United States Patent
Shresta

(10) Patent No.: US 11,806,393 B2
(45) Date of Patent: Nov. 7, 2023

(54) FLAVIVIRUS PEPTIDE SEQUENCES, EPITOPES, AND METHODS AND USES THEREOF

(71) Applicant: La Jolla Institute for Allergy and Immunology, La Jolla, CA (US)

(72) Inventor: Sujan Shresta, La Jolla, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 0 days.

(21) Appl. No.: 16/537,447

(22) Filed: Aug. 9, 2019

(65) Prior Publication Data

US 2020/0237892 A1 Jul. 30, 2020

Related U.S. Application Data

(63) Continuation-in-part of application No. PCT/US2018/017554, filed on Feb. 9, 2018.

(60) Provisional application No. 62/845,414, filed on May 9, 2019, provisional application No. 62/457,753, filed on Feb. 10, 2017.

(51) Int. Cl.
*A61K 39/12* (2006.01)
*G01N 33/50* (2006.01)
*G01N 33/68* (2006.01)
*C07K 7/06* (2006.01)

(52) U.S. Cl.
CPC ............ *A61K 39/12* (2013.01); *C07K 7/06* (2013.01); *G01N 33/505* (2013.01); *G01N 33/6893* (2013.01)

(58) Field of Classification Search
None
See application file for complete search history.

(56) References Cited

U.S. PATENT DOCUMENTS

| 10,350,285 B2 * | 7/2019 | Reyes-Sandoval .... A61K 39/12 |
| 2009/0221005 A1 | 9/2009 | Kelleher et al. |
| 2016/0130305 A1 * | 5/2016 | Shresta .................... C12N 7/00 |
| | | 424/186.1 |

FOREIGN PATENT DOCUMENTS

| EP | 2 853 590 A1 | 4/2015 | |
| WO | WO-2011/163628 A2 | 12/2011 | |
| WO | WO-2016181147 A1 * | 11/2016 | ............ A61K 39/12 |
| WO | WO-2017015463 A2 * | 1/2017 | ............ A61K 39/12 |
| WO | WO-2017147458 A1 * | 8/2017 | ............ A61K 39/12 |
| WO | WO-2019092142 A1 * | 5/2019 | ............ A61K 39/12 |

OTHER PUBLICATIONS

Falcao et al., "Management of infection by the Zika virus," Ann Clin Microbiol Antimicrob 15:57 (Year: 2016).*

(Continued)

*Primary Examiner* — M Franco G Salvoza
(74) *Attorney, Agent, or Firm* — Foley & Lardner LLP

(57) ABSTRACT

The present application relates to composition of matter, processes and use of composition of matter relating to flavivirus peptides and epitopes, for example, for therapeutic or preventative vaccination against a flavivirus, and/or for inducing, enhancing, or sustaining an immune response against a flavivirus, and/or for detecting an infection with or an exposure to a flavivirus in a subject. The flavivirus may be for example the Zika and/or Dengue virus.

11 Claims, 93 Drawing Sheets

Specification includes a Sequence Listing.

(56) References Cited

OTHER PUBLICATIONS

Badwai M. M. et al., "Highly Conserved Epitopes of ZIKA Envelope Glycoprotein May Act as a Novel Peptide Vaccine with High Coverage: Immunoinformatics Approach", American Journal of Biomedical Research, 2016, vol. 4, No. 3, pp. 46-60.
International Search Report and Written Opinion issued in PCT/US2018/017554 dated Jun. 7, 2018, 11 pages.
Janahi E. M. et al., "In silico CD4+ , CD8+ T-cell and B-CELL immunity associated immunogenic epitope prediction and HLA distribution analysis of Zika virus", EXCLI Journal, Jan. 13, 2017, 16, pp. 63-72.
Mirza M. U. et al., "Towards peptide vaccines against Zika virus: Immunoinformatics combined with molecular dynamics simulations to predict antigenic epitopes of Zika viral proteins", Scientific Reports, Dec. 9, 2016, 6, 37313, pp. 1-17.
Ngono A. E. et al., "Mapping and Role of the CD8+ T Cell Response During Primary Zika Virus Infection in Mice", Cell host & microbe, Jan. 11, 2017, vol. 21, No. 1, pp. 35-46.
Sarma K. et al., "Immunoinformatics screening of prospective MHC class I restricted cytotoxic T-cell based epitopes in Zika virus", International Journal of Current Advanced Research, Sep. 2016, vol. 5, Issue 9, pp. 1229-1235.

\* cited by examiner

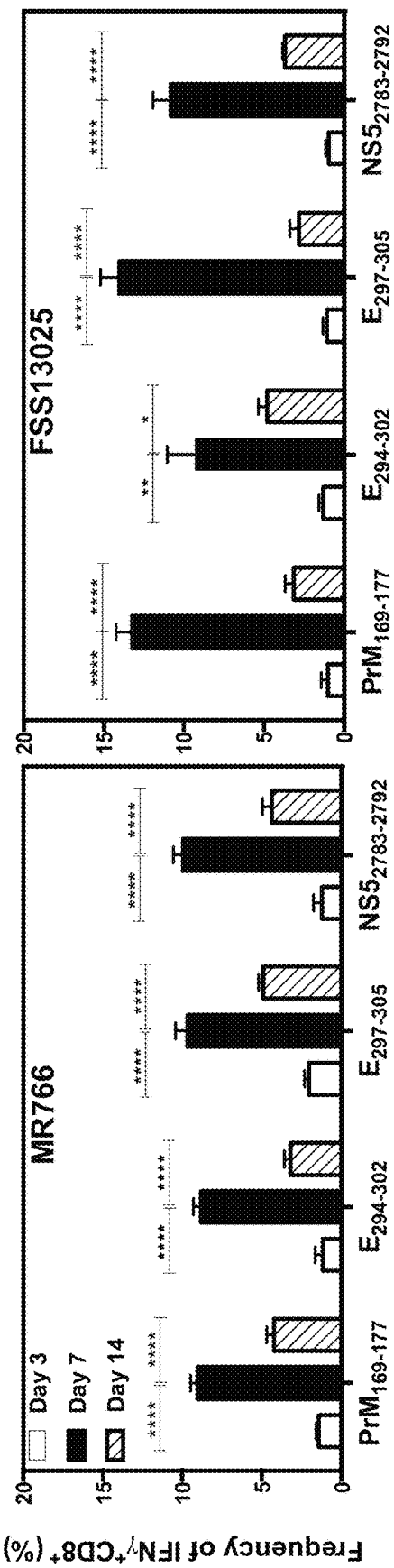
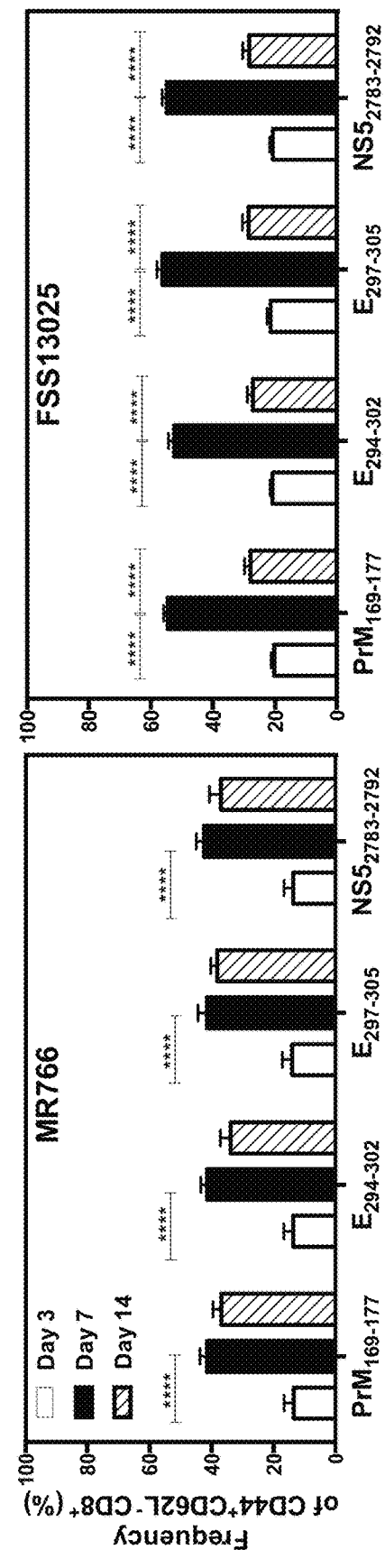
FIG. 5A
FIG. 5B

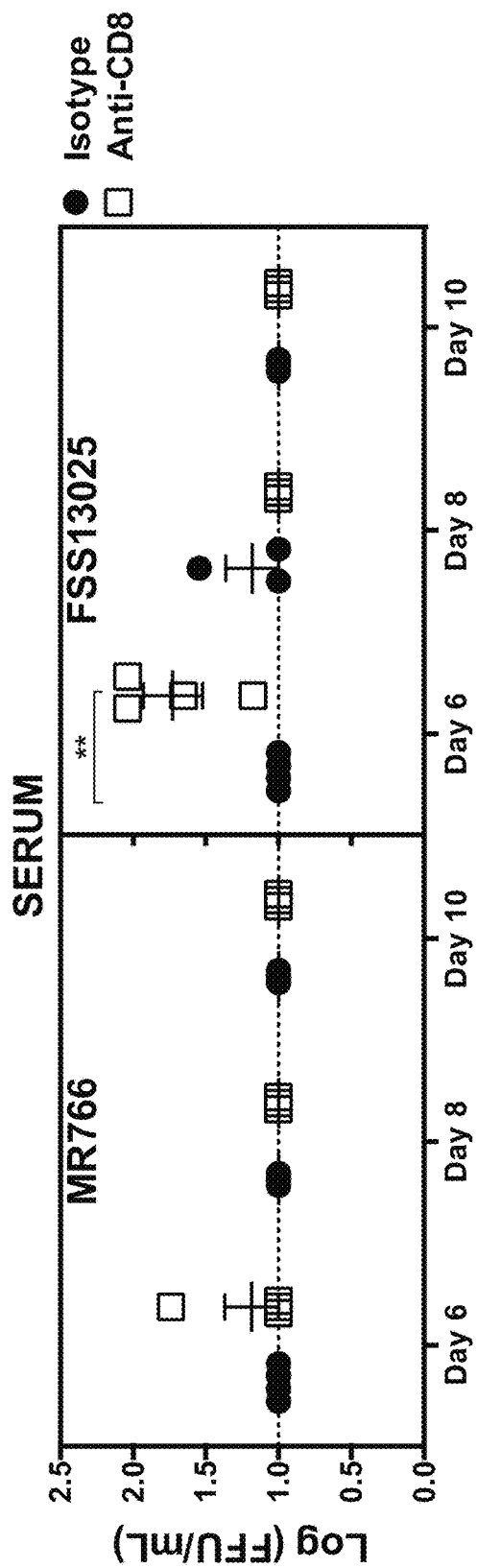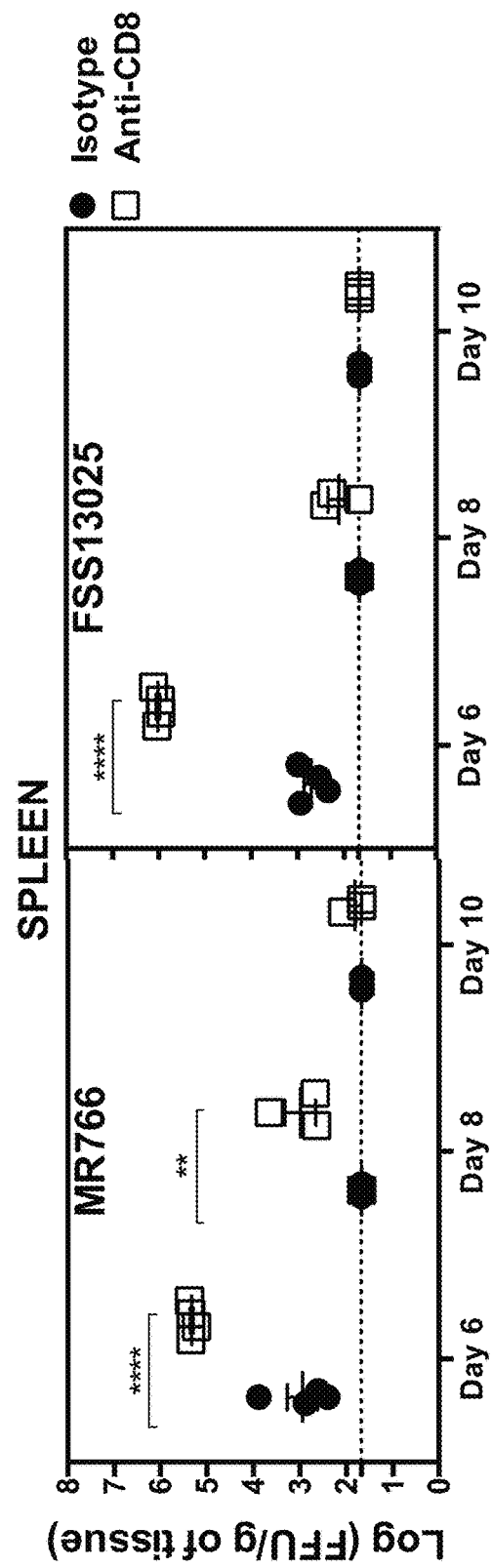

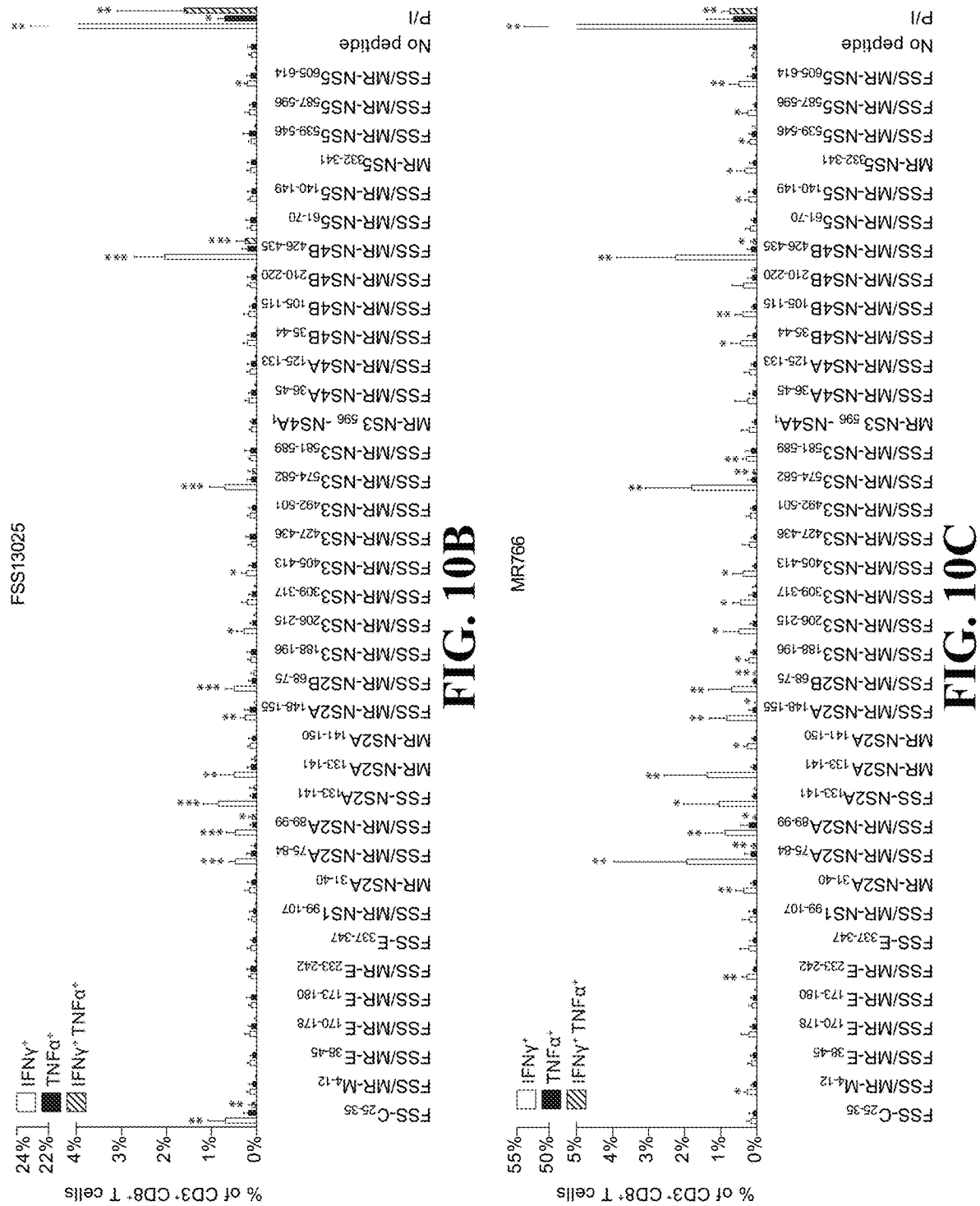

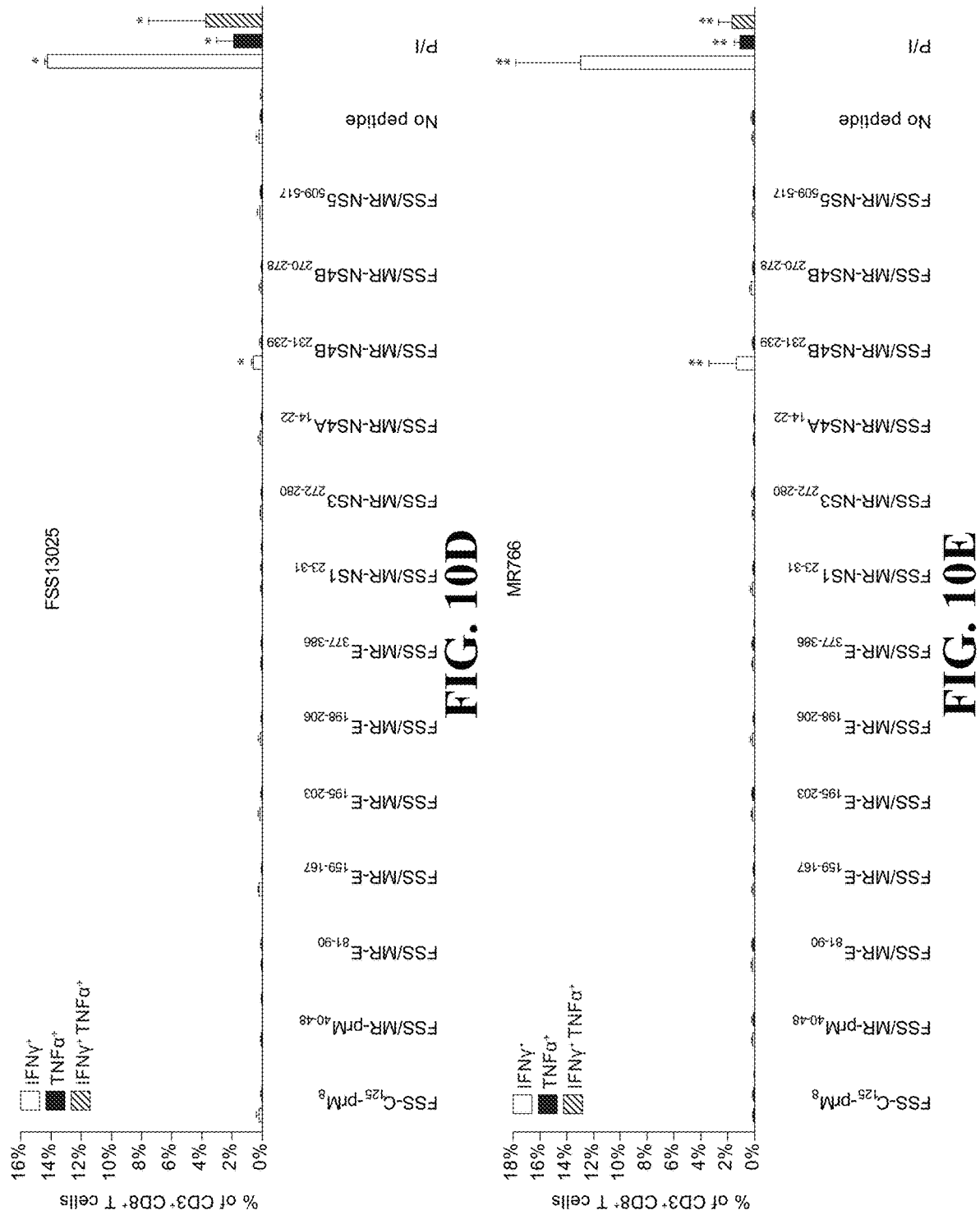

FLAVIVIRUS PEPTIDE SEQUENCES, EPITOPES, AND METHODS AND USES THEREOF

CROSS-REFERENCE TO RELATED APPLICATION

The present application is a continuation-in-part of PCT/US18/17554, filed Feb. 9, 2018, which claims the benefit of U.S. provisional patent application Ser. No. 62/457,753 filed on Feb. 10, 2017, and also claims priority to U.S. Provisional Application Ser. No. 62/845,414, filed May 9, 2019, the contents of each of which is incorporated herein by reference in their entirety.

GOVERNMENT SUPPORT

This invention was made with support under grants AI116813, AI140063 and NS106387 awarded by the National Institutes of Health. The government has certain rights in this invention.

TECHNICAL FIELD

The present application relates to composition of matter, processes and use of composition of matter relating to flavivirus peptides and epitopes.

SEQUENCE LISTING

The instant application contains a Sequence Listing which has been submitted electronically in ASCII format and is hereby incorporated by reference in its entirety. Said ASCII copy, created on Aug. 6, 2019, is named 116639-1020_SL.txt and is 41,683 bytes in size.

BACKGROUND

Flavivirus is a genus of viruses in the family Flaviviridae. This genus includes the West Nile virus, dengue virus (DENV), tick-borne encephalitis (TBE) virus, yellow fever virus, Zika virus (ZIKV) and several other viruses which may cause encephalitis, as well as insect-specific flaviviruses (ISFs) such as cell fusing agent virus (CFAV), Palm Creek virus (PCV), and Parramatta River virus (PaRV).

Flaviviruses are share several common aspects: common size (40-65 nm), symmetry (enveloped, icosahedral nucleocapsid), nucleic acid (positive-sense, single-stranded RNA around 10,000-11,000 bases), and appearance in the electron microscope. Flaviviruses are globally emerging and cause significant human disease in the form of encephalitis or hemorrhagic fever. Most flaviviruses are maintained in animal reservoirs in nature and are transmitted to humans primarily through the bite of an infected mosquito or tick. Other virus transmission routes can include handling infected animal carcasses, blood transfusion, child birth and through consumption of unpasteurized milk products.

Most cases of ZIKA infection have no symptoms, but when present they are usually mild and can resemble dengue fever, and may cause fever, rash, headache, pain behind the eyes, conjunctivitis, muscle or joint pain, nausea, vomiting, or loss of appetite.

Further, a causal relationship between ZIKV and a congenital syndrome including microcephaly has been confirmed in the 2015 Brazilian outbreak, and signs of microcephaly have been seen in ZIKV-infected mice. ZIKV has also been linked to Guillain-Barre Syndrome (GBS) and case reports of sexual transmission are mounting. Recently there was a major outbreak of ZIKV in the Western Hemisphere, which also was associated with GBS. Additionally, infection of pregnant women was confirmed to cause Congenital ZIKV Syndrome, which includes microcephaly and other birth defects. (Mlakar, J., et al., *Zika Virus Associated with Microcephaly*. N Engl J Med, 2016. 374(10): p. 951-8; Driggers, R. W., et al., *Zika Virus Infection with Prolonged Maternal Viremia and Fetal Brain Abnormalities*. N Engl J Med, 2016. 374(22): p. 2142-51; Hennessey, M., M. Fischer, and J. E. Staples, *Zika Virus Spreads to New Areas—Region of the Americas, May 2015-January 2016*. MMWR Morb Mortal Wkly Rep, 2016. 65(3): p. 55-8; Rasmussen, S. A., et al., *Zika Virus and Birth Defects—Reviewing the Evidence for Causality*. N Engl J Med, 2016. 374(20): p. 1981-7).

There are, however, fundamental gaps in the understanding of flaviviruses immunology and pathogenesis.

Vaccines are currently available for only yellow fever and Japanese and TBE; however, new vaccines for dengue and West Nile are in clinical trials in humans. In recent years, many studies have shown that flaviviruses, especially dengue virus has the ability to inhibit the innate immune response during the infection (Diamond M S (September 2009), *J. Interferon Cytokine Res.* 29 (9): 521-30; Jones M, Davidson A, Hibbert L, et al. (May 2005). *J. Virol.* 79 (9): 5414-20). Indeed, the dengue virus has many nonstructural proteins that allow the inhibition of various mediators of the innate immune system response. Disease diagnosis can be difficult as all flaviviruses are antigenically and genetically closely related. There are no effective antiviral therapies that exist for any flavivirus so the main approach to disease control is through vaccination and vector control.

As mosquito control has failed, and with the new disease syndromes caused by and associated with ZIKV infection, there is an urgent need to address the fundamental gaps in the understanding of flaviviruses immunology and pathogenesis so as to be able to develop more effective flavivirus vaccines, diagnosis assays, and/or treatment approaches.

ZIKV and DENV share similar amino acid sequences, with 43% overall homology and up to 68% identity for the non-structural proteins (Lazear, H. M. et al., Journal of virology 90, 4864-4875, 2016), (Wen, J. & Shresta, Current opinion in immunology 59, 1-8, 2019). Additionally, ZIKV and DENV utilize the same vectors for transmission and have overlapping geographical ranges. Cross-reactivity has been demonstrated between ZIKV and DENV at antibody (Ab) (Dejnirattisai, W. et al., Nature immunology 17, 1102-1108, 2016); (Castanha, P. M. S. et al., The Journal of infectious diseases 215, 781-785, 2017); (Charles, A. S. & Christofferson, R. C., PLoS Curr 8, 2016); (Kawiecki, A. B. & Christofferson, R. C., The Journal of infectious diseases 214, 1357-1360, 2016); (Paul, L. M. et al., Clinical & translational immunology 5, e117, 2016); (Priyamvada, L. et al., Proceedings of the National Academy of Sciences of the United States of America 113, 7852-7857, 2016); (Swanstrom, J. A. et al., Zika Virus. mBio 7, 2016); and both CD4[+] and CD8[+] T cell levels (Paquin-Proulx, D. et al., Pathogens & immunity 2, 274-292, 2017); (Grifoni, A. et al., Journal of virology 91, e01469-01417, 2017); (Lim, M. Q. et al., Frontiers in immunology 9, 2225, 2018). Moreover, studies using mouse models have shown that DENV/ZIKV-cross-reactive Abs play a dual role in mediating both protection and pathogenesis (Fernandez, E. et al., Nature immunology 18, 1261-1269, 2017); (Kam, Y. W. et al., JCI insight 2, 2017); (Slon Campos, J. L. et al., PLoS one 12, e0181734, 2017); (Bardina, S. V. et al., Science, 2017); (Bardina, S. V. et al., Science, 2017). It is well established that cross-reactive Abs produced during a primary infection with one DENV serotype can exacerbate, rather than protect against, secondary infection with a different DENV serotype (Katzelnick, L. C. et al., Science 358, 929-932, 2017); (Salje, H. et al., Nature 557, 719-723, 2018). This occurs through a process known as Ab-dependent enhancement (ADE) of infection and can lead to a potentially life-threatening infection with hemorrhagic fever/shock (severe dengue) (Halstead, S. B. Dengue. Lancet 370, 1644-1652, 2007). Considering the close homology and overlapping endemicity of the four DENV serotypes and ZIKV, there is a strong possibility that natural infection and/or vaccination against heterologous viruses could have disastrous consequences. Thus, it is crucial to deepen the understanding of the extent to which DENV/ZIKV-cross-reactive Ab and T cell immunity can be protective vs. pathogenic during secondary ZIKV or DENV infection.

SUMMARY

This Summary is provided to introduce a selection of concepts in a simplified form that are further described below in the Detailed Description. This Summary is not intended to identify key aspects or essential aspects of the claimed subject matter.

This disclosure provides a composition comprising, or consisting essentially of, or yet consisting of an acceptable carrier or diluent, and one or more peptide selected from the group of:
a) a peptide comprising an amino acid sequence which is at least 95% identical to the amino acid sequence set forth in any one of SEQ ID NO: 1 to SEQ ID NO: 93 or SEQ ID NO: 97 to SEQ ID NO: 131, or a subsequence, portion, homologue, variant or derivative of each thereof;
b) a peptide comprising an amino acid sequence which is at least 95% identical to the amino acid sequence set forth in any one of SEQ ID NO: 1 to SEQ ID NO: 93, or a subsequence, portion, homologue, variant or derivative of each thereof;
c) a peptide comprising an amino acid sequence which is at least 95% identical to the amino acid sequence set forth in any one of SEQ ID NO: 97 to SEQ ID NO: 131, or a subsequence, portion, homologue, variant or derivative of each thereof;
d) a peptide comprising an amino acid sequence which is at least 95% identical to any one of FSS/MR-NS2A$_{75-84}$ (SEQ ID NO: 39), FSS/MR-NS2A$_{89-99}$ (SEQ ID NO: 40), FSS-NS2A$_{133-141}$ (SEQ ID NO: 41), MR-NS2A$_{133-141}$ (SEQ ID NO: 42), FSS/MR-NS2A$_{148-155}$ (SEQ ID NO: 44), FSS/MR-NS2B$_{68-75}$ (SEQ ID NO: 45), FSS/MR-NS3$_{206-215}$ (SEQ ID NO: 47), FSS/MR-NS3$_{574-582}$ (SEQ ID NO: 52), FSS/MR-NS4B$_{426-435}$ (SEQ ID NO: 60), FSS/MR-E$_{159-167}$ (SEQ ID NO: 70), FSS/MR-E$_{195-203}$ (SEQ ID NO: 71), FSS/MR-NS1$_{23-31}$ (SEQ ID NO: 74), FSS/MR-NS4B$_{231-239}$ (SEQ ID NO: 77), C$_{27-41}$ (SEQ ID NO: 97), C$_{53-67}$ (SEQ ID NO: 98), C$_{81-95}$ (SEQ ID NO: 99), E$_{134-148}$ (SEQ ID NO: 102), E$_{450-464}$ (SEQ ID NO: 104), NS2A$_{66-80}$, (SEQ ID NO: 108), NS3$_{601}$-NS4A$_{12}$, NS4B$_{40-54}$ (SEQ ID NO: 118), or NS5$_{222-236}$ (SEQ ID NO: 125), or a subsequence, portion, homologue, variant or derivative of each thereof;
e) a peptide consisting of an amino acid sequence which is at least 95% identical to the amino acid sequence set forth in any one of SEQ ID NO: 1 to SEQ ID NO: 93 or SEQ ID NO: 97 to SEQ ID NO: 131, or a subsequence, portion, homologue, variant or derivative thereof;
f) a peptide consisting of an amino acid sequence which is at least 95% identical to the amino acid sequence set forth in any one of SEQ ID NO: 1 to SEQ ID NO: 93, or a subsequence, portion, homologue, variant or derivative thereof;
g) a peptide consisting of an amino acid sequence which is at least 95% identical to the amino acid sequence set forth in any one of SEQ ID NO: 97 to SEQ ID NO: 131, or a subsequence, portion, homologue, variant or derivative thereof;
h) a peptide consisting of an amino acid sequence which is at least 95% identical to any one of FSS/MR-NS2A$_{75-84}$ (SEQ ID NO: 39), FSS/MR-NS2A$_{89-99}$ (SEQ ID NO: 40), FSS-NS2A$_{133-141}$ (SEQ ID NO: 41), MR-NS2A$_{133-141}$ (SEQ ID NO: 42), FSS/MR-NS2A$_{148-155}$ (SEQ ID NO: 44), FSS/MR-NS2B$_{68-75}$ (SEQ ID NO: 45), FSS/MR-NS3$_{206-215}$ (SEQ ID NO: 47), FSS/MR-NS3$_{574-582}$ (SEQ ID NO: 52), FSS/MR-NS4B$_{426-435}$ (SEQ ID NO: 60), FSS/MR-E$_{159-167}$ (SEQ ID NO: 70), FSS/MR-E$_{195-203}$ (SEQ ID NO: 71), FSS/MR-NS1$_{23-31}$ (SEQ ID NO: 74), FSS/MR-NS4B$_{231-239}$ (SEQ ID NO: 77), C$_{27-41}$ (SEQ ID NO: 97), C$_{53-67}$ (SEQ ID NO: 98), C$_{81-95}$ (SEQ ID NO: 99), E$_{134-148}$ (SEQ ID NO: 102), E$_{450-464}$, NS2A$_{66-80}$ (SEQ ID NO: 108), NS3$_{601}$-NS4A$_{12}$, NS4B$_{40-54}$ (SEQ ID NO: 118), or NS5$_{222-236}$ (SEQ ID NO: 125) or a subsequence, portion, homologue, variant or derivative of each thereof;
i) a peptide of any of a) through h), wherein the peptide comprises a Zika T cell epitope;
j) a peptide of any of a) through h), wherein the peptide comprises a Zika CD4+ T cell epitope;
k) a peptide of any of a) through h), wherein the peptide comprises a Zika T cell epitope;
l) a peptide of any of a) through h), wherein the peptide comprises a Zika T cell epitope that is not conserved in another flavivirus;
m) a peptide of any of a) through h), wherein the peptide comprises a Zika T cell epitope, that is conserved in another flavivirus;
n) a peptide of any of a) through h), wherein the peptide includes a Dengue T cell epitope;
o) a peptide of any of a) through h), wherein the peptide includes a Zika T cell epitope and a Dengue T cell epitope;
p) a peptide of any of a) through h), wherein the peptide comprises a CD8 T cell epitope;
q) a peptide of any of a) through h), wherein the peptide elicits, stimulates, induces, promotes, increases or enhances a T cell or B cell response to Zika virus; or
r) a peptide of any of a) through h), wherein the peptide elicits, stimulates, induces, promotes, increases or enhances the T cell or B cell response to a Zika virus envelope, NS2, NS4 or NS5 protein or peptide, or a variant, homologue, derivative or subsequence thereof.

In one aspect, the composition comprises, or consists essentially of, or yet further consisting of 30, 40, 50, 60, 70 or more peptides of any of a) through r) and wherein each peptide comprises a different amino acid sequence from each other.

The compositions can be in any acceptable diagnostic, therapeutic or form for an in vitro or in vivo assay. Non-limiting examples of such include a form from the group of: lyophilized form, frozen form, or in the form of an injectable preparation.

Also provided is an in vitro method for detecting an infection with or an exposure to a flavivirus in a subject, the method comprising, or consisting essentially of, or yet further consisting of contacting a sample comprising T cells with the composition of claim 1, processing the sample to detect the presence of a T cell response, and detecting the presence or absence of the T cell response, wherein the presence of the T cell response is indicative that the subject has been infected with or exposed to the flavivirus. The flavivirus can be a Zika virus or a Dengue virus.

Further provided is a method of inducing, enhancing, or sustaining an immune response against a flavivirus in a subject, the method comprising, or consisting essentially of, or yet further consisting of, contacting T cells of the subject with an effective amount of the composition as described herein. In one aspect, the method is conducted more days following the date of suspected infection by or exposure to the flavivirus virus.

In yet a further aspect, provided herein is a method diagnosing flavivirus infection or flavivirus exposure in a subject, the method comprising, or consisting essentially of, or yet further consisting of, contacting cells of a subject with the composition as described herein and determining if the composition elicits a response from the contacted cells, wherein a response identifies that the subject has been infected with or exposed to a flavivirus. In one aspect, the method is conducted more days following the date of suspected infection by or exposure to the flavivirus.

Further provided is a method of stimulating, inducing, promoting, increasing, or enhancing an immune response against a flavivirus in a subject, the method comprising, or consisting essentially of, or yet further consisting of administering to a subject an effective amount of the composition of claim 1, effective to stimulate, induce, promote, increase, or enhance an immune response against flavivirus in the subject. In one embodiment, the immune response provides the subject with protection against a flavivirus infection or pathology, or one or more physiological conditions, disorders, illnesses, diseases or symptoms caused by or associated with a flavivirus infection or pathology.

Also provided herein is method for treating, reducing or inhibiting susceptibility to flavivirus infection or pathology in a subject, the method comprising, or consisting essentially of, or yet further consisting of, administering to a subject an amount of the composition as described herein, sufficient to treat the subject for the flavivirus infection. In one aspect, the method elicits, stimulates, induces, promotes, increases, or enhances an anti-flavivirus T cell response or a CD4+ T cell response. In another aspect, the composition is administered prior to exposure to the virus or within 2-72 hours after a rash develops.

Also provided herein is a method of inducing, increasing, promoting or stimulating anti-flavivirus activity of T cells in a subject, the method comprising, or consisting essentially of, or yet further consisting of, administering to a subject an amount of the composition as described herein sufficient to induce, increase, promote or stimulate anti-flavivirus activity of T cells in the subject.

In another aspect, a method of stimulating, inducing, promoting, increasing, or enhancing an immune response against flavivirus in a subject is provided, the method comprising, or consisting essentially of, or yet further consisting of, administering to a subject an amount of the composition as described herein, sufficient to stimulate, induce, promote, increase, or enhance an immune response against flavivirus in the subject.

Also provided herein is a method of treating a subject for a flavivirus infection, the method comprising, or alternatively consisting essentially of, or yet further consisting of, administering to a subject an amount of the composition as described herein, sufficient to treat the subject for the flavivirus infection. In one aspect, the method reduces flavivirus titer, increases or stimulates flavivirus clearance, reduces or inhibits flavivirus proliferation, reduces or inhibits increases in flavivirus titer or flavivirus proliferation, reduces the amount of a flavivirus protein or the amount of a flavivirus nucleic acid, or reduces or inhibits synthesis of a flavivirus protein or a flavivirus nucleic acid or reduces or improves one or more adverse physiological conditions, disorders, illness, diseases, symptoms or complications caused by or associated with flavivirus infection or pathology.

In one aspect, a method of inducing, increasing, promoting or stimulating anti-flavivirus activity of T cells in a subject is provided, the method comprising, or consisting essentially of, or yet further consisting of, administering to a subject an amount of the composition as described herein, sufficient to induce, increase, promote or stimulate anti-flavivirus activity of T cells in the subject.

In the methods as described above and herein, the flavivirus is a Zika virus or a Dengue virus and the subject can be a mammal, such as for example, a human patient.

BRIEF DESCRIPTION OF THE DRAWINGS

A detailed description of specific exemplary embodiments is provided herein below with reference to the accompanying drawings in which:

FIGS. 5A-5B: shows exemplary non-limiting results of kinetics of the ZIKV-specific CD8$^+$ T cell response in LysMCre$^+$IFNAR$^{fl/fl}$ mice in accordance with an embodiment of the present disclosure;

FIGS. 6A-6F: shows graphs that illustrate non-limiting levels of infectious virus in the serum of LysMCre$^+$IFNAR$^{fl/fl}$ treated with depleting anti-CD8 or isotype control antibody on days 3 and 1 before infection with 10$^5$ FFU of MR766 or FSS13025 in accordance with an embodiment of the present disclosure;

FIG. 8 discloses SEQ ID NOS: 130-145, 24 and 146-157, respectively, in order of appearance;

FIGS. 10A-10E: shows graphs that illustrate non-limiting results of cytokine secretion pattern of CD8+ T cells directed to HLA-B*0702- and HLA-A*0101-binding epitopes identified via IFNγ ELISPOT in accordance with an embodiment of the present disclosure;

FIGS. 11A-11E: shows graphs that illustrate non-limiting results that demonstrate the impact of prior DENV2 infection on the ZIKV-specific CD8+ T cell response in accordance with an embodiment of the present disclosure;

FIGS. 12A-12H: shows graphs that illustrate non-limiting results that demonstrate ZIKV-specific and ZIKV/DENV cross-reactive peptide immunization elicited CD8+ T cell response and mediated protection against ZIKV in accordance with an embodiment of the present disclosure;

Figure 1A:
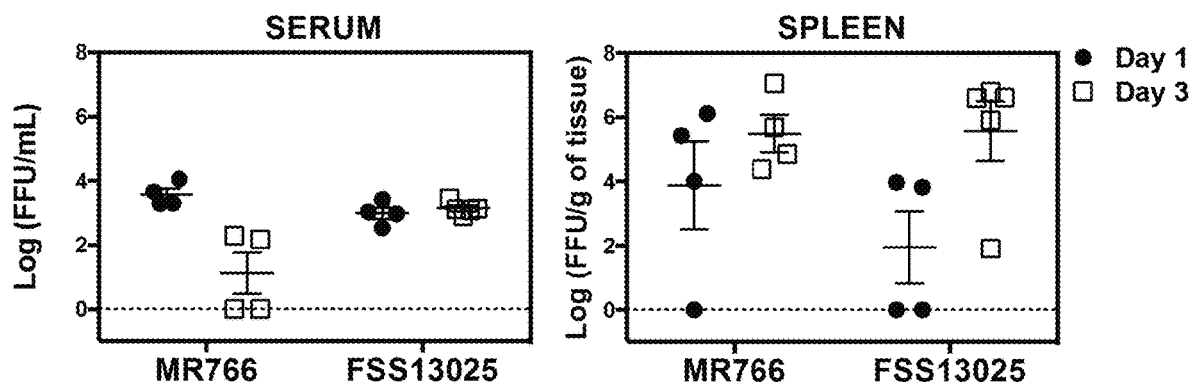
FIGS. 1A-1C: shows non-limiting characterization of ZIKV infection and identification of epitopes recognized by CD8$^+$ T cells in WT C57BL/6 mice treated with IFNAR-blocking antibody in accordance with an embodiment of the present disclosure.

In the drawings, exemplary embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

A detailed description of one or more embodiments of the invention is provided below along with accompanying figures that illustrate the principles of the invention. The invention is described in connection with such embodiments, but the invention is not limited to any embodiment. The scope of the invention is limited only by the claims. Numerous specific details are set forth in the following description in order to provide a thorough understanding of the invention. These details are provided for the purpose of non-limiting examples and the invention may be practiced according to the claims without some or all of these specific details. For the purpose of clarity, technical material that is known in the technical fields related to the invention has not been described in detail so that the invention is not unnecessarily obscured.

The present application describes experimental results and line of reasoning which supports the development of more effective flavivirus vaccine, diagnosis assay, and/or treatment approach, than what has been previously described.

In one embodiment, the flavivirus vaccine, diagnosis assay, and/or treatment approach relates to ZIKV.

In one embodiment, the flavivirus vaccine, diagnosis assay, and/or treatment approach relates to DENV.

In one embodiment, the flavivirus vaccine, diagnosis assay, and/or treatment approach relates to ZIKV and DENV.

$CD8^+$ cytotoxic T cells play a key role in the defense against intracellular pathogens and tumor cells. $CD8^+$ T cell immune responses are driven by the recognition of foreign peptides presented by major histocompatibility complex class I (MHC I) molecules at the cell surface. The identification of these peptides ($CD8^+$ T cell epitopes) is therefore important for understanding disease pathogenesis and etiology as well as for vaccine design.

A large body of literature has provided evidence for a potential dual role for $CD8^+$ T cells in protection and pathogenesis during dengue virus (DENV) infection (Screaton et al., 2015; Tang et al., 2015; Weiskopf and Sette, 2014; Zellweger and Shresta, 2014). Epidemiologic studies indicate that Severe Dengue is most often seen in individuals experiencing a heterotypic DENV infection after prior seroconversion to at least one of the other three serotypes (Guzman et al., 2000; Sangkawibha et al., 1984). Some studies showed cross-reactive $CD8^+$ T cells are more activated during secondary infection (Mongkolsapaya et al., 2003) with a suboptimal T cell phenotype (Mongkolsapaya et al., 2006) (Imrie et al., 2007; Mangada and Rothman, 2005) suggesting a possible pathogenic role for cross-reactive T cells. However, recently emerging literature points to a protective role for T cells in DENV infection (Weiskopf et al., 2013; Weiskopf et al., 2015), and our previous work on DENV using mouse models (Prestwood et al., 2012b; Yauch et al., 2010; Yauch et al., 2009; Zellweger et al., 2014; Zellweger et al., 2013; Zellweger et al., 2015) in C57BL/6 and 129/Sv mice lacking type I IFN receptor (IFNAR) alone or both type I and II IFN receptors (AB6, A129, and AG129) has provided multiple lines of evidence indicating a protective role for $CD8^+$ T cells.

Signs of clinical Zika disease have historically been similar to signs of dengue fever, and ZIKV's immunologic similarity to DENV has also been documented. Blast search results show that ZIKV and DENV have about 52%-57% amino acid sequence homology. Indeed, serologic cross-reactivity of these two viruses has probably contributed to misdiagnosis and underdiagnosis of ZIKV, and cases of concurrent infection with ZIKV and DENV have also been documented. Cellular immunity to flaviviruses is also cross-reactive, and cross-reactive T cells may play a dual role in protection and pathogenesis. However, to date ZIKV epitopes recognized by human $CD4^+$ or $CD8^+$ T cells have not been identified, and their identification would accelerate investigations of immunity and pathogenesis, and development of vaccines and potentially diagnostics.

Epidemiologic and laboratory studies from the relatively large body of knowledge on the 4 serotypes of DENV indicate that the severe and potentially fatal form of dengue disease occurs most commonly when patients are infected with a second DENV serotype after infection by and recovery from a first heterologous DENV serotype. One hypothesis deemed "original T cell antigenic sin" suggests that disease severity increases in secondary infection because T cells primed during the first DENV infection predominate in the subsequent infection with a different DENV serotype, and these serotype-cross-reactive T cells fail to mount an appropriate immune response to the second DENV serotype. Similar T cell cross-reactivity may exist between ZIKV and DENV, as ZIKV and DENV share high amino acid identity. Consistent with this homology, several recent studies have revealed cross-reactivity between ZIKV and DENV at the antibody response level. In particular, both plasma and monoclonal antibodies isolated from DENV-exposed donors can have potent neutralizing activity against ZIKV and can mediate antibody-dependent enhancement (ADE) of ZIKV infection. In fact, monoclonal antibodies isolated from ZIKV-immune donors can induce ADE of DENV infection in vitro and in vivo in mice.

Very little is known, however, about T cell-mediated responses to ZIKV at present. As ZIKV and DENV will continue to co-circulate in many regions of the world due to their common vectors and geographical distributions, it is critical to start exploring the protective vs. potentially pathogenic influence of T cells induced by prior DENV exposure on ZIKV infection. Knowledge about the T cell epitopes that are unique to ZIKV or shared with DENV is lacking. As a consequence, suitable tools for investigating ZIKV-specific T cell immunity and vaccine development are not available.

Cellular immunity to flaviviruses is also cross-reactive, and cross-reactive T cells may play a dual role in protection and pathogenesis.

Definitions

Unless otherwise defined, all technical and scientific terms used herein have the same meaning as commonly understood by a person of ordinary skill in the art to which the present invention pertains. As used herein, and unless stated otherwise or required otherwise by context, each of the following terms shall have the definition set forth below.

"Administering" an expression vector, nucleic acid molecule, or a delivery vehicle (such as a chitosan nanoparticle) to a cell comprises transducing, transfecting, electroporation, translocating, fusing, phagocytosing, shooting or ballistic methods, etc., i.e., any means by which a protein or nucleic acid can be transported across a cell membrane and preferably into the nucleus of a cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide. The nucleotide sequences are displayed herein in the conventional 5'-3' orientation.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and 0-phosphoserine. The expression "amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid and nucleic acid sequences, individual substitutions, deletions or additions that alter, add or delete a single amino acid or-nucleotide or a small percentage of amino acids or nucleotides in the sequence create a "conservatively modified variant," where the alteration results in the substitution of an amino acid with a chemically similar amino acid. Conservative substitution tables providing functionally similar amino acids are well known in the art.

For example, the following groups each contain amino acids that are conservative substitutions for one another (see, e.g., Creighton, Proteins (1984) W.H. Freeman, New York, pages 6-20, for a discussion of amino acid properties):

Alanine (A), Glycine (G)
Serine (S), Threonine (T)
Aspartic acid (D), Glutamic acid (E)
Asparagine (N), Glutamine (Q)
Cysteine (C), Methionine (M)
Arginine (E), Lysine (K), Histidine (H)
Isoleucine (I), Leucine (L), Valine (V)
Phenylalanine (F), Tyrosine (Y), Tryptophan (W)

In light of the present disclosure, in particular in view of the experimental data described in the examples of the present text, the person of skill will readily understand which amino acid may be substituted, deleted or added to a given sequence to create a conservatively modified variant comprising an amino acid sequence which is at least at least 95%, or at least 96%, or at least 97%, or at least 98%, or at least 99%, identical to the amino acid sequence set forth in any one of set forth in any one or more of SEQ ID NO: 1 to SEQ ID NO: 131, or alternatively in any one or more of SEQ IDS NO: 1 to SEQ ID NO: 93; or alternatively any one or more of SEQ ID NO: 94 to SEQ ID NO: 131, Table 10 and Table 11, without undue effort.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods, such as qPCR.

The phrases "coding sequence," "structural sequence," and "structural nucleic acid sequence" refer to a physical structure comprising an orderly arrangement of nucleic acids. The nucleic acids are arranged in a series of nucleic acid triplets that each form a codon. Each codon encodes for a specific amino acid. Thus, the coding sequence, structural sequence, and structural nucleic acid sequence encode a series of amino acids forming a protein, polypeptide, or peptide sequence. The coding sequence, structural sequence, and structural nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The phrases "DNA sequence," "nucleic acid sequence," and "nucleic acid molecule" refer to a physical structure comprising an orderly arrangement of nucleic acids. The DNA sequence or nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

The term "treating" refers to a process by which an infection or a disease or the symptoms of an infection or a disease associated with a flavivirus strain are alleviated or completely eliminated. As used herein, the term "preventing" refers to a process by which an infection or a disease or symptoms of an infection or a disease associated with a flavivirus are obstructed or delayed.

The expression "an acceptable carrier" may refer to a vehicle for containing a compound that can be administered to a subject without significant adverse effects.

As used herein, the term "adjuvant" means a substance added to the composition of the invention to increase the composition's immunogenicity. The mechanism of how an adjuvant operates is not entirely known. Some adjuvants are believed to enhance the immune response (humoral and/or cellular response) by slowly releasing the antigen, while other adjuvants are strongly immunogenic in their own right and are believed to function synergistically.

The expression "ELISPOT" refers to the known Enzyme-Linked ImmunoSpot assay which typically allows visualization of the secretory product(s) of individual activated or responding cells. Each spot that develops in the assay represents a single reactive cell. Thus, the ELISPOT assay provides both qualitative (regarding the specific cytokine or other secreted immune molecule) and quantitative (the frequency of responding cells within the test population) information. Generally speaking, in an ELISPOT assay, the membrane surfaces in a 96-well PVDF-membrane microtiter plate are coated with capture antibody that binds a specific epitope of the cytokine being assayed. During the cell incubation and stimulation step, a biological sample (typically containing PBMCs) is seeded into the wells of the plate along with the antigen (which can be a peptide as described in the present disclosure), and forms a monolayer on the membrane surface of the well. As the antigen-specific cells are activated, they release the cytokine, which is captured directly on the membrane surface by the immobilized antibody. The cytokine is thus "captured" in the area directly surrounding the secreting cell, before it has a chance to diffuse into the culture media, or to be degraded by proteases and bound by receptors on bystander cells. Subsequent detection steps visualize the immobilized cytokine as an ImmunoSpot; essentially the secretory footprint of the activated cell.

The terms "determining," "measuring," "evaluating," "assessing," and "assaying," as used herein, generally refer to any form of measurement, and include determining if an element is present or not in a biological sample. These terms include both quantitative and/or qualitative determinations, which both require sample processing and transformation steps of the biological sample. Assessing may be relative or absolute. The phrase "assessing the presence of" can include determining the amount of something present, as well as determining whether it is present or absent.

The expression "biological sample" includes in the present disclosure any biological sample that is suspected of comprising a T cell, such as for example but without being limited thereto, blood and fractions thereof, urine, excreta, semen, seminal fluid, seminal plasma, prostatic fluid, pre-ejaculatory fluid (Cowper's fluid), pleural effusion, tears, saliva, sputum, sweat, biopsy, ascites, amniotic fluid, lymph, vaginal secretions, endometrial secretions, gastrointestinal secretions, bronchial secretions, breast secretions, and the like.

The expression "treatment" includes inducing, enhancing, or sustaining an immune response against a flavivirus infection or symptoms associated thereto. For example, the treatment may induce, increase, promote or stimulate anti-flavivirus activity of immune system cells in a subject following the treatment. For example, the immune system cells may include T cells, preferably $CD8^+$ T cells.

The expression "therapeutically effective amount" may include the amount necessary to allow the component or composition to which it refers to perform its immunological role without causing overly negative effects in the host to which the component or composition is administered. The exact amount of the components to be used or the composition to be administered will vary according to factors such as the type of condition being treated, the type and age of the subject to be treated, the mode of administration, as well as the other ingredients in the composition.

Modes for Carrying Out the Disclosure

The flaviviruses Zika virus (ZIKV) and dengue virus (DENV) share substantial sequence similarity, have the same mosquito vector, and have overlapping geographic ranges. Although DENV/ZIKV-cross-reactive $CD4^+$ T cells have been identified in humans, very little is known about the protective and/or pathogenic effects of these cells during ZIKV or DENV infection. Here, using a human HLA-DRB1*0101 transgenic interferon $\alpha/\beta$ receptor-deficient mouse model that supports robust DENV and ZIKV replication, Applicants examined the epitope cross-reactivity of $CD4^+$ T cells in DENV-immune animals infected with ZIKV, and valuated the ability of DENV/ZIKV-cross-reactive $CD4^+$ T cells to protect against ZIKV infection. Mapping of the HLA-DRB1*0101-restricted $CD4^+$ T cell response identified four DENV/ZIKV-cross-reactive Th1 $CD4^+$ T cell epitopes. Vaccination of mice with either ZIKV-specific or DENV2/ZIKV-cross-reactive epitopes induced a $CD4^+$ T cell response sufficient to reduce tissue viral burden following ZIKV challenge, and this vaccine-elicited CD4+ T cell response conferred protection via secretion of IFNγ and TNF. These data reveal DENV/ZIKV-cross-reactive CD4+ T cells producing the canonical Th1 cytokines as a novel correlate of protection against ZIKV, and demonstrates that the efficacy of DENV and ZIKV vaccines could be optimized by including one or more virus-specific and/or cross-reactive CD4+ T cell epitopes (including but not limited to Th1 CD4+ T cell epitopes) disclosed herein.

Antigenic Peptides and Compositions

As embodied and broadly described herein, the present disclosure relates to a composition comprising at least one isolated peptide and an acceptable carrier or diluent, the at least one peptide comprising an amino acid sequence which is at least 95%, or at least 96%, or at least 97%, or at least 98%, or at least 99%, or 100% identical to the amino acid sequence set forth in any one or more of SEQ ID NO: 1 to SEQ ID NO: 93 and SEQ ID NO: 97-131, or alternatively in any one of or more SEQ IDS NO: 1 to SEQ ID NO: 93; or alternatively any one or more of SEQ ID NO: 97 to SEQ ID NO: 131. In certain non-limiting embodiments of the composition described herein, the composition comprises a plurality of the isolated peptide, where each peptide of the plurality of the isolated peptide comprises a respective amino acid sequence which is different from one another. For example, a first peptide in the plurality of the isolated peptide may comprise an amino acid sequence which is 95% identical with the amino acid sequence set forth in SEQ ID NO: 1 and at least a second peptide in the plurality of the isolated peptide may comprise an amino acid sequence which is 98% identical with the amino acid sequence set forth in SEQ ID NO: 2. In another aspect, a first peptide in the plurality of the isolated peptide may comprise an amino acid sequence which is 95% identical with the amino acid sequence set forth in any one set forth in SEQ ID NO: 97 to SEQ ID NO: 131 and at least a second peptide in the plurality of the isolated peptide may comprise an amino acid sequence which is 98% identical with the amino acid sequence set forth in any one set forth in SEQ ID NO: 97 to SEQ ID NO: 131. The various possibilities of having different peptide sequence in a plurality of peptides will be apparent to the person of skill in light of the present disclosure, and for conciseness sake will not be further described here.

As embodied and broadly described herein, the present disclosure relates to a composition comprising a protein or peptide comprising, consisting of or consisting essentially of an amino acid sequence set forth in set forth in any one of SEQ ID NO: 1 to SEQ ID NO: 93, or SEQ ID NO: 97 to SEQ ID NO: 131, or alternatively in any one or more of SEQ IDS NO: 1 to SEQ ID NO: 93; or alternatively any one or more of SEQ ID NO: 97 to SEQ ID NO: 131, or a subsequence, portion, homologue, variant or derivative thereof. In certain embodiments, the composition comprises two or more proteins or peptides comprising, consisting of or consisting essentially of an amino acid sequence set forth in set forth in any one or more of SEQ ID NO: 1 to SEQ ID NO: 93, or SEQ ID NO: 97 to SEQ ID NO: 131, or alternatively in any one or more of SEQ IDS NO: 1 to SEQ ID NO: 93; or alternatively any one or more of SEQ ID NO: 97 to SEQ ID NO: 131, or a subsequence, portion, homologue, variant or derivative thereof. In certain alternative compositions, the two or more proteins or peptides each comprise, consist of or consist essentially of a different amino acid sequence set forth in set forth in any one of SEQ ID NO: 1 to SEQ ID NO: 93, or SEQ ID NO: 97 to SEQ ID NO: 131, or alternatively in any one or more of SEQ IDS NO: 1 to SEQ ID NO: 93; or alternatively any one or more of SEQ ID NO: 97 to SEQ ID NO: 131, or a subsequence, portion, homologue, variant or derivative thereof.

In one aspect, Applicants identified a panel of ZIKV peptides (set forth in SEQ ID NO: 94 to SEQ ID NO: 131) predicted to bind to HLA-DRB1*0101 and characterized the CD4+ T cell response to the peptides in Ifnar1−/− $^{HLA\text{-}DRB}$1*0101 mice infected with ZIKV or DENV2. Of the thirty ZIKV peptides screened, nine were shown to be CD4+ T cell epitopes by intracellular cytokine staining (ICS), and four of these were recognized by cross-reactive DENV2-primed T cells. Vaccination with DENV/ZIKV-cross-reactive CD4+ T cell epitopes induced a cellular response that reduced viral burden in ZIKV-challenged mice via production of IFNγ and TNF. These findings reveal the importance of DENV-reactive Th1 CD4+ T cells in mediating cross-protection against ZIKV in an antibody-independent manner, with significant implications for development of pan-flavivirus vaccines that maximize protection and minimize ADE.

As embodied and broadly described herein, the present disclosure relates to a composition comprising a protein or peptide comprising, consisting of or consisting essentially of an amino acid sequence set forth in any one or more of SEQ ID NO: 1 to SEQ ID NO: 93, or SEQ ID NO: 97 to SEQ ID NO: 131, Table 10 or 11, or a subsequence, portion, homologue, variant or derivative thereof. In certain embodiments, the composition comprises two or more proteins or peptides comprising, consisting of or consisting essentially of an amino acid sequence set forth in any one or more of SEQ ID NO: 1 to SEQ ID NO: 93, or SEQ ID NO: 97 to SEQ ID NO: 131, Table 10 or Table 11, or a subsequence, portion, homologue, variant or derivative thereof. In certain alternative compositions, the two or more proteins or peptides each comprise, consist of or consist essentially of a different amino acid sequence set forth in any one or more of SEQ ID NO: 1 to SEQ ID NO: 93, or SEQ ID NO: 97 to SEQ ID NO: 131, Table 10 or Table 11, or a subsequence, portion, homologue, variant or derivative thereof.

In certain embodiments, the protein or peptide comprises a Zika T cell epitope. In certain alternative embodiments, wherein the protein or peptide comprises a Zika CD4+ T cell epitope.

In certain embodiments, the Zika T cell epitope is not conserved in another flavivirus. In certain alternative embodiments, the Zika T cell epitope is conserved in another flavivirus. In certain specific embodiments, the protein or peptide has a length from about 10-15, 15-20, 20-25, 25-30, 30-40, 40-50, 50-75 or 75-100 amino acids.

In certain embodiments, the composition comprises 30, 40, 50, 60, 70 or more proteins or peptides comprising, consisting of or consisting essentially of an amino acid sequence set forth in set forth in any one or more of SEQ ID NO: 1 to SEQ ID NO: 93, or SEQ ID NO: 97 to SEQ ID NO: 131, or alternatively in any one or more of SEQ IDS NO: 1 to SEQ ID NO: 93; or alternatively any one or more of SEQ ID NO: 97 to SEQ ID NO: 131, or a subsequence, portion, homologue, variant or derivative thereof, wherein each protein or peptides comprises, consists of or consists essentially of a different amino acid sequence set forth in set forth in any one or more of SEQ ID NO: 1 to SEQ ID NO: 93, or SEQ ID NO: 97 to SEQ ID NO: 131, or alternatively in any one or more of SEQ IDS NO: 1 to SEQ ID NO: 93; or alternatively any one or more of SEQ ID NO: 97 to SEQ ID NO: 131, or a subsequence, portion, homologue, variant or derivative thereof. In certain specific embodiments, the protein or peptide comprises, consists, or consists essentially of one or more of the peptides selected from $C_{27\text{-}41}$ (SEQ ID NO: 97), $C_{53\text{-}67}$ (SEQ ID NO: 98), $C_{81\text{-}95}$ (SEQ ID NO: 99), $E_{134\text{-}148}$ (SEQ ID NO: 102), $E_{450\text{-}464}$ (SEQ ID NO: 104), NS2A$_{66-80}$ (SEQ ID NO: 108), NS3$_{601}$-NS4A$_{12}$(SEQ ID NO: 115), NS4B$_{40-54}$, (SEQ ID NO: 118) or NS5$_{222-236}$ (SEQ ID NO: 125).

In one aspect, the present disclosure relates to a composition comprising at least one isolated peptide and an acceptable carrier or diluent, the at least one peptide comprising an amino acid sequence which is at least 95%, or at least 96%, or at least 97%, or at least 98%, or at least 99%, or 100% identical to the amino acid sequence set forth in SEQ ID NO: 1 to SEQ ID NO: 93, or SEQ ID NO: 97 to SEQ ID NO: 131, Table 10 or Table 11. In certain non-limiting embodiments of the composition described herein, the composition comprises a plurality of the isolated peptide, where each peptide of the plurality of the isolated peptide comprises a respective amino acid sequence which is different from one another. For example, a first peptide in the plurality of the isolated peptide may comprise an amino acid sequence which is 95% identical with an amino acid sequence set forth in any one or more of SEQ ID NO: 1 SEQ ID NO: 1 to SEQ ID NO: 93 or SEQ ID NO: 97 to SEQ ID NO: 131, Table 10 or Table 11 and at least a second peptide in the plurality of the isolated peptide may comprise an amino acid sequence which is 98% identical with a second amino acid sequence set forth in any one or more of any one or more of SEQ ID NO: 1 to SEQ ID NO: 93 or SEQ ID NO: 97 to SEQ ID NO: 131, Table 10 or Table 11. The various possibilities of having different peptide sequence in a plurality of peptides will be apparent to the person of skill in light of the present disclosure, and for conciseness sake will not be further described here.

In certain alternative embodiments, the protein or peptide comprises, consists of or consists essentially of an amino acid sequence set forth in any one or more of SEQ ID NO: 1 to SEQ ID NO: 93 or SEQ ID NO: 97 to SEQ ID NO: 131, Table 10 or Table 11, or a subsequence, portion, homologue, variant or derivative thereof.

In certain embodiments, the flavivirus is Dengue virus or a Zika virus.

In certain embodiments, the composition comprises a protein or peptide that elicits, stimulates, induces, promotes, increases or enhances a T cell or B cell response to Zika virus. In certain alternative embodiments, the protein or peptide that elicits, stimulates, induces, promotes, increases or enhances the T cell or B cell response to Zika virus is a Zika virus envelope, NS2, NS4 or NS5 protein or peptide, or a variant, homologue, derivative or subsequence thereof.

In one non-limiting embodiment, the composition of the present disclosure may include one or more acceptable carrier selected from the acceptable carriers described herein. For example, an acceptable carrier may be selected from gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

Additionally, or alternatively, the composition of the present disclosure may include one or more pharmaceutically acceptable salt selected from the pharmaceutically acceptable salts described herein. For example, a pharmaceutically acceptable salt may be selected from sodium chloride, potassium chloride, sodium sulfate, ammonium sulfate, or sodium citrate. The concentration of the pharmaceutically acceptable salt can be any suitable concentration known in the art, and may be selected from about 10 mM to about 200 mM.

Additionally, or alternatively, the composition of the present disclosure may include one or more adjuvant selected from the adjuvants described herein. For example, an adjuvant may be selected from aluminum hydroxide or mineral oil, and a stimulator of immune responses, such as *Bordetella pertussis* or *Mycobacterium tuberculosis* derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes; biodegradable microspheres; and Quil A. Suitable adjuvants also include, but are not limited to, toll-like receptor (TLR) agonists, particularly toll-like receptor type 4 (TLR-4) agonists (e.g., monophosphoryl lipid A (MPL), synthetic lipid A, lipid A mimetics or analogs), aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, oil-in-water emulsions, MF59, and squalene. In some embodiments, the adjuvants are not bacterially-derived exotoxins. In one embodiment, adjuvants may include adjuvants which stimulate a Th1 type response such as 3DMPL or QS21. Adjuvants may also include certain synthetic polymers such as poly amino acids and co-polymers of amino acids, saponin, paraffin oil, and muramyl dipeptide. Adjuvants also encompass genetic adjuvants such as immunomodulatory molecules encoded in a co-inoculated DNA, or as CpG oligonucleotides. The coinoculated DNA can be in the same plasmid construct as the plasmid immunogen or in a separate DNA vector. The reader can refer to Vaccines (Basel). 2015 June; 3(2): 320-343 for further examples of suitable adjuvant.

Additionally or alternatively, the composition of the present disclosure and/or the method of the present disclosure whereby T cells are introduced into a subject after the T cells are contacted with the composition of the present disclosure may further include one or more components, such as drugs, immunostimulants (such as α-interferon, β-interferon, γ-interferon, granulocyte macrophage colony stimulator factor (GM-CSF), macrophage colony stimulator factor (M-CSF), and interleukin 2 (IL2)), antioxidants, surfactants, flavoring agents, volatile oils, buffering agents, dispersants, propellants, and preservatives.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Detection and Diagnosis

As embodied and broadly described herein, the present disclosure further relates to an in vitro method for detecting an infection with or an exposure to a flavivirus in a subject. The method comprises providing a biological sample from the subject, the biological sample comprising T cells from the subject. The method further comprises contacting the sample with the composition of the present disclosure. The method also comprises processing the sample to detect the presence of a T cell response, and detecting the presence or absence of the T cell response. The presence of the T cell response being indicative that the subject has been infected with or exposed to the flavivirus. The method may further include causing a transmission of an electronic notification data conveying information indicative of whether the subject has been infected with or exposed to the flavivirus.

In one non-limiting embodiment, the electronic notification data is transmitted to a computing device associated with a particular user, which can be a medical expert or the subject. In some specific practical implementations, the computing device associated with the particular medical expert may include a smartphone, a tablet, a general purpose computer and/or any other suitable computing device and the electronic notification data may convey an e-mail message, an SMS message and/or or any other suitable electronic message.

Therapeutic Methods

As embodied and broadly described herein, the present disclosure further relates to a method of inducing, enhancing, or sustaining an immune response against a flavivirus in a subject, the method comprising contacting T cells of the subject with an effective amount of the composition of the present disclosure.

In one non-limiting embodiment, the contacting includes administrating the effective amount of the composition to the subject.

In one non-limiting embodiment, the contacting includes contacting T cells ex vivo with the effective amount of the composition, and administrating the contacted T cells to the subject. The method may further comprise expansion of the T cells in vitro prior to administrating the contacted T cells to the subject.

In non-limiting embodiments, the herein described method of inducing, enhancing, or sustaining an immune response against a flavivirus in a subject may afford one to obtain at least one of the following features: reduce flavivirus titer, increase or stimulate flavivirus clearance, reduce or inhibit flavivirus proliferation, reduce or inhibit increases in flavivirus titer or flavivirus proliferation, reduce the amount of a flavivirus protein or the amount of a flavivirus nucleic acid, or reduce or inhibit synthesis of a flavivirus protein or a flavivirus nucleic acid.

In one non-limiting embodiment, the herein described method of inducing, enhancing, or sustaining an immune response against a flavivirus in a subject includes contacting T cells of the subject with the effective amount of the composition of the present disclosure prior to, substantially contemporaneously with or following exposure to or infection of the subject with the flavivirus. For example, contacting T cells of the subject with the effective amount of the composition of the present disclosure may occur within 2-72 hours, 2-48 hours, 4-24 hours, 4-18 hours, or 6-12 hours after a rash develops.

In one non-limiting embodiment, the flavivirus is a Zika virus.

In one non-limiting embodiment, the flavivirus is a Dengue virus.

In the case where the flavivirus is a Zika virus, the herein described method of inducing, enhancing, or sustaining an immune response against a flavivirus in a subject may treat or mitigate symptoms associated with a Zika virus infection such as, but not limited to, fever, rash, headache, pain behind the eyes, conjunctivitis, muscle or joint pain, nausea, vomiting, or loss of appetite.

In one non-limiting embodiment, the herein described biological sample can be obtained by any known technique, for example by drawing, by non-invasive techniques, or from sample collections or banks, etc.

Additionally or alternatively, the composition of the present disclosure and/or the method of the present disclosure whereby T cells are introduced into a subject after the T cells are contacted with the composition of the present disclosure may further include one or more components, such as drugs, immunostimulants (such as α-interferon, β-interferon, γ-interferon, granulocyte macrophage colony stimulator factor (GM-CSF), macrophage colony stimulator factor (M-CSF), and interleukin 2 (IL2)), antioxidants, surfactants, flavoring agents, volatile oils, buffering agents, dispersants, propellants, and preservatives.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

The compositions of the present disclosure may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

For instance, the composition of the present disclosure may be administered in the form of an injectable preparation, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or subcutaneously by injection, by infusion or per os. Suitable dosages will vary, depending upon factors such as the amount of each of the components in the composition, the desired effect (short or long term), the route of administration, the age and the weight of the subject to be treated. Any other methods well known in the art may be used for administering the composition of the present disclosure.

The composition of the present disclosure may be formulated as a dry powder (i.e., in lyophilized form). Freeze-drying (also named lyophilisation) is often used for preservation and storage of biologically active material because of the low temperature exposure during drying. Typically, the liquid antigen is freeze dried in the presence of agents to protect the antigen during the lyophilization process and to yield a cake with desirable powder characteristics. Sugars such as sucrose, mannitol, trehalose, or lactose (present at an initial concentration of 10-200 mg/mL) are commonly used for cryoprotection of protein antigens and to yield lyophilized cake with desirable powder characteristics. Lyophilizing the composition theoretically results in a more stable composition.

In certain embodiments, the composition of the present disclosure may be formulated as a liquid (e.g. aqueous formulation), e.g., as syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Where the composition of the present disclosure is intended for delivery to the respiratory (e.g. nasal) mucosa, typically it is formulated as an aqueous solution for administration as an aerosol or nasal drops, or alternatively, as a dry powder, e.g. for rapid deposition within the nasal passage. Compositions for administration as nasal drops may contain one or more excipients of the type usually included in such compositions, for example preservatives, viscosity adjusting agents, tonicity adjusting agents, buffering agents, and the like. Viscosity agents can be microcrystalline cellulose, chitosan, starches, polysaccharides, and the like. Compositions for administration as dry powder may also contain one or more excipients usually included in such compositions, for example, mucoadhesive agents, bulking agents, and agents to deliver appropriate powder flow and size characteristics. Bulking and powder flow and size agents may include mannitol, sucrose, trehalose, and xylitol.

In one embodiment, the herein described subject can be a mammal, preferably a human.

Kits

As embodied and broadly described herein, the present disclosure also relates to a kit comprising an antigenic component of the present disclosure and instructions for use. For example, in such kit, the antigenic component may contain cells producing or releasing at least one peptide comprising an amino acid sequence which is at least 95%, or at least 96%, or at least 97%, or at least 98%, or at least 99%, or 100% identical to the amino acid sequence set forth in any one or more of SEQ ID NO: 1 to SEQ ID NO: 93 or SEQ ID NO: 97 to SEQ ID NO: 131, or alternatively in any one or more of SEQ IDS NO: 1 to SEQ ID NO: 93; or alternatively any one or more of SEQ ID NO: 97 to SEQ ID NO: 131. Alternatively, the antigenic component may contain such at least one peptide. In certain non-limiting embodiments of the kit described here, the kit may comprise a plurality of the isolated peptide, where each peptide of the plurality of the isolated peptide comprises a respective amino acid sequence which is different from one another, as described above with respect to the composition. The instructions for use may be to implement any one of the herein described methods, for example for therapeutic or preventative vaccination against a flavivirus.

In one non-limiting embodiment, the flavivirus is a Zika virus.

In one non-limiting embodiment, the flavivirus is a Dengue virus.

In one non-limiting embodiment, the herein described methods and/or kits described herein may employ, for example, a dipstick, a membrane, a chip, a disk, a test strip, a filter, a microsphere, a slide, a multi-well plate, an optical fiber, and the like, or any other variant available to the person skilled in the art without departing from the present disclosure. For example, a test strip may be used where a sample to be tested can be added dropwise to a sample application pad present on the test strip, and the presence of at least an isolated peptide comprising an amino sequence which is at least 95%, or at least 96%, or at least 97%, or at least 98%, or at least 99%, or 100% identical to the amino acid sequence set forth in any one of in any one or more of SEQ ID NO: 1 to SEQ ID NO: 93 or SEQ ID NO: 97 to SEQ ID NO: 131, or alternatively in any one or more of SEQ IDS NO: 1 to SEQ ID NO: 93; or alternatively any one or more of SEQ ID NO: 97 to SEQ ID NO: 131 is made based on an immunodetection method which detects presence of the at least one such peptide. As discussed earlier in the text, the person of skill will readily understand that such test strip may make use of an immunodetection method which detects presence of a plurality of the isolated peptide, where each peptide of the plurality of the isolated peptide comprises a respective amino acid sequence which is different from one another, as described above with respect to the composition. Such immunodetection method may include an immunochromatographic test, an ELISA or ELISPOT or variant thereof, and the like, or any other suitable method available to the person skilled in the art without departing from the present disclosure.

In one non-limiting embodiment, the herein described kit may include at least one detecting agent which is "packaged". As used herein, the term "packaged" can refer to the use of a solid matrix or material such as glass, plastic, paper, fiber, foil and the like, capable of holding within fixed limits the at least one detection reagent. Thus, in one non-limiting embodiment, the kit may include the at least one detecting agent "packaged" in a glass vial used to contain microgram or milligram quantities of the at least one detecting agent. In another non-limiting embodiment, the kit may include the at least one detecting agent "packaged" in a microtiter plate well to which microgram quantities of the at least one detecting agent has been operatively affixed. In another non-limiting embodiment, the kit may include the at least one detecting agent coated on microparticles entrapped within a porous membrane or embedded in a test strip or dipstick, etc. In another non-limiting embodiment, the kit may include the at least one detecting agent directly coated onto a membrane, test strip or dipstick, etc. which contacts the sample fluid. Many other possibilities exist and will be readily recognized by those skilled in this art without departing from the invention.

All features of exemplary embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with the accompanying Figures.

EXAMPLES

The following examples describe some exemplary modes of making and practicing certain compositions that are described herein. It should be understood that these examples are for illustrative purposes only and are not meant to limit the scope of the compositions and methods described herein.

Example 1

Example 1 refers to the results shown in FIG. 1A to FIG. 8.

Example 1 can be summarized as follows:

H-2b mouse models of ZIKV infection recently have been established in WT C57BL/6 mice treated with blocking anti-IFNAR monoclonal antibody and in gene-deficient mice that globally lack IFNAR or both IFNAR and type II IFN receptors (Dowall et al., 2016; Govero et al., 2016; Lazear et al., 2016; Rossi et al., 2016). To investigate IFN receptor-competent CD8$^+$ T cell responses in H-2b mice, a model of ZIKV infection was established in LysMCre$^+$ IFNAR$^{fl/fl}$ C57BL/6 mice, which lack IFNAR in a subset of myeloid cells but express normal IFNAR levels on T cells, B cells, and most dendritic cells (Clausen et al., 1999; Diamond et al., 2011). Both LysMCre$^+$IFNAR$^{fl/fl}$ C7BL/6 mice and anti-IFNAR antibody-treated wild-type (WT) C57BL/6 mice were infected with ZIKV MR766 and FSS13025 strains and mapped the H-2b-restricted CD8+ T cell responses. Additionally, a protective role was demonstrated for CD8$^+$ T cells in controlling ZIKV infection in LysMCre$^+$IFNAR$^{fl/fl}$ mice.

The CD8$^+$ T cell response in ZIKV-infected LysMCre$^+$ IFNAR$^{fl/fl}$ C57BL/6 (H-2b) mice lacking the type I interferon receptor was evaluated in a subset of myeloid cells. IFNγ-ELISPOT analysis identified 26 and 15 reactive peptides for ZIKV African (MR766) and Asian (FSS13025) lineage strains, respectively. Intracellular cytokine staining validated the identity of these epitopes and demonstrated induction of polyfunctional ZIKV-specific CD8$^+$ T cells. Furthermore, CD8$^+$ T cells from infected mice mediated cytotoxicity. Adoptive transfer of ZIKV-immune CD8$^+$ T cells reduced viral burdens, whereas depletion of CD8$^+$ T cells led to higher tissue burdens and mortality was increased in ZIKV-infected CD8$^{-/-}$ mice compared to Wild-type. Collectively, these results demonstrate that CD8$^+$ T cells protect against ZIKV infection and provide an immunocompetent and thoroughly characterized H-2b mouse model for investigating ZIKV-specific T cell responses.

1. Materials & Methods for Example 1

1.1 Viral Strains and Mice

ZIKV strains MR766 and FSS13025 were obtained from the World Reference Center for Emerging Viruses and Arboviruses (WRCEVA). MR766, African lineage was isolated from a sentinel monkey rhesus (766) in east Africa (Dick, 1952). Since this isolation, the MR766 isolate has been passaged over 100 times in mice using intracerebral inoculations (Dick, 1952). ZIKV FSS13025 was isolated in 2010 from a Cambodian pediatric case (Heang et al., 2012) and has been passaged a low number of times. MR766 and FSS13025 were cultured using C6/36 Aedes albopictus mosquito cells as described previously (Prestwood et al., 2008). Virus was harvested from cell supernatants 7-10 days after infection, followed by clarification via centrifugation, and concentration via ultracentrifugation as previously described (Prestwood et al., 2012a). Virus was titrated using Baby hamster kidney (BHK)-21 cell-based focus-forming assay (FFA). ZIKV strain Dakar 41519, isolated in Senegal in 1984, was also obtained from WRCEVA, passaged four times in RAG-/-mice and amplified once in Vero cells (African green Monkey Kidney Epithelial Cells) as described (Govero et al., 2016; Sapparapu et al., 2016). Next generation sequencing of ZIKV stocks confirmed the sequence of each strain and the absence of adventitious pathogens.

Wild type mice were purchased from the Jackson laboratories, and LysMCre$^+$IFNAR$^{fl/fl}$ and CD8α$^{-/-}$ C57BL/6 mice were bred at La Jolla Institute for Allergy & Immunology and Washington University School of Medicine Animal Facilities. Wild type (WT) mice were treated with 1 or 2 mg of mouse anti-IFNAR (MAR1-5A3) depending on the experiment or isotype control (MOPC-21) monoclonal antibody one day prior to infection. All experiments were performed following the institutional Animal Care and Use Committee-approved animal protocols. Both male and female mice between 5-7 weeks of age were used in this study and all in vivo infections were performed either retro-orbital or subcutaneous inoculations with 200 μl of ZIKV in 10% FBS/PBS buffer containing $10^4$, $10^5$, or $10^6$ Focus Forming Units (FFU) of virus. In all experiments, mice receiving 10% FBS/PBS buffer, are designated as MOCK. For survival study, mice were infected with 50 μl of Dakar 41519 ZIKV strain diluted in PBS.

To assess the clinical features, mice were checked each day and assigned a score between 1 and 7 as previously described (Tang et al., 2016). Weights were recorded, reported and compared to the initial weight obtained on the day of infection.

1.2 Titration of Virus by FFA

BHK-21 cells were plated at $2 \times 10^5$ cells per well in a 24-well plate and incubated at 37° C., 5% $CO_2$ overnight. Following mouse perfusion with PBS, organs were harvested in 1 ml of MEM-alpha-medium (Invitrogen) in pre-weighed tubes containing steel beads, followed by homogenization and then centrifugation at 2000 g for 5 minutes. The clarified supernatant was used to infect BHK cells following serial dilution, and cells were infected for 1 hour with gentle shaking every 15 minutes. After infection, wells were overlaid with carboxymethyl cellulose (CMC) (Sigma). Two days after infection, cells were fixed with 4% formalin (Fisher Chemicals), permeabilized with 1% TRITON™ X (Sigma), and blocked with 10% FBS-PBS. Viral antigen was detected using 4G2, a pan-flavivirus anti-envelope (E) antibody, following by a secondary antibody, horseradish peroxidase (HRP)-conjugated goat anti-mouse IgG (Sigma). Foci were revealed after incubation with True Blue substrate (KPL) and were counted manually.

1.3 Peptide Prediction Approaches

All known ZIKV polyprotein sequences for African and Asian lineages were obtained from the NCBI protein database in January 2016. MHC class I-peptide binding affinity predictions were performed at the Immune Epitope Database (IEDB) Tools website using "IEDB-recommended" method selection, as previously described (Kim et al., 2012). Predicted binding affinities for all non-redundant 8-11mer peptides that bound H2-Kb and H2-db were obtained. For each allele, the lists of peptides obtained above were sorted by increasing consensus percentile rank and restricted to the top 1%.

The E protein from ZIKV strains MR766 and FSS13025 was selected to identify epitopes using the overlapping methods (FIG. 8). 15-mer peptides that overlapped by 11 amino acids were designed from the E protein sequence and synthesized.

1.4 Peptide Synthesis

All peptides were synthesized by Synthetic Biomolecules, San Diego, Calif. All 9-, 10-, 11- and 15-mer peptides for ELISPOT were synthesized as crude material on a 1-mg scale and mass spectral analysis of each peptide was performed to validate the synthesis. Peptides for flow cytometric analyses were synthesized and purified by reverse-phase HPLC to ≥95% purity. Peptides were dissolved in DMSO and aliquoted.

1.5 Ex Vivo Gamma Interferon (IFNγ) ELISPOT

CD8$^+$ T cells were isolated by magnetic bead positive selection (Miltenyi Biotec, Germany). A total of $2\times10^5$ CD8$^+$ T cells were stimulated with $1\times10^5$ LPS-blast cells as antigen presenting cells (APCs) and 10 μg of individual ZIKV-derived peptide in 96-well flat-bottom plates (IMMOBILON™-P; Millipore, MA) coated with anti-mouse IFNγ monoclonal antibody (mAb) (clone AN18; Mabtech, Sweden) in triplicate. IFNγ-ELISPOT was performed as previously detailed (Elong Ngono et al., 2016). Positive peptides were those with a number of spot-forming cells (SFC) per $10^6$ CD8$^+$ T cells ≥20 and a stimulation index ≥2 based on the negative control (DMSO).

1.7 Flow Cytometric Analyses

For intracellular cytokine staining (ICS), splenocytes were counted after red blood cell lysis and resuspended in 10% FBS/RPMI medium at $40\times10^6$ cells per ml. Splenocytes ($2\times10^6$) were plated and stimulated with 1 μg of individual peptide as previously detailed (Elong Ngono et al., 2016). Positive (PMA-Ionomycin) and negative (No stimulation) controls were added for all experiments. Cells were labeled with anti-CD3 (Clone 145-2C11), anti-CD8 (clone 53-67), anti-CD44 (clone IM7), and anti-CD62L (clone Mel-14). Cells then were fixed and permeabilized, followed by staining with anti-granzyme B (clone NGZB), anti-IFNγ (clone XMG 1.2) and anti-TNFα (clone MP6-XT22). Samples were read on an LSR II (BD Biosciences) and were analyzed using FLOWJO™ software X 10.0.7 (Tree Star, Ashland, Oreg.).

1.8 In Vivo Cytotoxicity Assay

LysMCre$^+$IFNAR$^{fl/fl}$ and WT mice were infected with $10^4$ FFU of MR766 or FSS13025. Seven days post-infection, splenocytes were harvested from naïve donor mice, followed by stimulation with a pool of H-2b-restricted ZIKV-peptides (PrM$_{169-177}$(SEQ ID NO: 19), E$_{297-305}$ (SEQ ID NO: 25), N552783-2792 (SEQ ID NO: 20)) referred to as "Target Cells" or with DMSO for 3 h at 37° C. The cells were washed and labeled with CSFE (Invitrogen) in PBS/0.1% BSA for 10 min at 37° C. Target cells were labeled with 1 μM CSFE (High) or 100 nM CSFE (Low) for unstimulated cells. After washing, $10^7$ of labeled cells ($5\times10^6$ of each population) were injected intravenously into MOCK and infected recipients. Splenocytes from recipients were harvested 4 (Wild type) or 12 h later (LysMCre$^+$ IFNAR$^{fl/fl}$) and analyzed by flow cytometry. The percentage of killing is calculated as followed: 100−(% ZIKV-peptide stimulated in infected mice/% DMSO-stimulated in infected mice)/(% ZIKV-peptide stimulated in naïve mice/% DMSO-stimulated in naïve mice)×100).

1.9 Depletion and Adoptive Transfer of CD8$^+$ T Cells

All antibodies for depletion studies were purchased from BioXCell. Mice were injected intraperitoneally (i.p.) with CD8 cell-depleting (clone YTS 169.4) or rat IgG2 isotype control (clone LTF-2) antibodies on days 3 and 1 prior to infection with $10^5$ FFU of ZIKV MR766 or ZIKV FSS13025. Organs were harvested at day 6, 8 or 10 after infection and levels of infectious virus were determined using BHK-21 cell-based FFA.

ZIKV-immune CD8$^+$ T cells were isolated from LysM-Cre$^+$IFNAR$^{fl/fl}$ mice on day 120 after infection with $10^5$ FFU of MR766 or FSS13025 using magnetic positive CD8$^+$ T cells selection kit (Miltenyi Biotech, CD8a Ly-2). $7.5\times10^6$ CD8$^+$ T cells were transferred into 5 week-old naïve mice, and recipient mice were challenged with either MR766 or FSS13025 one day after cell transfer. Viral titers in tissues were measured using BHK-21 cell-based FFA three days post-challenge.

1.10 Statistical Analyses

All data were analyzed with PRISM™ software version 5.0 (GraphPad Software, Inc., San Diego, Calif.) and expressed as mean±SEM. Statistical significance was determined using the non-parametric Mann-Whitney test to compare two groups and the Wilcoxon test to compare two parameters from the same group. Two-way ANOVA or the Kruskal-Wallis test was used to compare more than 2 groups. P<0.05 was considered as significant.

2. Results 2.1. Characterization of CD8$^+$ T Cell Response in WT C57BL/6 Mice Treated with IFNAR-Blocking Antibody H-2b mice that are genetically deficient in IFNAR or treated with IFNAR-blocking antibody are susceptible to ZIKV infection (Dowall et al., 2016; Lazear et al., 2016; Miner et al., 2016; Rossi et al., 2016). To characterize the CD8$^+$ T cell response in H-2b mice, WT C57BL/6 mice were treated with an IFNAR-blocking antibody MAR1-5A3 (Sheehan et al., 2006) prior to inoculation with ZIKV strains MR766 or FSS13025 and infectious virus particles in serum and spleen were measured at days 1 and 3 post-infection.

Figure 1B:
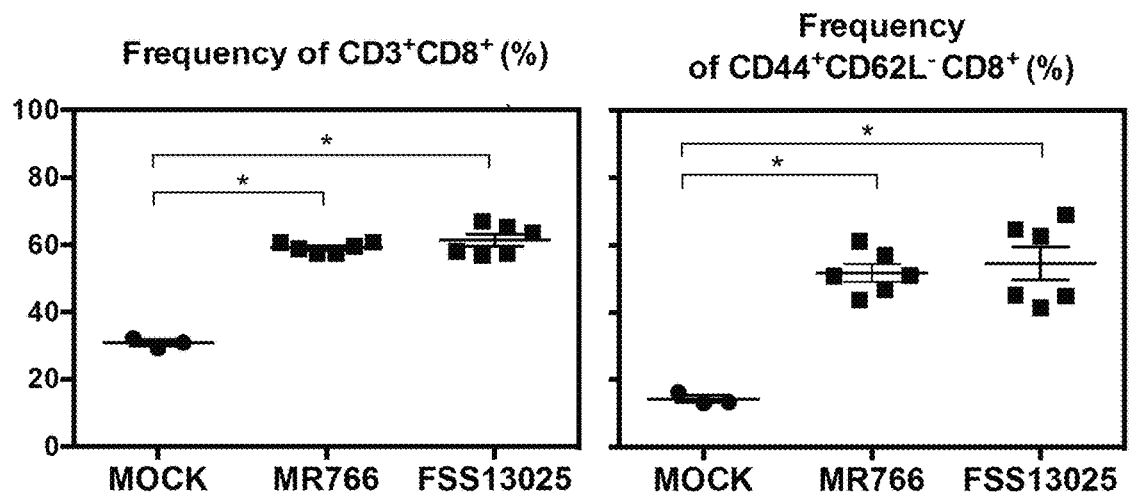
Figure 1C:
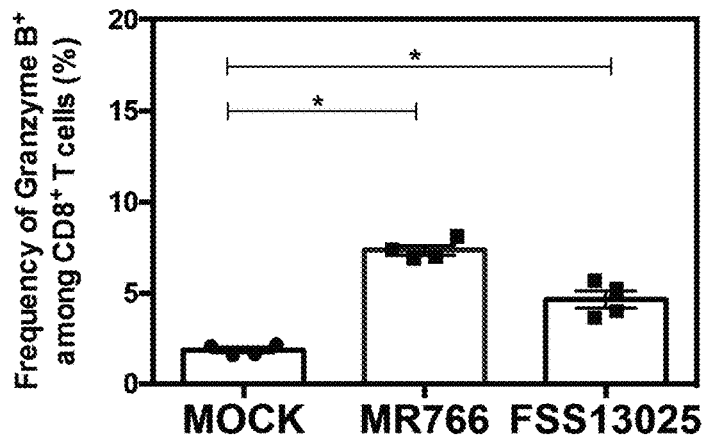

The following results are with reference to FIG. 1A to FIG. 1C, where WT C57BL/6 mice were administered IFNAR-blocking antibody (MAR1-5A3) one day prior to infection with $10^4$ Focus Forming Units (FFU) of ZIKV strains MR766 (n=4) or FSS13025 (n=4). MOCK represents control mice injected with 10% FBS/PBS. In FIG. 1A levels of infectious ZIKV in serum and spleen on day 1 or 3 post-infection were measured by BHK-21 cell-based FFA. In FIG. 1B, the expansion of total CD8$^+$ T cells and CD44$^+$CD62L$^−$ CD8$^+$ T cells in MOCK group (n=3) or ZIKV-infected mice (MR766 and FSS13025, n=4) was determined on day 7 post-infection. In FIG. 1C, the percentage of granzyme B produced by infected (n=4) and MOCK mice (n=4) is represented. Kruskall Wallis test was used first to compare all groups following by Mann-Whitney test to compare MOCK vs. each ZIKV-infected mouse group. See also FIG. 7.

The results obtained are the following:

At day 1, infectious ZIKV was detectable in all of the sera and some spleens from mice treated with anti-IFNAR antibody (FIG. 1A). Three days after infection, the viral load decreased in serum of mice infected with MR766 but not those infected with FSS13025. In the spleen, the level of infectious virus in both groups increased at day 3 compared to day 1.

Having confirmed replication of both ZIKV strains in this mouse model, the CD8$^+$ T cell response was assessed in the spleen 7 days after infection. The frequencies of total CD8$^+$ T cells and antigen-experienced (CD44$^+$CD62L$^−$) CD8$^+$ T cells were increased in infected mice with IFNAR blockade relative to MOCK mice (FIG. 1B). Infected mice contained 2-fold more total or antigen-experienced CD8+ T cells than MOCK mice. In addition, ZIKV MR766- and FSS13025-infected mice, respectively, contained 5- and 3-fold more CD8$^+$ T cells expressing granzyme B (a marker of cytotoxicity) compared to controls (FIG. 1C). No difference in CD8$^+$ T cell response was observed between MR766 and FSS13025 groups. These results indicate that ZIKV induces CD8$^+$ T cell expansion and activation in WT mice treated with IFNAR-blocking antibody, and that this model is suitable for identifying ZIKV-derived epitopes recognized by CD8+ T cells.

2.2 Identification of ZIKV-Derived Epitopes Recognized by CD8+ T Cells from WT C57BL/6 Mice Treated with IFNAR-Blocking Antibody To map the specificity of the MHC class I-restricted CD8+ T cell response, the proteome of ZIKV was first inspected for the presence of peptides predicted to bind H-2b class I molecules (Kb and db) with high affinity using a bioinformatic prediction program (Kim et al., 2012).

Figure 7A:
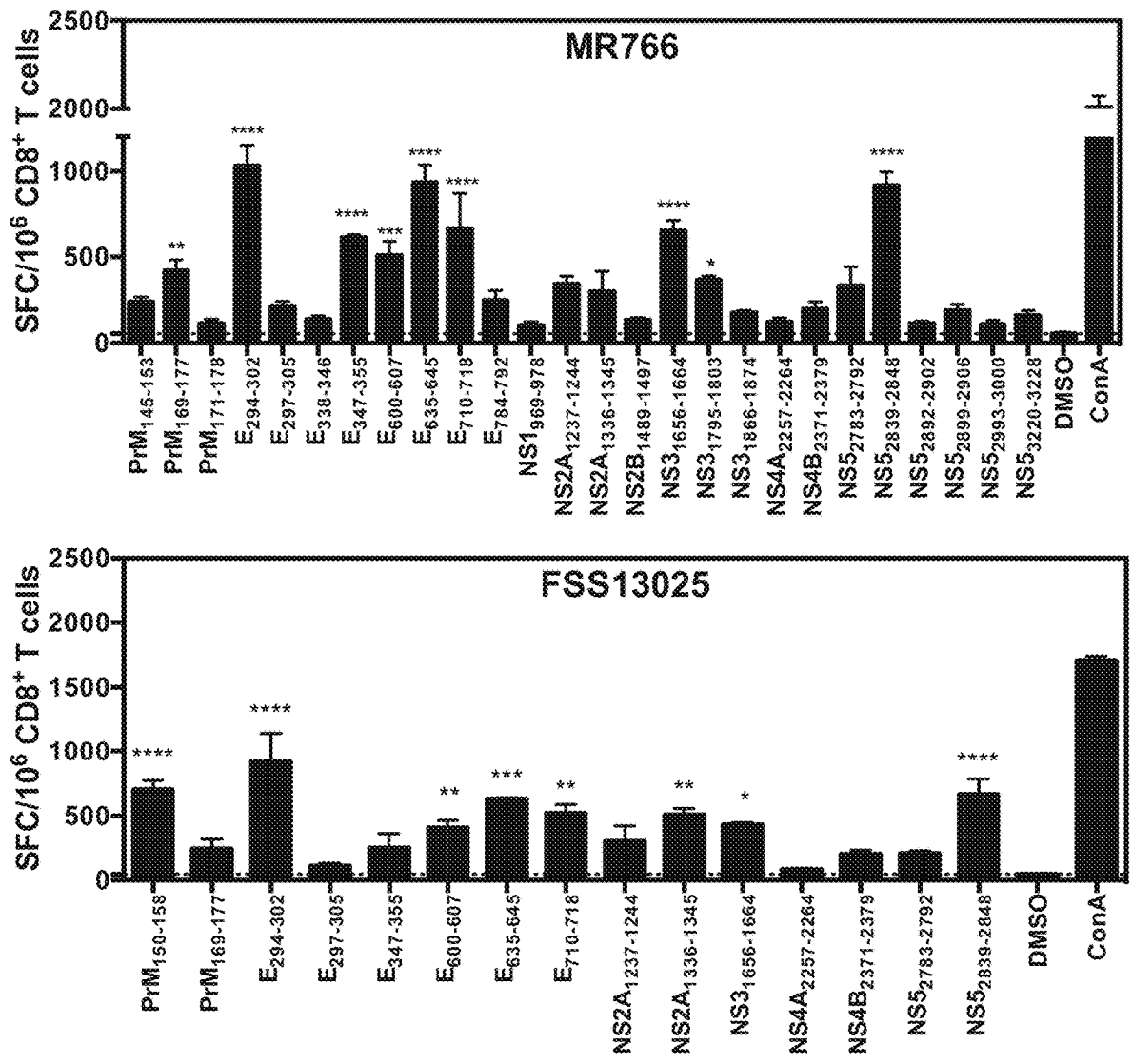
FIGS. 7A-7D: shows graphs that illustrate non-limiting results of the identification of epitopes recognized by CD8$^+$ T cells in WT C57BL/6 mice treated with IFNAR-blocking antibody in accordance with an embodiment of the present disclosure.
Figure 7B:
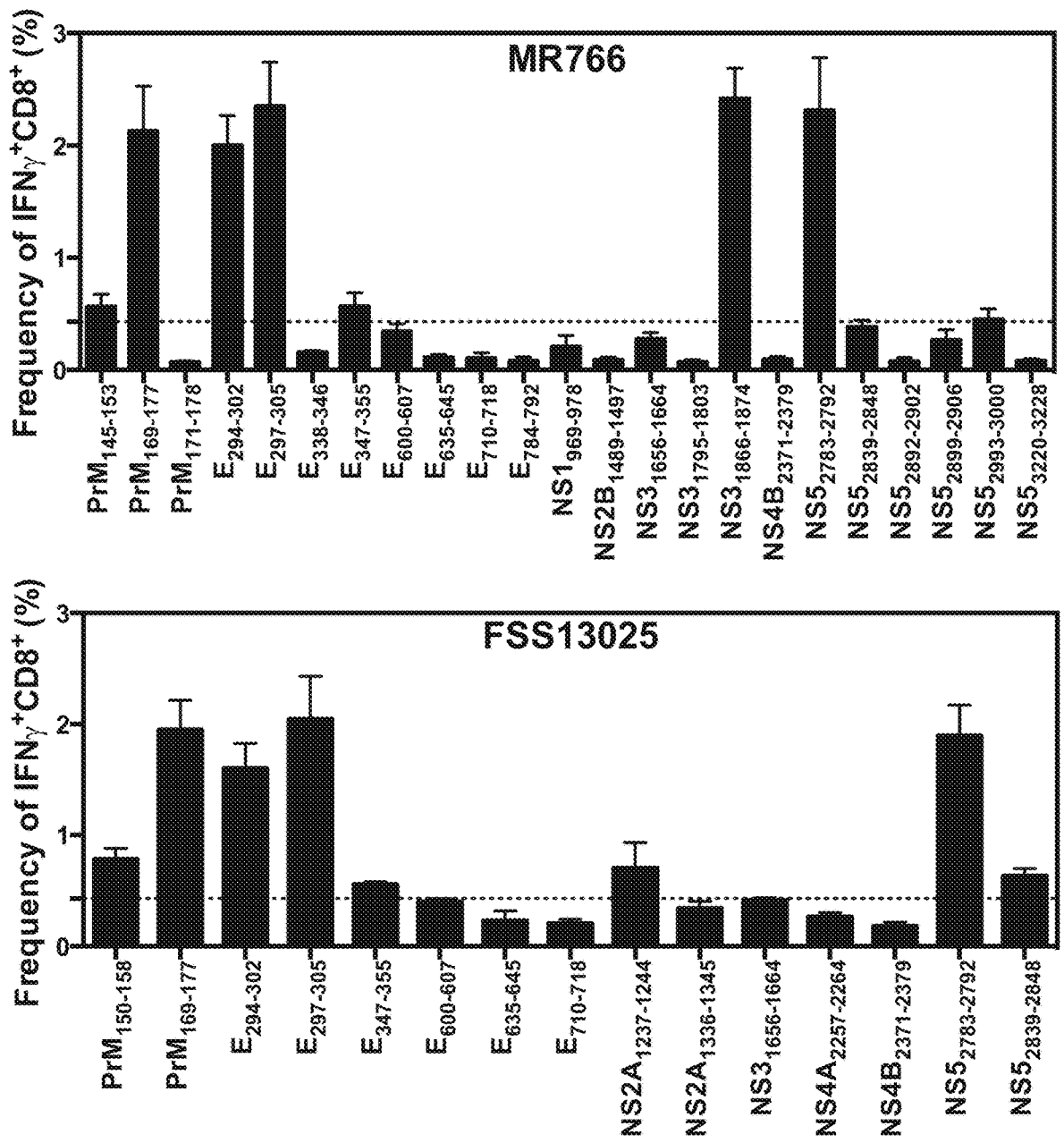
Figure 7C:
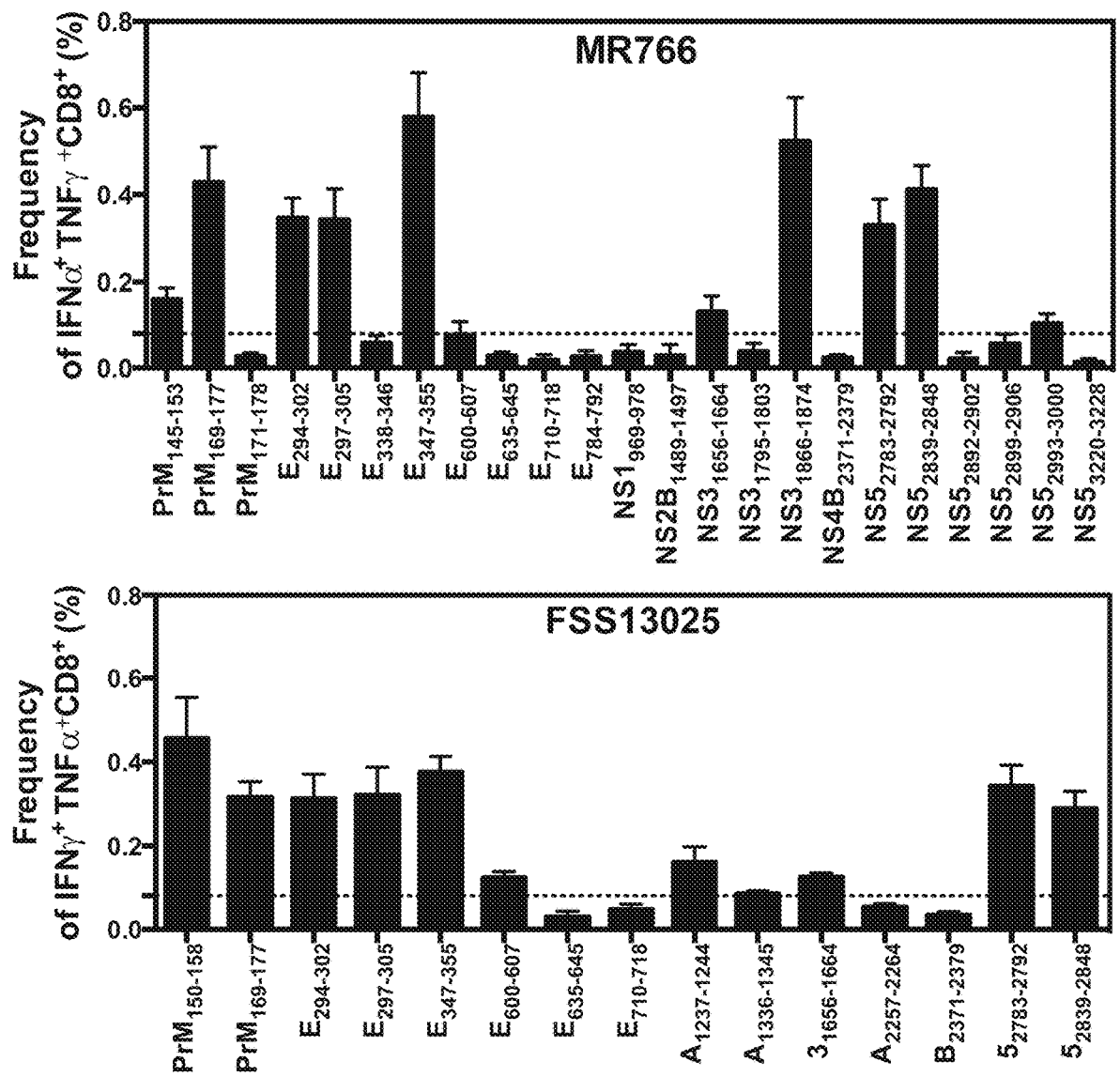
Figure 7C:
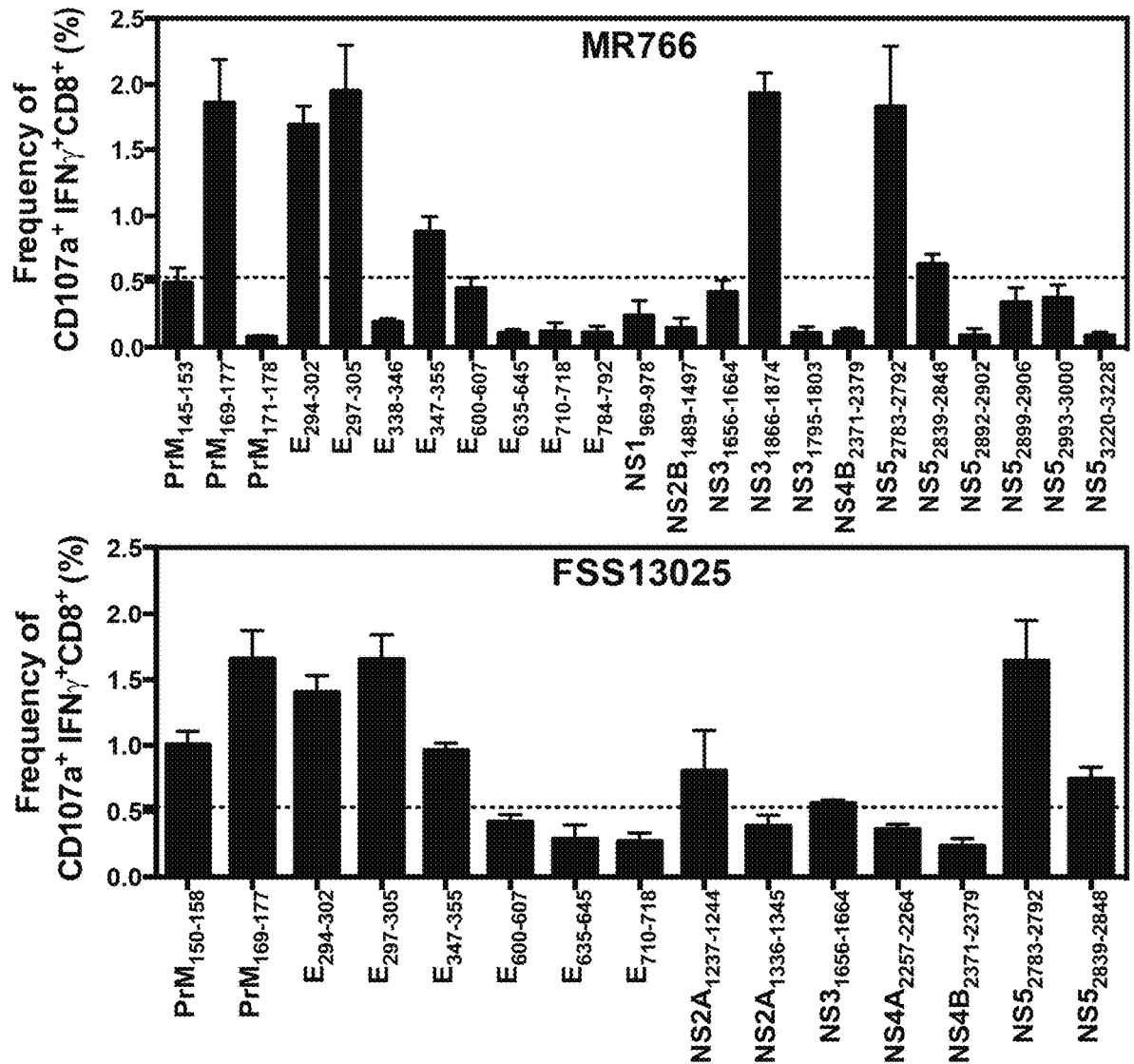
Figure 7D:
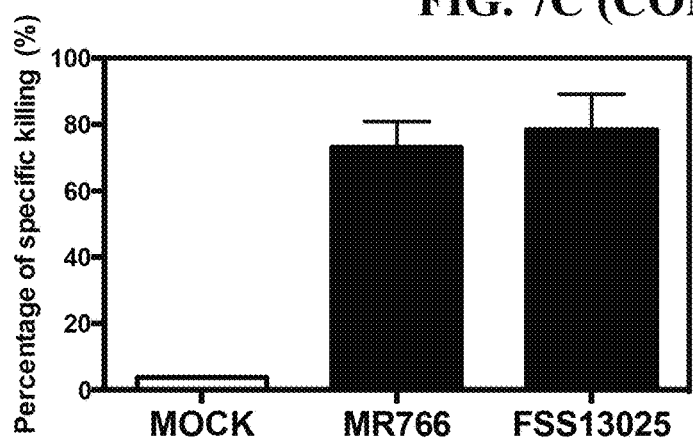

The following results are with respect to FIG. 7A to FIG. 7E, where WT C57BL/6 mice treated with type I IFN receptor-blocking antibody on day 1 prior to infection were inoculated with $10^4$ FFU of ZIKV strain MR766 (n=3) or FSS (n=3), or injected with 10% FBS/PBS (MOCK, n=2). FIG. 7A shows results where seven days post-infection, IFNγ-ELISPOT was performed using CD8+ T cells isolated from the spleen to screen 244 peptides from both ZIKV strains that were predicted to bind H-2Kb and H-2db. Four independent experiments for MR766 (n=8 mice per experiment) and two independent experiments for FSS13025 (n=8 mice per experiment) were performed in triplicate for each peptide. The data are expressed as the mean of spot forming cells (SFC) per $10^6$ CD8+ T cells. One-way ANOVA was used to compare the mean of each peptide with the control (DMSO). FIG. 7B shows the frequency of CD8+ T cells producing IFNγ upon stimulation with MR766 and FSS13025-derived peptides, as detected via intracellular cytokine staining (ICS), using splenocytes from mice infected with MR766 (n=5), FSS13025 (n=5), or MOCK (n=4). Pooled data from two independent experiments are shown. The dotted line corresponds to the average value obtained by MOCK after stimulation (0.43% of IFNγ+CD8+ T cells). Splenocytes were harvested on day 7 post-infection, followed by stimulation with 1 μg of IFNγ-ELISPOT-positive ZIKV-derived peptides in presence of Brefeldin A (BFA) and CD107a for 4 hours, and the production of IFNγ and TNFα was assessed via ICS. FIG. 7C shows the frequency of CD8+ T cells producing both IFNγ and TNFα upon stimulation with MR766-derived peptides (top panel) or FSS13025-derived peptides (bottom panel). FIG. 7D shows the frequency of CD107a+IFNγ+ CD8+ T cells obtained after stimulation with MR766- (top panel) or FSS13025-derived (bottom panel) peptides. FIG. 7E shows results where seven days after infection, splenocytes from naïve mice that were pulsed with ZIKV-derived peptides (prM$_{169-177}$ (SEQ ID NO: 19); E297-305 (SEQ ID NO: 25); NS5$_{2783-2792}$ (SEQ ID NO: 20)) as "target" were injected into infected and MOCK mice 4 hours prior to harvest, and shows the percentage of "target cells" killed in mice infected with MR766 (n=2) or FSS13025 (n=3). All experiments were performed twice and error bars are represented in SEM.

The results obtained are the following:

A total of 244 predicted H-2b-binding peptides were identified with 202 shared between both ZIKV strains, and 42 specific for FSS13025. Among these peptides, 96 were specific for H-2Kb, 148 for H-2db, and 22 were predicted to bind both MHC class I alleles. Next, all peptides were tested individually in an IFNγ-ELISPOT assay using CD8+ T cells from mice infected with either MR766 or FSS13025. Twenty-six peptides were positive for ZIKV MR766 (FIG. 7A, top panel) and 15 peptides were positive for ZIKV FSS13025 (FIG. 7A, bottom panel).

The identified ZIKV epitopes are derived from 9 (for MR766) and from 7 (for FSS13025) of the 10 ZIKV proteins including structural proteins prM and E, and non-structural proteins NS1, NS2B (only MR766), NS2A, NS3, NS4A, NS4B and NS5 (FIG. 7A). Although the CD8+ T cell responses to ZIKV MR766 and ZIKV FSS13025 were not identical, the E protein-derived epitopes predominated in both ZIKV strains.

To validate the identification of these ZIKV-derived peptides, intracellular cytokine staining (ICS) was performed. Splenocytes were stimulated with all positive peptides and the frequency of IFNγ-producing CD8+ T cells was reported for each peptide for both ZIKV strains (FIG. 7B). Five of 26 MR766-derived peptides (top panel) and four of 15 FSS13025-derived peptides (bottom panel) induced a high frequency of IFNγ-expressing cells. The following 4 peptides were shared between both ZIKV strains: prM$_{169-177}$ (SEQ ID NO: 19), E294-302 (SEQ ID NO: 21), E297-305 (SEQ ID NO: 25), and NS5$_{2783-2792}$ (SEQ ID NO: 20). Only NS3$_{1866-1874}$ (SEQ ID NO: 5) was specific for ZIKV MR766. For both ZIKV strains, all positive peptides confirmed by IFNγ-ICS induced a high frequency of IFNγ+ TNFα+ and CD107a+IFNγ+ double-positive cells (FIG. 7C and FIG. 7D). CD8+ T cells from mice infected with both ZIKV strains exhibited cytolytic activity by killing approximately 70% of splenocytes loaded with prM$_{169-177}$ (SEQ ID NO: 19), E$_{297-305}$ (SEQ ID NO: 25), and NS5$_{2783-2792}$ (SEQ ID NO: 20) peptides (FIG. 7E). These results demonstrate a polyfunctional phenotype of ZIKV antigen-specific CD8+ T cells upon infection with either ZIKV strain in C57BL/6 mice after IFNAR blockade.

2.3 LysMCre+IFNAR$^{fl/fl}$ Mice, a Novel H-$2^b$ Model Susceptible to ZIKV Infection To investigate the role of CD8+ T cells during ZIKV infection in a more immunocompetent model than mice with global IFNAR blockade, LysMCre+IFNAR$^{fl/fl}$ C57BL/6 mice, recently published for utility in studying DENV infection (Pinto et al., 2015), were evaluated; these mice display normal T and B cell immune responses and lack IFNAR expression only in a subset of myeloid cells. The Ifnar gene deletion is efficient in mature macrophages (83-98%) and granulocytes (100%) but partial for CD11C+ splenic dendritic cells (16%) (Clausen et al., 1999; Diamond et al., 2011). LysMCre+IFNAR$^{fl/fl}$ and WT C57BL/6 mice were infected intravenously with MR766 or FSS13025, and levels of infectious virus in serum, liver, spleen, and brain at 1 and 3 days after infection were determined.

Figure 2A:
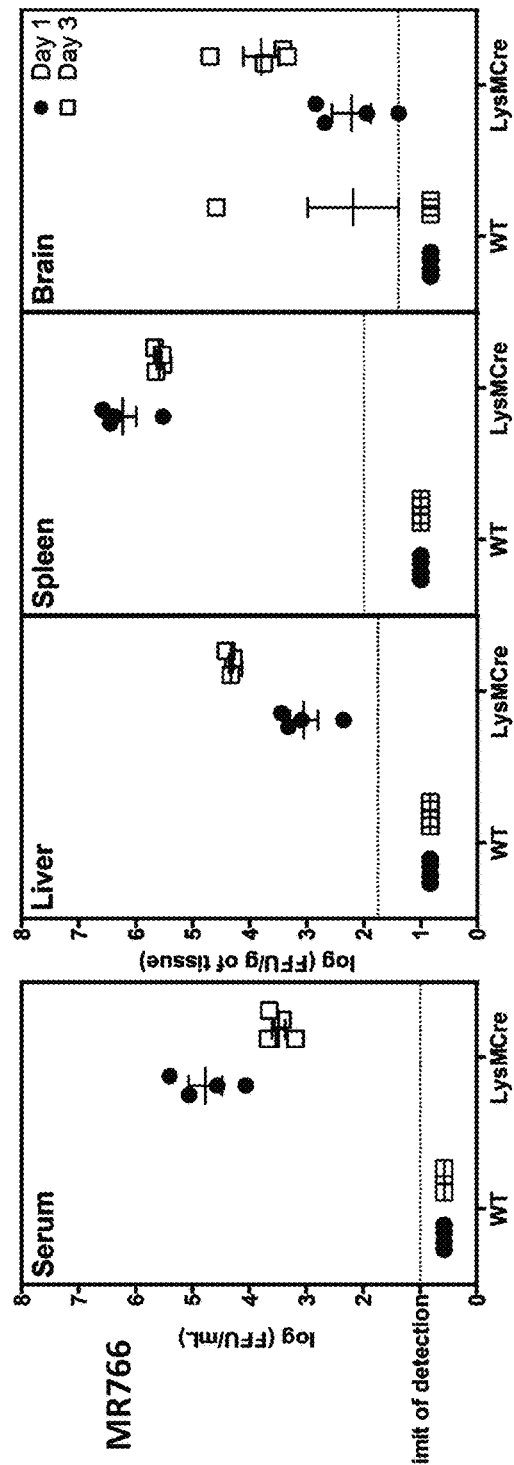
FIGS. 2A-2E: shows exemplary non-limiting results obtained with a LysMCre$^+$IFNAR$^{fl/fl}$ mouse model of ZIKV infection in accordance with an embodiment of the present disclosure.
Figure 2B:
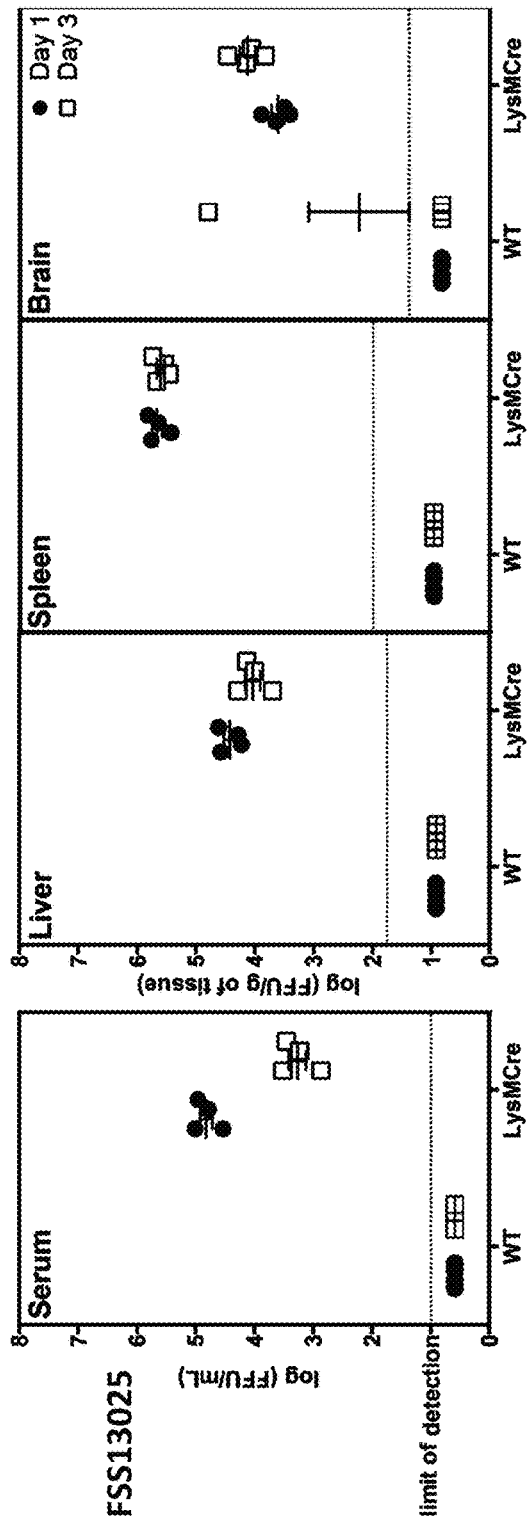
Figure 2C:
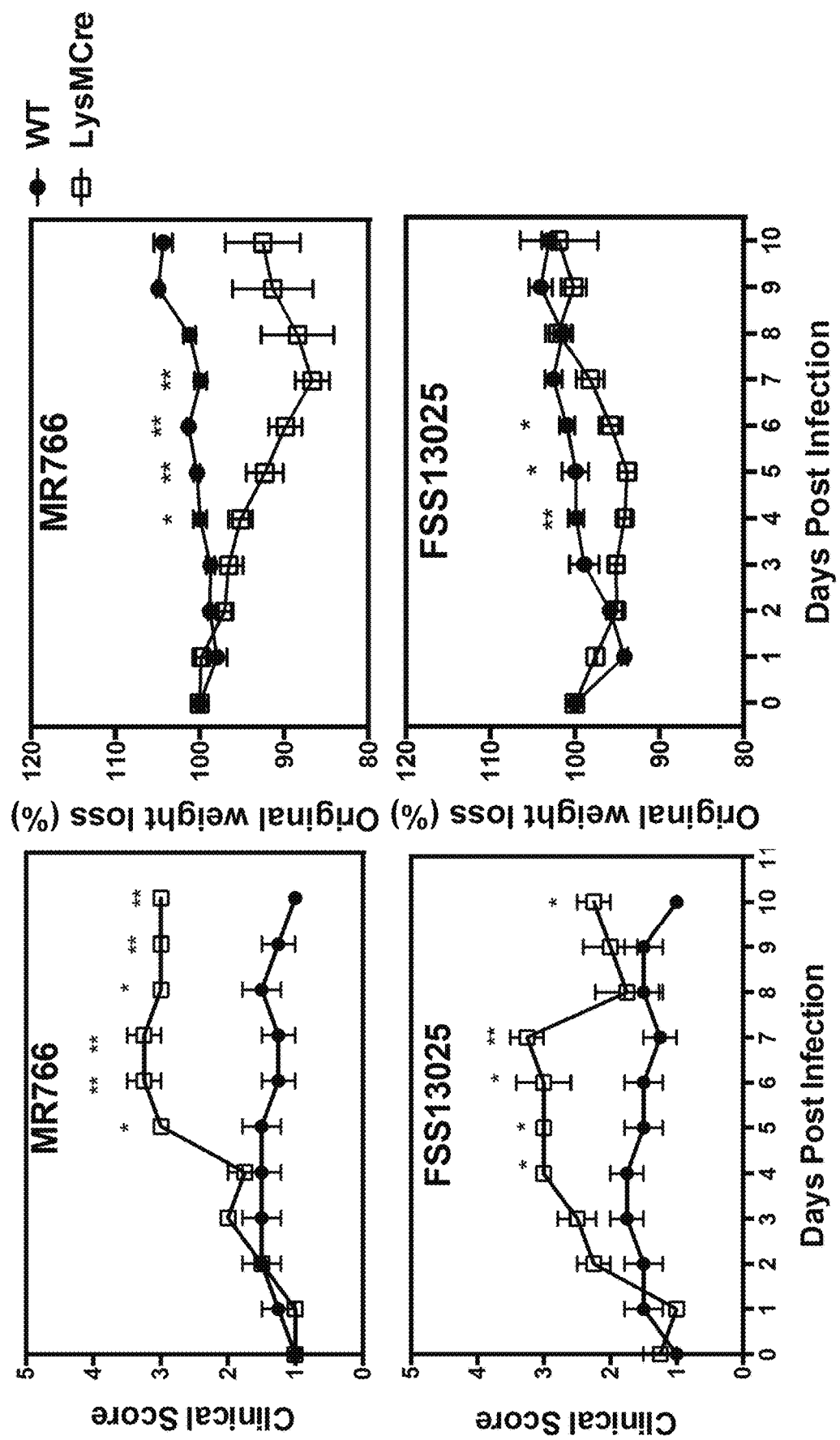
Figure 2D:
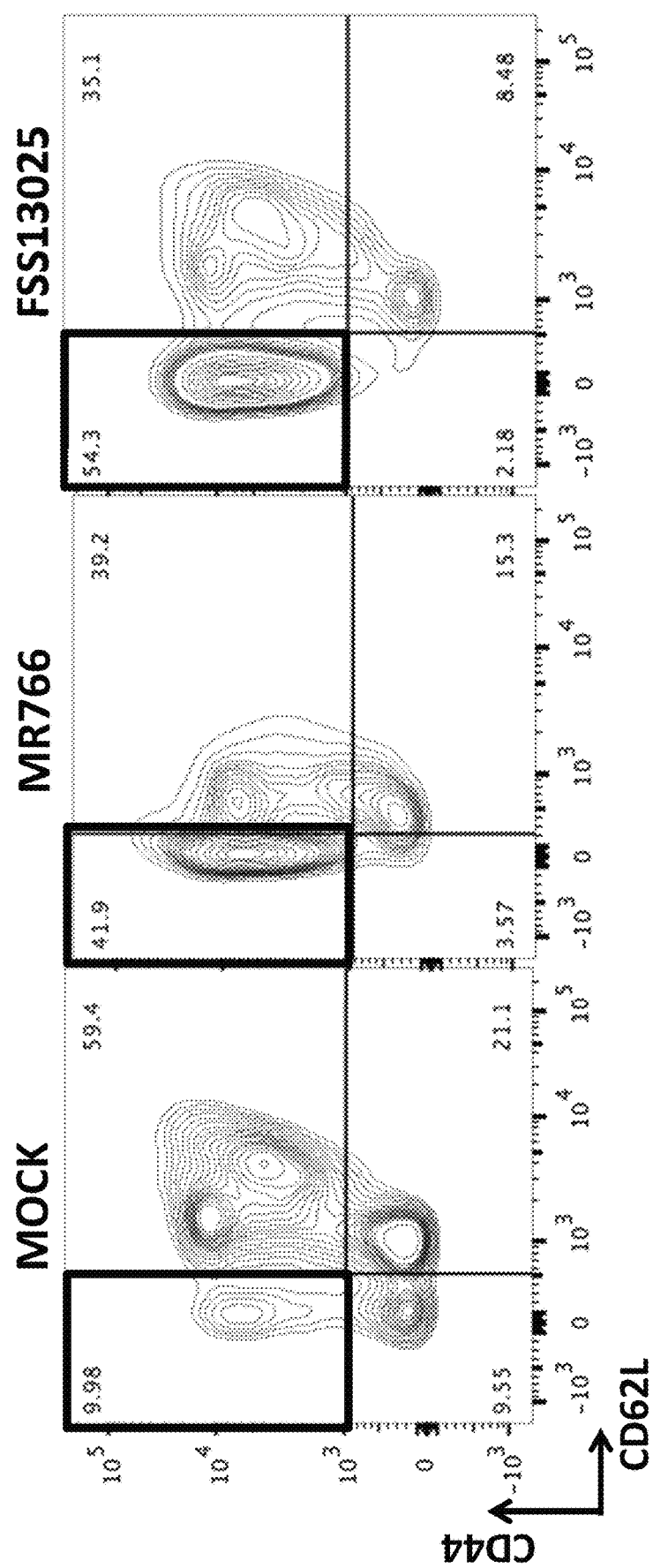

The following results are with reference to FIG. 2A to FIG. 2C, where WT and LysMCre+IFNAR$^{fl/fl}$ C57BL/6 mice at 5 weeks of age were infected with $10^6$ FFU of MR766 or FSS13025. Serum, liver, spleen, and brain were harvested at day 1 and 3 post-infection, and the levels of infectious ZIKV were determined using BHK-21 cell-based FFA. The quantities of infectious in FIG. 2A MR766 virus or in FIG. 2B FSS13025 virus at day 1 (black circles) and day 3 (white squares) post-infection are shown. Four mice were included in each group. In FIG. 2C the weight and clinical scores of infected WT and LysMCre+IFNAR$^{fl/fl}$ mice were monitored and unpaired t test with Welch's correction was used to compare the two groups at each time point. In FIG. 2D, a representative density plot showing CD44 and CD62L expression and in FIG. 2E, the frequency of CD3+CD8+ T cells and CD44+CD62L− CD8+ T cells from LysMCre+ IFNAR$^{fl/fl}$ mice infected with $10^4$ FFU of ZIKV or MOCK are shown. Kruskall Wallis test was used first to compare all groups and the Mann-Whitney test was used to compare MOCK and each ZIKV-infected group. All error bars correspond to SEM.

The results obtained are the following:

At day 1 post-infection, the infectious virus was detectable in all of the tissues tested in LysMCre⁺IFNAR^(fl/fl) mice infected with MR766 (FIG. 2A) and FSS13025 (FIG. 2B), whereas virus was undetectable in WT mice. At day 3 post-infection, infectious ZIKV were still detectable in tissues of LysMCre⁺IFNAR^(fl/fl) mice. Based on these results, LysMCre⁺IFNAR1^(fl/fl) mice, unlike WT mice, are susceptible to ZIKV infection.

To evaluate whether LysMCre⁺IFNAR^(fl/fl) mice demonstrate a clinical phenotype of ZIKV infection, the clinical scores and the weights of LysMCre⁺IFNAR^(fl/fl) vs. WT mice were compared. Using a clinical criteria scale, it was observed that LysMCre⁺IFNAR^(fl/fl) mice developed clinical features up to score 3, corresponding to ruffling of their fur. The infection also induced weight loss in LysMCre⁺IFNAR^(fl/fl) mice between days 4 and 7 post-infection (FIG. 2C). However, no signs of paralysis, a dominant phenotype of ZIKV-infected IFNAR⁻/⁻ mice, and death were observed.

Figure 2E:
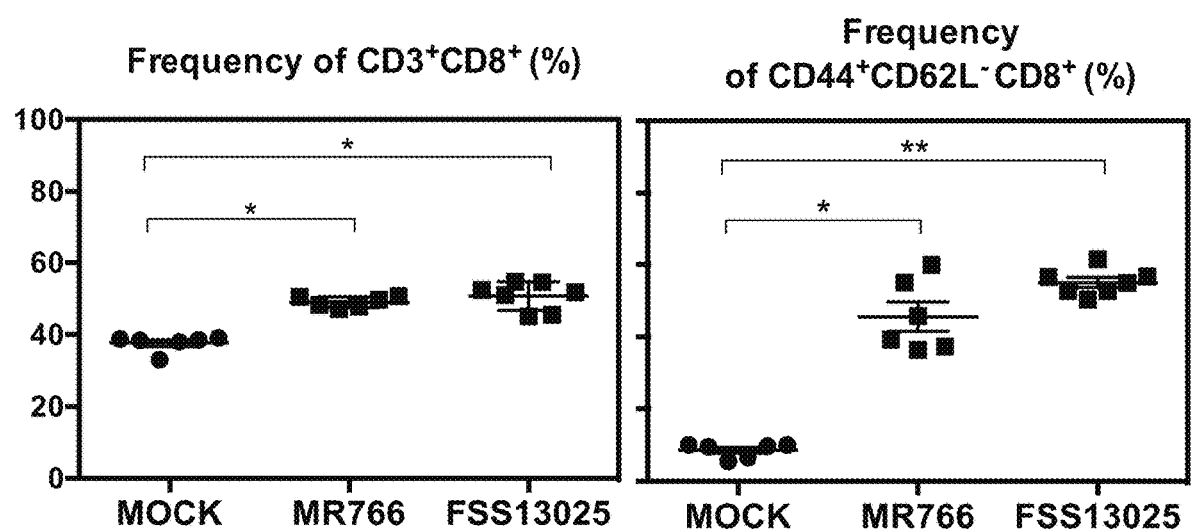

Next, CD8⁺ T cell expansion and activation following ZIKV infection of LysMCre⁺IFNAR^(fl/fl) mice was explored. CD44 and CD62L markers differentiated the antigen-experienced CD8⁺ T cell subset as represented in the gating strategy (FIG. 2D) for splenocytes from MOCK and ZIKV-infected (MR766 and FSS13025) mice. ZIKV infection led to an increase in the number of total CD8⁺ T cells and approximately 5- and 6-fold expansion of CD44⁺CD62L⁻ CD8⁺ T cells in mice infected with MR766 and FSS13025, respectively, as compared to uninfected mice (FIG. 2E). Thus, LysMCre⁺IFNAR^(fl/fl) mice mount a robust CD8⁺ T cell response to ZIKV infection.

2.4 Identification and Validation of ZIKV-Derived Epitopes Recognized by CD8⁺ T Cells in LysMCre⁺IFNAR^(fl/fl) Mice All 244 peptides were tested by IFNγ-ELISPOT assay using CD8⁺ T cells from ZIKV-infected mice.

Figure 3A:
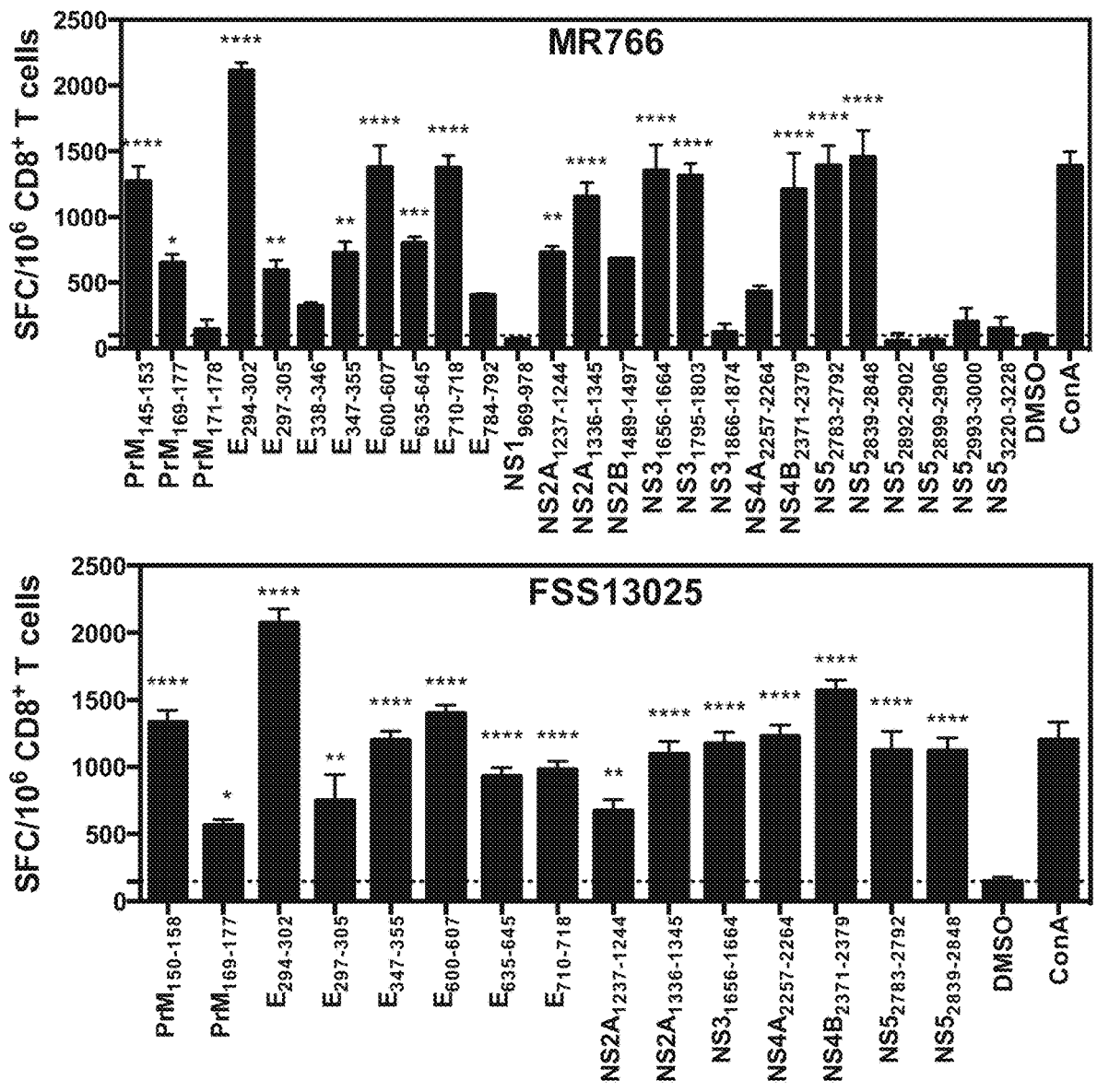
FIGS. 3A-3B: shows exemplary non-limiting results obtained from the identification of ZIKV epitopes recognized by CD8$^+$ T cells in LysMCre$^+$IFNAR$^{fl/fl}$ mice in accordance with an embodiment of the present disclosure.
Figure 3B:
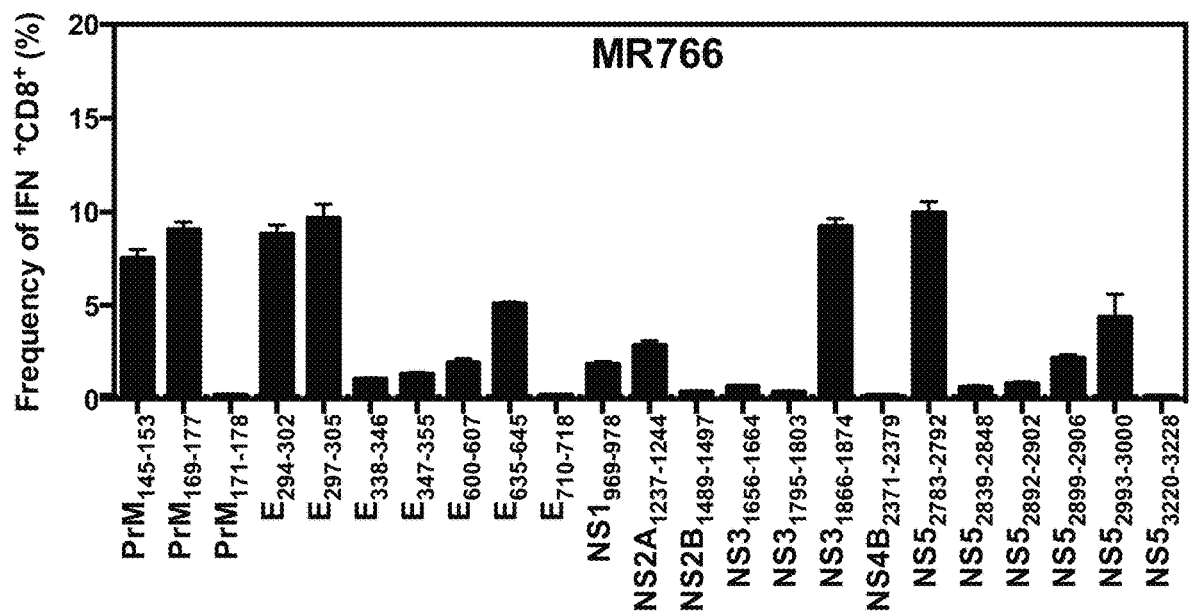
Figure 3B:
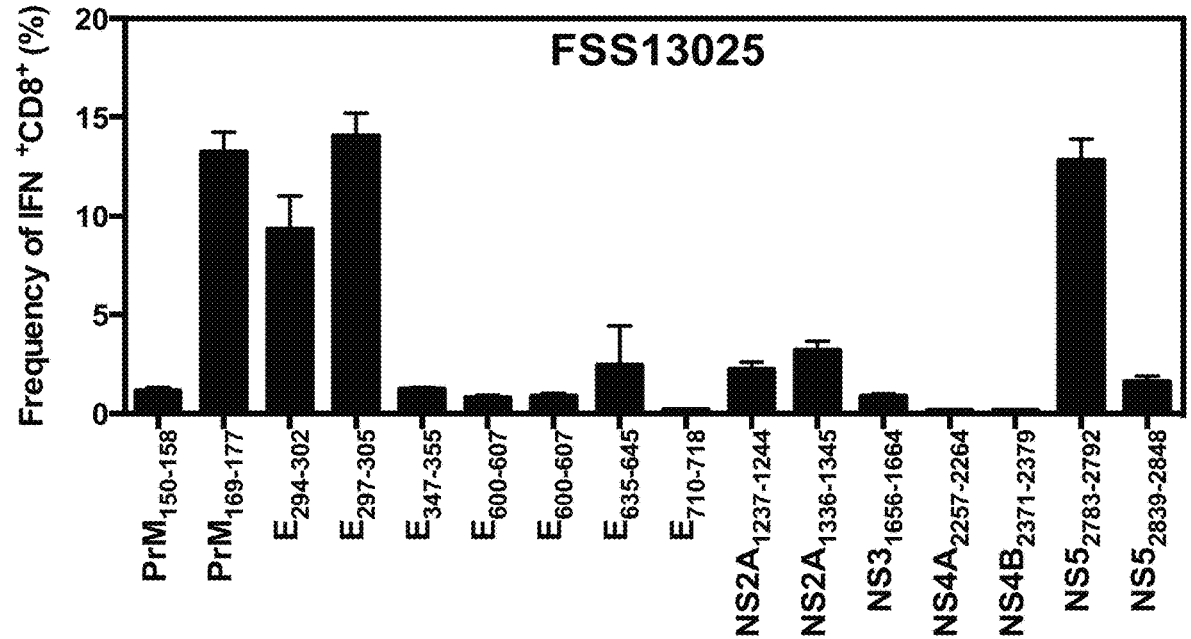

The following results are with reference to FIG. 3A and FIG. 3B, where five-week-old LysMCre⁺IFNAR^(fl/fl) were infected retro-orbitally with $10^4$ FFU of ZIKV MR766 or FSS13025. FIG. 3A shows a graph that illustrates the results from an IFNγ-ELISPOT which was performed using CD8⁺ T cells isolated from infected mice. A total of 244 peptides from ZIKV strains predicted to bind H-2Kb and H-2db with high affinity were screened. Two independent experiments for each ZIKV strain (n=5 mice for each experiment) were performed in triplicate per peptide. The data are expressed as the mean of spot forming cells (SFC) per $10^6$ CD8⁺ T cells, and error bars are represented as SEM. One-way ANOVA was used to compare the mean of each peptide with the control (DMSO) (P>0.05). FIG. 3B shows a graph that illustrates the results to confirm ZIKV-derived epitopes recognized by CD8⁺ T cells in LysMCre⁺IFNAR^(fl/fl) mice and IFNγ production via intracellular cytokine staining ("ICS"), determined seven days post-infection with positive peptides. The dotted line corresponds to the average amount of IFNγ produced by MOCK mice when stimulated with positive ZIKV-derived peptides (0.19% of IFNγ+CD8⁺ T cells).

The results obtained are the following:

Fifteen peptides were statistically positive for both MR766 (FIG. 3A, top panel) and FSS13025 (FIG. 3A, bottom panel). Eight and 7 proteins of the 10 ZIKV proteins are represented among these positive peptides from MR766 and FSS13025, respectively: 40% are from E protein, 13% from prM, NS2A, NS3 or NS5, and 6% from NS2B, NS4A, or NS4B for MR766. FSS13025 epitopes are similarly represented as MR766. All epitopes identified by IFNγ-ELISPOT for both ZIKV strains are indicated in Table 1 (SEQ ID Nos: 1-29). Fourteen peptides are recognized only by MR766-primed CD8⁺ T cells, 3 are specific for FSS13025-primed CD8⁺ T cells, and twelve are recognized by both MR766- and ZIKV FSS13025-primed CD8⁺ T cells (Table 1, see next page).

Peptides from MR766 and FSS13025 ZIKV strains were predicted to bind H-$2^b$ class I molecules (db and Kb). The positions, sequences, and lengths of each of the 29 peptides that induced a positive T cell response, as determined via IFNγ-ELISPOT assay, are shown. The sequence conservation among more than 100 ZIKV strains was obtained using the program BLASTP 2.5.1 on NCBI, and 80% of these strains represent 2015-2016 isolates from Japan, Florida, Singapore, Venezuela, Australia, and Brazil. Y corresponds to highly conserved peptides, sharing 100% (Y(100%)) or 80% (Y(80%)) of sequence identity with the majority of the published strains.

To verify the map of the CD8⁺ T cell response to ZIKV, the computational epitope prediction approach was compared to the overlapping peptide method (screening 15-mer peptides that overlap by 11 amino acids in the E protein from both ZIKV strains).

TABLE 1

| SEQ ID NO: | Sequence | Length | Db | Kb | Protein | Start-position | End-position | Conserved | Strains |
|---|---|---|---|---|---|---|---|---|---|
| 1 | AAFTFTKV | 8 | | X | E | 600 | 607 | Y (100%) | MR766 |
| 2 | AAGAWYVYV | 9 | | X | NS2B | 1489 | 1497 | Y (100%) | MR766 |
| 3 | ISFATTLGV | 9 | | X | PrM | 145 | 153 | Y (80%) | MR766 |
| 4 | MSYECPML | 8 | X | X | PrM | 171 | 178 | Y (100%) | MR766 |
| 5 | PSVRNGNEI | 9 | X | | NS3 | 1866 | 1874 | Y (100%) | MR766 |
| 6 | RAIWYMWL | 8 | X | X | NS5 | 2993 | 3000 | Y (100%) | MR766 |
| 7 | RQVMNIVSSWL | 11 | X | | NS5 | 2892 | 2902 | Y (100%) | MR766 |
| 8 | SSIAARGYI | 9 | X | | NS3 | 1795 | 1803 | Y (100%) | MR766 |
| 9 | SSLVNGVVRL | 10 | X | | NS5 | 2839 | 2848 | Y (100%) | MR766 |
| 10 | SSWLWKEL | 8 | | X | NS5 | 2899 | 2906 | Y (100%) | MR766 |

TABLE 1-continued

| SEQ ID NO: | Sequence | Length | Db | Kb | Protein | Start-position | End-position | Conserved | Strains |
|---|---|---|---|---|---|---|---|---|---|
| 11 | TGWSNWEEV | 9 | X | | NS5 | 3220 | 3228 | Y (100%) | MR766 |
| 12 | TTVSNMAEV | 9 | X | | E | 338 | 346 | Y (100%) | MR766 |
| 13 | VMIFLSTAV | 9 | X | X | E | 784 | 792 | Y (80%) | MR766 |
| 14 | YSLECDPAVI | 10 | X | | NS1 | 969 | 978 | Y (100%) | MR766 |
| 15 | AAFTFTKI | 8 | X | X | E | 600 | 607 | Y (100%) | FSS |
| 16 | SSLINGVVRL | 10 | X | | NS5 | 2839 | 2848 | Y (80%) | FSS |
| 17 | TLGMNKCYI | 9 | X | | PrM | 150 | 158 | Y (100%) | FSS |
| 18 | IMVAVGLL | 8 | | X | NS4A | 2257 | 2264 | Y (100%) | MR766/FSS |
| 19 | ATMSYECPM | 9 | | X | PrM | 169 | 177 | Y (100%) | MR766/FSS |
| 20 | CAEAPNMKVI | 10 | X | | NS5 | 2783 | 2792 | Y (100%) | MR766/FSS |
| 21 | IGVSNRDFV | 9 | X | | E | 294 | 302 | Y (100%) | MR766/FSS |
| 22 | MAVDMQTLTPV | 11 | X | | E | 635 | 645 | Y (100%) | MR766/FSS |
| 23 | RMAVLGDTA | 9 | X | | E | 710 | 718 | Y (100%) | MR766/FSS |
| 24 | RSYCYEASI | 9 | | X | E | 347 | 355 | Y (100%) | MR766/FSS |
| 25 | SNRDFVEGM | 9 | | X | E | 297 | 305 | Y (100%) | MR766/FSS |
| 26 | SQLTPLTLI | 9 | X | | NS4B | 2371 | 2379 | Y (100%) | MR766/FSS |
| 27 | SVKKNLPFVM | 10 | X | | NS2A | 1336 | 1345 | Y (100%) | MR766/FSS |
| 28 | VSFIFRAN | 8 | X | X | NS2A | 1237 | 1244 | Y (100%) | MR766/FSS |
| 29 | VVIKNGSYV | 9 | X | | NS3 | 1656 | 1664 | Y (100%) | MR766/FSS |

The results obtained are the following:

In total, 14 and 15 peptides generated by overlap were positive for MR766 and FSS13025, respectively. Six of the 8 computationally predicted MR766 peptides and 4 of the 5 computationally predicted FSS13025-peptides were identified as positive using the overlapping approach (FIG. 8).

Figure 4A:
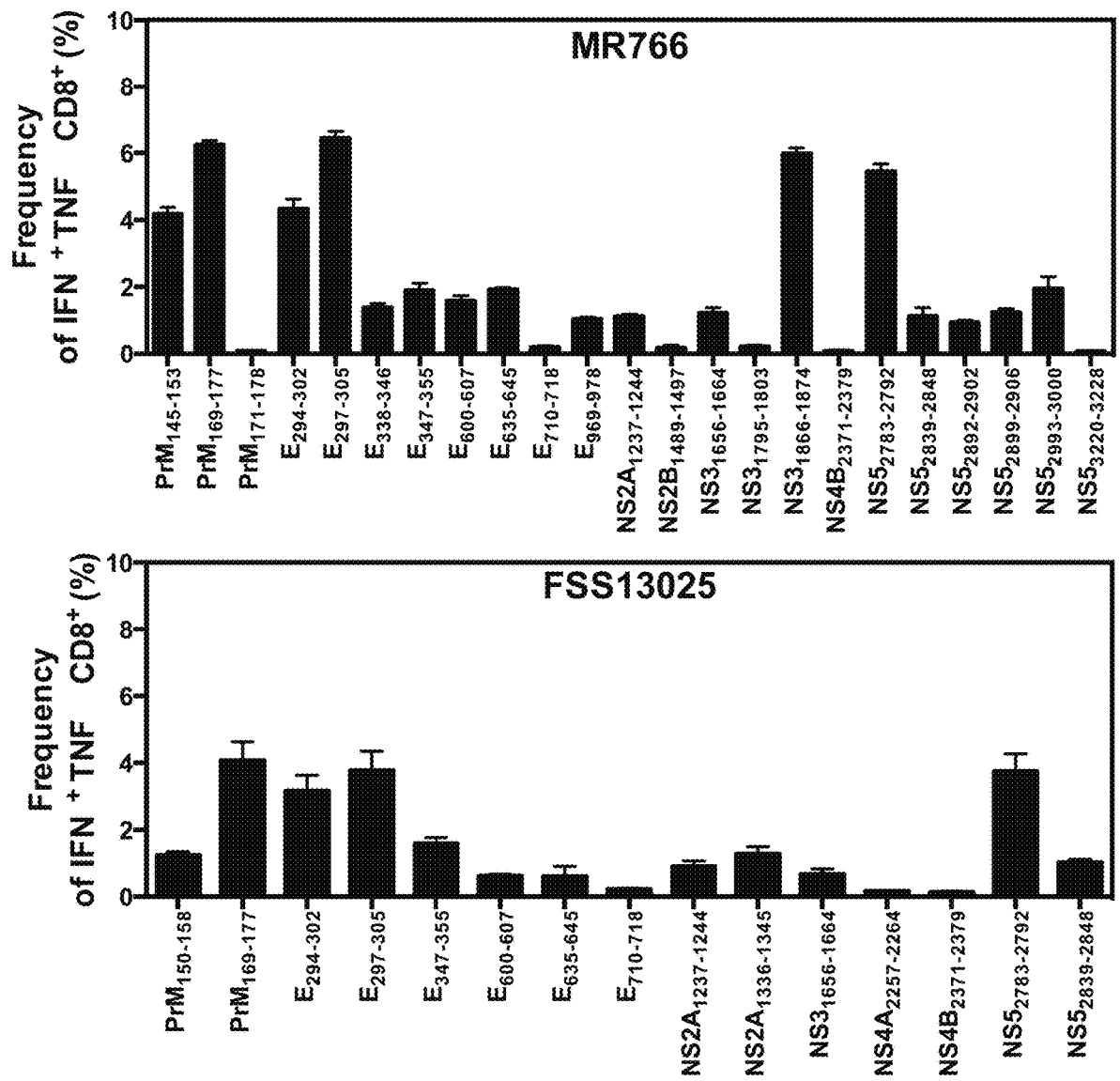
FIGS. 4A-4F: shows exemplary non-limiting results of polyfunctional phenotype of ZIKV epitope-specific CD8$^+$ T cells in LysMCre$^+$IFNAR$^{fl/fl}$ mice in accordance with an embodiment of the present disclosure.
Figure 4B:
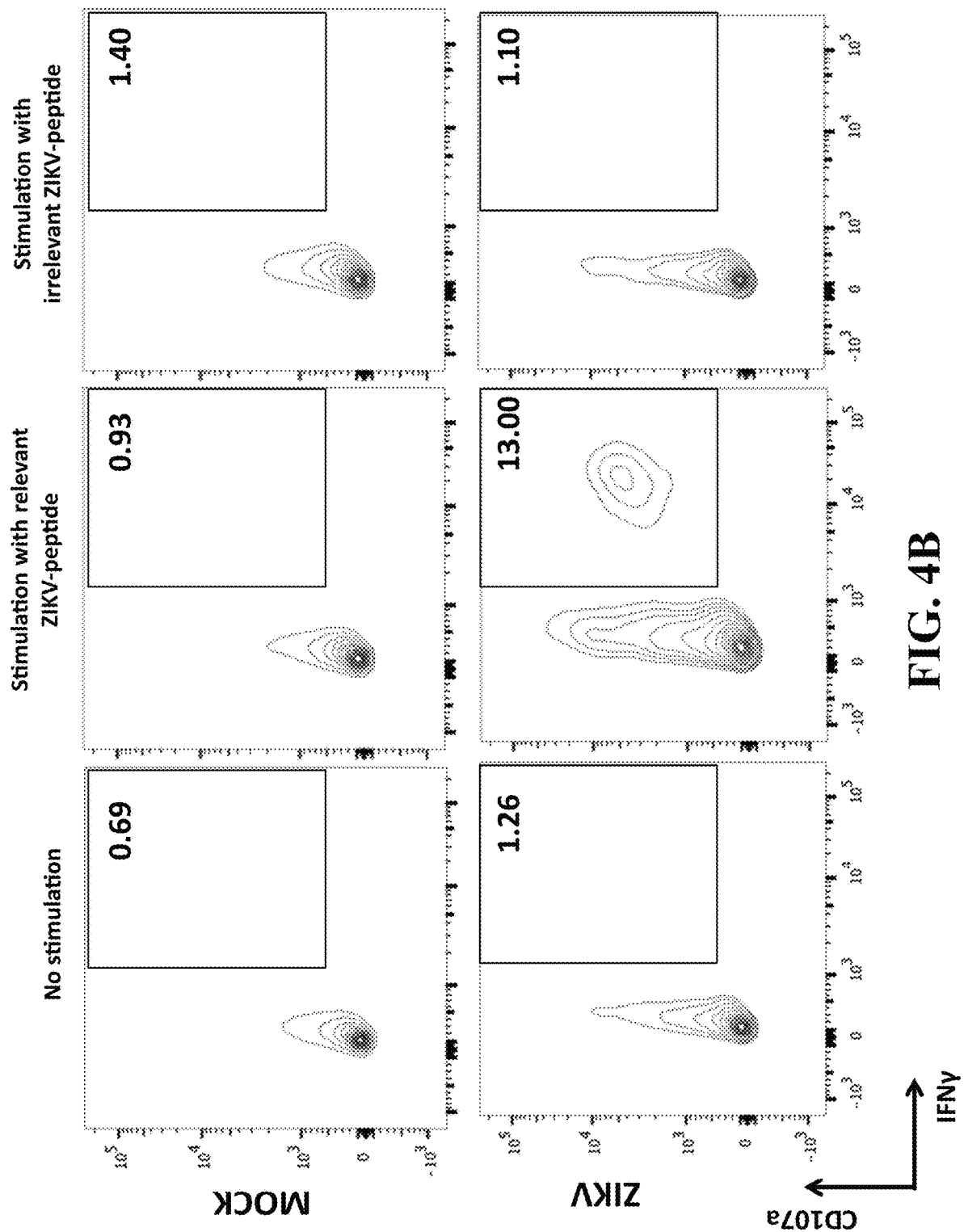
Figure 4C:
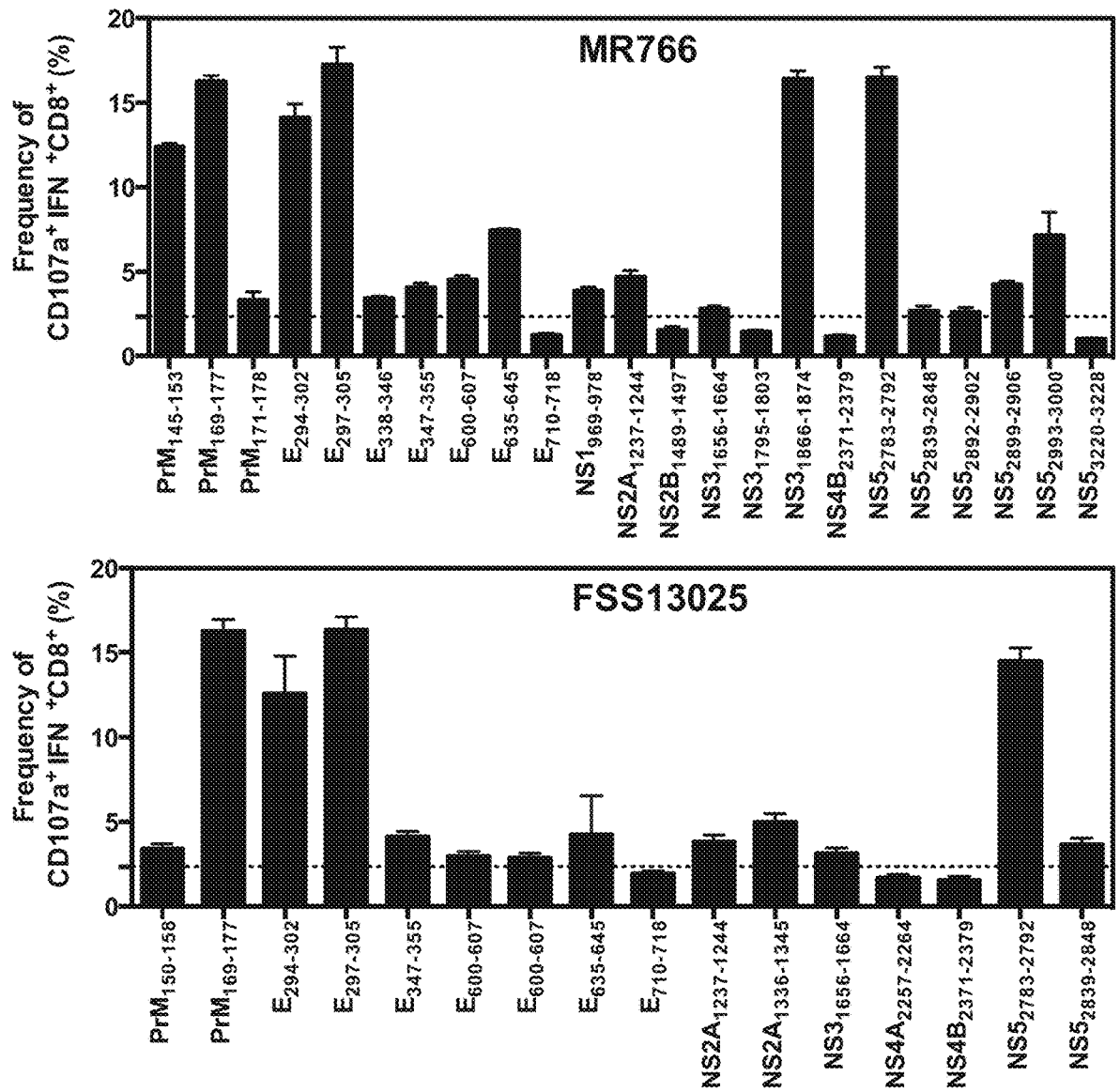
Figure 4D:
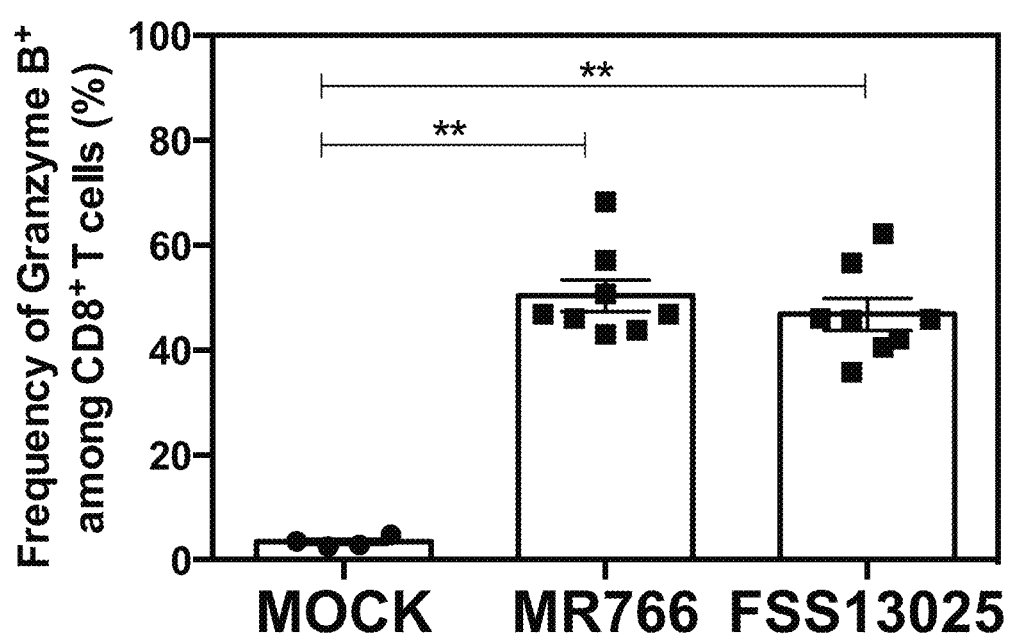
Figure 4E:
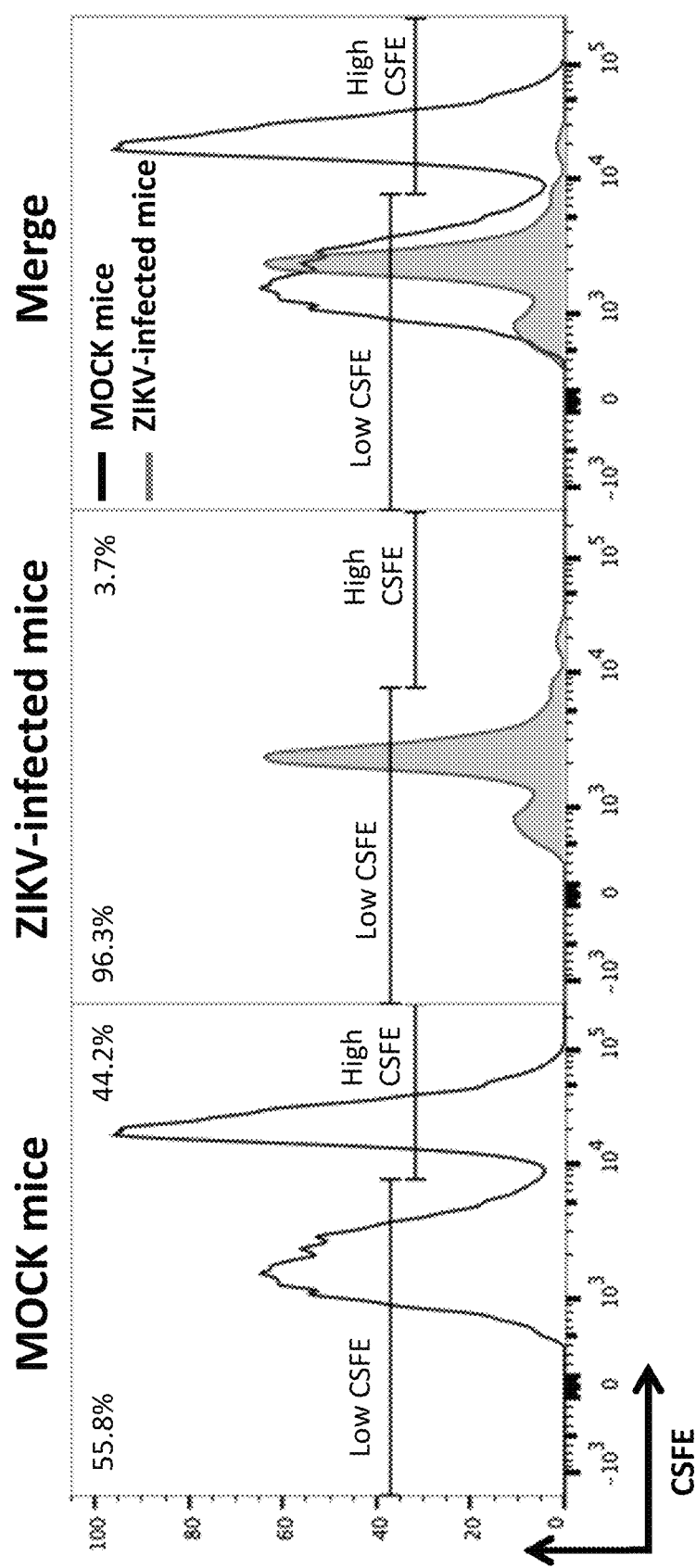
Figure 4F:
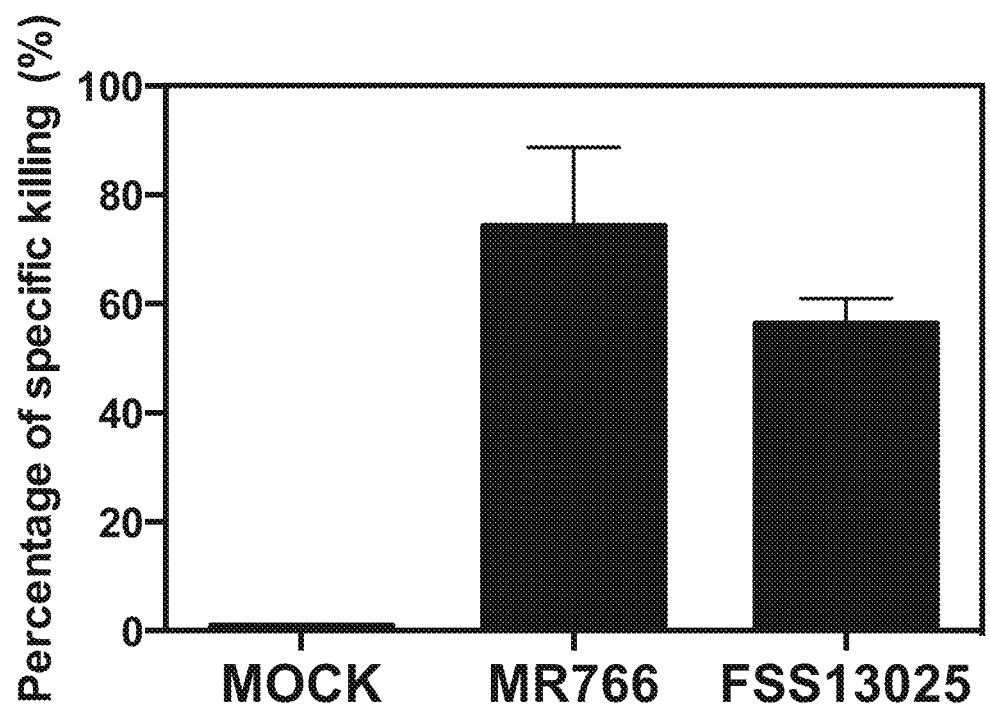
Figure 8:
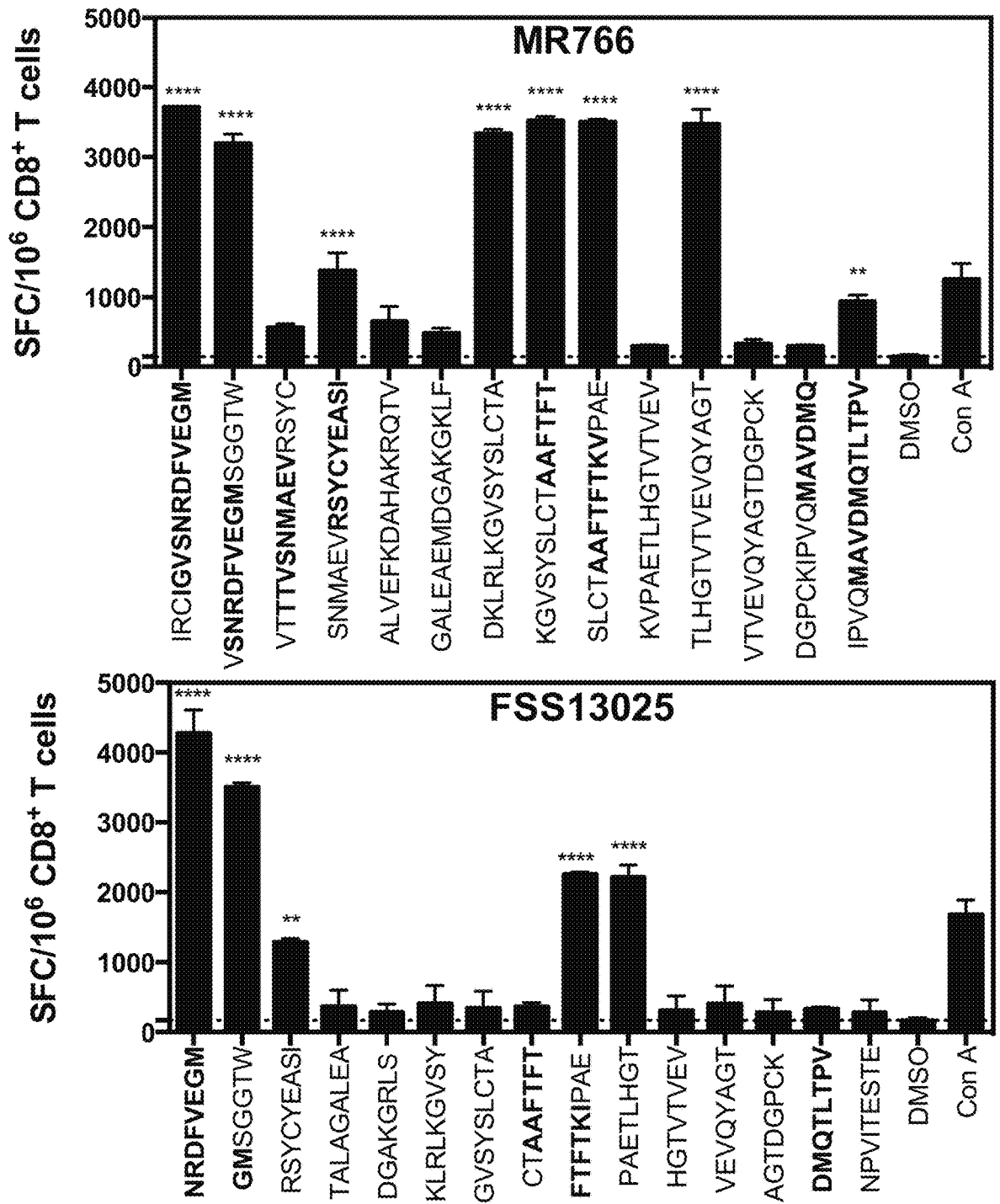
FIG. 8: shows graphs that illustrate a non-limiting experimental procedure for the peptide prediction approaches to identify ZIKV-derived epitopes recognized by CD8+ T cells via screening of 15-mer overlapping peptides in accordance with an embodiment of the present disclosure.

The following results are with respect to FIG. 8, where six-week-old LysMCre$^+$IFNAR$^{fl/fl}$ were infected retro-orbitally with 1×10$^4$ FFU of MR766 or FSS13025. A total of 127 peptides spanning the E protein of both MR766 and FSS13025 were screened and all peptides were tested by IFNγ-ELISPOT in triplicates. The data are expressed as the mean of Spot Forming Cells (SFC) per $10^6$ CD8$^+$ T cells and error bars are represented as SEM. A positive peptide induced a SFC value per $10^6$ CD8$^+$ T cells greater than 20 and a stimulation index factor greater than 2 in comparison to the negative control (DMSO). All peptide sequences previously identified by computational approach are identified in bold. Fourteen peptides are positive for MR766 (top panel) and fifteen for FSS13025 (bottom panel). One-way ANOVA was used to compare the mean of each peptide with the negative control ($p<0.05$).

To validate the epitopes identified via the IFNγ-ELISPOT assay, ICS was performed and CD8$^+$ T cell production of IFNγ, TNFα, and CD107a after stimulation with individual peptides was quantified. Among all positive peptides identified by IFNγ-ELISPOT assay, 8 peptides from MR766-infected mice (FIG. 3B, top panel) and 4 peptides from FSS13025-infected mice (FIG. 3B, bottom panel) induced a high frequency of IFNγ+ cells. For MR766, epitopes were derived from prM (25%), E (37%), NS3 (12%) and NS5 (25%). For FSS13025, 50% of epitopes were from the E protein and 16% were from prM, NS2A, and NS5.

Polyfunctionality of CD8$^+$ T cells after peptide stimulation was evaluated based on the frequency of IFNγ$^+$TNFα$^+$ and CD107a$^+$IFNγ$^+$ (gating strategy, FIG. 4B) double-positive cells in MR766-primed (FIG. 4A and FIG. 4C, top panel) and FSS13025-primed CD8$^+$ T cells (FIG. 4A and FIG. 4C, bottom panel).

The following results are with reference to FIG. 4A to FIG. 4F, where splenocytes from LysMCre$^+$IFNAR$^{fl/fl}$ mice were infected with $10^4$ FFU of ZIKV strain MR766 (n=4) or FSS13025 (n=5). FIG. 4A shows the frequency of CD8$^+$ T cells producing IFNγ and TNFα upon stimulation with MR766-derived peptides (top panel) and FSS13025-derived peptides (bottom panel). All experiments were performed twice and error bars are represented in SEM. FIG. 4B shows the gating strategy used to select cells expressing both CD107a and IFNγ in MOCK and infected mice upon stimulation with relevant ZIKV-peptide (E294-302) or with irrelevant ZIKV-peptide ($E_{710-718}$). FIG. 4C shows the frequency of CD107a$^+$IFNγ+CD8$^+$ T cells obtained after stimulation with MR766- or FSS13025-derived peptides. The background obtained in MOCK mice is represented by dotted lines and corresponded to 0.07% for IFNγ$^+$TNFα$^+$ (panel A) and 2.36% for CD107a$^+$IFNγ$^+$ double-positive CD8$^+$ T cells (panel C). FIG. 4D shows the percentage of granzyme B produced by CD8$^+$ T cells from mice infected with MR766

(n=8) or FSS13025 ZIKV (n=8) and MOCK (n=4). FIG. 4E shows a representation of In vivo cytotoxicity of target cells in ZIKV-infected mice. FIG. 4F shows the percentage of killing was obtained in mice infected with ZIKV (n=4) for 7 days or in MOCK (n=4).

The results obtained are the following:

The results confirmed that prM$_{169-177}$ (SEQ ID NO: 19), E$_{294-302}$ (SEQ ID NO: 21), E$_{297-305}$ (SEQ ID NO: 25), and NS5$_{2783-2792}$ (SEQ ID NO: 20) are the immunodominant epitopes. The investigation was expanded by assessing granzyme B expression in CD8$^+$ T cells. The percentages of granzyme CD8$^+$ T cells in infected mice were similar for both ZIKV strains for MR766 and FSS13025, and were 15- and 14-fold higher, respectively, relative to uninfected animals (FIG. 4D). To verify cytolytic activity of the ZIKV-specific CD8$^+$ T cells, an in vivo cytotoxicity assay was performed using splenocytes pulsed with three immunodominant peptides (prM$_{169-177}$ (SEQ ID NO: 19); E$_{297-305}$ (SEQ ID NO: 25); NS5$_{2783-2792}$ (SEQ ID NO: 20)) as targets (FIG. 4E). As expected, a high percentage of cytotoxicity was observed in both MR766- and FSS13025-infected mice (FIG. 4F). Taken together, these results demonstrate that the epitope-specific CD8$^+$ T cells exhibit a polyfunctional phenotype.

2.5 Kinetics of the ZIKV-Specific CD8$^+$ T Cell Response in LysMCre$^+$IFNAR$^{fl/fl}$ Mice The following results are with respect to FIG. 5A and FIG. 5B, where LysMCre$^+$IFNAR$^{fl/fl}$ mice were infected with 10$^4$ FFU of ZIKV strain MR766 or FSS13025. Splenocytes were harvested at 3, 7, and 14 days post-infection and stimulated with immunodominant ZIKV-derived peptides to assess cytokine production by ICS. FIG. 5A shows the frequency of IFNγ-producing CD8$^+$ T cells and FIG. 5B shows the frequency of CD44$^+$CD62L$^-$ CD8$^+$ T cells at day 3 (white), 7 (black), and 14 (grey) post-infection. The background production of IFNγ obtained in MOCK was subtracted from all values. Two-way ANOVA test was used to compare the time points for each peptide (P>0.05). The error bars correspond to SEM.

The results obtained are the following:

The kinetics of the splenic CD8$^+$ T cell response induced by the immunodominant epitopes at days 3, 7 and 14 post-infection were measured in LysMCre$^+$IFNAR$^{fl/fl}$ mice infected with MR766 or FSS13025. The percentage of IFNγ$^+$CD8$^+$ T cells was higher at day 7 than day 3 or day 14 post-infection for both MR766 and FSS13025-infected mice (FIG. 5A). Similarly, the frequency of CD44$^+$CD62L$^-$ cells in infected mice was higher at day 7 than day 3 (FIG. 5B). These results demonstrate that, among the time points measured, the CD8$^+$ T cell response in ZIKV-infected mice peaks at day 7 post-infection.

2.6 CD8$^+$ T Cells Control ZIKV Infection in LysMCre$^+$ IFNAR$^{fl/fl}$ Mice

The following results explore the role of CD8$^+$ T cells in controlling ZIKV infection by performing antibody-mediated depletion studies.

Figure 6C:
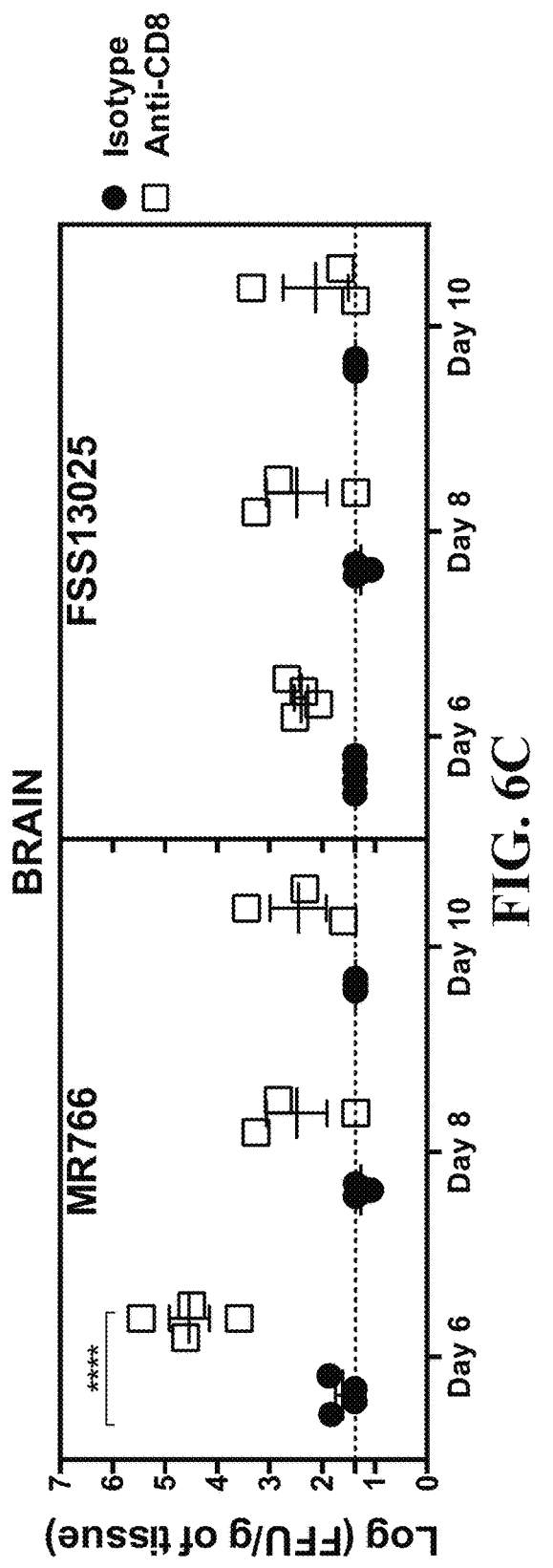
Figure 6D:
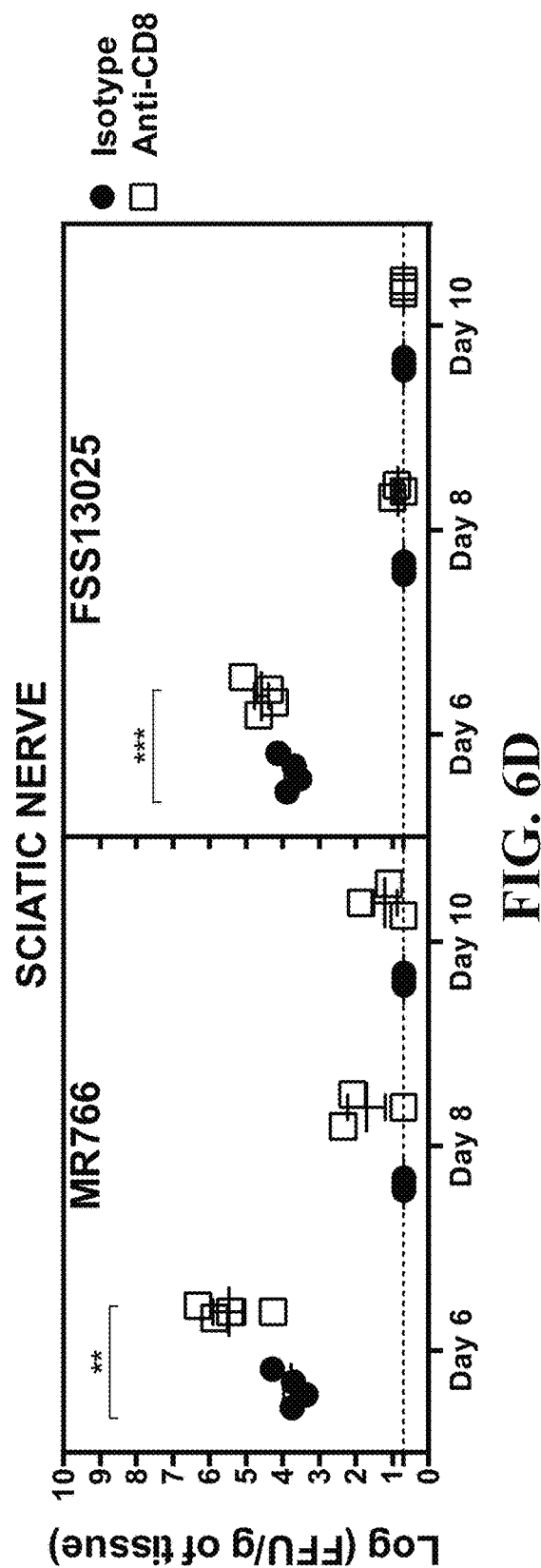
Figure 6E:
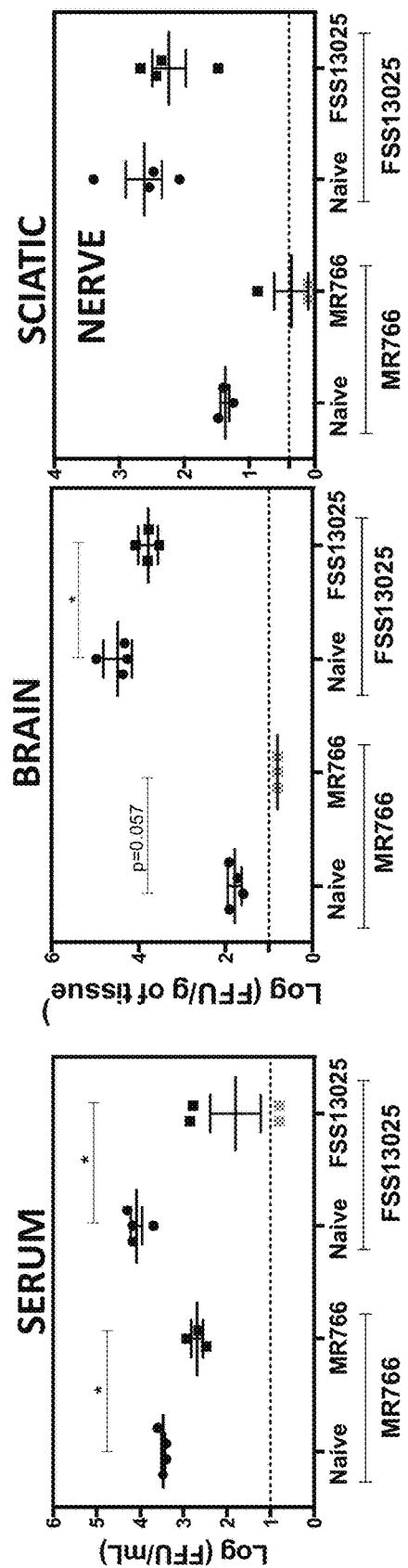
Figure 6F:
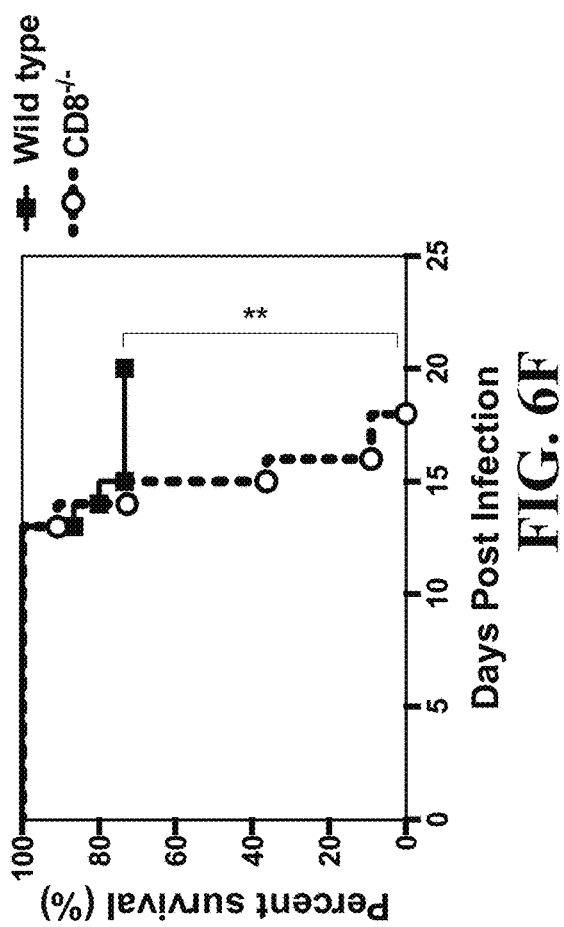

The following results are with respect to FIG. 6A to FIG. 6F, where LysMCre$^+$IFNAR$^{fl/fl}$ were treated with depleting anti-CD8 or isotype control antibody on days 3 and 1 before infection with 10$^5$ FFU of MR766 or FSS13025. Mice were sacrificed and tissues harvested at 6, 8 and 10 days post-infection. The levels of infectious virus in the (FIG. 6A) serum, (FIG. 6B) spleen, (FIG. 6C) brain, and (FIG. 6D) sciatic nerve were quantified using BHK-21 cell-based FFA. A two-way ANOVA test was used to compare the levels of infectious ZIKV between the isotype and the anti-CD8 antibody-administered groups for all time points and tissues. FIG. 6E, on day 120 after infection with MR766 or FSS13025, 7.5×10$^6$ CD8$^+$ T cells were transferred into 5-week-old naive mice one day before challenge with 10$^5$ FFU of MR766 or FSS13025. For controls, CD8$^+$ T cells were isolated from naive LysMCre$^+$IFNAR$^{fl/fl}$ mice. Infectious ZIKV was quantified. Mann-Whitney test was used to compare naïve CD8$^+$ T cells vs. ZIKV-immune CD8$^+$ T cells. FIG. 6F, seven-week-old WT and CD8α$^{-/-}$ that were treated with 2 mg of IFNAR-blocking antibody at day −1, and then inoculated subcutaneously with 10$^5$ PFU of mouse adapted Dakar 41519 ZIKV strain at day 0. Survival was monitored for 21 days in both groups and reported for WT (n=15, Black square) and CD8$^{-/-}$ (n=11, Red circle) mice. Pooled data from three independent experiments are represented and the log-rank (Mantel-cox) test was used to compare groups.

The results obtained are the following:

Levels of infectious virus in serum (FIG. 6A), spleen (FIG. 6B), brain (FIG. 6C) and sciatic nerve (FIG. 6D) were assessed 6, 8 or 10 days after infection of CD8$^+$ T cell-sufficient and -depleted mice. At day 6 post-infection, CD8$^+$ T cell-depleted mice infected with MR766 or FSS13025 contained higher viral burdens in the serum, spleen, brain, and sciatic relative to the CD8$^+$ T cell-sufficient control mice. At day 8 post-infection, the amount of virus decreased in all tissues, in both control and CD8-depleted groups. At day 10, the level of infectious ZIKV was undetectable in almost all of the tissues (FIG. 6A, FIG. 6B, and FIG. 6D) except the brain (FIG. 6C).

Next, memory CD8$^+$ T cells were adoptively transferred from LysMCre$^+$IFNAR$^{fl/fl}$ donor mice infected with MR766 or FSS13025 for 120 days. ZIKV-immune memory CD8$^+$ T cells were transferred to naïve recipient LysMCre$^+$IFNAR$^{fl/fl}$ mice one-day prior to infection with MR766 or FSS13025. Transfer of 7.5×10$^6$ memory CD8$^+$ T cells resulted in decreased ZIKV burden compared to control T cells from naïve mice (FIG. 6E) in the serum and brain (FIG. 6E).

During its generation in the 1940s and 1950s, ZIKV MR766 was passaged serially more than 100 times in mouse brains, leading to a neurologically adapted virus (Haddow et al., 2012). To confirm the role of CD8+ T cells during ZIKV infection using a second ZIKV strain of African lineage as well as another loss-of-function model for CD8$^+$ T cells, a survival study was performed using mouse-adapted ZIKV strain Dakar 41519 and Cd8a gene-deficient mice lacking CD8+ T cells. Survival was monitored in IFNAR-blocking antibody-treated WT and congenic CD8+ T cell-deficient (CD8−/−) C57BL/6 mice (FIG. 6F). Mice started to die 12 days after infection with mouse-adapted ZIKV Dakar 41519. Eighteen days later, all CD8−/− mice were dead compared to only 25% of WT mice. Thus, a lack of CD8+ cells significantly increased susceptibility to lethal ZIKV infection. Collectively, these results demonstrate a critical role for CD8+ T cells in controlling ZIKV infection and pathogenesis in mice.

3. Discussion on Example 1

Based on the results obtained in example 1, it is reasonable to conclude that CD8$^+$ T cells play a protective role against ZIKV infection in an animal model with IFN receptor-competent T cells and dendritic cells, and that the specificity of the CD8$^+$ T cell response varies slightly among ZIKV strains. The present disclosure provides a validated map of the CD8$^+$ T cell response to ZIKV strains MR766 and FSS130125 with identification of 26 and 15 epitopes, respectively. Moreover, all three immunodominant peptides are highly conserved. These maps establish a foundation for investigating CD8+ T cell responses to ZIKV. The results demonstrate that an effective ZIKV vaccine should induce a broad CD8+ T cell response.

ZIKV publications through November 2016 have not described any data on the T cell response to ZIKV in humans or animal models. Currently DENV mouse models provide the largest body of information regarding CD8+ T cell responses to systemic *Aedes*-transmitted flavivirus infection. Similar to our present results with ZIKV, a protective role for CD8+ T cells against DENV was established as increased viral loads were observed following CD8+ T cell depletion (Yauch et al., 2009). In addition, adoptive transfer of DENV-primed CD8+ T cells (Zellweger et al., 2014) and effective epitope vaccination studies (Yauch et al., 2009) provided further indication of CD8+ T cells' protective role against DENV.

The present data shows broad CD8+ T cell responses to ZIKV MR766 and FSS13025 that target all viral proteins with the exception of NS1 and NS2B in the FSS13025 response. In H-2$^b$ mice, E protein appeared to be the main target of the anti-ZIKV CD8+ T cell response, whereas for DENV dominant epitopes are within NS3, NS4B, and NS5 (Weiskopf et al., 2013; Yauch et al., 2009). When grouped by protein, epitope immunodominance between the two ZIKV strains was similar for the prM, E, and NS5 epitopes. However, a stronger response was seen for MR766 NS31866-1874 (SEQ ID NO: 5). Overall, the H-2b CD8+ T cell response to MR766 was broader than to FSS13025, especially for NS1, NS3, and NS5 epitopes.

The contribution of CD8+ T cells to protection vs. pathogenesis in ZIKV infection, and whether cross-reactive antibodies or T cells can worsen the course of ZIKV infection following infection with a similar flavivirus through antibody-dependent enhancement or original T cell antigenic sin, respectively, remain to be determined (Lazear and Diamond, 2016). However, evidence of these phenomena (Halstead, 2007; Mongkolsapaya et al., 2003) from cases of severe DENV would indicate that vaccine developers need to consider the effects of ZIKV vaccine if recipients subsequently become infected with DENV. Therefore, the use of epitopes to design a subunit vaccine may be a good alternative for ZIKV.

The results shown in example 1 lay the groundwork for investigating the function of CD8+ T cells in ZIKV infection of immunologically specialized sites. Unlike dengue disease in which systemic infection dominates the clinical course (Mongkolsapaya et al., 2006), it is the localized events preceding and following systemic infection that are the most threatening components of ZIKV's clinical picture. Documentation of mucosal transmission by vaginal and anal intercourse leading to systemic infection is growing (D'Ortenzio et al., 2016; Deckard et al., 2016; Foy et al., 2011; Hills et al., 2016; Musso et al., 2015; Venturi et al., 2016). Once maternal systemic infection has been established, transplacental infection and transmission allows for infection of the fetal brain and devastating consequences including microcephaly (Brasil et al., 2016; Lazear and Diamond, 2016; Malone et al., 2016; Mlakar et al., 2016; Oliveira Melo et al., 2016; Tetro, 2016; Ventura et al., 2016). Post-systemic infection entry of the virus into semen-producing tissues (Atkinson et al., 2016; Govero et al., 2016) allows the virus to be transmitted without its mosquito vector. Finally, evidence is also mounting that autoimmune disease such as Guillain-Barré syndrome (GBS) can follow systemic infection with ZIKV (Deckard et al., 2016; Lazear and Diamond, 2016; Malone et al., 2016; Oehler et al., 2014).

ZIKV's most devastating clinical effects result from infection of the fetal brain, and CD8+ T cell-dependent clearance of other neurotropic flaviviruses is well documented (Shrestha and Diamond, 2004). ZIKV burden observed in the brains of both CD8+ T cell-sufficient and -depleted LysMCre+IFNAR$^{fl/fl}$ mice is consistent with published evidence of ZIKV's neurotropism in mice (Cugola et al., 2016; Dowall et al., 2016; Lazear et al., 2016; Li et al., 2016a; Li et al., 2016$^b$; Miner et al., 2016; Rossi et al., 2016). In the latter mice, disproportionately increased levels of ZIKV MR766 in the brain seen at day 6 post-infection may reflect the strain's passage history through mouse brains (Dick, 1952). This observation in the brains of mice infected with MR766 relative to FSS13025 highlights one of the differences between these two strains, albeit this difference was not observed at earlier time points (days 1 and 3 post-infection).

The susceptibility of LysMCre+IFNAR$^{fl/fl}$ mice to ZIKV indicates that loss of type I IFN response in myeloid cells is sufficient to permit robust ZIKV infection. This finding is consistent with reported permissiveness of monocytes and macrophages to replication of other flaviviruses (Mangada et al., 2002; Prestwood et al., 2012a; Shrestha et al., 2008; Yang et al., 2014). Transplacental ZIKV transmission was recently reported in SJL mice, which also have an intact IFN response, but no mention of the specific cellular tropism was made (Cugola et al., 2016). The exact effects of the myeloid cell type I IFN response on the anti-ZIKV CD8+ T cell response remain unknown. Similar to Zika fever in adult humans (Lazear and Diamond, 2016; Malone et al., 2016), LysMCre+IFNAR$^{fl/fl}$ mice become transiently ill (ruffled coat, hunched posture, weight loss) and recover from clinical signs at day 6-7 after infection, which corresponds to peak CD8+ T cell IFNγ and CD107a expression. Based on CD8+ T cell expansion, polyfunctional phenotype of ZIKV epitope-specific CD8+ T cells, and CD8+ T cell-mediated viral clearance, it is reasonable to conclude that myeloid type I IFN response is not necessary for priming an efficient CD8+ T cell response in these mice. This conclusion is similar to studies of DENV (Yauch et al., 2009), vaccinia virus, vesicular stomatitis virus (Thompson et al., 2006), and Sendai virus (Lopez et al., 2006) in IFNAR-deficient mice. Further characterization of the LysMCre+IFNAR$^{fl/fl}$ mouse model should provide a platform for studying ZIKV-specific T cell responses, and for testing vaccine and antiviral candidates.

Example 2

Example 2 refers to the results shown in FIG. 9 to FIG. 14B.

Example 2 can be summarized as follows:

CD8+ T cells play an important role in controlling Flavivirus infection, but the CD8+ T cell response to Zika virus (ZIKV) is as yet to be defined. Due to sharing of host space with other flaviviruses, an understanding of cross-reactive immunity is also essential. Using computational analysis, the present inventors predicted 107 ZIKV peptides to bind HLA-B*0702 and 90 ZIKV peptides to bind HLA-A*0101, and screened CD8+ T cells for IFNγ response from ZIKV-infected interferon (IFN)α/β receptor (Ifnar)$^{-/-}$ HLA-B*0702 and HLA-A*0101 transgenic mice. The data in example 2 identified 37 HLA-B*0702-restricted epitopes and 13 HLA-A*0101-restricted epitopes using ELISPOT with 18 and 7 peptides common to both African (MR766) and Asian (FSS13025) lineages, respectively. Twenty-five HLA-B*0702-binding peptides and 1 HLA-A*0101-binding peptide were confirmed to stimulate CD8+ T cell IFNγ production by intracellular cytokine staining (ICS). The cross-reactivity of ZIKV epitopes to Dengue virus (DENV) was tested using IFNγ-ELISPOT and IFNγ-ICS on CD8+ T cells from DENV-infected mice, and 5 cross-reactive HLA-B*0701-binding peptides were identified by both assays. ZIKV/DENV cross-reactive CD8+ T cells in DENV-immune mice expanded post ZIKV challenge and dominated in subsequent CD8+ T cell response, reminiscent of heterotypic DENV reinfection. ZIKV challenge following immunization of mice with ZIKV-specific and ZIKV/DENV cross-reactive epitopes elicited antigen-experienced CD8+ T cell response and reduced infectious ZIKV levels. CD8+ T cell depletion confirmed epitope-specific CD8+ T cells mediated this protection. These results identify ZIKV-specific and ZIKV/DENV cross-reactive epitopes, and demonstrate an altered immunodominance pattern in the DENV-immune setting relative to naive and a protective role for epitope-specific CD8+ T cells against ZIKV. These results have important implications for ZIKV vaccine development and testing efforts, and provide a new mouse model for evaluating anti-ZIKV CD8+ T cell responses of human relevance.

4. Materials & Methods for Example 2

4.1 Mice and Ethics Statement

Ifnar$^{-/-}$ HLA-B*0702 and Ifnar$^{-/-}$ HLA-A*0101 transgenic mice were previously generated via intercrossing of HLA-B*0702 and HLA-A*0101 transgenic mice with Ifnar$^{-/-}$ mice[22]. Mice were bred at the La Jolla Institute for Allergy and Immunology under standard pathogen free conditions. All experiments involving these mice were approved by the Institutional Animal Care and Use Committee under protocol #AP028-SS1-0615. Sample sizes were estimated based on experiments in similar studies. Animal experiments were not randomized and blinded.

4.2 Epitope Prediction and Peptide Synthesis

The HLA-B*0702- and HLA-A*0101-binding peptides were predicted using the IEDAR website online software. Peptides were chosen if their predictive scores ranked in the top 2% of all candidates. One hundred seven HLA-B*0702-binding and 90 HLA-A*0101-binding epitope candidates were synthesized by Synthetic Biomolecules (San Diego, USA) as crude materials which were confirmed by mass spectrometry analysis. Six immunodominant HLA-B*0702-binding peptides, 5 HLA-A*0101-binding peptides and a Hepatitis C virus (HCV)-core helper peptide TPPAY-RRPPNAPIL (SEQ ID NO: 80) restricted by mouse MHC molecule I-Ab were synthesized with a purity of >99% and used for immunizing mice. All peptides were dissolved in DMSO with a concentration of 40 mg/ml and stored at −20° C.

4.3 Viral Strains and Mouse Infection

Two ZIKV strains, MR766 (Uganda, 1947) and FSS13025 (Cambodia, 2010), were obtained from the World Reference Center for Emerging Viruses and Arboviruses (WRCEVA). The mouse-adapted DENV2 strain S221 is a triple-plaque purified clone derived from DENV2 D2S1038. Both ZIKV and DENV2 were amplified in C6/36 mosquito cells, and viral titers were measured using baby hamster kidney (BHK)-21 cell-based focus forming assay (FFA). For epitope screening, 5-week old mice (female or male) were infected retro-orbitally (R.O.) with either 1×10² FFU of ZIKV FSS13025 or ZIKV MR766, or 2×10⁴ FFU of DENV2 S221 in 200 µl 10% FBS/PBS. Seven days after infection, CD8+ T cells were isolated from splenocytes and used for ELISPOT assay, while the splenocytes were directly used for ICS assay. Additionally, 5-week old mice were inoculated I.P. with 2×10³ FFU of DENV2 S221 for 4 weeks. DENV2 S221-immune mice were challenged R.O. with 1×10⁴ FFU of ZIKV FSS13025 for 3 days or 7 days, and the percentages of peptide-specific IFNγ+ and/or TNFα+ CD8+ T cells were detected by ICS.

4.4 ZIKV Challenge of Peptide-Immunized Mice

Two HLA-B*0702-binding ZIKV-specific peptides (FSS-NS2A133-141(SEQ ID NO: 41) and FSS/MR766-NS2B$_{68-75}$ (SEQ ID NO: 45)) and four ZIKV/DENV cross-reactive peptides (FSS/MR766-NS4B$_{426-435}$ (SEQ ID NO: 60), FSS/MR766-NS2A$_{75-84}$ (SEQ ID NO: 39), FSS/MR766-NS3$_{206-215}$ (SEQ ID NO: 47), and FSS/MR766-NS3$_{574-582}$ (SEQ ID NO: 52)) were chosen for synthesis. Five HLA-A*0101-binding peptides (FSS/MR-E$_{159-167}$ (SEQ ID NO: 70), FSS/MR-E$_{195-203}$ (SEQ ID NO: 71), FSS/MR-NS1$_{23-31}$ (SEQ ID NO: 74), FSS/MR-NS4B$_{231-239}$ (SEQ ID NO: 77), and FSS/MR-NS5$_{509-517}$ (SEQ ID NO: 79)) were chosen for synthesis. Mice (both female and male; 5-6 weeks of age) were immunized subcutaneously with a mixture of HCV helper peptide (100 µg/mouse) and 3 or 4 HLA-B*0702-binding peptides (50 µg/peptide/mouse) emulsified in Complete Freund's Adjuvant (CFA). Mock group mice received the same immunization strategy but without any ZIKV-specific or ZIKV/DENV cross-reactive peptide. On the 21st day, mice were boosted with the same peptide mixtures emulsified in Incomplete Freund's Adjuvant (IFA). On the 30th day, all mice were challenged R.O. with 1×10⁴ FFU of ZIKV FSS13025. Three days post ZIKV infection mice were sacrificed, and serum and spleen were harvested. The splenocytes were used for ICS assay. After cardiac perfusion with PBS, brain was harvested. The levels of infectious ZIKV in serum and brain were measured using FFA.

4.5 ZIKV Challenge of CD8+ T Cell-Depleted, Peptide-Immunized Mice

Both 6 HLA-B*0702-binding peptides and 5 HLA-A*0101-binding peptides were used to immunize corresponding mice using the method as described above. Mock and peptide-immunized mice were injected I.P. with either anti-mouse CD8 monoclonal antibody (250 µg/mouse, rat anti-mouse CD8, clone YTS 169.4) or isotype control monoclonal antibody (250 µg/mouse, rat IgG2, clone LTF-2) at 3 days and 1 day before ZIKV challenge. Mice were injected R.O. with 1×10⁴ FFU ZIKV FSS13025. Three days after infection mice were sacrificed, and spleen and serum were used for ICS assay and FFA, respectively. After cardiac perfusion with PBS, liver and brain were harvested. ZIKV titers in tissues were measured using FFA.

4.6 LPS-Blast Preparation

LPS-blasts were prepared as previously described[52]. Briefly, spleens were harvested from Ifnar$^{-/-}$ HLA-B*0702 or Ifnar$^{-/-}$HLA-A*0101 transgenic mice and homogenized through a 70 µm cell strainer. A single-cell splenocyte suspension was placed into a non-vented culture flask with RPMI-1640 complete medium supplemented with 6 µg/ml Lipopolysaccharide (LPS) and 7 µg/ml Dextran Sulfate. Cells were incubated for 3 days at 37° C. with 5% CO$_2$. Cells were collected and washed three times with RPMI-1640 medium and adjusted to 4×106/ml.

4.7 IFNγ ELISPOT Assay

CD8+ T cells were isolated from splenocytes using magnetic bead positive selection (Miltenyi Biotec, Germany) 7 days after virus infection. 2×10⁵ CD8+ T cells were stimulated with 1×10⁵ LPS-blasts loaded with 10 µg of individual peptide in 96-well flat-bottom plates (IMMOBILON™-P; Millipore, Bedford, Mass.) that were coated with anti-IFNγ mAb (clone AN18; Mabtech, Stockholm, Sweden) in triplicate. Concanavalin A (ConA) was used as positive control. After 20 hours of incubation, biotinylated anti-mouse IFNγ mAb (R4-6A2; Mabtech), followed by ABC peroxidase (Vector Laboratories, Burlingame, Calif., USA) and then 3-amino-9-ethylcarbazole (Sigma-Aldrich, St. Louis, Mo., USA) were added into the wells. Responses are expressed as number of IFNγ spot-forming cells (SFCs) per 1×10⁶ CD8⁺ T cells and were considered positive if the magnitude of response was >20 SFCs, and had a stimulation index (SI; ratio of test SFCs to control SFCs) of >2. A peptide inducing a magnitude of >500 SFCs/10⁶ CD8⁺ T cells was considered as an immunodominant peptide.

4.8 ICS Assay

Spleens were harvested from virus-infected, mock-immunized, or peptide-immunized mice. 1×10⁶ splenocytes were plated in each well of 96-well U-bottom plates and stimulated with individual peptide (10 μg crude peptide or 1 μg pure peptide per well) for 6 hours. Five hours before the end of incubation, Brefeldin A (GolgiPlug; BD Biosciences) and PE-conjugated anti CD107a mAb (clone 1D4B, eBioscience) were added to the cells. Splenocytes stimulated with PMA-ionomycin were used as the positive control, while cells without any stimulation were the negative control. After incubation, cells were first stained with PERCPCY™ 5.5-conjugated anti-CD3 mAb (Clone 145-2C11, TONBO), PE-CY7™-conjugated anti-CD8 mAb (clone 53-67, BD Biosciences), EFLUOR™ 450-conjugated anti-CD44 mAb (clone IM7, eBioscience), and APC eFluor 780-conjugated anti-CD62L mAb (clone Mel-14, eBioscience). Cells were then fixed and permeabilized using CYTOFIX/CYTOPERM™ solution (BD Biosciences), followed by staining with FITC-conjugated anti-IFNγ mAb (clone XMG 1.2, TONBO) and APC-conjugated anti-TNFα mAb (clone MP6-XT22, eBioscience). Samples were run using an LSR™ II (BD Biosciences) and analyzed using FLOWJO™ software X 10.0.7 (Tree Star, Ashland, Oreg.).

4.9 Statistical Analyses

All data were analyzed with PRISM™ software version 6.0 (GraphPad Software, Inc., San Diego, Calif.) and expressed as mean±SEM. Grubbs' test was performed to determine whether one of the values is a significant outlier from the rest. Statistical significance was determined using the non-parametric Mann-Whitney test to compare two groups. P<0.05 was considered as significant.

5. Results 5.1 Identification of HLA-B*0702- and HLA-A*0101-Restricted ZIKV-Derived Epitopes Previously generated in vivo models of DENV infection in HLA transgenic Ifnar mice. Ifnar⁻/⁻ mice were used instead of wild-type mice, because DENV cannot block type I IFN signaling and replicate in murine cells. The HLA transgenic Ifnar⁻/⁻ mouse models of DENV infection have been validated by several observations:

(i) The epitopes identified in mice were also recognized by peripheral blood mononuclear cells (PBMC) from DENV-exposed humans[22];

(ii) A dominance of HLA B*0702-restricted response was observed in both mice and humans;

(iii) CD8⁺ T cell response targets both structural and nonstructural (NS) proteins in DENV3 but predominantly NS proteins in the other three DENV serotypes in both mice and humans;

(iv) CD8⁺ T cell responses were broad (targeting both structural and nonstructural (NS) proteins) following primary and homotypic secondary DENV infection in both mice and humans, whereas CD8⁺ T cell responses following heterotypic secondary infection in mice[23] and natural reinfections in humans focused towards the conserved NS proteins. Similar to DENV, ZIKV cannot evade type I IFN-mediated immunity.

In view of such validation, the Ifnar1-HLA-B*0702 and HLA-A*0101 transgenic mice were, therefore, used to identify ZIKV-derived HLA-restricted epitopes.

Figure 9:
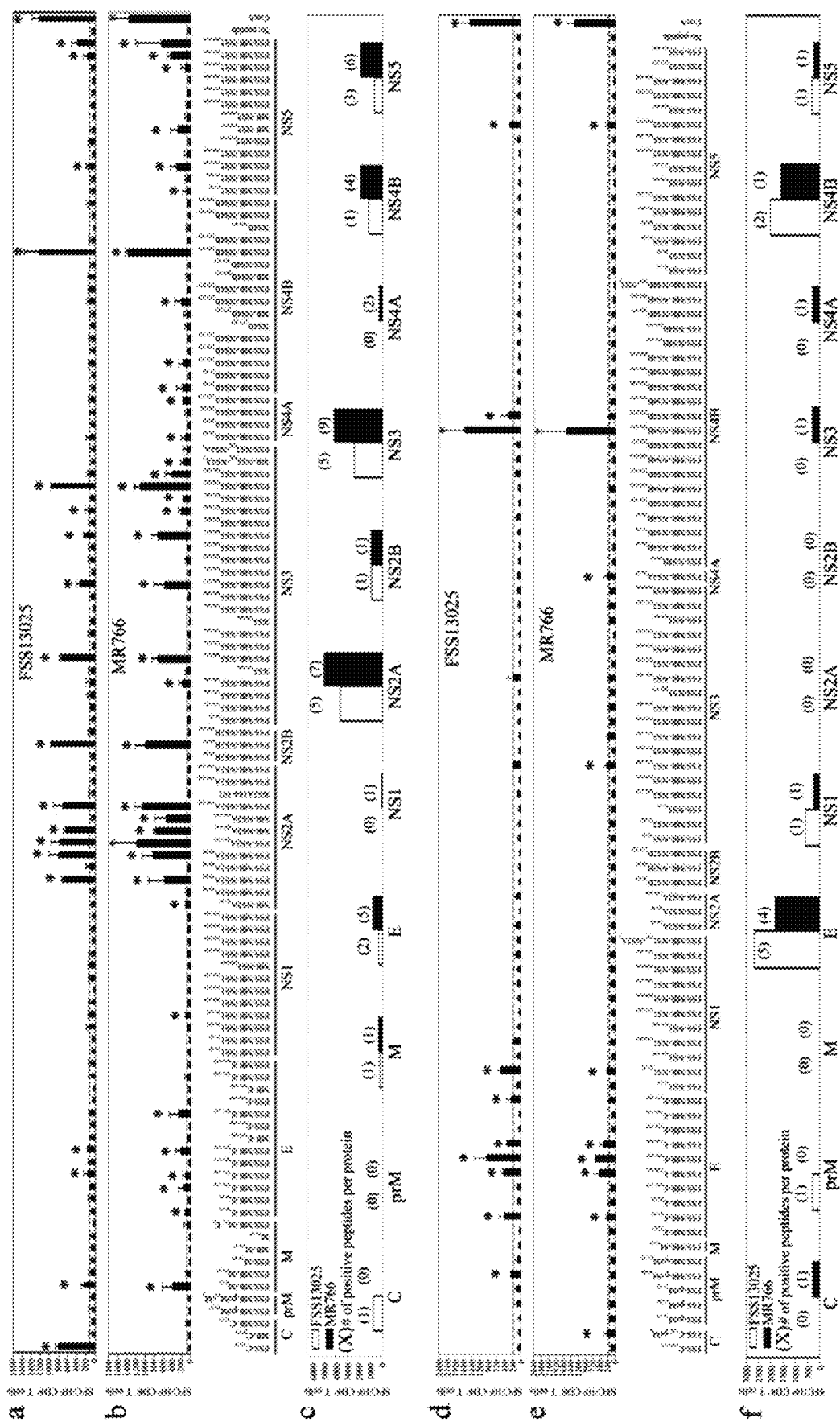
FIG. 9: illustrates a non-limiting screening of ZIKV-derived HLA-B*0702 and HLA-A*0101-restricted epitope candidates in Ifnar$^{-/-}$ HLA transgenic mice in accordance with an embodiment of the present disclosure.

The following results are with respect to FIG. 9, where IFNγ ELISPOT was performed using CD8+ T cells isolated from Ifnar⁻/⁻ HLA-B*0702 transgenic mice (a and b) and Ifnar⁻/⁻ HLA-A*0101 transgenic mice (d and e) 7 days after retro-orbital (R.O.) infection with 1×10² FFU of ZIKV strain FSS13025 or MR766. Two independent experiments performed in triplicate were averaged and the error bars represent the SEM. The data are expressed as the mean number of spot forming cells (SFC) per 10⁶ CD8⁺ T cells. The criteria for positivity were net SFC per 10⁶ cells of >20, and a stimulation index of >2.0 when compared with the negative control. Dotted lines represent the cutoff value. * Indicates a positive response. All positive peptides were grouped according the corresponding ZIKV protein (c and f); white and black bars are the total IFNγ response of all identified positive peptides from an indicated protein; numbers in parentheses are the number of positive peptides in this protein. ConA denotes Concanavalin A.

One hundred seven HLA-B*0702-binding epitope candidates (8-, 9-, 10-, and 11-mers), representing the top 2% of candidates predicted by the Immune Epitope Database and Analysis Resource (IEDAR), were chosen for synthesis. The numbers of peptides in C, prM, M, E, NS1, NS2A, NS2B, NS3, NS4A, NS4B, and NS5 were 3, 2, 6, 13, 12, 12, 3, 23, 4, 16, 13, respectively. Seven days after infection of Ifnar⁻/⁻ HLA-B*0702 transgenic mice with ZIKV strain FSS13025 or MR766, CD8⁺ T cells were isolated from splenocytes and screened by IFNγ ELISPOT assay. ZIKV MR766 infection induced a stronger and broader CD8⁺ T cell response than ZIKV FSS13025 in Ifnar⁻/⁻ HLA-B*0702 transgenic mice (FIGS. 9A and 9C). The frequencies of peptide-specific IFNγ-producing CD8⁺ T cells in mice infected with ZIKV FSS13025 and ZIKV MR766 ranged from 140-1223 SFC/10⁶ CD8+ T cells and 98-1362 SFC/10⁶ CD8⁺ T cells, respectively. Table 2 (see next page) shows the key characteristics of positive peptides. A total of 19 and 36 epitopes were derived from ZIKV FSS13025 and ZIKV MR766, respectively. The two ZIKV strains shared 18 epitopes, including the following 9 immunodominant peptides: FSS/MR-NS2A$_{75-84}$ (SEQ ID NO: 39), FSS/MR-NS2A$_{89-99}$ (SEQ ID NO: 40), FSS-NS2A133-141 (SEQ ID NO: 41), MR-NS2A133-141 (SEQ ID NO: 42), FSS/MR-NS2A$_{148-155}$ (SEQ ID NO: 44), FSS/MR-NS2B$_{68-75}$ (SEQ ID NO: 45), FSS/MR-NS3$_{206-215}$ (SEQ ID NO: 47), FSS/MR-NS3$_{574-582}$ (SEQ ID NO: 52), and FSS/MR-NS4B$_{426-435}$ (SEQ ID NO: 60) (Table 2). The FSS-C25-35 (SEQ ID NO: 30) epitope is present in ZIKV FSS13025 but not ZIKV MR766. The NS3 protein contained the largest number of epitopes and NS2A induced the highest magnitude of CD8⁺ T cell responses. The majority of immunodominant epitopes was located in NS2A, but the most immunodominant epitope, FSS/MR-NS4B$_{426-435}$ (SEQ ID NO: 60), was contained in NS4B (FIGS. 9A-9C).

TABLE 2

| SEQ ID NO | Peptides[a] | Sequences | HLA | IEDB prediction Percentile rank | Conservation[b] FSS13025 | Conservation[b] MR766 | Conservation[b] SPH2015 | SFC/$10^6$ $CD8^+$ T cells (% IFNγ+ $CD8^+$ T cells)[c] FSS13025 | SFC/$10^6$ $CD8^+$ T cells (% IFNγ+ $CD8^+$ T cells)[c] MR766 | SFC/$10^6$ $CD8^+$ T cells (% IFNγ+ $CD8^+$ T cells)[c] S221 |
|---|---|---|---|---|---|---|---|---|---|---|
| 30 | FSS-$C_{25-35}$ | SPFGGLKRLPA | B*0702 | 0.75 | Y | Y | | 802 (0.79%) | | |
| 31 | FSS/MR-$M_{4-12}$ | LPSHSTRKL | B*0702 | 0.4 | Y | Y | Y | 235 | 398 (0.28%) | |
| 32 | FSS/MR-$E_{38-45}$ | KPTVDIEL | B*0702 | 1.45 | Y | Y | Y | | 103 | 51 |
| 33 | FSS/MR-$E_{170-178}$ | TPNSPRAEA | B*0702 | 0.8 | Y | Y | Y | | 155 | |
| 34 | FSS/MR-$E_{173-180}$ | SPRAEATL | B*0702 | 0.25 | Y | Y | Y | 167 | 108 | |
| 35 | FSS/MR-$E_{233-242}$ | TPHWNNKEAL | B*0702 | 0.35 | Y | Y | Y | 158 | 218 (0.3%) | |
| 36 | FSS-$E_{337-347}$ | GPCKVPAQMAV | B*0702 | 1.7 | Y | | Y | | 271 | |
| 37 | FSS/MR-$NS1_{99-107}$ | GPQRLPVPV | B*0702 | 1.4 | Y | Y | Y | | 103 | |
| 38 | MR-$NS2A_{31-40}$ | VVMILGGFSM | B*0702 | 1.6 | | Y | | | 106 (0.37%) | 51 |
| 39 | FSS/MR-$NS2A_{75-84}$ | RPALLVSFIF | B*0702 | 1.6 | Y | Y | Y | 713 (0.53%) | 582 (2.04%) | 88 (0.58%) |
| 40 | FSS/MR-$NS2A_{89-99}$ | TPRESMLLAL | B*0702 | 0.15 | Y | Y | Y | 807 (0.56%) | 823 (0.95%) | 55 |
| 41 | FSS-$NS2A_{133-141}$ | VPRTDNITL | B*0702 | 0.3 | Y | | Y | 786 (0.9%) | 1182 (1.07%) | |
| 42 | MR-$NS2A_{133-141}$ | VPRTDNIAL | B*0702 | 0.2 | | Y | | 648 (0.54%) | 776 (1.39%) | |
| 43 | MR-$NS2A_{141-150}$ | LPILAALTPL | B*0702 | 0.2 | | Y | | | 540 (0.28%) | |
| 44 | FSS/MR-$NS2A_{148-155}$ | TPLARGTL | B*0702 | 0.45 | Y | Y | Y | 706 (0.28%) | 1055 (0.87%) | |
| 45 | FSS/MR-$NS2B_{68-75}$ | SPRLDVAL | B*0702 | 0.6 | Y | Y | Y | 963 (0.56%) | 993 (0.77%) | |
| 46 | FSS/MR-$NS3_{188-196}$ | LPEIVREAI | B*0702 | 1.2 | Y | Y | Y | | 179 (0.23%) | 63 |

TABLE 2-continued

| SEQ ID NO | Peptides[a] | Sequences | HLA | IEDB prediction Percentile rank | Conservation[b] FSS13025 | MR766 | SPH2015 | SFC/10$^6$ CD8$^+$ T cells (% IFNγ+ CD8$^+$ T cells)[c] FSS13025 | MR766 | S221 |
|---|---|---|---|---|---|---|---|---|---|---|
| 47 | FSS/MR-NS3$_{206-215}$ | APTRVVAAEM | B*0702 | 0.2 | Y | Y | Y | 749 (0.3%) | 724 (0.53%) | 606 (0.33%) |
| 48 | FSS/MR-NS3$_{309-317}$ | FPDSNSPINI | B*0702 | 1.2 | Y | Y | Y | 335 | 565 (0.49%) | |
| 49 | FSS/MR-NS3$_{405-413}$ | RVIDSRRCL | B*0702 | 1.1 | Y | Y | Y | 236 (0.23%) | 718 (0.4%) | |
| 50 | FSS/MR-NS3$_{427-436}$ | GPMPVTHASA | B*0702 | 0.25 | Y | Y | Y | 140 | 204 | 136 |
| 51 | FSS/MR-NS3$_{492-501}$ | RPEADKVAAI | B*0702 | 0.55 | Y | Y | Y | | 157 | |
| 52 | FSS/MR-NS3$_{574-582}$ | KPRWMDARV | B*0702 | 0.3 | Y | Y | Y | 969 (0.79%) | 1095 (1.9%) | 350 (0.63%) |
| 53 | FSS/MR-NS3$_{581-589}$ | RVCSDHAAL | B*0702 | 1.3 | Y | Y | Y | | 411 (0.31%) | 44 |
| 54 | MR-NS3$_{596}$_NS4A$_1$ | AAGKRGAAL | B*0702 | 0.6 | | Y | | | 148 | |
| 55 | FSS/MR-NS4A$_{36-45}$ | RPYKAAAAQL | B*0702 | 0.25 | Y | Y | Y | | 120 | |
| 56 | FSS/MR-NS4A$_{125-133}$ | SPQDNQMAI | B*0702 | 0.5 | Y | Y | Y | | 159 | |
| 57 | FSS/MR-NS4B$_{35-44}$ | RPASAWAIYA | B*0702 | 0.35 | Y | Y | Y | | 180 (0.49%) | |
| 58 | FSS/MR-NS4B$_{105-115}$ | TPLTLIVAIIL | B*0702 | 1.55 | Y | Y | Y | | 163 (0.4%) | |
| 59 | FSS/MR-NS4B$_{210-220}$ | SPNKYVVNSSTA | B*0702 | 0.45 | Y | Y | Y | | 195 | 49 |
| 60 | FSS/MR-NS4B$_{426-435}$ | RPGAPCIKVL | B*0702 | 0.3 | Y | Y | Y | 1223 (2.28%) | 1362 (2.36%) | 90 (0.3%) |
| 61 | FSS/MR-NS5$_{61-70}$ | APTQSASSL | B*0702 | 0.3 | Y | Y | Y | | 98 | 47 |
| 62 | FSS/MR-NS5$_{140-149}$ | RPRVCTKEEF | B*0702 | 0.1 | Y | Y | Y | 162 | 311 (0.24%) | 0.28% |
| 63 | MR-NS5$_{332-341}$ | RPAEGGKTVM | B*0702 | 0.1 | | Y | | | 277 (0.35%) | |
| 64 | FSS/MR-NS5$_{539-546}$ | VPTGRTTVV | B*0702 | 0.4 | Y | Y | Y | | 121 (0.25%) | 54 (0.18%) |

TABLE 2-continued

| SEQ ID NO | Peptides[a] | Sequences | HLA | IEDB prediction Percentile rank | Conservation[b] FSS13025 | MR766 | SPH2015 | SFC/$10^6$ $CD8^+$ T cells (% IFNγ+ $CD8^+$ T cells)[c] FSS13025 | MR766 | S221 |
|---|---|---|---|---|---|---|---|---|---|---|
| 65 | FSS/MR-$NS5_{587-596}$ | IPYLGKREDL | B*0702 | 0.95 | Y | Y | Y | 178 | 438 (0.26%) | |
| 66 | FSS/MR-$NS5_{605-614}$ | RPRTTVVAENI | B*0702 | 0.25 | Y | Y | Y | 383 (0.22%) | 641 (0.55%) | |
| 67 | FSS-$C_{125}$-prM8 | VTRRGNAYY | A*0101 | 0.7 | Y | | | | 266 | |
| 68 | FSS/MR-$prM_{40-48}$ | HMCDATMSY | A*0101 | 1 | Y | Y | Y | 288 | | |
| 69 | FSS/MR-$E_{81-90}$ | YLDKQSDTQY | A*0101 | 0.25 | Y | Y | Y | 495 | 258 | |
| 70 | FSS/MR-$E_{159-167}$ | ETDENRAKV | A*0101 | 1.3 | Y | Y | Y | 512 | 516 | |
| 71 | FSS/MR-$E_{195-203}$ | GLDFSDLYY | A*0101 | 0.2 | Y | Y | Y | 993 | 647 | |
| 72 | FSS/MR-$E_{198-206}$ | FSDLYYLTM | A*0101 | 0.25 | Y | Y | Y | 398 | 388 | |
| 73 | FSS/MR-$E_{377-386}$ | ELDPPFGDSY | A*0101 | 0.25 | Y | Y | Y | 286 | | |
| 74 | FSS/MR-$NS_{123-31}$ | DVEAWRDRY | A*0101 | 0.95 | Y | Y | Y | 583 | 260 | |
| 75 | FSS/MR-$NS3_{272-280}$ | FTDPSSIAA | A*0101 | 0.25 | Y | Y | Y | | 286 | |
| 76 | FSS/MR-$NS4A_{14-22}$ | MTERFQEAI | A*0101 | 1.15 | Y | Y | Y | | 266 | |
| 77 | FSS/MR-$NS4B_{231-239}$ | YLAGASLIY | A*0101 | 0.55 | Y | Y | Y | 1646 (0.60%) | 1574 (1.38%) | |
| 78 | FSS/MR-$NS4B_{270-278}$ | MSALEFYSY | A*0101 | 0.3 | Y | Y | Y | 378 | | |
| 79 | FSS/MR-$NS5_{509-517}$ | YAQMWQLLY | A*0101 | 0.2 | Y | Y | Y | 313 | 225 | |

[a]The position of peptides was determined according to the amino acid sequence of ZIKV FSS13025. FSS and MR are abbreviations for FSS13025 and MR766, respectively;
[b]"Y" means having the same sequence;
[c]Peptides are positive based on IFNγ ELISPOT count and/or IFNγ ICS percentage in parenthesis.

Ninety HLA-A*0101-binding epitope candidates were also chosen for synthesis. The numbers of peptides in C, prM, M, E, NS1, NS2A, NS2B, NS3, NS4A, NS4B, and NS5 were 2, 5, 1, 10, 11, 3, 3, 18, 1, 20, 16, respectively. In contrast to HLA B*0702 mice, FSS13026 induced a stronger CD8$^+$ T cell response than MR766 in Ifnar$^{-/-}$ HLA-A*0101 transgenic mice (FIG. 9D-9F). As shown in Table 2, the frequencies of peptide-specific IFNγ-producing CD8$^+$ T cells in mice infected with ZIKV FSS13025 and ZIKV MR766 ranged from 286-1646 SFC/10$^6$ CD8$^+$ T cells and 225-1574 SFC/10$^6$ CD8$^+$ T cells, respectively. Thirteen peptides were identified as positive in total. The two ZIKV strains shared 7 positive peptides, including 4 immunodominant peptides: FSS/MR-E$_{159-167}$ (SEQ ID NO: 70), FSS/MR-E$_{195-203}$ (SEQ ID NO: 71), FSS/MR-NS1$_{23-31}$ (SEQ ID NO: 74), FSS/MR-NS4B$_{231-239}$ (SEQ ID NO: 77) (Table 2). E protein contained the largest number of epitopes and induced the highest magnitude of CD8$^+$ T cell response. The most immunodominant epitope, FSS/MR-NS4B$_{231-239}$ (SEQ ID NO: 77), was contained in NS4B (FIG. 9D-9F).

5.2 Epitope Confirmation and Characterization of Cytokine Secretion

To further characterize the epitopes identified via IFNγELISPOT analysis, splenocytes were isolated from ZIKV-infected Ifnar$^{-/-}$ HLA-B*0702 transgenic mice, stimulated with each of 37 positive peptides, and the frequency of IFNγ- and/or TNFα-producing CD3$^+$CD8$^+$ T cells was determined by ICS.

Figure 10A:
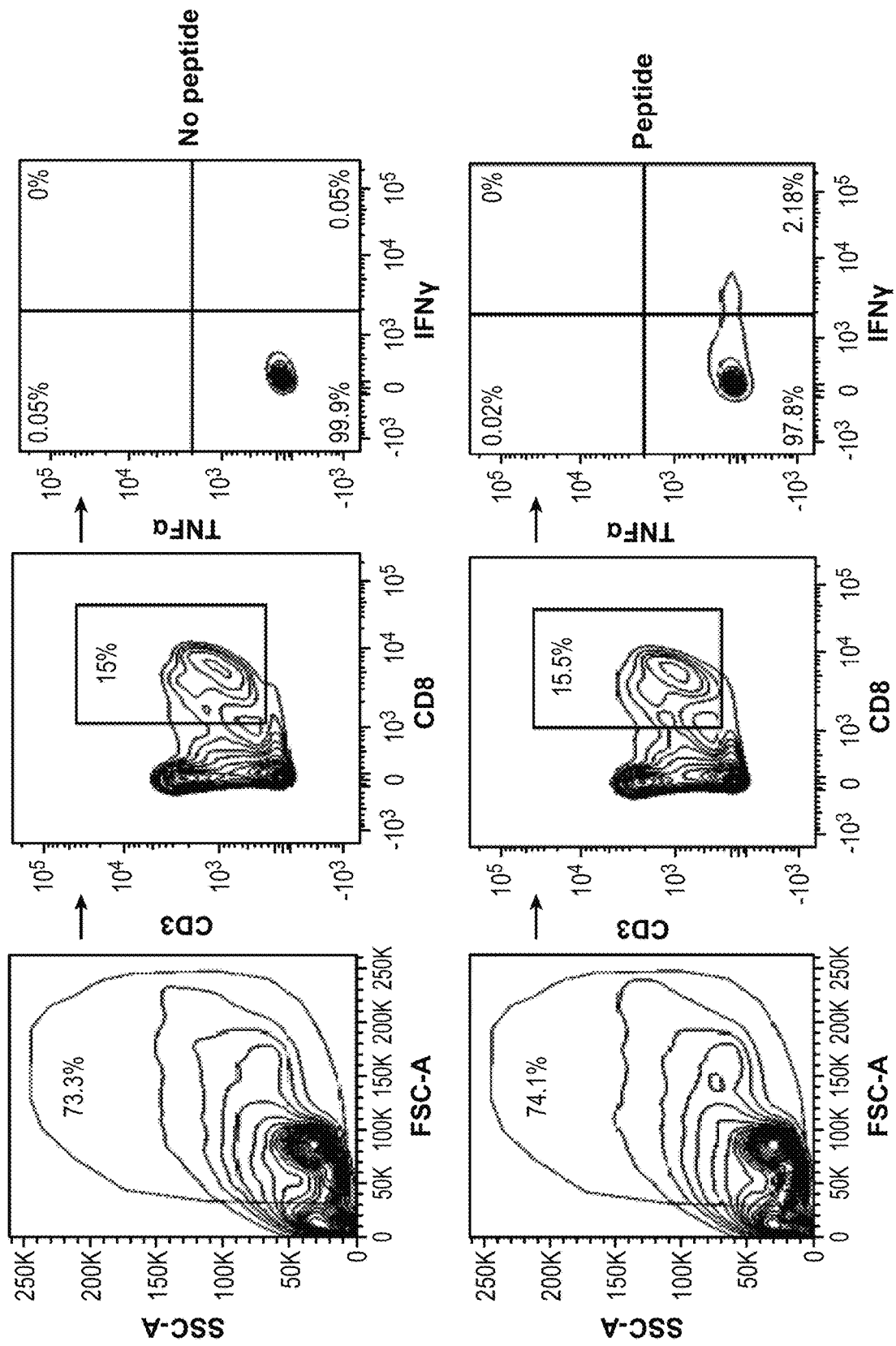

The following results are with respect to FIG. 10B to FIG. 10E, where splenocytes isolated from Ifnar$^{-/-}$ HLA-B*0702 transgenic mice (FIG. 10B, n=7 mice; c, n=6 mice) and Ifnar$^{-/-}$ HLA-A*0101 transgenic mice (FIG. 10D, n=4 mice; FIG. 10E, n=6 mice) 7 days after R.O. infection with 1×10$^2$ FFU of ZIKV strain FSS13025 or MR766 were stimulated with each of the 37 positive HLA-B*0702-binding peptides or 13 positive HLA-A*0101-binding peptides identified via IFNγ ELISPOT and then ICS assay was performed. A representative figure shows the CD3$^+$CD8$^+$ T cell gate and the percentages of IFNγ$^+$ and/or TNFα$^+$ cells (FIG. 10A). Data represent the average of two independent experiments and are expressed as mean±SEM. *, P<0.05; **, P<0.01; Two-tailed Mann-Whitney test. P/I denotes PMA/ionomycin.

The results obtained are as follows:

The percentages of IFNγ-producing CD8$^+$ T cells ranged from 0.22% to 2.28% and 0.23% to 2.36% of total CD3$^+$CD8$^+$ T cells in ZIKV FSS13025-infected mice and ZIKV MR766-infected mice, respectively (Table 2). Twenty-five of the 37 IFNγ ELISPOT-positive peptides were confirmed by IFNγ ICS. Some of the FSS/MR-NS2A$_{89-99}$ (SEQ ID NO: 40) and FSS/MR-NS4B$_{426-435}$ (SEQ ID NO: 60) peptide-stimulated CD8$^+$ T cells simultaneously secreted both IFNγ and TNFα in mice infected with either ZIKV FSS13025 or ZIKV MR766. In ZIKV FSS13025-infected mice, FSS-C$_{25-35}$ (SEQ ID NO: 30) also stimulated production of both IFNγ and TNFα(FIG. 10B). In ZIKV MR766-infected mice, four additional peptides (FSS/MR-NS2A$_{75-84}$ (SEQ ID NO: 39), FSS/MR-NS2A$_{148-155}$ (SEQ ID NO: 44), FSS/MR-NS2B$_{68-75}$ (SEQ ID NO: 45), and FSS/MR-NS3$_{574-582}$ (SEQ ID NO: 47)) stimulated simultaneous production of IFNγ and TNFα (FIG. 10C). Collectively, these results define the specificity of the anti-ZIKV CD8$^+$ T cell response restricted by HLA-B*0702 in this mouse model. The epitope map shows that NS proteins NS2A, NS3, NS4B, and NS5 are the major targets of the HLA-B*0702-restricted CD8$^+$ T cell response to both African and Asian lineage ZIKV, and that the African lineage ZIKV MR766 contained more HLA-B*0702-restricted CD8$^+$ T cell epitopes than the Asian lineage ZIKV FSS13025. However, among 13 IFNγ ELISPOT-positive HLA-A*0101-binding peptides, only FSS/MR-NS4B$_{231-239}$ (SEQ ID NO: 77) was confirmed by IFNγ ICS in mice infected with either FSS13025 or MR766 (FIGS. 10E and 10E). The percentages of IFNγ-producing CD8$^+$ T cells in ZIKV FSS13025- and ZIKV MR766-infected Ifnar$^{-/-}$ HLA-A*0101 transgenic mice were 0.6% and 1.38%, respectively (Table 2).

5.3 Cross-Reactivity of ZIKV Epitopes with DENV

To evaluate potential cross-reactivity of the HLA-B*0702-restricted ZIKV-derived epitopes with DENV, CD8$^+$ T cells from spleens of Ifnar$^{-/-}$ HLA-B*0702 transgenic mice infected with DENV2 strain 5221 were stimulated by each of 37 ZIKV-derived epitopes identified by IFNγ ELISPOT analysis.

Figure 14A:
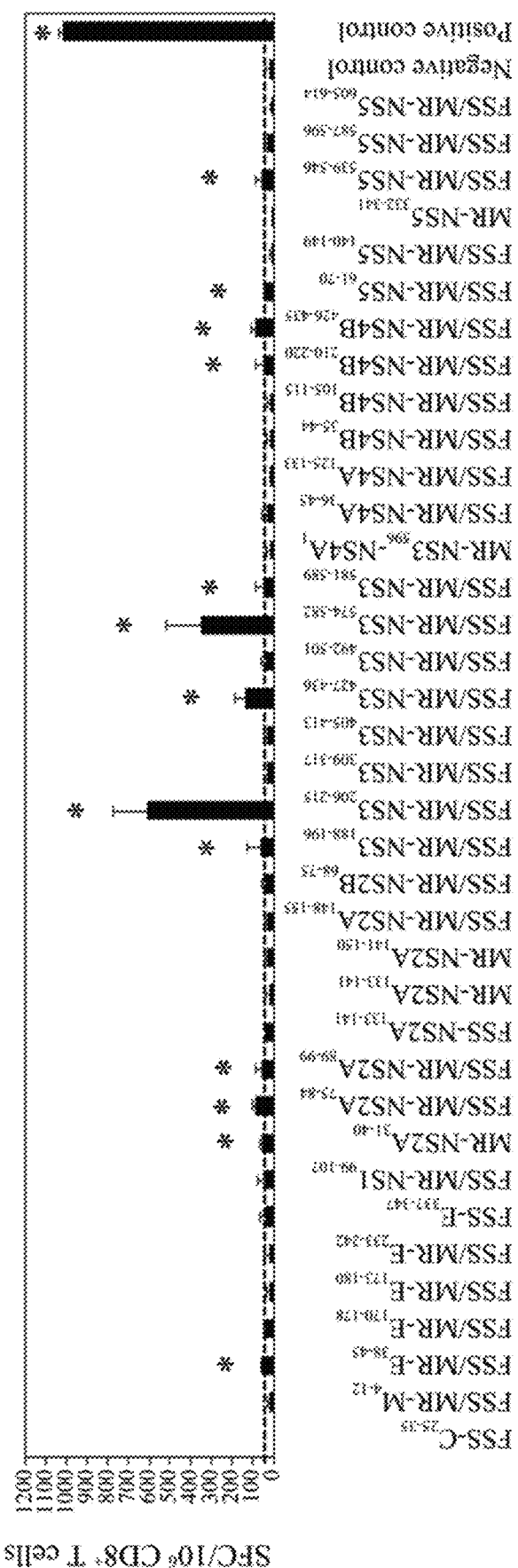
FIGS. 14A-14B: shows graphs that illustrate non-limiting results that demonstrate the identification of ZIKV epitopes that are cross-reactive with DENV in accordance with an embodiment of the present disclosure.
Figure 14B:
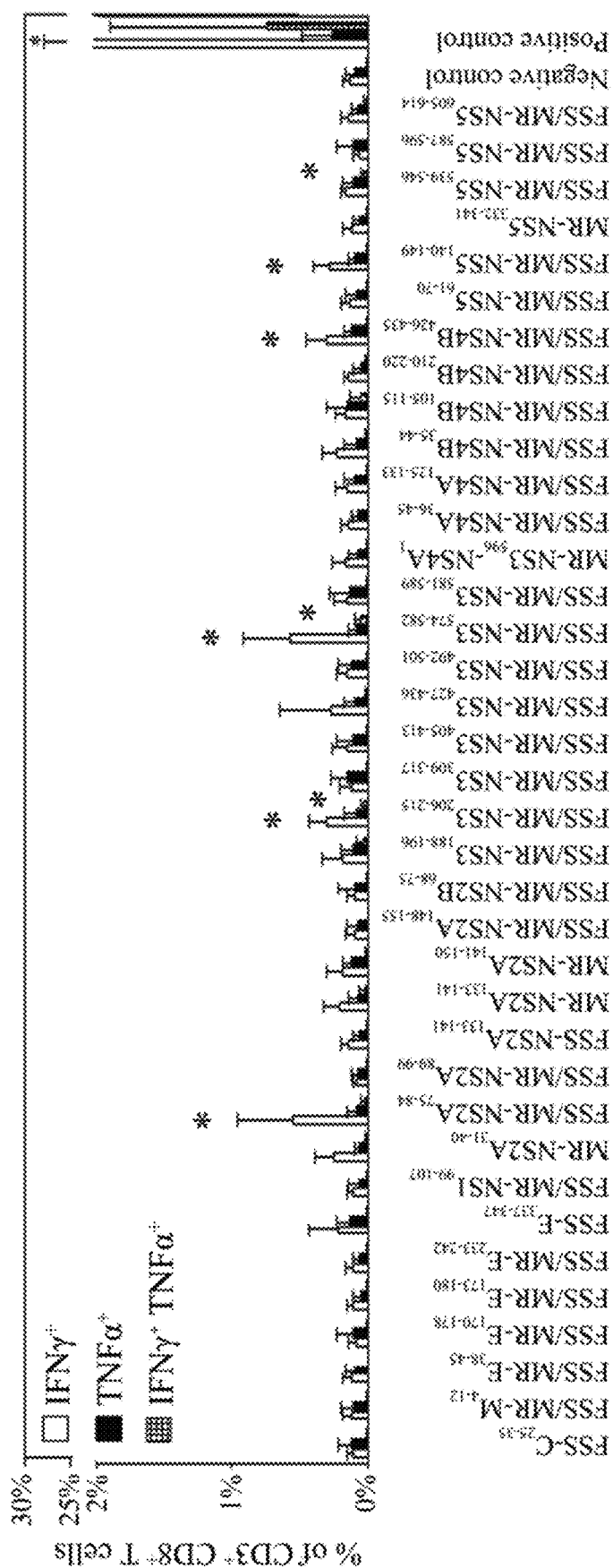

The following results are with respect to FIG. 14A and FIG. 14B, where Ifnar$^{-/-}$ HLA-B*0702 transgenic mice were infected R.O. with 2×10$^4$ FFU of DENV2 strain S221 for 7 days. CD8$^+$ T cells isolated from splenocytes were stimulated with each of the 37 ZIKV epitopes identified via IFNγELISPOT to perform (FIG. 14A) IFNγELISPOT and (FIG. 14B) ICS assay. Data represent the average of two independent IFNγELISPOT experiments and two independent ICS experiments (n=7 mice) and are expressed as mean±SEM. Dotted line corresponds to the cutoff value. *, P<0.05.

The results obtained are as follows:

Cross-reactivity was determined using both IFNγ ELISPOT and IFNγ ICS assays (FIG. 14A and FIG. 14B). Thirteen peptides were positive, as determined via IFNγELISPOT (FIG. 14A), and the frequency of epitope specific IFNγ$^+$CD8$^+$ T cells ranged from 44 to 606 SFC/10$^6$ CD8$^+$ T cells (Table 2). Six peptides were positive based on IFNγICS assay, and the percentages of IFNγ-producing CD8$^+$ T cells ranged from 0.18% to 0.63% (FIG. 14B and Table 2). Of these 6 IFNγ ICS-positive peptides, 5 epitopes (FSS/MR-NS2A$_{75-84}$ (SEQ ID NO: 39),FSS/MR-NS3$_{206-215}$ (SEQ ID NO: 47), FSS/MR-NS3$_{574-582}$ (SEQ ID NO: 52), FSS/MR NS4B$_{426-435}$ (SEQ ID NO: 60), and FSS/MR-N55539-546 (SEQ ID NO: 64)) were positive in both IFNγ ELISPOT and IFNγICS assays (Table 2). These results thus identified at least 5 HLA-B*0702-restricted ZIKV/DENV cross-reactive epitopes with as many as 13 additional HLA B*0702-restricted epitopes possibly being cross-reactive as determined by the IFNγELISPOT assay alone. Thirteen positive HLA-A*0101-binding peptides were tested in DENV2 S221-infected Ifnar$^{-/-}$ HLA-A*0101 transgenic mice but no positive peptide was found by IFNγICS (data not shown).

5.4 Immunodominance of Cross-Reactive Memory CD8$^+$ T Cells During ZIKV Infection of DENV-Immune Mice The majority of people in the Latin American countries with recent ZIKV outbreaks have previously been exposed to DENV36. To investigate how prior exposure to DENV impacts ZIKV-specific CD8$^+$ T cell response, Ifnar$^{-/-}$ HLA-B*0702 transgenic mice were infected with DENV2 strain S221 for 4 weeks, followed by challenge of these DENV-immune mice with ZIKV FSS13025. On day 3 post-ZIKV infection (a time point that is too early for development of DENV-specific naïve CD8$^+$ T cell response in mouse models[37,38]), splenocytes from mock-infected and DENV2-immune mice were stimulated by each of 23 ZIKV epitopes that were identified by IFNγ ICS.

Figure 11A:
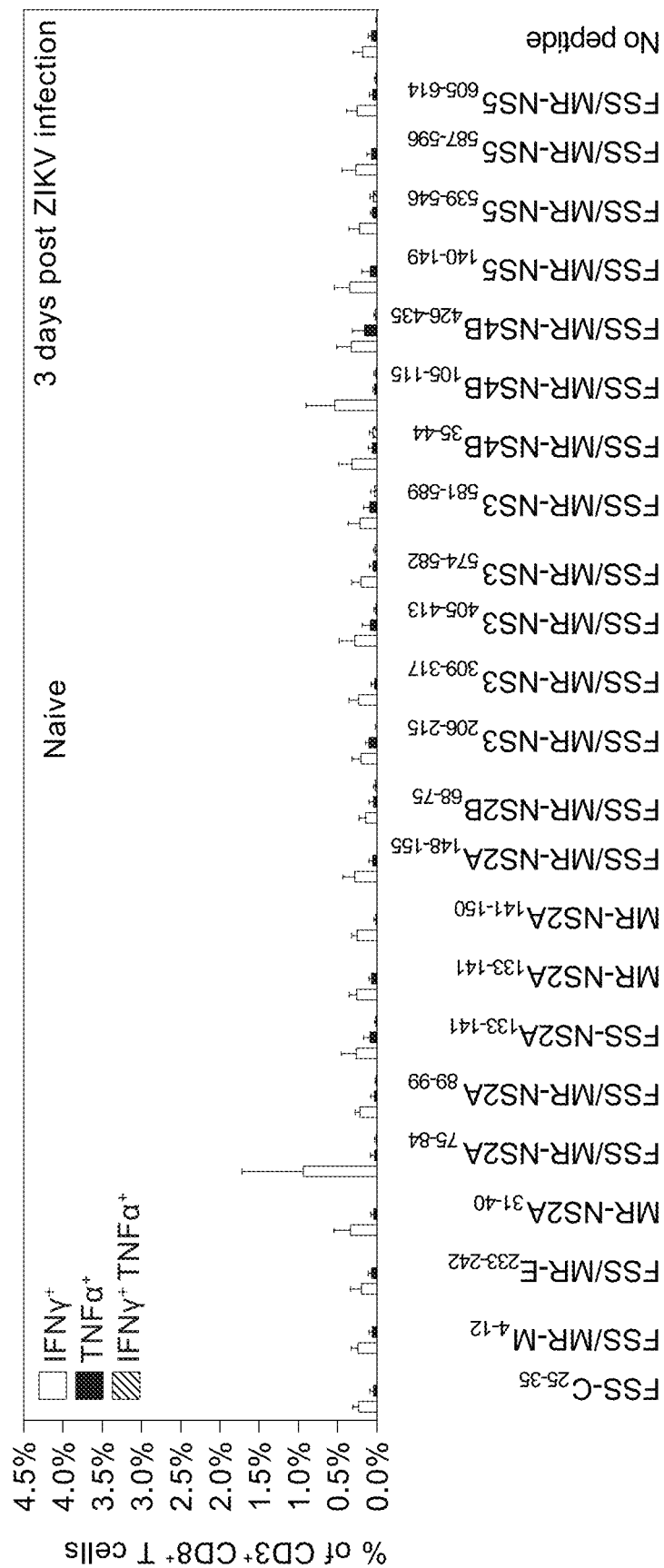
Figure 11B:
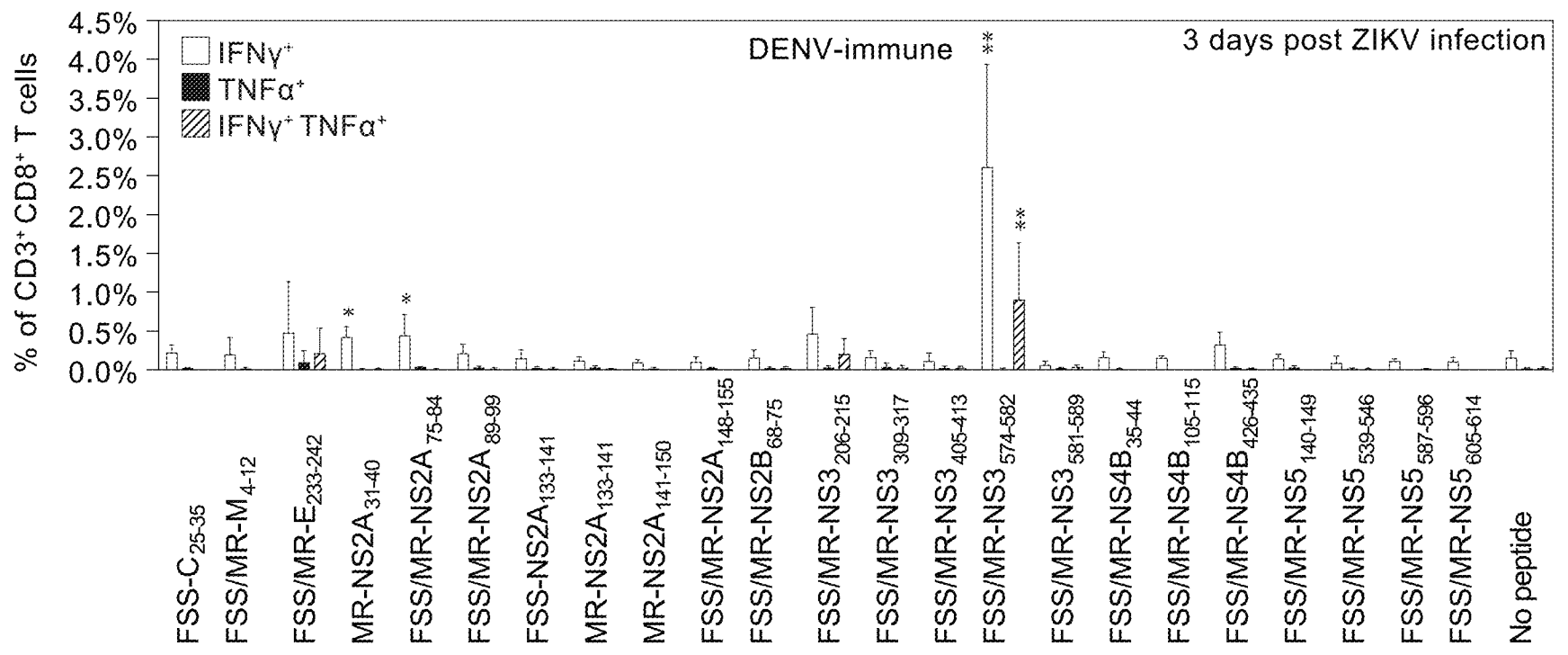
Figure 11C:
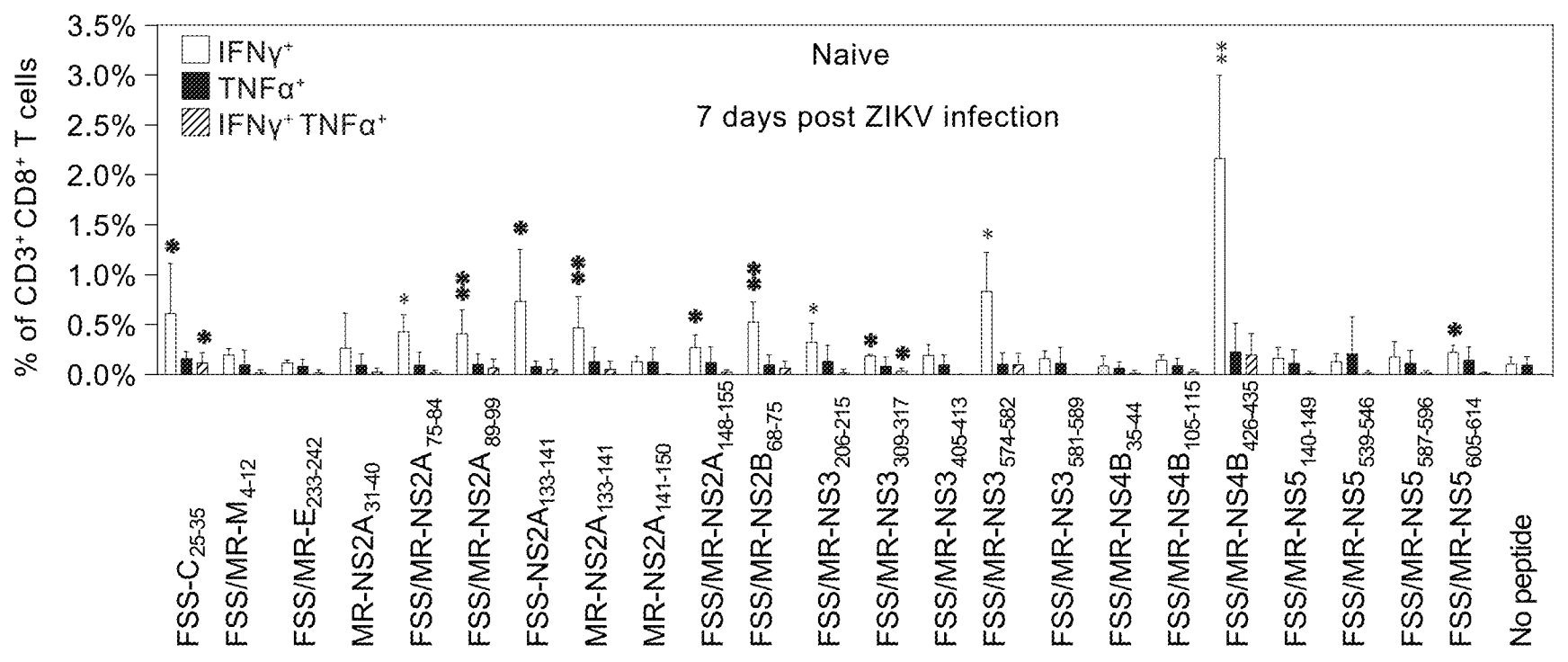
Figure 11D:
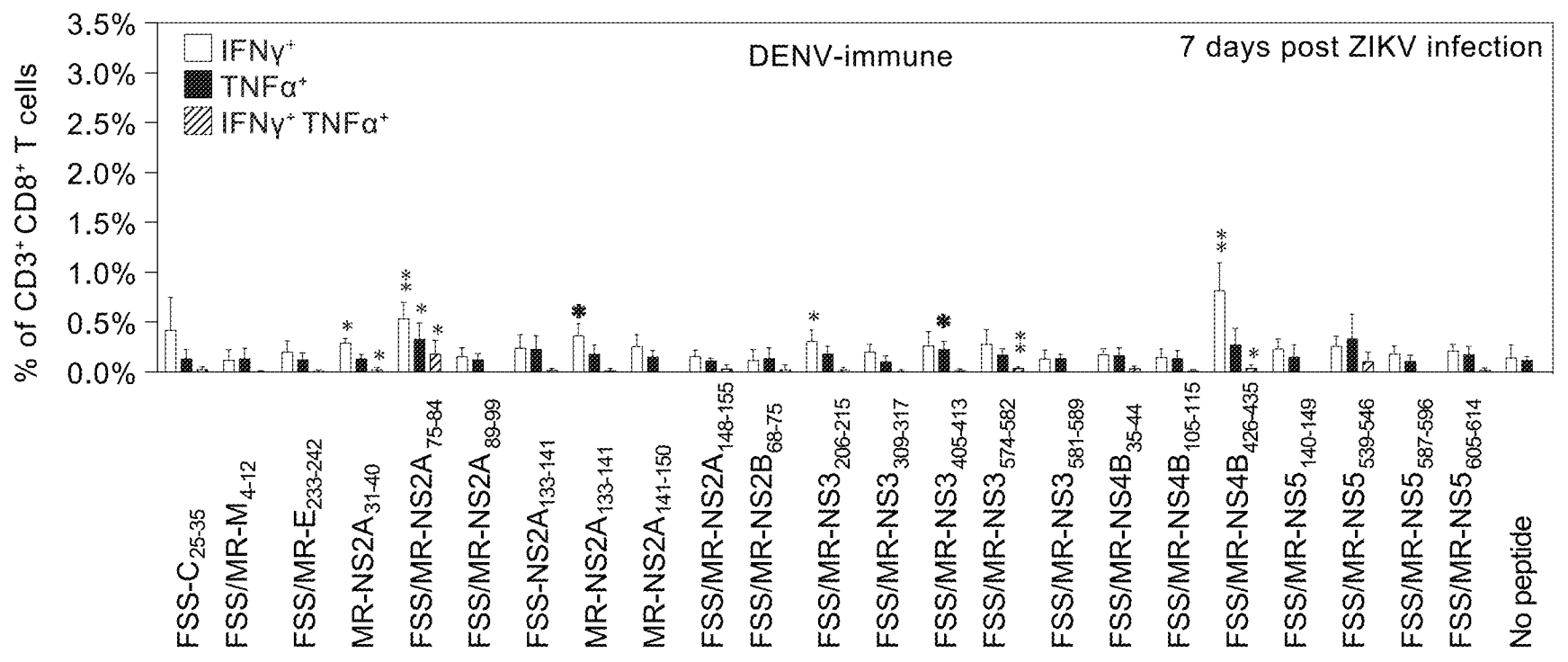
Figure 11E:
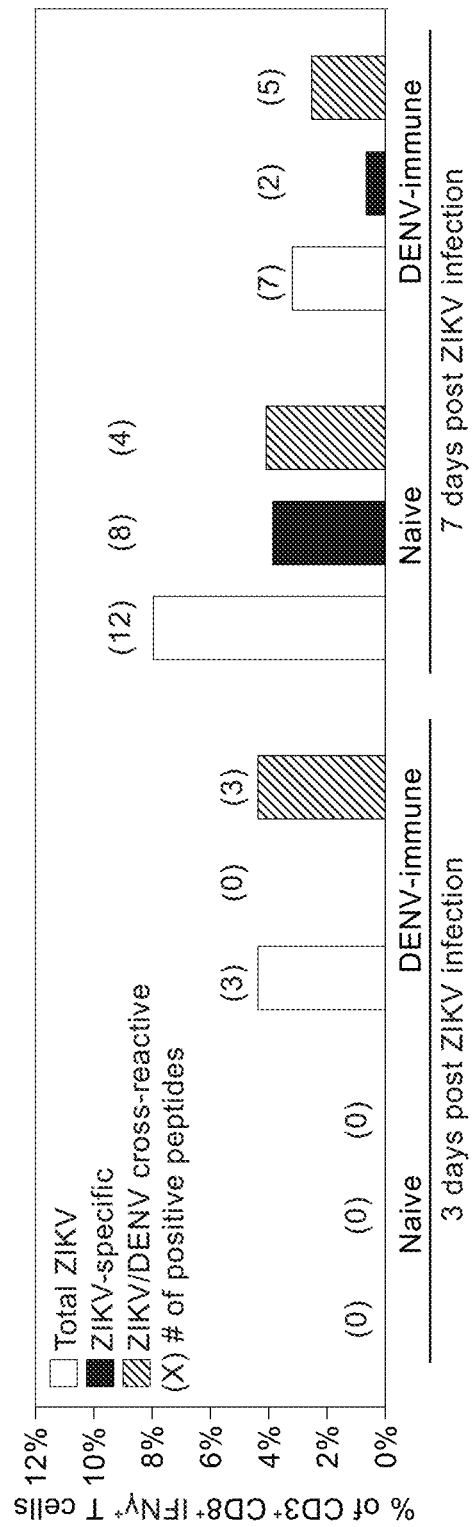

The following results are with respect to FIG. 11 to FIG. 11E, where Ifnar$^{-/-}$ HLA-B*0702 transgenic mice were inoculated I.P. with 2×10$^3$ FFU of DENV2 strain S221 for 4 weeks. Naive mice (n=5) and DENV2 strain S221-immune mice (n=5) were challenged R.O. with 1×10$^4$ FU of ZIKV FSS13025 for three days, and the percentages of peptide-specific IFNγ$^+$ and/or TNFα$^+$ CD8$^+$ T cells were detected by ICS (FIG. 11A and FIG. 11B). In addition, separate groups of naive mice (n=5) and DENV2 strain S221-immune mice (n=5) were challenged R.O. with 1×10$^4$ FFU of ZIKV FSS13025 for seven days, and the percentages of peptide-specific IFNγ$^+$ and/or TNFα$^+$ CD8$^+$ T cells were detected by ICS assay (FIG. 11C and FIG. 11D). Data were expressed as mean±SEM. *, P<0.05; **, P<0.01; Two-tailed ann-Whitney test. Black "*" indicates ZIKV-specific response while bold "*" represents ZIKV/DENV cross-reactive response. All positive peptides were grouped according the ZIKV specificity of immune response (FIG. 11E). Numbers in parentheses indicate the number of positive peptides in this group.

The results obtained are as follows:

In naive mice, no significant epitope-specific CD8$^+$ T cells were induced (FIG. 11A). In DENV2-immune mice, IFNγ-expressing CD8$^+$ T cells directed to the 3 ZIKV/DENV cross-reactive peptides (MR-NS2A31-40 (SEQ ID NO: 38), FSS/MR-NS2A$_{75-84}$ (SEQ ID NO: 39), and FSS/MR-NS3$_{574-582}$ (SEQ ID NO: 52)) were detected (FIG. 11B). The percentages of these 3 epitope-specific IFNγ-producing CD8$^+$ T cells were 0.42±0.12%, 0.44±0.24%, and 2.61±1.19%, respectively. FSS/MR-NS2A$_{75-84}$ (SEQ ID NO: 39) and FSS/MR-NS3$_{574-582}$ (SEQ ID NO: 52) specific CD8$^+$ T cells were double-positive with expression of both IFNγ and TNFα. Similar analysis on day 7 post-ZIKV infection revealed that 8 ZIKV-specific and 4 ZIKV/DENV cross-reactive CD8$^+$ T cell responses were induced in naive mice (FIG. 11C); in comparison, 2 ZIKV-specific and 5 ZIKV/DENV cross-reactive CD8$^+$ T cell responses were elicited in DENV2-immune mice (FIG. 11D). FIG. 11E summarizes the frequency and magnitude of ZIKV-specific, ZIKV/DENV cross-reactive, and total epitope-specific (both ZIKV-specific and ZIKV/DENV cross-reactive) CD8$^+$ T cell responses in naïve vs. DENV-immune mice at 3 and 7 days following ZIKV infection. The results demonstrate that, upon ZIKV challenge of DENV-immune mice, memory ZIKV/DENV cross-reactive CD8$^+$ T cells are activated and the immunodominance pattern of the CD8$^+$ T cell response to ZIKV infection is altered relative to naïve mice. The anti-ZIKV CD8$^+$ T cell response in naïve mice is broad and includes recognition of both ZIKV-specific and cross-reactive epitopes, whereas the CD8$^+$ T cell response to ZIKV infection in DENV-immune mice is directed to cross-reactive epitopes.

5.5 Protective Immunity Conferred by Immunization of Mice with ZIKV-Specific and ZIKV/DENV Cross-Reactive Peptides Based on increasing numbers of recent studies using mouse models and human donor samples that implicate a protective role for serotype-cross-reactive CD8$^+$ T cells against DENV[13,27,39,40], it was next hypothesized that ZIKV/DENV cross-reactive CD8$^+$ T cells play a protective role against ZIKV infection. To directly address the role of ZIKV epitope-specific and ZIKV/DENV cross-reactive CD8$^+$ T cells in protection against ZIKV infection, Ifnar$^{-/-}$ HLA-B*0702 transgenic mice were immunized with a cocktail of either 3 ZIKV immunodominant peptides (FSS-NS2A$_{133-141}$ (SEQ ID NO: 41), FSS/MR766-NS2B$_{68-75}$ (SEQ ID NO: 45), and FSS/MR-NS4B$_{426-435}$ (SEQ ID NO: 60)) or 4 ZIKV/DENV cross-reactive peptides (FSS/MR766-NS4B$_{426-435}$ (SEQ ID NO: 60), FSS/MR766-NS2A$_{75-84}$ (SEQ ID NO: 39), FSS/MR766-NS3$_{206-215}$ (SEQ ID NO: 47), and FSS/MR766-NS3$_{574-582}$ (SEQ ID NO: 52), followed by challenge with ZIKV FSS13025.

Figure 12A:
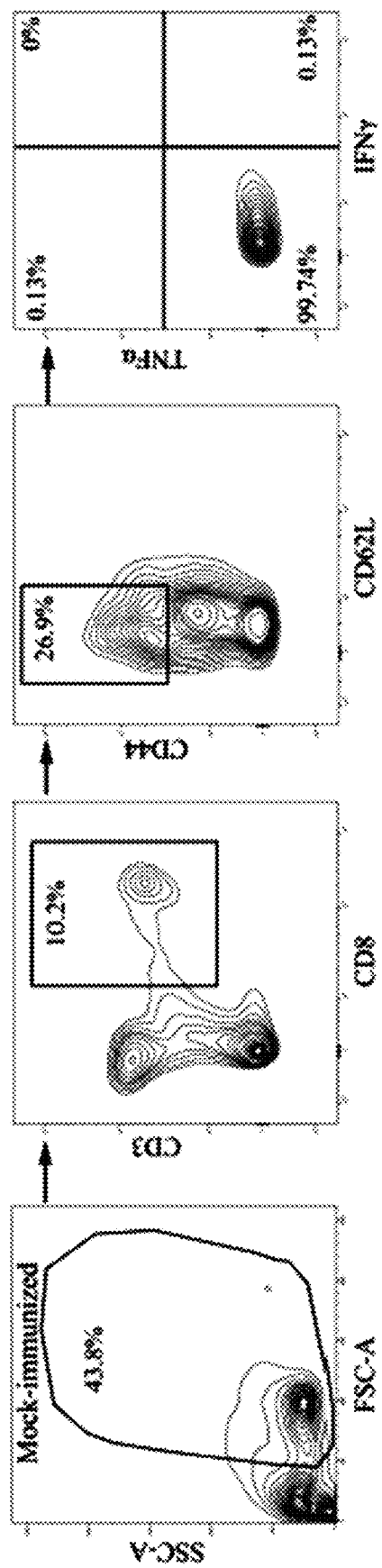
Figure 12B:
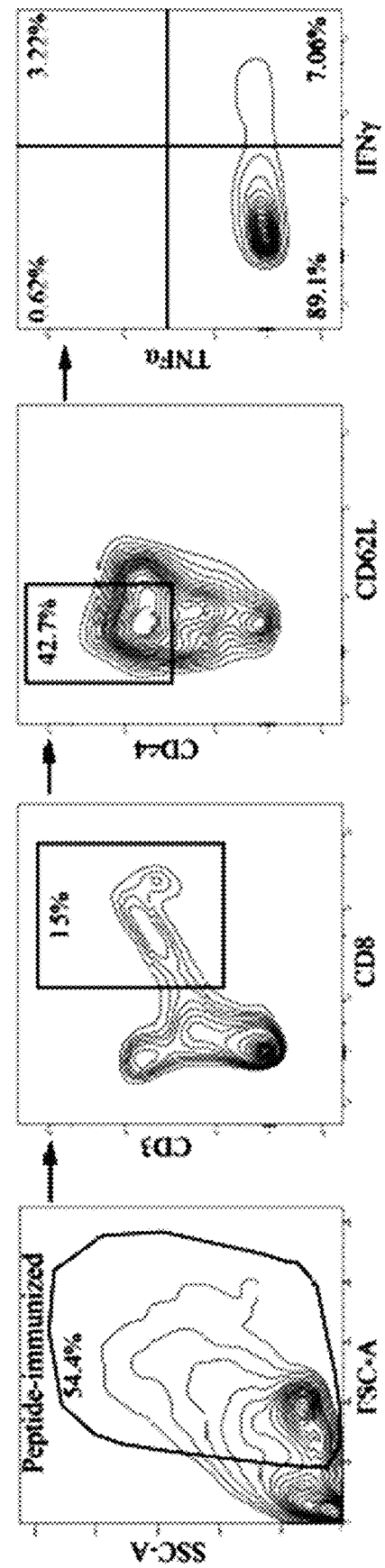
Figure 12C:
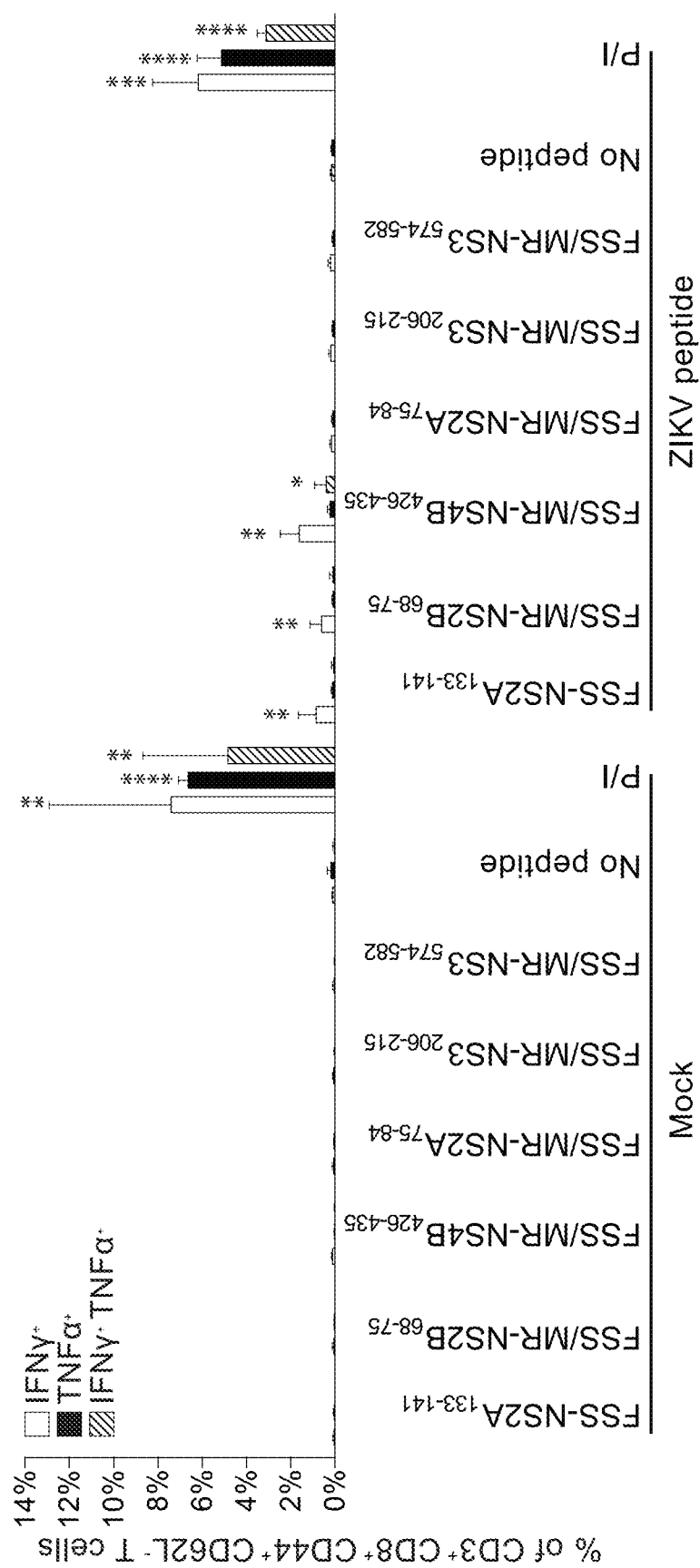
Figures 12D, 12E:
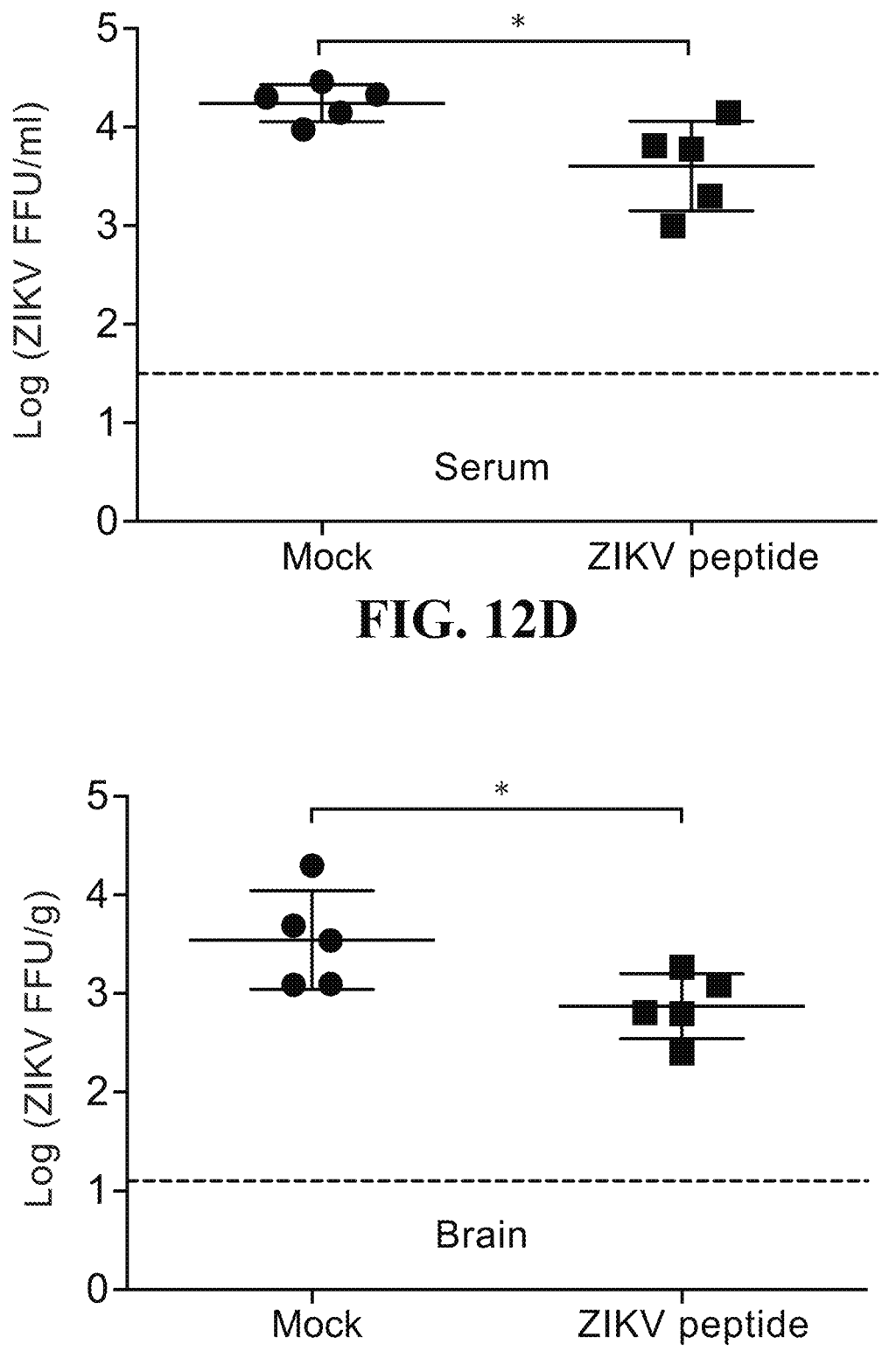
Figure 12F:
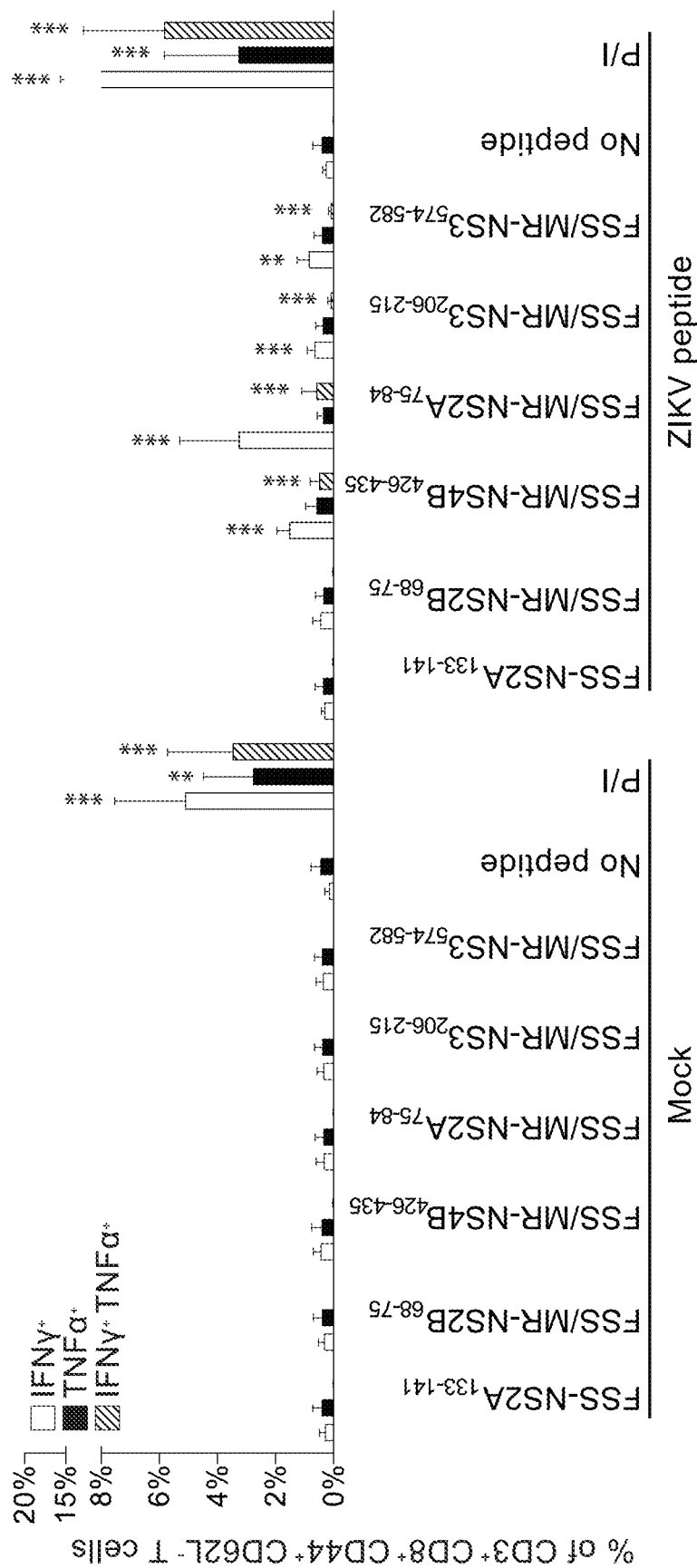

The following results are with respect to FIG. 12A-12F, where five-week-old Ifnar$^{-/-}$ HLA-B*0702 transgenic mice were divided into four groups: mock (5 mice) vs. ZIKV peptide (5 mice) (FIG. 12C and FIG. 12D) and mock (7 mice) vs. ZIKV/DENV cross-reactive peptide (8 mice) (FIG. 12E and FIG. 12F). Peptide groups received corresponding peptide immunizations as described in Materials and Methods. All groups were challenged R.O. with 1×10$^4$ FFU of ZIKV FSS13025 for 3 days. CD3$^+$CD8$^+$CD44$^+$CD62L− T cells were gated and the percentages of IFNγ$^+$ and/or TNFα$^+$ cells in a representative mouse from mock (FIG. 12A) and peptide (FIG. 12B) groups were determined by ICS. The levels of infectious ZIKV in sera and brains were measured via FFA. Data were expressed as mean±SEM. *, P<0.05; , P<0.01; *, P<0.001. Two-tailed Mann-Whitney test.

The results obtained are as follows:

On day 3 after viral challenge, epitope-specific CD8$^+$ T cells in the spleen were examined via ICS and viral titers in the sera and brain assessed via focus-forming assay. Infectious virus measurement was focused in these two tissues because viremia is a defining feature of human ZIKV infection, and the brain appears to be a major target of ZIKV in both fetal and adult infection settings.

Figure 12G:
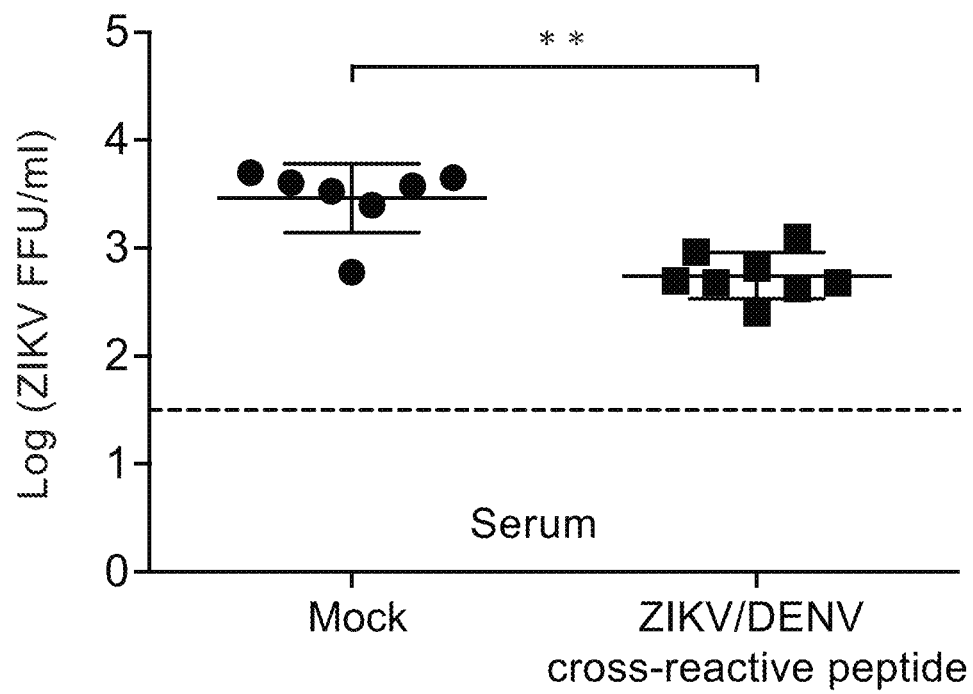
Figure 12H:
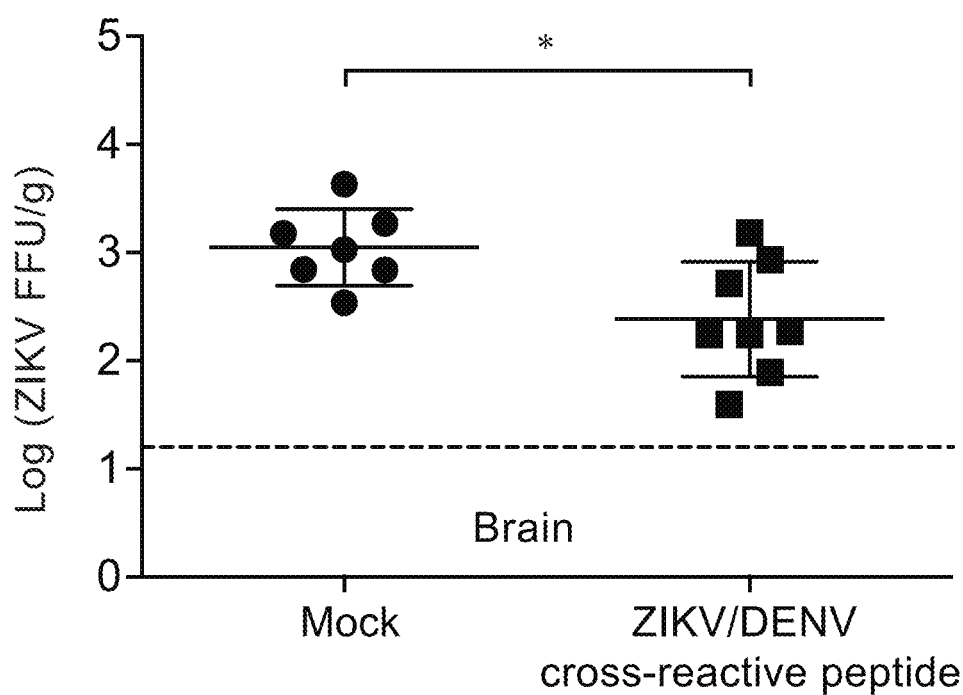

As expected, no significant epitope-specific CD8$^+$ T cell responses were detected in mock-immunized mice (FIG. 12A, FIG. 12C, and FIG. 12F). In comparison, a significant frequency of each individual epitope-specific CD8$^+$ T cells was observed in mice immunized with the 3 ZIKV immunodominant epitopes; the percentages of IFNγ-producing cells among antigen experienced (CD44$^+$CD62L$^-$) CD8$^+$ T cells directed to the FSS-NS2A$_{133-141}$ (SEQ ID NO: 41), FSS/MR766-NS2B$_{68-75}$ (SEQ ID NO: 45), and FSS/MR766-NS4B$_{426-435}$ (SEQ ID NO: 60) epitopes were 0.86%±0.71%, 0.61±0.47%, and 1.63±0.76%, respectively (FIG. 12C). In addition, the levels of infectious virus in the sera and brain of mice immunized with these 3 ZIKV immunodominant epitopes were significantly lower than those of mock-immunized mice (FIG. 12D and FIG. 12E). Similarly, in mice that were immunized with the 4 ZIKV/DENV cross-reactive peptides, antigen experienced (CD44$^+$CD62L$^-$) CD8$^+$ T cells recognizing 4 epitopes were detectable: The percentages of FSS/MR766-NS4B$_{426-435}$ (SEQ ID NO: 60), FSS/MR766-NS2A$_{75-84}$ (SEQ ID NO: 39), FSS/MR766-NS3$_{206-215}$ (SEQ ID NO: 47), and FSS/MR766-NS3$_{574-582}$ (SEQ ID NO: 52) specific cells were 1.52±0.42%, 3.27±1.91%, 0.66±0.24%, and 0.84±0.39%, respectively (FIG. 12F). Infectious ZIKV in both sera and brains of these mice immunized with the 4 ZIKV/DENV cross-reactive peptides were significantly lower relative to mock-immunized mice (FIG. 12G and FIG. 12H).

Taken together, these results demonstrate that both peptide immunization protocols (i.e., the 3 ZIKV immunodominant and the 4 ZIKV/DENV cross-reactive epitope cocktails) elicit antigen-experienced, epitope-specific CD8$^+$ T cells upon ZIKV challenge and reduce infectious ZIKV titers in tissues. Importantly, they indicate that CD8$^+$ T cells recognizing not only ZIKV immunodominant epitopes but also ZIKV/DENV cross-reactive epitopes can contribute to reduction in infectious ZIKV titers in vivo.

5.6 CD8$^+$ T Cell Depletion Confirms Epitope-Specific CD8$^+$ T Cell-Mediated Protection To confirm the protective role of epitope-specific CD8$^+$ T cells in ZIKV infection, the present inventors firstly immunized Ifnar$^{-/-}$ HLA-B*0702 and HLA-A*0101 transgenic mice with 6 HLA-B*0702-restricted epitopes and 5 HLA-A*0101-restricted epitopes, respectively; and then treated the peptide-immunized mice with anti-CD8 antibody to deplete $CD8^+$ T cells.

Figure 13A:
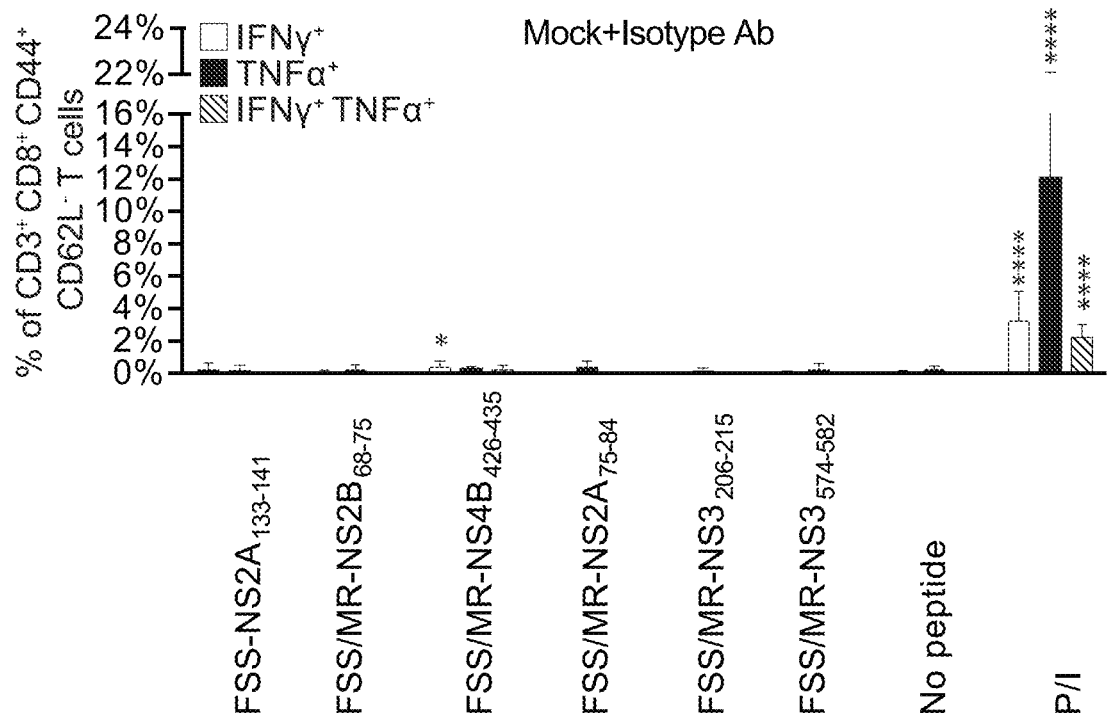
FIGS. 13A-13N: show graphs that illustrate non-limiting results that demonstrate that HLA-B*0702- and HLA-A*0101-restricted ZIKV peptide immunization-mediated protection is mediated by CD8+ T cells in accordance with an embodiment of the present disclosure.
Figure 13B:
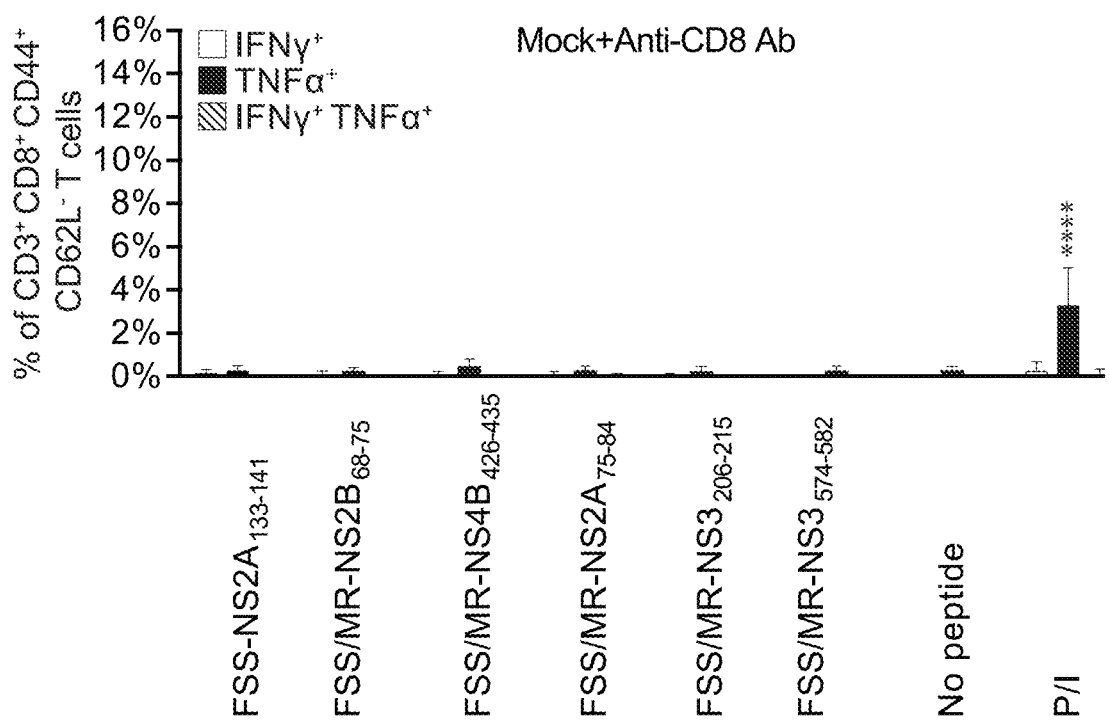
Figure 13C:
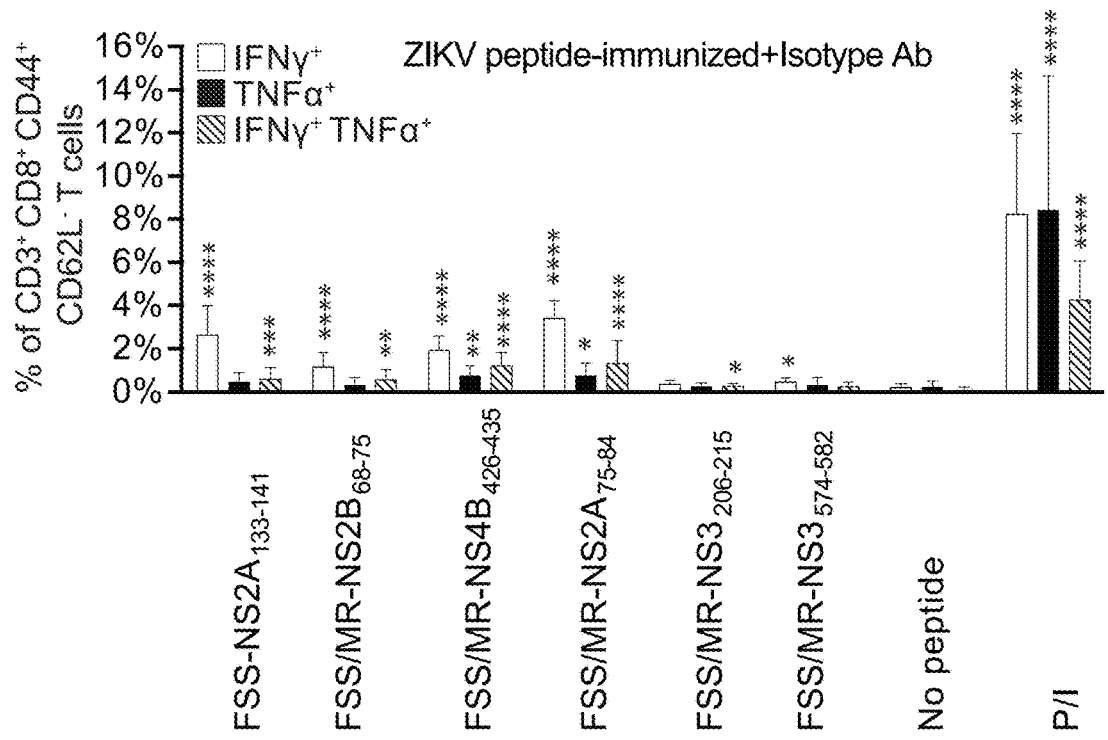
Figure 13D:
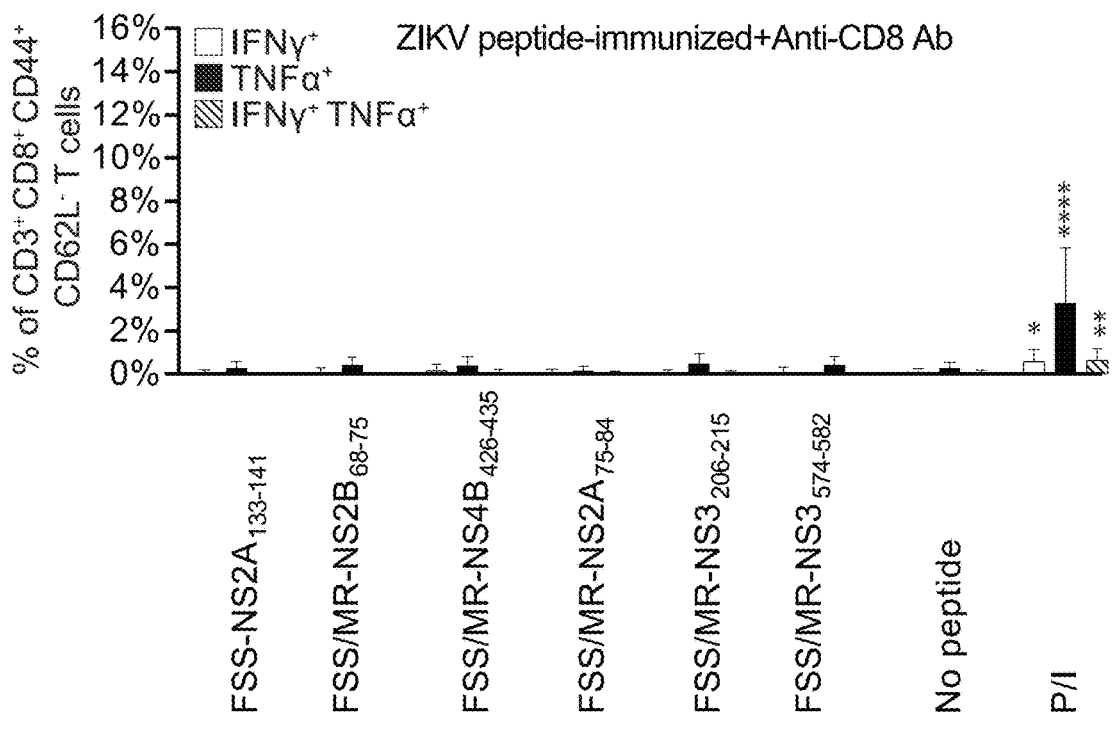
Figure 13E:
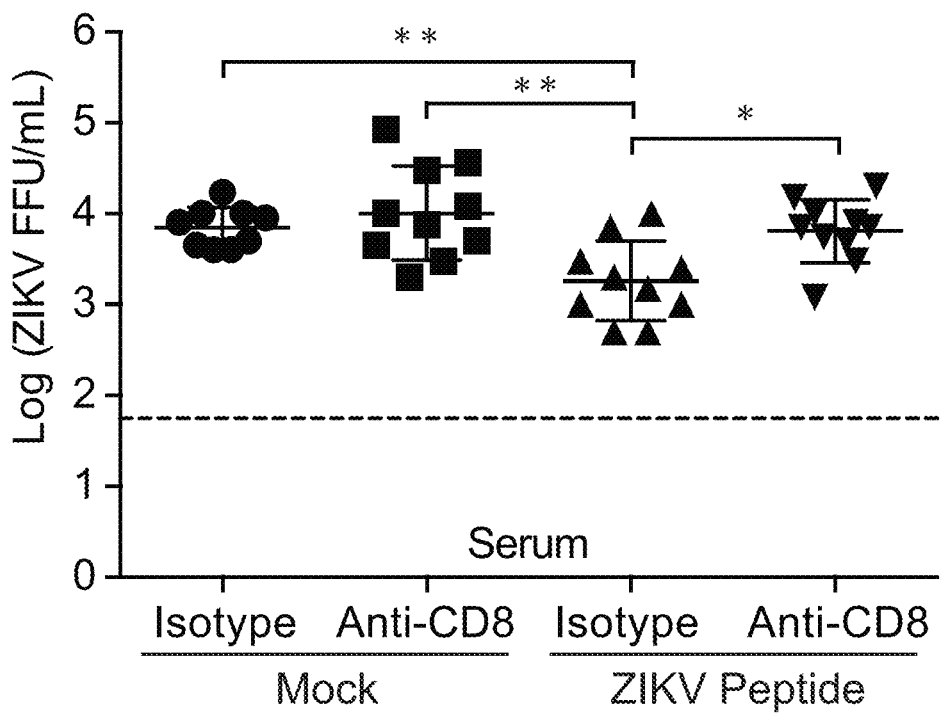
Figure 13F:
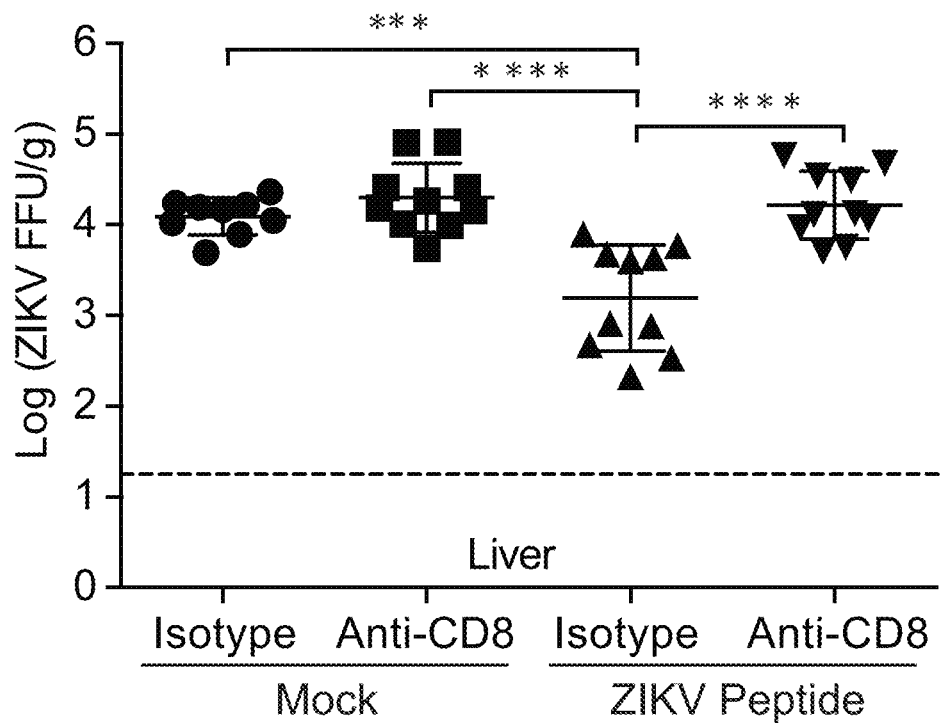
Figure 13G:
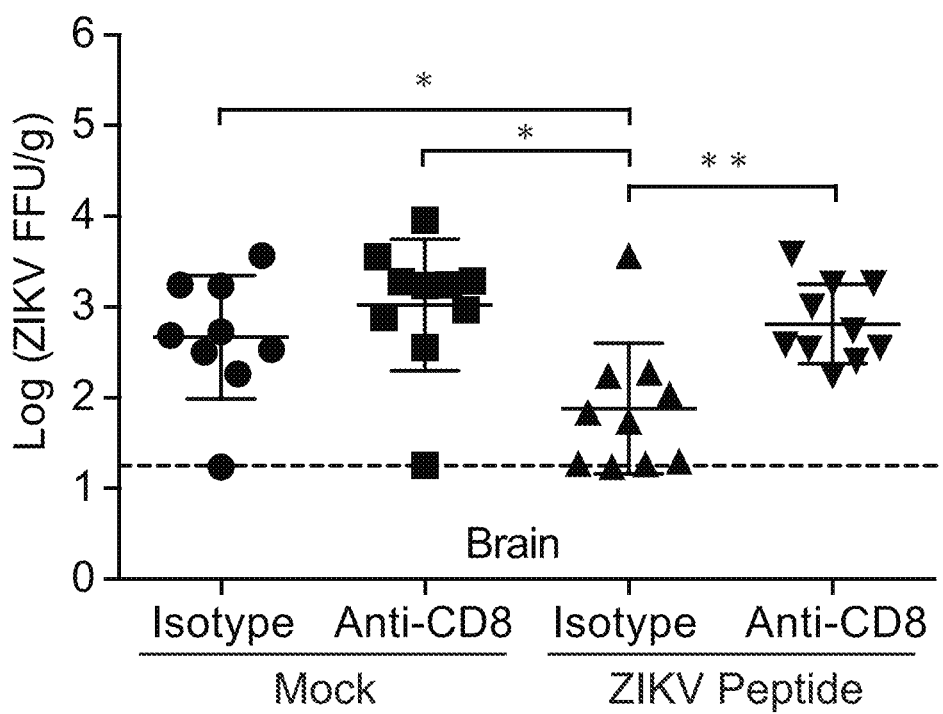
Figure 13H:
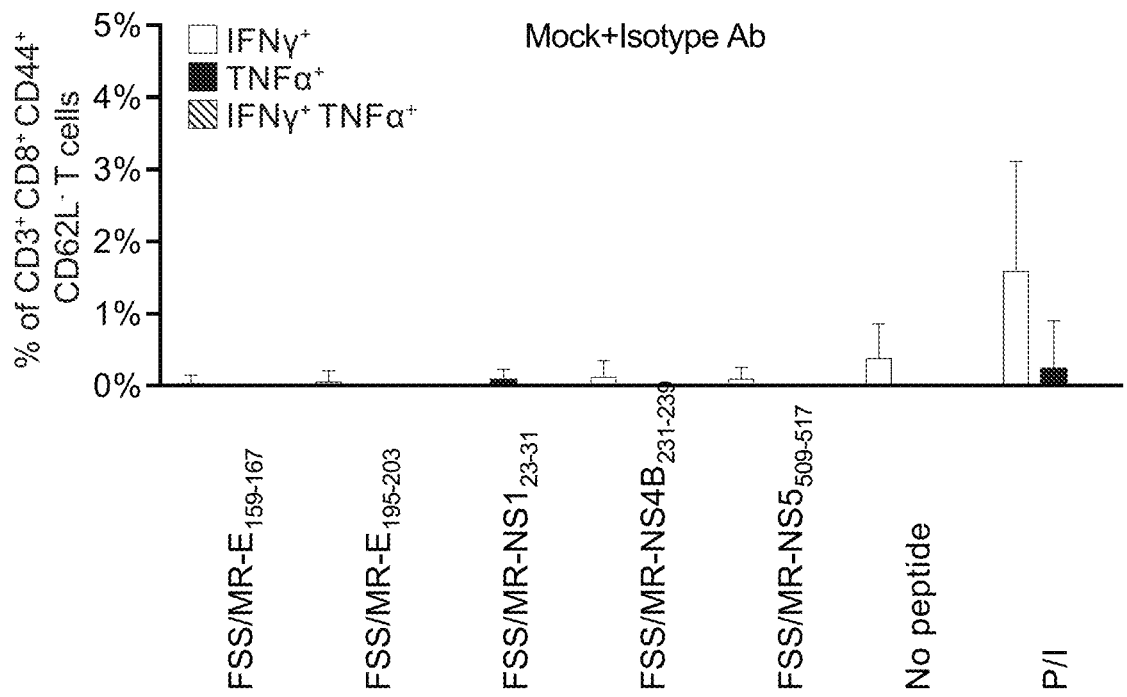
Figure 13I:
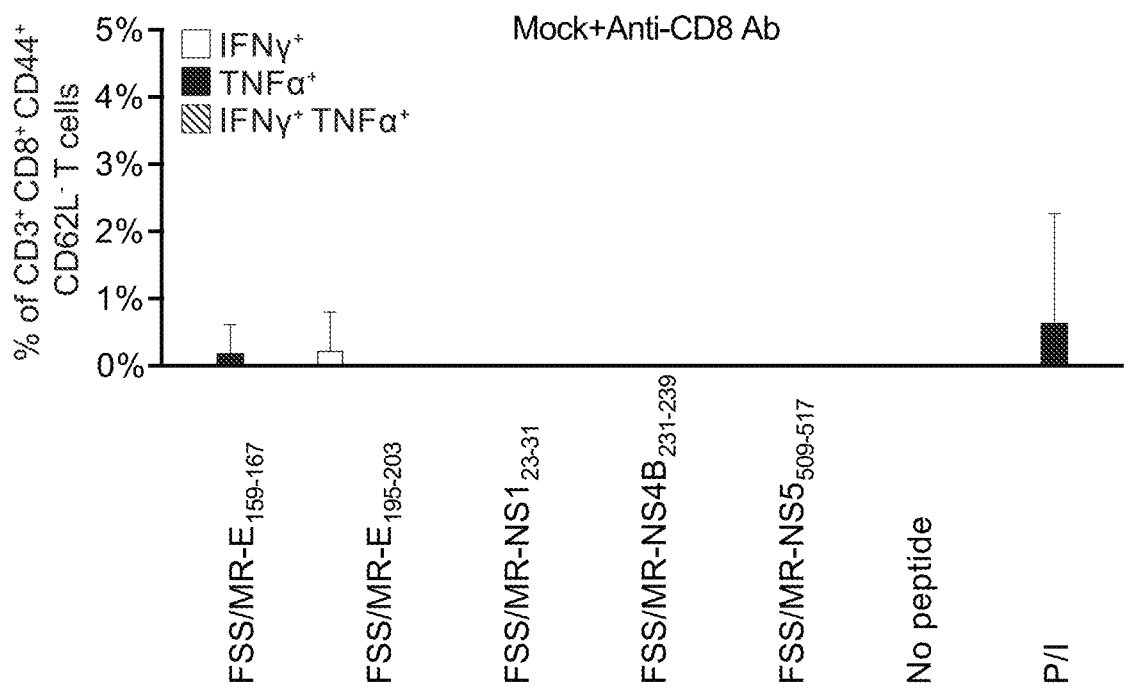
Figure 13J:
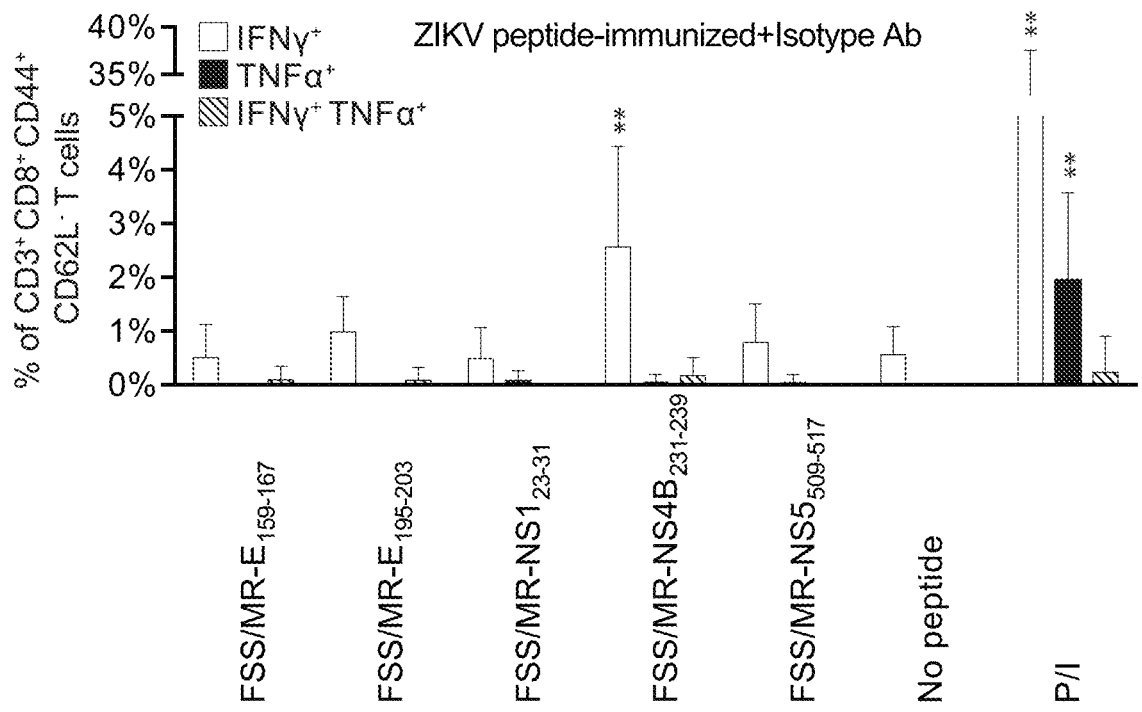
Figure 13K:
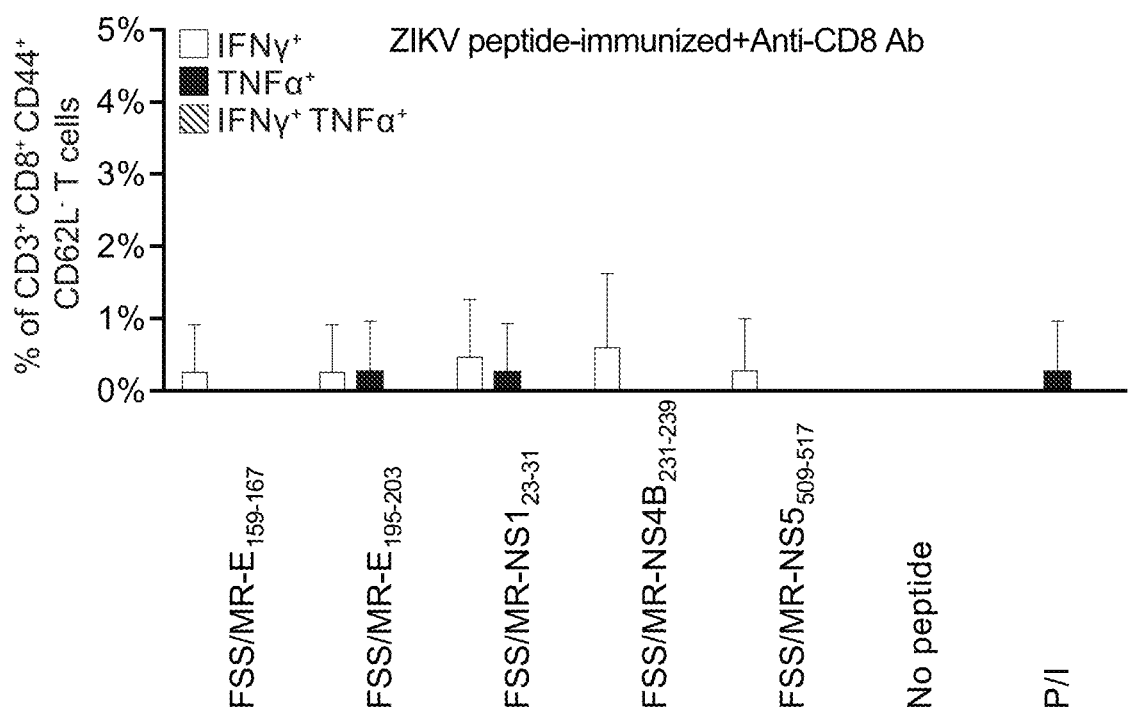
Figure 13L:
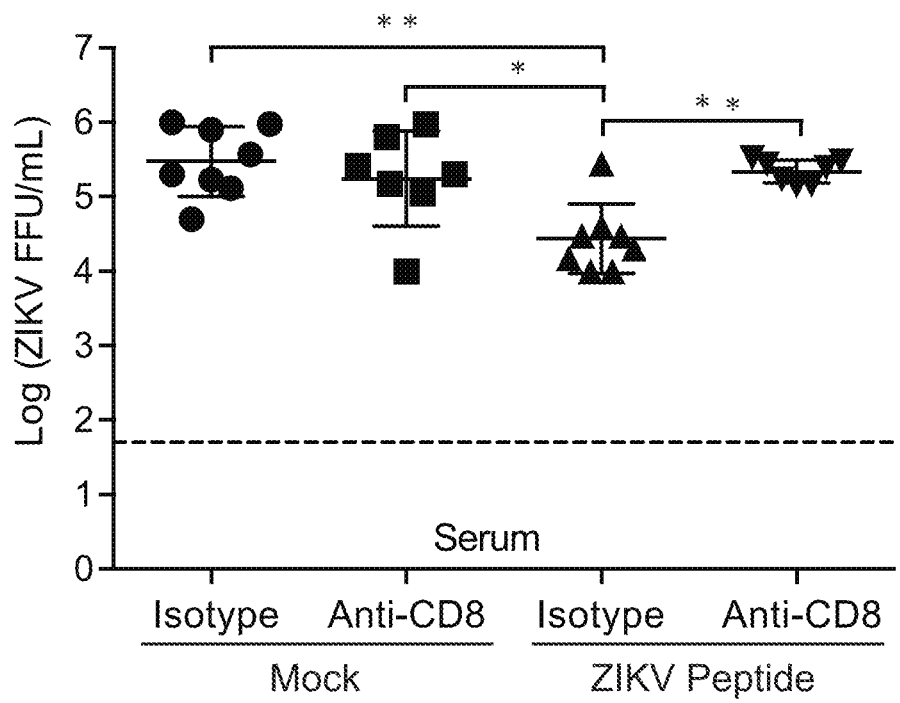
Figure 13M:
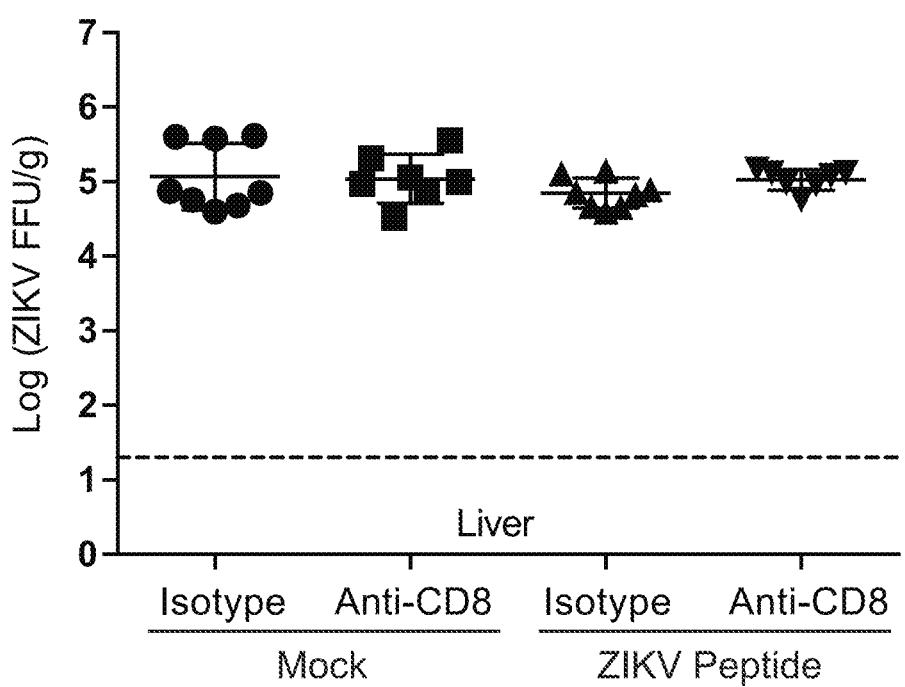
Figure 13N:
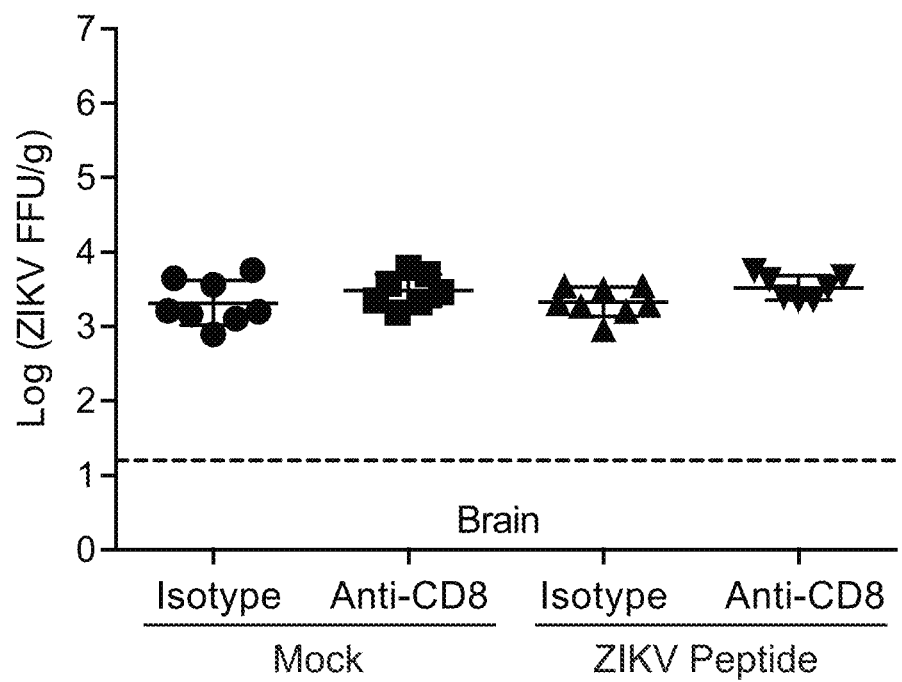

The following results are with respect to FIG. 13A to FIG. 13N, where five-week-old Ifnar$^{-/-}$ HLA-B*0702 transgenic mice were divided into four groups: mock+isotype antibody (Ab) (9 mice) vs. mock+anti-CD8 Ab (10 mice) vs. peptide-immunized+isotype Ab (10 mice) vs. peptide-immunized+anti-CD8 Ab (10 mice) (FIG. 13A to FIG. 13E). Peptide-immunized Ifnar1$^{-/-}$ HLA-B*0702 transgenic mice were immunized with a cocktail of 6 peptides as described in Materials and Methods. Five-week-old Ifnar$^{-/-}$ HLA-A*0101 transgenic mice were divided into four groups: mock+isotype Ab (8 mice) vs. mock+anti-CD8 Ab (7 mice) vs. peptide-immunized+isotype Ab (8 mice) vs. peptide-immunized+anti-CD8 Ab (7 mice) (FIG. 13H to FIG. 13N). Peptide-immunized Ifnar$^{-/-}$ HLA-A*0101 transgenic mice were immunized with a cocktail of 5 peptides as described in Materials and Methods. Mock-immunized mice and peptide-immunized mice were injected I.P. with isotype control Ab and anti-mouse CD8 Ab 3 days and 1 day before ZIKV challenge. All groups were challenged R.O. with $1\times10^4$ FFU of ZIKV FSS13025 for 3 days. $CD3^+CD8^+CD44^+CD62L^-$ T cells were gated and the percentages of IFN$\gamma^+$ and/or TNF$\alpha^+$ cells in mock and peptide groups were determined by ICS. The levels of infectious ZIKV in tissues were measured via FFA. Data were expressed as mean±SEM. *, P<0.05; , P<0.01; *, P<0.001;****, P<0.0001; Two-tailed Mann-Whitney test.

The results obtained are as follows:

As expected, antigen-experienced $CD8^+$ T cell responses were absent in mock-immunized mice (FIG. 13A, FIG. 13B, FIG. 13H and FIG. 13I) but present in peptide-immunized mice (FIG. 13C and FIG. 13J). Infectious ZIKV levels in the serum, liver, and brain of peptide-immunized mice were significantly lower than those in mock-immunized mice (Isotype peptide-immunized vs. Isotype mock in FIGS. 13E-13G and FIG. 13L). When $CD8^+$ T cell-depleting anti-CD8 antibody was administered to mice, the majority of peptide-specific $CD8^+$ T cells were absent (FIG. 13D and FIG. 13K) and infectious ZIKV levels in the serum, liver, and brain of $CD8^+$ T cell-depleted peptide-immunized mice were the same as in anti-CD8 antibody-treated mock-immunized mice, but significantly higher than levels in isotype control antibody-treated peptide-immunized mice that were $CD8^+$ T cell-sufficient (Anti-CD8 peptide-immunized vs. Isotype peptide-immunized in FIGS. 13E-13G, and FIG. 13L). Collectively, these results confirmed that protective immunity induced by ZIKV peptide immunization was mediated by $CD8^+$ T cells.

6. Discussion on Example 2

The goals of example 2 were to define specificity and role of ZIKV-specific and ZIKV/DENV cross-reactive $CD8^+$ T cell epitopes that are restricted by common HLA molecules using the Ifnar$^{-/-}$ HLA-B*0702 and HLA-A*0101 transgenic mouse models. Prior studies have shown the value of using these mouse models to investigate DENV epitopes of relevance to human T cell responses. Therefore, in a first step, HLA-B*0702-restricted and HLA-A*0101-restricted CD8+ T cell epitopes were identified that were recognized in Ifnar$^{-/-}$ HLA-B*0702 and HLA-A*0101 transgenic mice infected with either the African or Asian lineage ZIKV. Most identified epitopes are conserved in not only ZIKV FSS13025 and ZIKV MR766, but also in the Brazilian outbreak strain SPH2015. The majority of HLA-B*0702-restricted CD8+ T cell epitopes identified in ZIKV are located in nonstructural proteins. In contrast, fewer HLA-A*0101-restricted epitopes were identified (13 HLA-A*0101-restricted vs. 37 HLA-B*0702-restricted, as identified via IFN$\gamma$ ELISPOT), and the majority of HLA-A*0101-restricted ZIKV epitopes resided in the structural protein E.

To assess the magnitude and functional quality of cross-reactive T cell responses between ZIKV and DENV, ZIKV/DENV cross-reactive epitopes were next identified using DENV2-infected mice. There were 37 IFN$\gamma$ ELISPOT-confirmed HLA-B*0702-restricted ZIKV epitopes tested in DENV2-infected mice and 14 peptides reactive with DENV2 in ELISPOT and/or ICS assays were identified, whereas none of the 13 HLA-A*0101-restricted ZIKV epitopes were cross-reactive with DENV2. These 14 HLA-B*0702-restricted ZIKV/DENV cross-reactive epitopes and their DENV2 variants have 0-8 amino acid substitutions (see Table 3 in next page). It is noteworthy that 5 DENV2 variants (RPTFAAGLLL (SEQ ID NO: 81), APTRVVAAEM (SEQ ID NO: 47), KPRWLDARI (SEQ ID NO: 82), TPRMCTREEF (SEQ ID NO: 85), LPAIVREAI (SEQ ID NO: 86)) had been identified as HLA-B*0702-restricted epitopes in both mouse models and humans[22]. Three ZIKV peptides and the corresponding DENV2 variants have the same C-terminal amino acid residue, suggesting these ZIKV peptides are probably human epitopes as well. Of these 5 peptides, FSS/MR766-NS3$_{206-215}$(SEQ ID NO: 47) (APTRVVAAEM (SEQ ID NO: 47)) is conserved among many Flaviviruses, including ZIKV, four DENV serotypes, West Nile Virus, Japanese Encephalitis Virus, Usutu Virus, Murray Valley Encephalitis Virus, and Kunjin Virus.

TABLE 3

| Peptides[a] | SEQ ID NO | Sequences[b] | Conservation[c] | Reference |
|---|---|---|---|---|
| FSS/MR766-NS2A$_{75-84}$ | 39 | RPALLVSFIF | 20% | (22) |
| DENV2-NS2A$_{74-83}$ | 81 | RPTFAAGLLL | | |
| FSS/MR766-NS3$_{206-215}$ | 47 | APTRVVAAEM | 100% | (22) |
| DENV2-NS3$_{205-214}$ | | | | |
| FSS/MR766-NS3$_{574-582}$ | 52 | KPRWMDARV | 78% | (22) |
| DENV2-NS3$_{575-583}$ | 82 | KPRWLDARI | | |
| FSS/MR766-NS4B$_{426-435}$ | 60 | RPGAFCIKVL | 60% | |
| DENV2-NS4B$_{423-432}$ | 83 | NTQFCIKVL | | |

TABLE 3-continued

| Peptides[a] | SEQ ID NO | Sequences[b] | Conservation[c] | Reference |
|---|---|---|---|---|
| FSS/MR-NS5$_{539-546}$ | 64 | VPTGRTTW | 88% | |
| DENV2-NS5$_{538-545}$ | 84 | VPTSRTTW | | |
| FSS/MR766-NS5$_{140-149}$ | 62 | RPRVCTKEEF | 70% | (22) |
| DENV2-NS5$_{140-149}$ | 85 | TPRMCTREEF | | |
| FSS/MR-NS3$_{188-196}$ | 46 | LPEIVREAI | 89% | (22) |
| DENV2-NS3$_{187-195}$ | 86 | LPAIVREAI | | |
| MR766-NS2A$_{31-40}$ | 38 | VVMILGGFSM | 40% | |
| DENV2-NS2A$_{31-40}$ | 87 | VTLITGNMSF | | |
| FSS/MR-NS2A$_{89-99}$ | 40 | TPRESMLLAL | 30% | |
| DENV2-NS2A$_{87-97}$ | 88 | TSKELMMTTI | | |
| FSS/MR-NS3$_{427-436}$ | 50 | GPMPVTHASA | 90% | |
| DENV2-NS3$_{428-437}$ | 89 | GPMPVTHSSA | | |
| FSS/MR-NS4B$_{210-220}$ | 59 | SPNKYWNSSTA | 36% | |
| DENV2-NS4B$_{208-218}$ | 90 | NPGRFWNTTIA | | |
| FSS/MR-NS5$_{61-70}$ | 61 | APTQGSASSL | 50% | |
| DENV2-NS5$_{61-70}$ | 91 | TKQTGSASSM | | |
| FSS/MR-E$_{38-45}$ | 32 | KPTVDIEL | 75% | |
| DENV2-E$_{38-45}$ | 92 | KPTLDFEL | | |
| FSS/MR-NS3$_{581-589}$ | 53 | RVCSDHAAL | 56% | |
| DENV2-NS3$_{582-590}$ | 93 | RIYSDPLAL | | |

[a]ZIKV peptides in bold are positive as determined via both IFNγ-ELISPOT and ICS assays in DENV2-infected mice.
[b]Underlined amino acid residues are conserved between ZIKV peptide and DENV2 variant.
[c]% shared amino acids between ZIKV and DENV2.

The present investigation of the effect of heterologous DENV/ZIKV infection on HLA-B*0702-restricted T cell response revealed that the ZIKV/DENV cross-reactive CD8$^+$ T cells elicited by prior DENV infection expanded in the early phase of ZIKV challenge and then dominated in the later CD8$^+$ T cell response to ZIKV. Moreover, both ZIKV-specific and ZIKV/DENV cross-reactive CD8$^+$ T cell responses in DENV2-immune mice were weaker in terms of both magnitude and breadth than responses in primary ZIKV infection. These results indicate that prior DENV immunity can affect both the specificity and magnitude of CD8$^+$ T cell response to ZIKV. This phenomenon was also observed during heterotypic DENV infection in mice and natural reinfections in humans, implying that ZIKV infection in DENV-immune people may behave similarly as heterotypic DENV infection.

In humans, congenital microcephaly and additional birth defects result from infection of the fetal neuronal stem cells. The data in the present disclosure show that ZIKV can also infect adult mouse neural progenitor cells, resulting in reduced cell proliferation and cell death. Therefore, in addition to minimizing viremia, ZIKV vaccine candidates should protect from brain infection (ZIKV encephalitis). In the present study, 6 immunodominant HLA-B*0702-restricted epitopes were selected for peptide immunization because (i) these peptides were positive in both IFNγ ELISPOT and ICS assays for both ZIKV FSS13025 and ZIKV MR766 infection; (ii) all six peptides were conserved in both ZIKV FSS13025 and ZIKV SPH2015 while five peptides were also shared by ZIKV MR766; and (iii) four peptides were cross-reactive with DENV2 as confirmed by IFNγ ELISPOT and ICS assays. These peptides were then divided into two groups for immunization: ZIKV peptide group (two ZIKV-specific peptides and one ZIKV/DENV cross-reactive peptide) and ZIKV/DENV cross-reactive peptide group (four ZIKV/DENV cross-reactive peptides). As expected, both ZIKV peptide and ZIKV/DENV cross-reactive peptide immunization elicited significant CD8$^+$ T cell responses and reduced infectious ZIKV levels in mouse sera and brains, revealing the potential of these epitopes for preventing ZIKV encephalitis. CD8$^+$ T cell depletion assays in mice immunized with 6 HLA-B*0702-restricted epitopes or 5 HLA-A*0101-restricted epitopes further confirmed epitope-specific CD8$^+$ T cell-mediated protection. The finding of cross-reactive peptides, combined with protection against ZIKV seen in the data of the present disclosure, raise the possibility of developing a single vaccine that can confer protection against multiple strains of ZIKV and DENV. Although recent studies have demonstrated that vaccination with subunit and inactivated ZIKV strains provides protection, antibody-dependent enhancement (ADE) may be caused by a waning vaccine-induced antibody response, and in domestic mammals the cytopathic effects of attenuated virus vaccine strains, such as the Rift Valley Fever vaccine, administered during pregnancy have caused teratogenesis and fetal demise. This also highlights the potential importance of using epitope-based ZIKV vaccines as a risk reduction strategy.

Among the pathogenic human flaviviruses, ZIKV is most closely related to DENV and these viruses share a high level of amino acid sequence homology. Accordingly, similar to the present inventors' recent DENV study with HLA-B*0702 transgenic Ifnar$^{-/-}$ mice[40], results of this example implicate a protective role for cross-reactive memory T cells. Despite several decades of research, no study to date has provided direct evidence supporting a pathogenic role for T cells during DENV infection. Instead, consistent with the present inventors' mouse findings[21,37-40,48-50], recent studies have begun to support a protective role for DENV-specific T cells in humans. In particular, the magnitude and breadth of DENV-specific CD8⁺ and CD4⁺ T cell responses are associated with particular HLA alleles that correlate with susceptibility vs. resistance to dengue disease, and HLA-B*0702 and HLA-A*0101, respectively, represent DENV-protective (i.e., associated with resistance to dengue disease) and DENV-susceptible alleles[27,29,51]. The identification in the present disclosure of a greater number of ZIKV-derived HLA-B*0702-restricted epitopes than HLA-A*0101-restricted epitopes and identification of ZIKV/DENV cross-reactive HLA-B*0702-restricted but not HLA-A*0101-restricted epitopes suggest that, similar to DENV, the CD8⁺ T cell response to ZIKV may be HLA-linked.

In summary, the ZIKV T cell immunity data in example 2 has identified HLA-B*0702 and HLA-A*0101 epitopes which are conserved between ZIKV lineages and cross-reactive with a DENV serotype. The HLA transgenic mouse model results in the present disclosure show that pre-existing DENV immunity modulates ZIKV-specific $CD8^+$ T cell response development, and that ZIKV-specific and ZIKV/DENV cross-reactive $CD8^+$ T cells play a protective role against ZIKV. The results on T cell mediated protection in mice in the present example are likely relevant to human infection, as the same mouse model has been validated in DENV infection by several independent observations. These results support that ZIKV vaccination approaches should include the induction of both ZIKV-specific and ZIKV/DENV cross-reactive $CD8^+$ T cell responses.

Example 3

Example 3 refers to the results shown in FIG. 15A to FIG. 24B.

Example 3 can be summarized as follows:

As ZIKV emerges into DENV-endemic areas, cases of ZIKV infection in DENV-immune pregnant women will rise. To investigate how prior DENV immunity affects maternal and fetal ZIKV infection in pregnancy, sequential DENV and ZIKV infection models were used. Fetuses in ZIKV-infected DENV-immune dams were of normal size, whereas fetal demise was observed in non-immune dams. Moreover, less ZIKV RNA was detected in the placenta and fetuses of ZIKV-infected DENV-immune than non-immune dams. DENV cross-reactive $CD8^+$ T cells expanded in the maternal spleen and decidua of ZIKV-infected dams, and their depletion led to increased ZIKV infection in the placenta and fetus, and fetal demise. Thus, in mice, prior DENV immunity can protect against ZIKV infection during pregnancy, and $CD8^+$ T cells are necessary for this cross-protection. This finding has implications for understanding the natural history of ZIKV in DENV-endemic areas and the development of optimal ZIKV vaccines.

7. Materials & Methods for Example 3

7.1 Ethics Statement

This study was performed following the guidelines of the Institutional Animal Care and Use Committee under protocol #AP028-SS1-0615. Inoculations were performed under isoflurane inhalation, and all efforts were made to minimize pain.

7.2 Viruses

ZIKV Asian lineage strain FSS13025 (Cambodia, 2010) was obtained from the World Reference Center for Emerging Viruses and Arboviruses (Galveston, Tex.). The mouse-adapted DENV2 strain S221 is a biological clone derived from DENV2 D2S10 (Shresta et al., 2006; Yauch et al., 2009). ZIKV and DENV2 were propagated in C6/36 *Aedes albopictus* cells, and viral titers were measured by focus forming assay (FFA) with baby hamster kidney (BHK)-21 cells (Elong Ngono et al., 2017) or by qRT-PCR (Lanciotti et al., 2008).

7.3 Mouse Experiments and Virus Infections

Ifnar1−/− and wild-type (WT) congenic C57BL/6J mice were bred in a specific-pathogen-free facility at La Jolla Institute for Allergy & Immunology, or WT mice (males, #000664) also were purchased from Jackson Laboratories. Two models of ZIKV pregnancy infection were used: (1) Ifnar1−/− females crossed to WT males and (2) WT females crossed to WT males. The type I IFN receptor (Ifnar1) signaling in WT females was transiently blocked via treatment with an Ifnar1-blocking monoclonal Ab (mAb), as described below.

To establish DENV immunity, 5-week-old Ifnar1 female mice were inoculated with $1\times10^3$ FFU of DENV2 via I.P. route or WT female mice were inoculated with $1\times10^4$ FFU of DENV2 via R.O. route. At 8 to 10 weeks of age, female mice were mated. Pregnancy was determined by the presence of a vaginal plug in the morning, and embryonic development was estimated as gestational age E0.5. Pregnant female mice were separated from male mice after plug detection. At E7.5, the females were inoculated with $1\times10^4$ FFU of ZIKV in 200 μL of PBS with 10% FBS or mock-infected with 200 μL of PBS with 10% FBS via R.O. route. Mice were sacrificed at E10.5 or E14.5 depending on the experimental design. Viral burden in the maternal tissues (serum, brain and spleen), placenta and fetal tissues (head and body) were quantified. Fetus weight and size were measured using an analytical balance (Catalog number: S94790A, Fisher Scientific) and Digital Caliper (Model number: 700-113-10, Mitutoyo), respectively.

7.4 Ifnar1-Blocking and T Cell-Depleting Antibodies

All antibodies (Abs) were purchased from BioXCell (USA). For Ifnar1 blocking, WT mice were treated with 2 mg Ifnar1-blocking mAb MAR1-5A3 via I.P. route 1 day before infection with ZIKV or DENV2 (WT mice only). To deplete $CD8^+$ T cells, mice were injected with either anti-mouse CD8 mAb (300 μg/mouse, rat IgG2b, clone 2.43) or isotype control mAb (300 μg/mouse, rat IgG2b, clone LTF-2) via R.O. route on days 3 and 1 prior to infection and every two days after ZIKV infection. The same protocol was used for $CD4^+$ T cell depletion (300 μg/mouse, clone GK1.5) or both $CD4^+$ and $CD8^+$ T cell depletion. All mice were monitored for $CD8^+$ T cell depletion in tissues after treatment using flow cytometry.

7.5 qRT-PCR Analysis of Viral Burdens

For RNA extraction, organs were collected in RNA later (Ambion) and stored at 4° C. Tissues were homogenized in BME/RLT buffer for 3 min using TISSUE IYSER™ II (QIAGEN™) and then centrifuged for 1 min at 6,010×g. RNA from tissue samples and serum obtained from ZIKV-infected mice were extracted using the RNEASY™ Mini Kit (tissues) and VIRAL RNA MINI™ Kit (serum) (QIAGEN), respectively. All RNA samples were stored at −80° C. For quantification of viral RNA, real-time qRT-PCR was performed using the qScript ONE-STEP™ qRT-PCR Kit (Quanta BioSciences) at the CFX96 TOUCH™ real-time PCR detection system (Bio-Rad CFX Manager 3.1). A published primer set [74] was used to detect ZIKV RNA:

TABLE 4

| Sequence | SEQ ID NO |
|---|---|
| Fwd, 5'-TTGGTCATGATACTGCTGATTGC-3' | 94 |
| Rev, 5'-CCTTCCACAAAGTCCCTATTGC-3' | 95 |
| Probe, 5'-6-FAM-CGGCATACAGCATCAGGTGCATAGGAG-Tamra-Q-3' | 96 |

Cycling conditions were set as following: 45° C. for 15 min, 95° C. for 15 min, followed by 50 cycles of 95° C. for 15 sec and 60° C. for 15 sec and a final extension of 72° C. for 30 min. Viral RNA concentration was determined based on an internal standard curve composed of serial dilutions of an in vitro transcribed RNA based on ZIKV strain FSS13025.

7.6 Peptide Synthesis

Peptides were purchased from Synthetic Biomolecules (A&A Labs). The 9- and 10-mer peptides used for flow cytometry were synthesized and purified by reverse-phase HPLC up to ≥95% purity. Peptides were stored at −20° C. after being dissolved in DMSO and aliquoted into small quantities to avoid freeze-thaw damage. The sequence and characteristics of all peptides used have been published (Wen et al., 2017a).

7.7 Cell Isolation and Flow Cytometric Analyses

For each pregnant mouse, placentas were harvested in 10% FBS/RPMI and pooled before processing as follows. Briefly, placentas without separation of maternal decidua were cut into small pieces and treated with 1 mg/ml of type I collagenase (Worthington) for 60 min at 37° C. After incubation, placentas were mechanically dissociated, filtered through over a 70-μtm cell strainer and the pellet was resuspended in 44% PERCOLL™ (GE Healthcare). Another layer of 67% PERCOLL™ was placed underneath before centrifugation at 376×g at room temperature for 20 min. The cell layer suspension was isolated between the different densities of Percoll and washed three times with PBS. Cells were counted after erythrocyte lysis using a cell counter (VI-CELL™ XR 2.04, Beckman Coulter).

For ICS, isolated splenocytes from all mice were plated as $2 \times 10^6$ splenocytes/well in 96-well U-bottom plates. Cells were stimulated with 1 μg of individual ZIKV peptides for 6 h in the presence of Brefeldin A (GolgiPlug; BD Biosciences) during the last 4 h, as previously described [41]. Cells from placenta/maternal decidua were plated and stimulated with a mixture of all 5 ZIKV peptides following the same conditions as splenocytes. Positive controls using a cell stimulation cocktail (commercial PMA-Ionomycin-500X, eBiosciences) and negative controls (10% FBS/RPMI) were added in each plate. Cells were washed after stimulation and labeled with viability dye EFLUOR™ 455 UV (Invitrogen) in PBS. All cells were stained with anti-CD3 PERCPCY™ 5.5 (Clone 145-2C11), anti-CD8 BV510 (clone 53-67), anti-CD44 BV785 (clone IM7), anti-CD62L APC eFluor 780 (clone Mel-14), followed by fixation and permeabilization using the BD CYTOFIX/CYTOPERM™ kit and then staining with a combination of anti-IFNγ FITC (clone XMG 1.2), anti-TNF ALEXA™ Fluor 700 (clone MP6-XT22) and granzyme B PE-CY™ (clone NGZB). Samples were acquired on LSR-Fortessa (BD Biosciences) and analyzed using FLOWJO™ software X 10.0.7 (Tree Star).

7.8 Statistical Analysis

All data were analyzed with PRISM™ software, version 7.0 (GraphPad Software). For ICS and viral burden data, a two-tailed Mann-Whitney test was used. For viral burden and morphological measurements, data were compared by one-way ANOVA with Tukey's multiple comparison test. Percentages of infection in placenta with decidua and fetal tissues were assessed via two-sided Fisher's exact test. All data were expressed as mean±SEM, and $p<0.05$ was considered as a significant difference.

8. Results 8.1 DENV2-Elicited CD8$^+$ T Cells Prevent Fetal Growth Restriction and Control ZIKV Burden in Ifnar1−/− Dams It has been recently demonstrated that DENV-elicited CD8$^+$ T cells mediated cross-protection against subsequent ZIKV infection in adult male and female Ifnar1$^{-/-}$ mice (Wen et al., 2017a). Previously, fetal growth restriction and demise have been observed in Ifnar1$^{-/-}$ pregnant mice following ZIKV infection (Miner et al., 2016; Yockey et al., 2016). To begin to evaluate the influence of prior DENV immunity on subsequent ZIKV infection during pregnancy, the present inventors utilized their published model of sequential DENV and ZIKV infection in which mice were primed with DENV2 strain S221 for 30 days prior to ZIKV challenge (Wen et al., 2017a).

The following results are with respect to FIG. 15A to FIG. 15D, where non-immune and DENV2-immune Ifnar1$^{-/-}$ dams that were administered isotype control Ab (Isotype), anti-CD4 Ab (Anti-CD4), anti-CD8 Ab (Anti-CD8) or both Abs (Anti-CD4+CD8) and were inoculated via a retro-orbital route (R.O.) at embryonic day 7.5 (E7.5) with $10^3$ FFU of ZIKV FSS13025 or 10% FBS-PBS as Mock. To generate DENV2-immune mice, mice were inoculated via an intraperitoneal route (I.P.) with $10^4$ FFU of DENV2 strain S221 for 30 days prior to mating. Fetal body weight (FIG. 15A and FIG. 15C) and size (FIG. 15B and FIG. 15D) were measured at E14.5. The populations were as follows:

TABLE 5

| n fetuses | Feature |
|---|---|
| 38 fetuses from 5 separate mothers | Non-immune-Mock |
| 34 fetuses from 4 separate mothers | Non-immune-ZIKV + isotype |
| 43 fetuses from 5 separate mothers | Non-immune-ZIKV + Anti-CD8 |
| 15 fetuses from 3 separate mothers | DENV2-immune-Mock |
| 22 fetuses from 3 separate mothers | DENV2-immune-ZIKV + isotype |
| 25 fetuses from 3 separate mothers | DENV2-immune-ZIKV + Anti-CD8 |
| 26 fetuses from 4 separate mothers | Non-immune-ZIKV + Anti-CD4 |
| 36 fetuses from 4 separate mothers | Non-immune-ZIKV + Anti-CD4 + CD8 |
| 35 fetuses from 4 separate mothers | DENV2-immune-ZIKV + Anti-CD4 |
| 38 fetuses from 5 separate mothers | DENV2-immune-ZIKV + Anti-CD4 + CD8 |

Weight and size were determined individually on the residual placenta if fetal resorption was observed. Data were pooled from two independent experiments. Tukey's one-way ANOVA with multiple comparisons was used, and data are expressed as mean±SEM. ****$p<0.0001$.

Figure 15A:
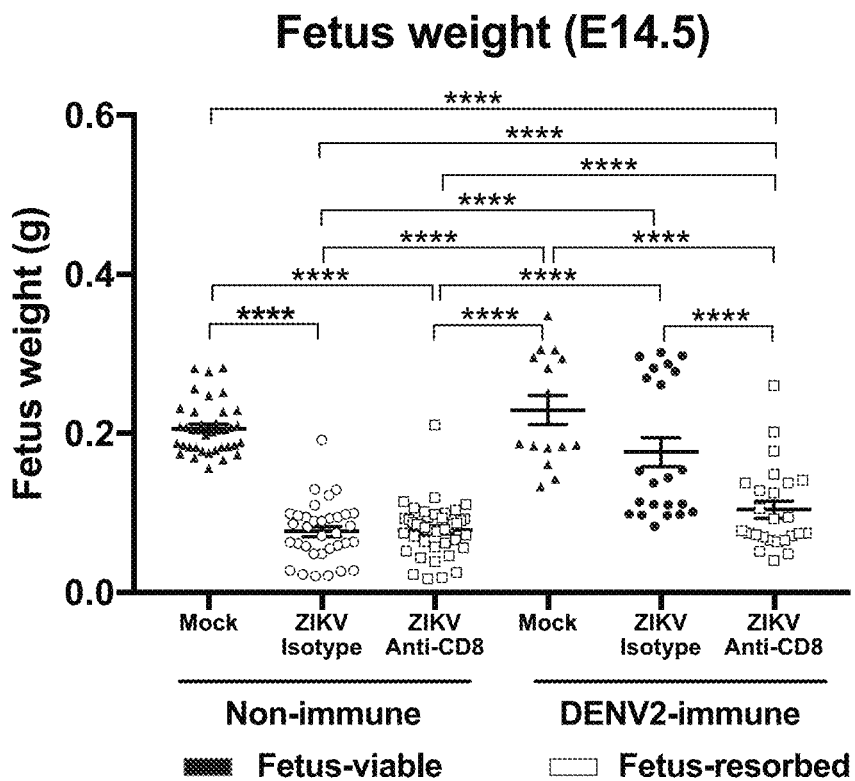
FIGS. 15A-15D: shows graphs that illustrate non-limiting results of fetal weight and size during maternal ZIKV infection in Ifnar1$^{-/-}$ mice with or without depletion of CD8+, CD4+, or both CD4+ and CD8+ T cells in accordance with an embodiment of the present disclosure.
Figure 15B:
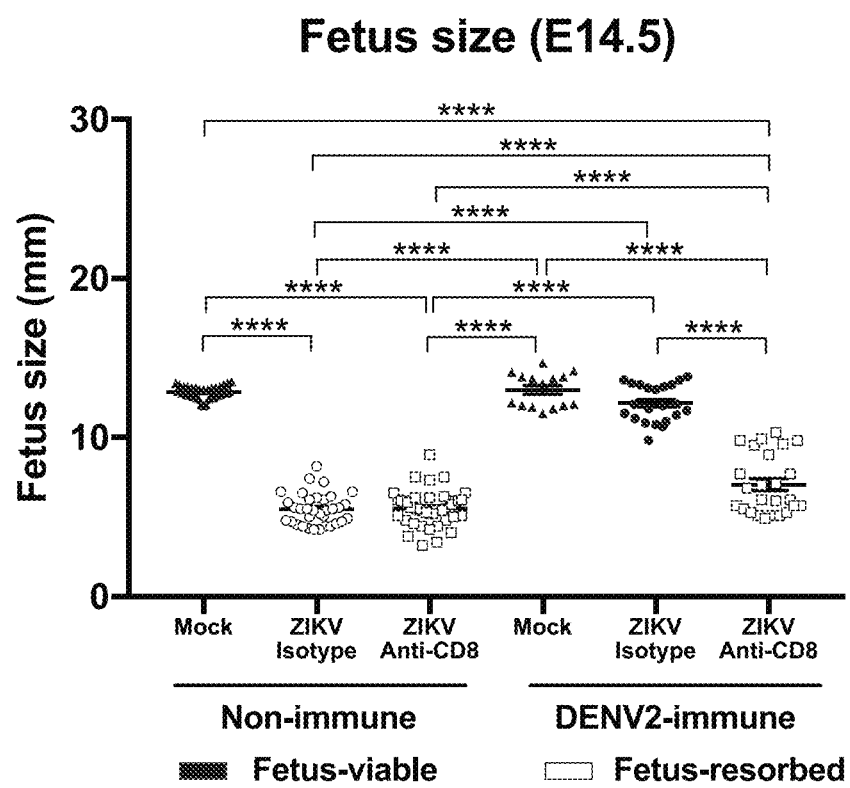
Figure 21A:
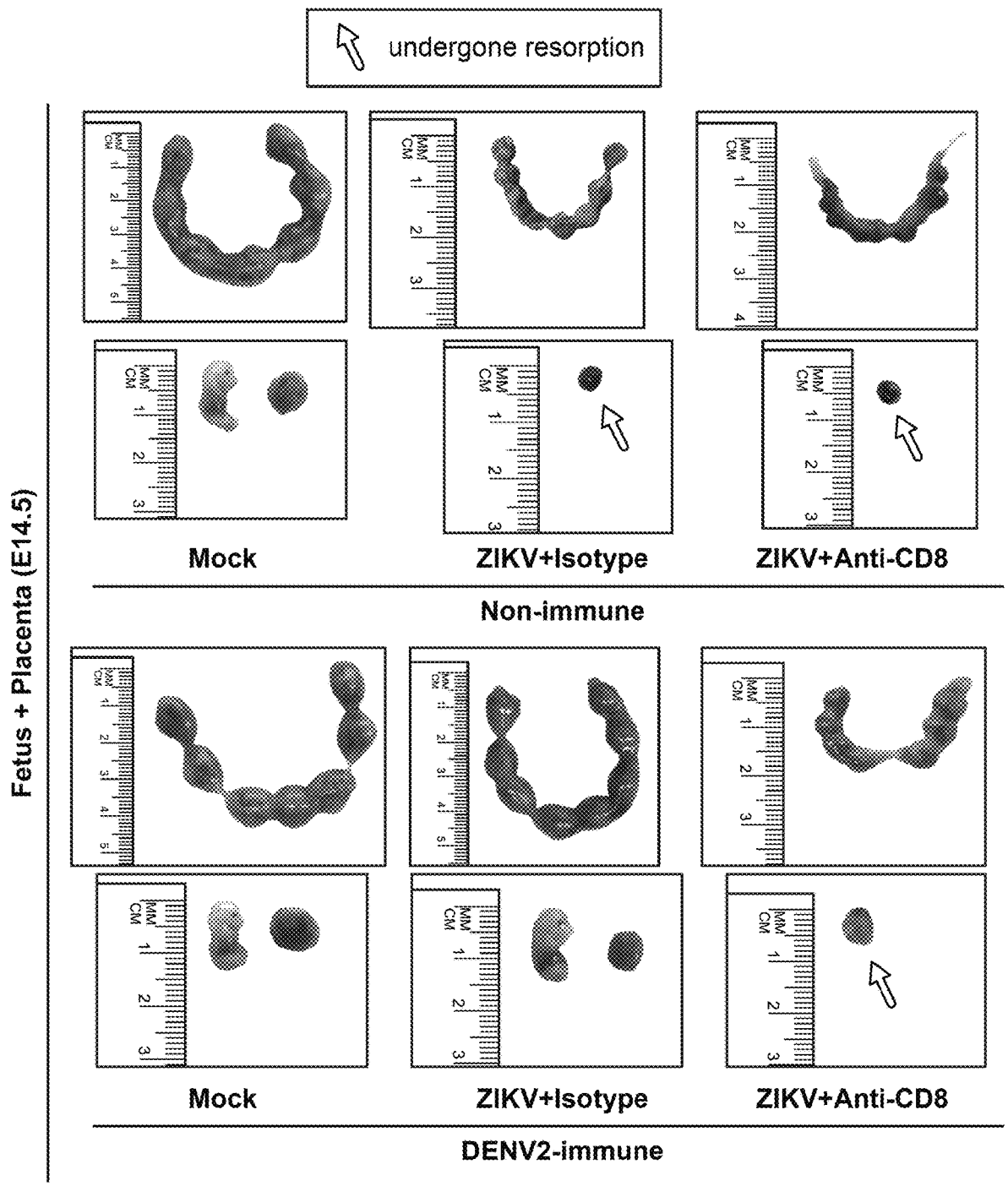
FIGS. 21A-21B: shows graphs that illustrate non-limiting results of a phenotype of fetuses from ZIKV-infected non-immune and DENV2-immune Ifnar1$^{-/-}$ dams that were depleted of CD8+, CD4+, or both CD4+ and CD8+ T cells in accordance with an embodiment of the present disclosure.
Figure 21B:
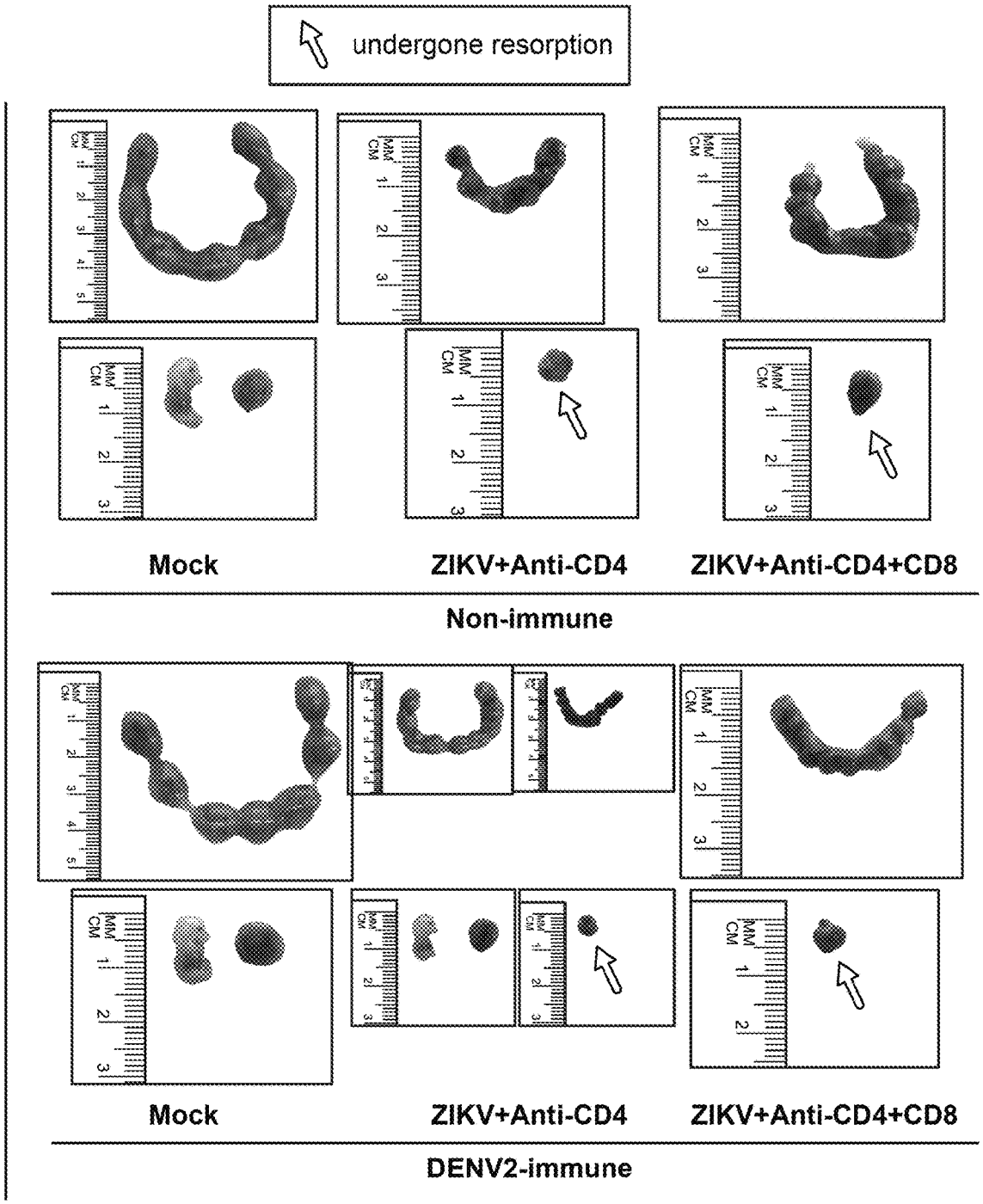

The results obtained are as follows:

Naïve and DENV-immune Ifnar1$^{-/-}$ pregnant mice were inoculated with $10^4$ focus forming units (FFU) of ZIKV FSS13025 (2010 Cambodian isolate) on embryonic day 7.5 (E7.5) and sacrificed 7 days later (E14.5). In the non-immune group, fetal resorption was observed after ZIKV-infection in all mice regardless of treatment with an isotype control or anti-CD8 Ab (FIG. 15A and FIG. 15B). Decreased fetal weight (FIG. 15A) and size (FIG. 15B) at E14.5 were consistently observed in the ZIKV-infected non-immune group. Remarkably, DENV-immune dams treated with isotype control Ab had normal fetuses that were similar in size to uninfected, naive control dams. Fetal resorption was observed in DENV2-immune mice only in the anti-CD8 Ab-treated group (FIG. 15A and FIG. 15B, and FIG. 21A). These results indicate that prior DENV immunity prevents fetal resorption induced by ZIKV infection during pregnancy, and CD8$^+$ T cells contribute to DENV immune-mediated protection against ZIKV in Ifnar1$^{-/-}$ pregnant mice.

Figure 15C:
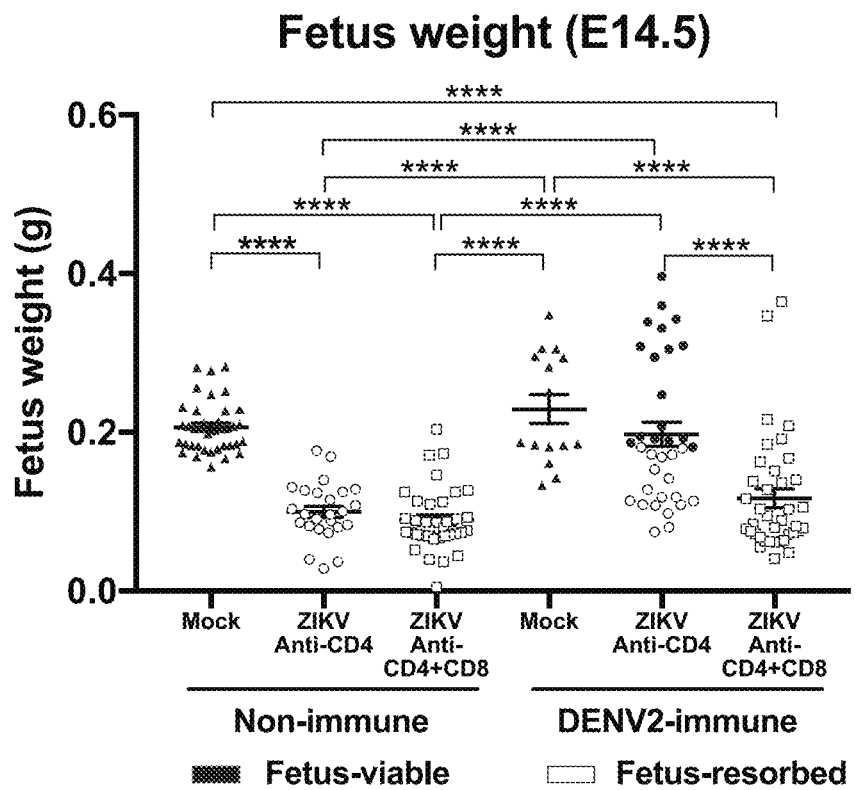
Figure 15D:
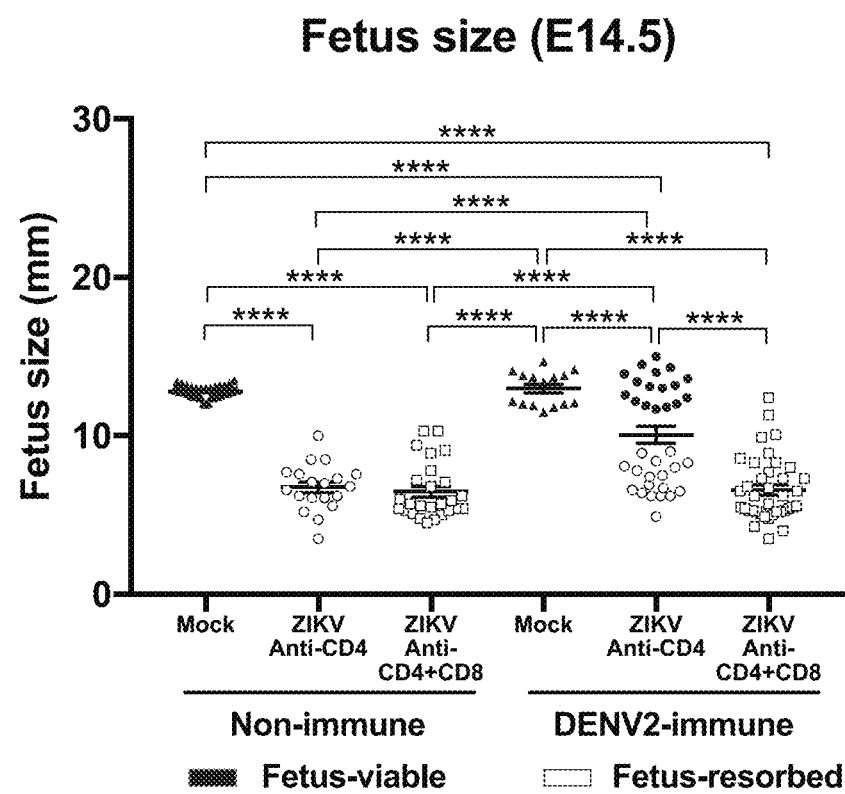

As CD4$^+$ T cell help may be required for development of an optimal CD8$^+$ T cell response (Swain et al., 2012), the present inventors examined their role in DENV immune-mediated protection against ZIKV during pregnancy. Non-immune and DENV2-immune dams were depleted of CD4$^+$ T cells or both CD4$^+$ and CD8$^+$ T cells via treatment with cell-depleting anti-CD4 or anti-CD4 plus anti-CD8 Abs. Fetuses undergoing resorption were seen in ZIKV-challenged, non-immune groups treated with anti-CD4 Ab alone or both anti-CD4 and anti-CD8 Abs (FIG. 15C and FIG. 15D). However, with prior DENV2 immunity, an intermediate phenotype with 47% of viable fetuses was found in mice treated with anti-CD4 Ab alone as compared with nearly 100% resorption in the group treated with both anti-CD4 and anti-CD8 Abs (FIG. 15C and FIG. 15D, and FIG. 24B). These results suggest that cross-reactive CD4$^+$ and CD8$^+$ T cells have subordinate and dominant roles, respectively, in mediating DENV immune protection against ZIKV-induced fetal damage.

The present inventors next determined the impact of prior DENV immunity on ZIKV burden in maternal tissues seven days after inoculation at E14.5.

Figure 22A:
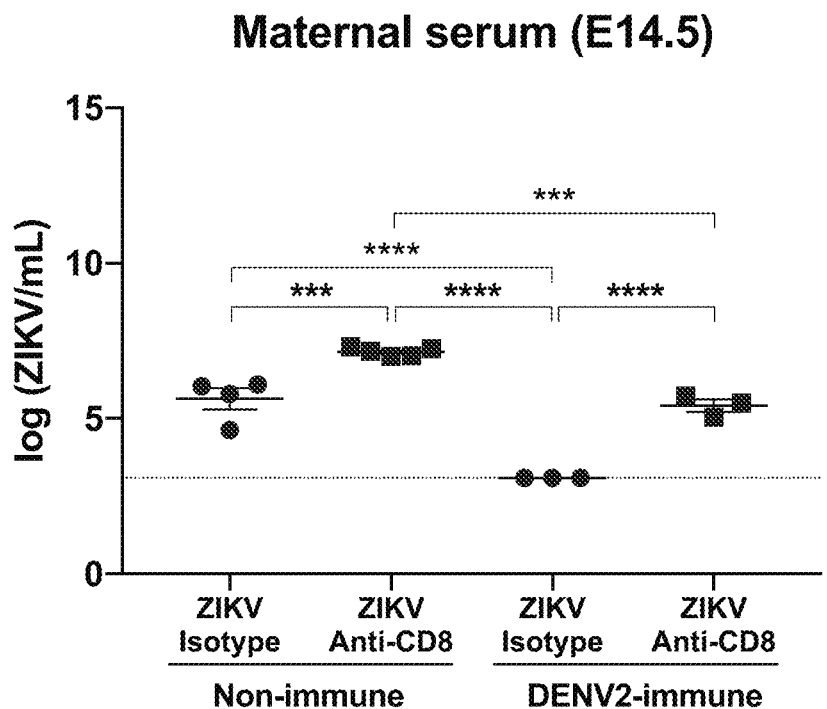
FIGS. 22A-22L: shows graphs that illustrate non-limiting results of the effect of CD4+, CD8+, or combined CD4+ and CD8+ T cell depletion on ZIKV viral burden in non-immune and DENV2-immune Ifnar1$^{-/-}$ dams in accordance with an embodiment of the present disclosure.
Figure 22B:
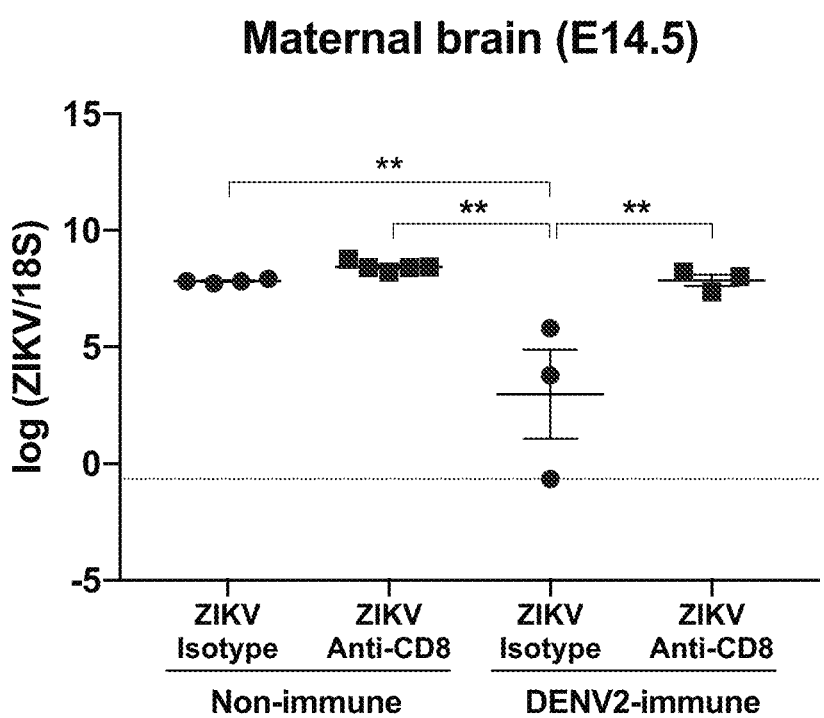
Figure 22C:
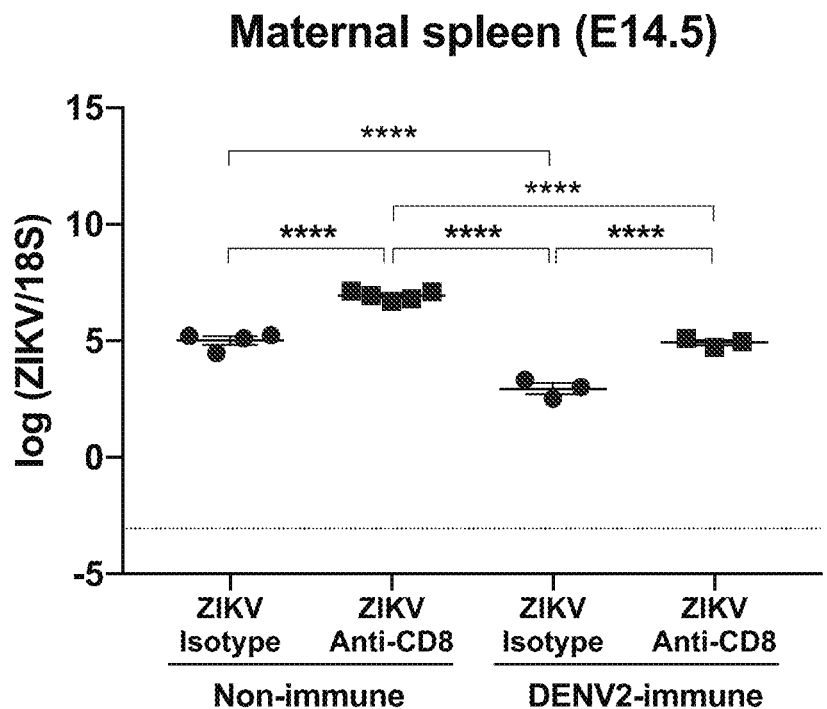
Figure 22D:
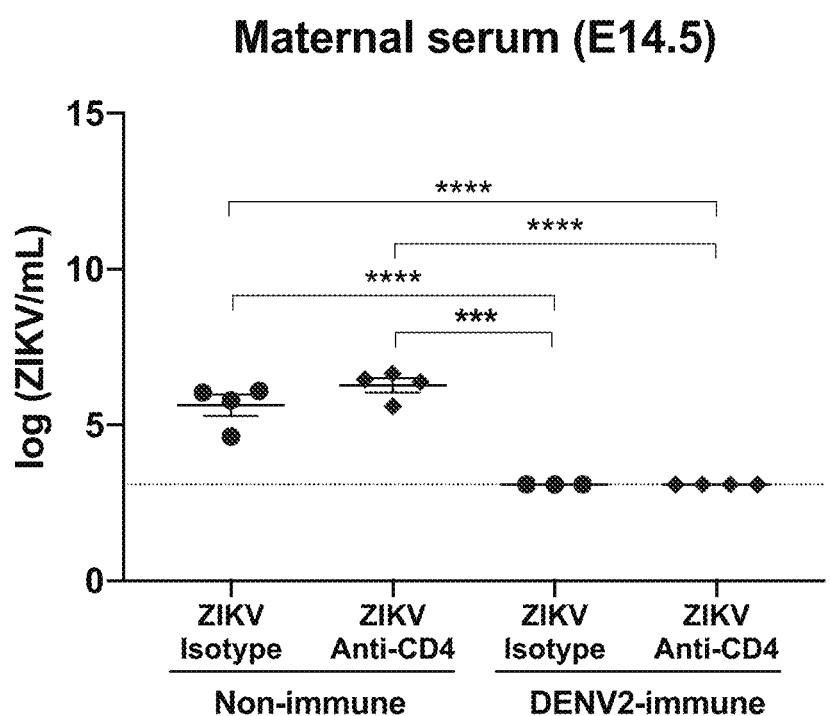
Figure 22E:
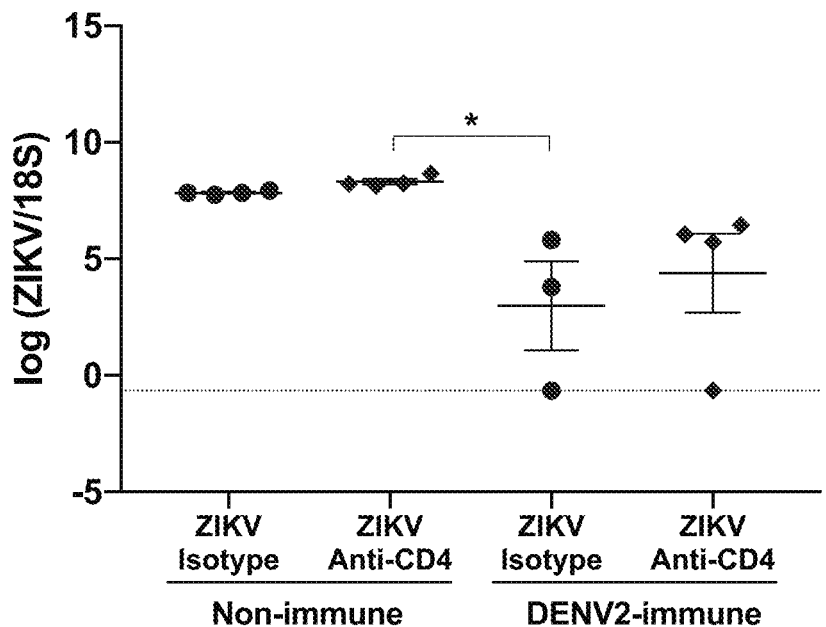
Figure 22F:
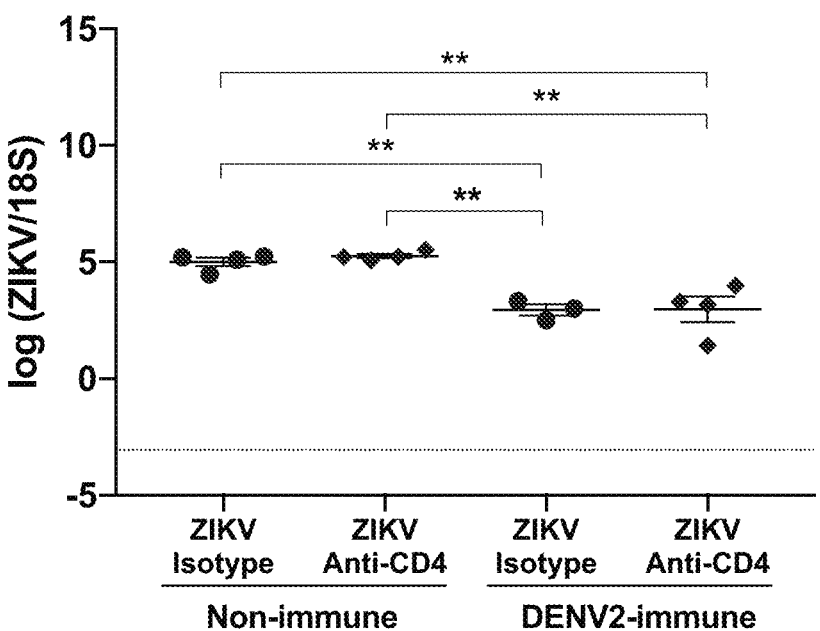
Figure 22G:
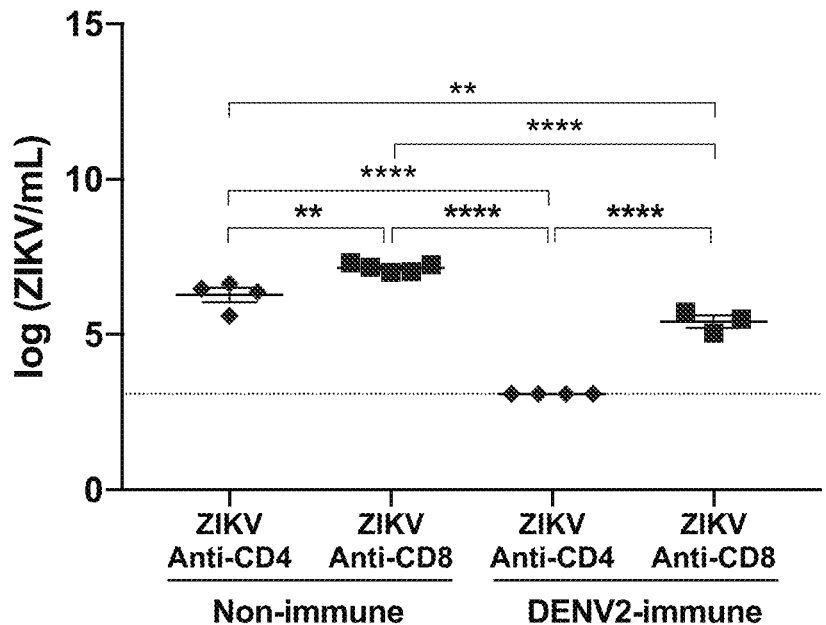
Figure 22H:
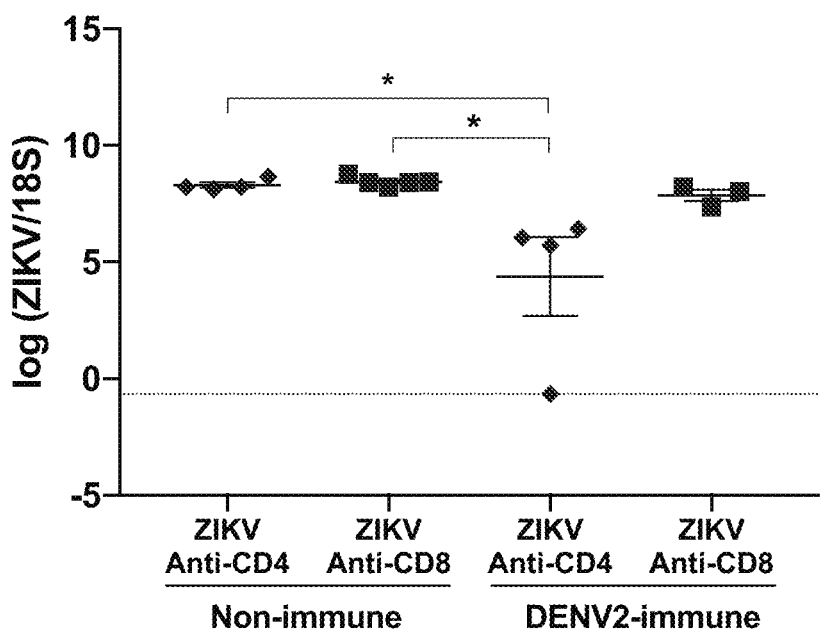
Figure 22I:
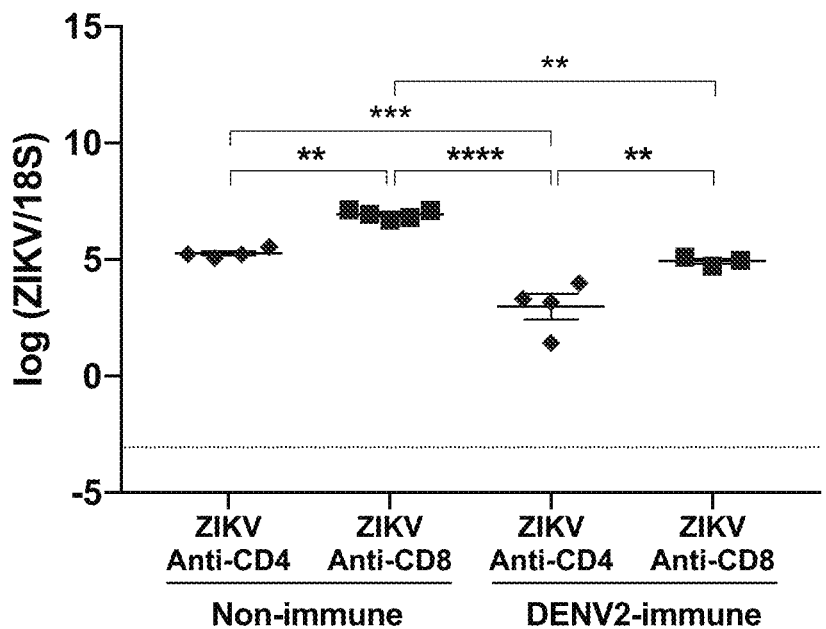
Figure 22J:
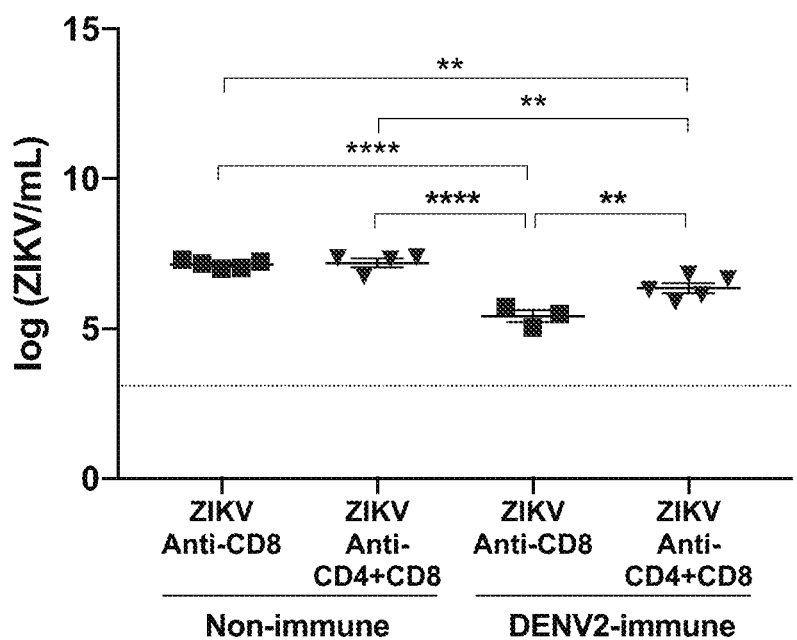
Figure 22K:
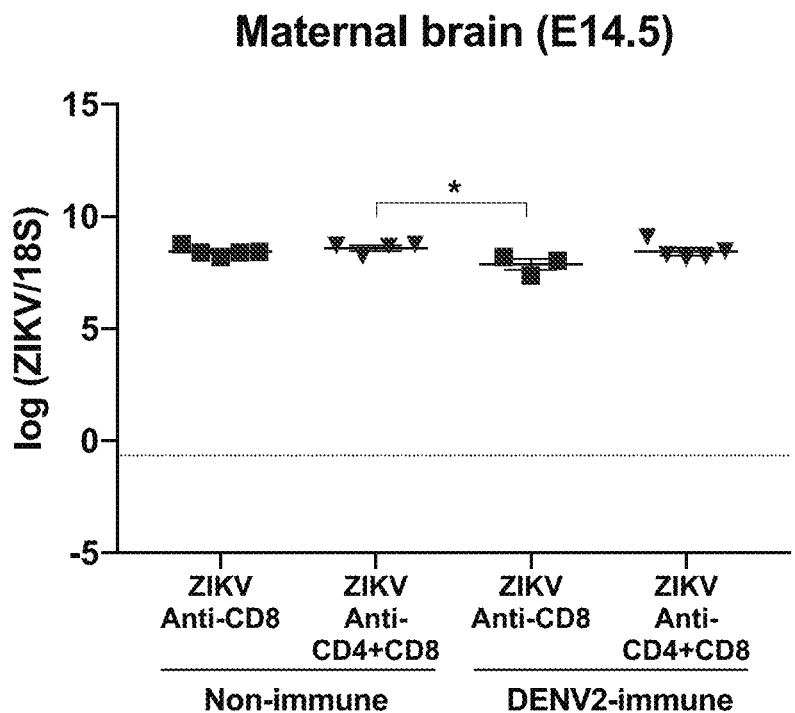

The following results are with respect to FIG. 22A to FIG. 22L, where non-immune and DENV2-immune WT dams that were administered isotype control Ab (Isotype) or anti-CD8 Ab (Anti-CD8) were inoculated R.O. at embryonic day 7.5 (E7.5) with 10$^4$ FFU of ZIKV FSS13025 or 10% FBS-PBS as Mock. All mice were injected I.P. with Ifnar1-blocking Ab on E6.5, one day prior to ZIKV challenge. DENV2-immune mice were generated after R.O. infection with 10$^4$ FFU of DENV2 strain S221 for 30 days prior to mating. FIG. 22A, fetus weight and (FIG. 22B) size at E14.5 were recorded. FIG. 22C to FIG. 22H, ZIKV RNA levels were measured by qRT-PCR of tissues collected from dams (serum, brain, and spleen), placentas with decidua, and fetuses (head and body) at E14.5. FIG. 22I to FIG. 22K, percentages of ZIKV infection in placentas with decidua, fetal heads, and fetal bodies at E14.5 were calculated. The populations were as follows:

TABLE 6

| n fetuses | Feature |
|---|---|
| 34 fetuses from 6 separate mothers | Non-immune-Mock |
| 35 fetuses from 5 separate mothers | Non-immune-ZIKV |
| 31 fetuses from 4 separate mothers | DENV2-immune-Mock |
| 43 fetuses from 5 separate mothers | DENV2-immune-ZIKV + isotype |
| 39 fetuses from 4 separate mothers | DENV2-immune-ZIKV + Anti-CD8 |

Total numbers of the fetal and placental units obtained from each dam in each group are indicated above each bar. Data were pooled from two independent experiments. Data are expressed as mean±SEM. *p<0.05, p<0.01, *p<0.001, ****p<0.0001. Tukey's one-way ANOVA for multiple comparisons was used for FIG. 22A to FIG. 22H, while two-sided Fisher's exact test was used for FIG. 22I to FIG. 22K.

Figure 22L:
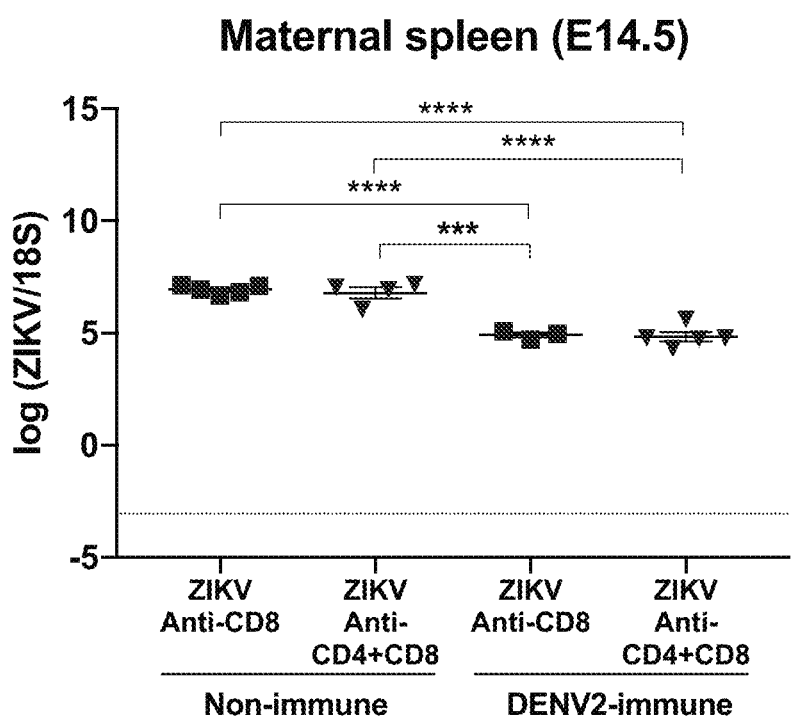

The results obtained are as follows:

In all cases, dams treated with anti-CD8 Ab had increased ZIKV RNA levels in the serum, brain, and spleen compared with those treated with isotype control Ab, and DENV immunity resulted in decreased viral RNA levels compared with the non-immune group (FIG. 22A to FIG. 22C). In contrast, dams treated with anti-CD4 Ab had similar maternal tissue viral burdens as isotype control Ab-treated animals (FIG. 22D to FIG. 22F). Comparison of anti-CD4 versus anti-CD8 Ab-treated groups also revealed that anti-CD8 but not anti-CD4 Ab treatment affected ZIKV RNA levels in maternal tissues (FIG. 22G to FIG. 22I). Finally, no difference was observed between the group treated with anti-CD8 Ab alone versus that treated with both anti-CD4 and anti-CD8 Abs in the brain and spleen of both non-immune and DENV-immune mice and serum of non-immune mice, whereas a higher ZIKV RNA burden was observed in DENV-immune mice administered both anti-CD4 and anti-CD8 Abs than in those treated with anti-CD8 Ab alone (FIG. 22J to FIG. 22L). Collectively, these results show a key role for CD8$^+$ T cells, with a more limited requirement for CD4$^+$ T cells, in DENV immune-mediated cross-protection of ZIKV infection in maternal tissues from Ifnar1$^{-/-}$ mice.

8.2 DENV2 Immunity Prevents Fetal Growth Restriction in Ifnar1 mAb-Treated WT Mice Via CD8$^+$ T Cells To confirm and extend the findings reported so far, the present inventors utilized a published model of ZIKV vertical transmission in WT mice with transient Ifnar1 blockade (Miner et al., 2016). Pretreatment with the Ifnar1-blocking Ab MAR1-5A3 (Sheehan et al., 2006) allows flaviviruses to replicate in WT mice without significantly impacting CD8$^+$ T cell differentiation into effector and memory cells (Pinto et al., 2011). WT C57BL/6 female mice were administered anti-Ifnar1 Ab one day before infection with DENV2, as DENV cannot inhibit type I interferon production and signaling in mouse cells, unlike in human cells (Aguirre and Fernandez-Sesma, 2017). Thirty days after DENV2 priming, mice were mated with male sires, followed by treatment of DENV2-immune and non-immune WT dams with anti-Ifnar1 Ab one day prior to ZIKV challenge on E7.5. Seven days later, at day E14.5, fetal weight, size, and characteristics were recorded, and maternal and fetal tissues were harvested.

The following results are with respect to FIG. 16A to FIG. 16D, where DENV2-immune WT dams were treated with anti-Ifnar1 mAb and challenged with ZIKV at E7.5 as described in FIG. 15A to FIG. 15K. Mice were administered isotype control or anti-CD8 Ab, also as described in FIG. 15A to FIG. 15K. On days 2 and 3 after ZIKV challenge (E9.5 and E10.5), ZIKV RNA levels in maternal (FIG. 16A) serum, (FIG. 16B) brain, and (FIG. 16C) spleen and (FIG. 16D) fetus+placenta+decidua were measured by qRT-PCR. The population was as follows:

TABLE 7

| n fetuses | Feature |
|---|---|
| 19 fetuses from 3 separate mothers | ZIKV + isotype |
| 35 fetuses from 4 separate mothers | ZIKV + Anti-CD8 at E9.5 |
| n = 46 fetuses from 6 separate mothers | ZIKV + isotype |
| 48 fetuses from 6 separate mothers | ZIKV + Anti-CD8 at E10.5 |

Data were pooled from two independent experiments. Data are expressed as mean±SEM. *p<0.05, p<0.01, **p<0.00001. Two-tailed Mann Whitney test was used.

Figure 16A:
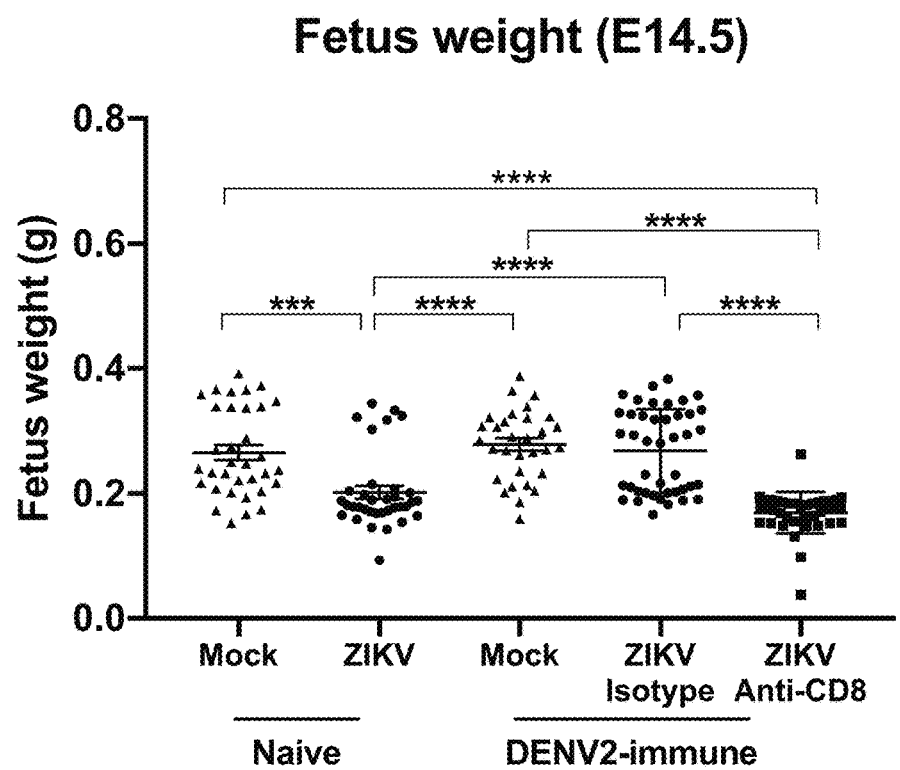
FIGS. 16A-16K: shows graphs that illustrate non-limiting results of fetal weight and size and viral burden in Ifnar1-blocking Ab-treated WT dams with or without CD8+ T cell depletion in accordance with an embodiment of the present disclosure.
Figure 16B:
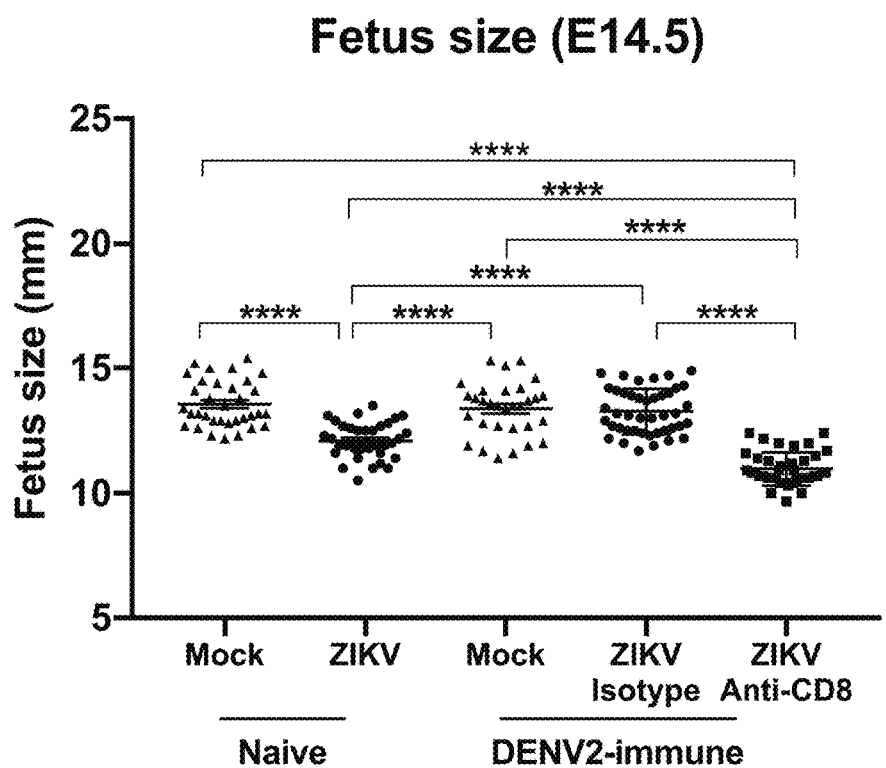
Figure 16C:
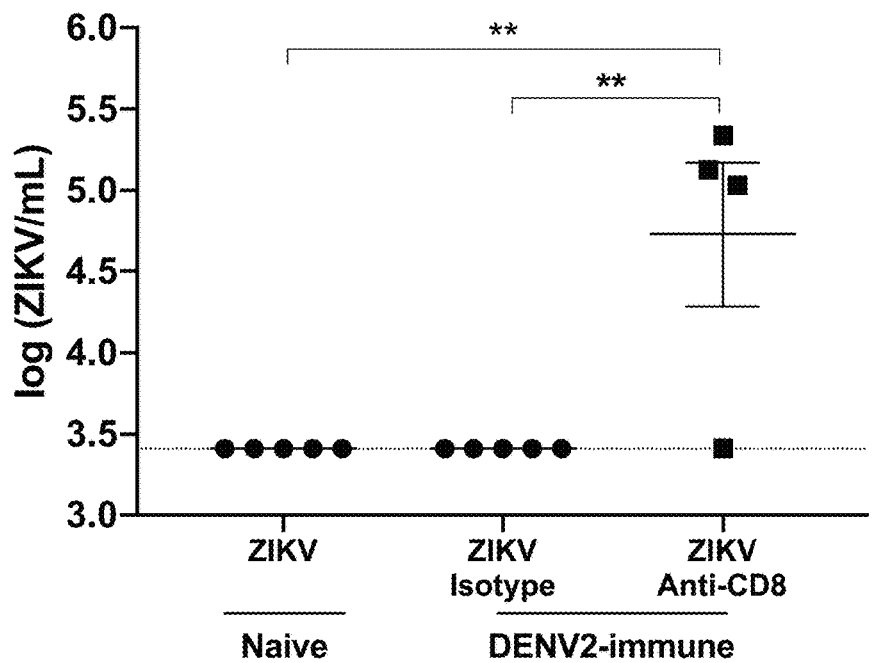
Figure 16D:
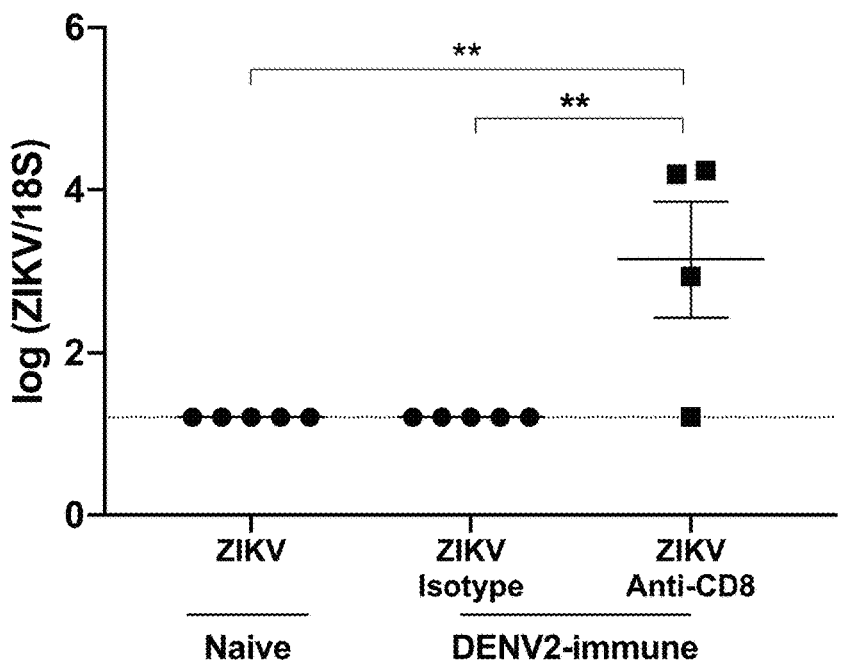
Figure 16E:
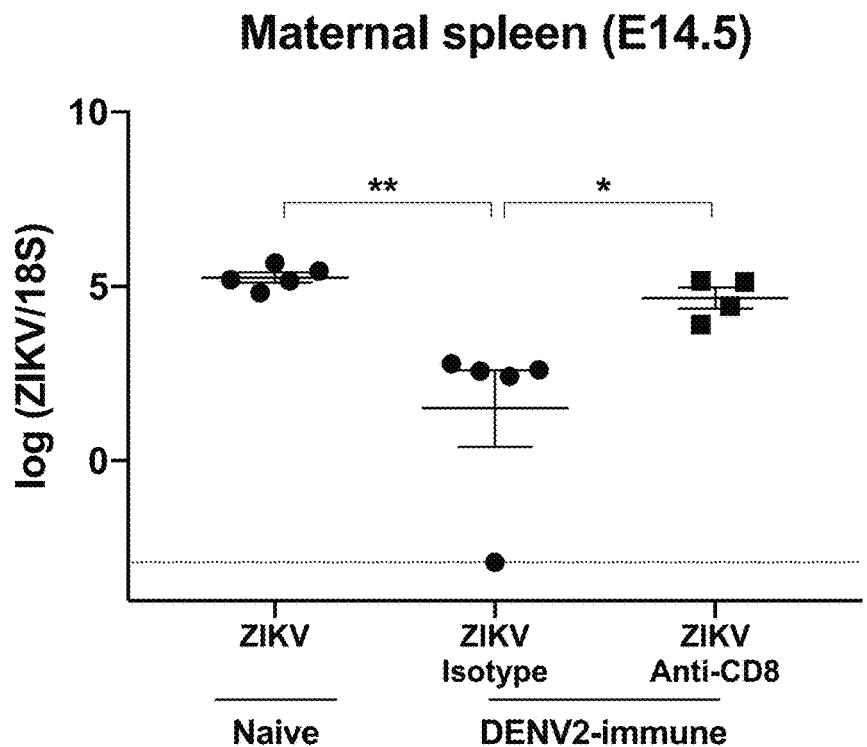
Figure 16F:
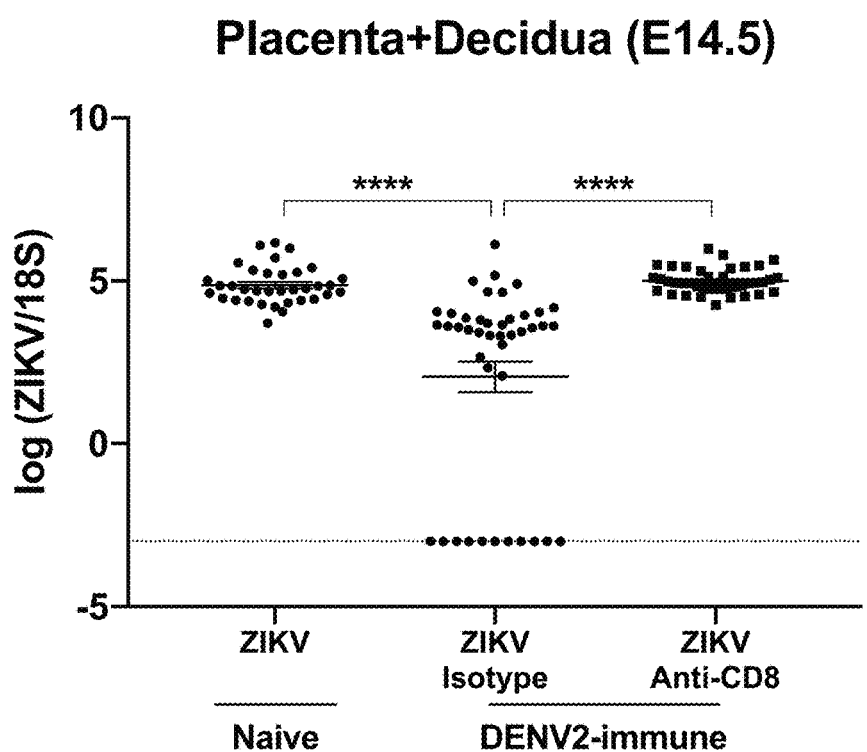
Figure 16G:
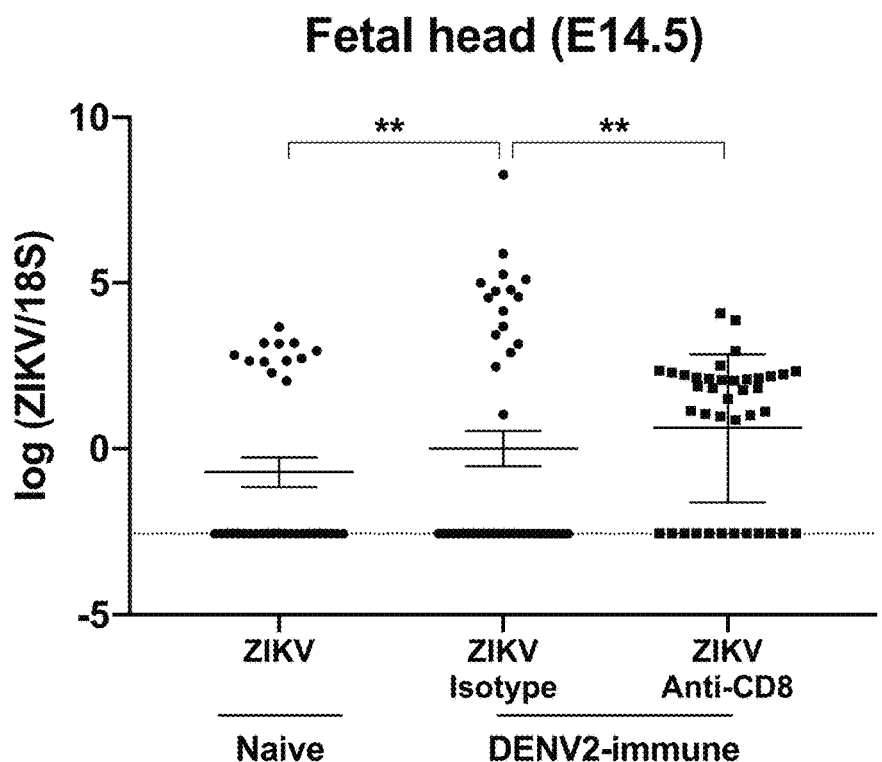
Figure 16H:
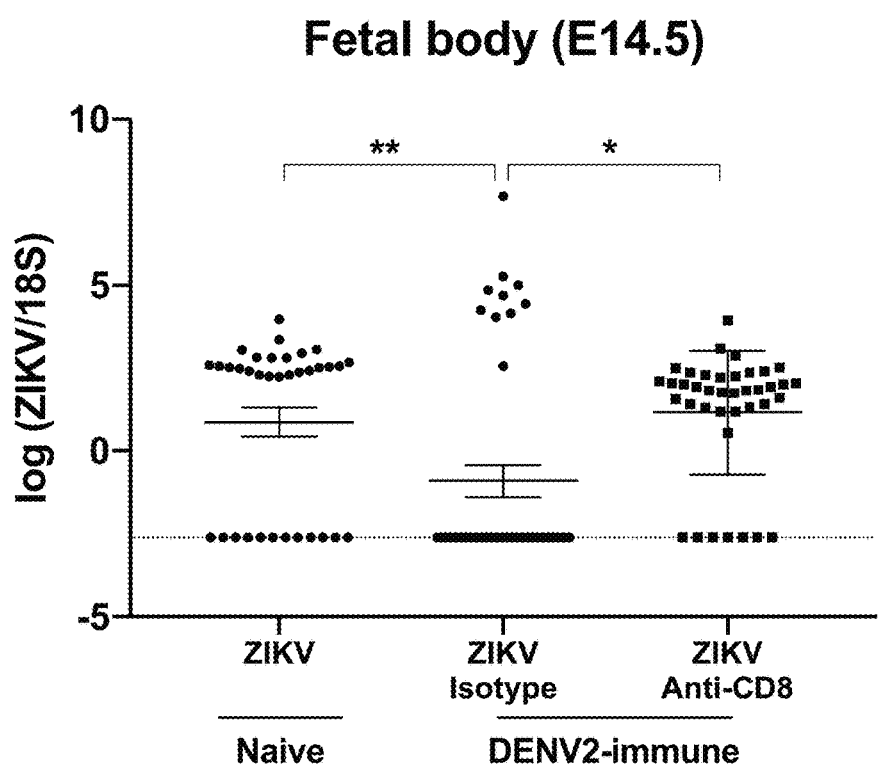
Figure 16I:
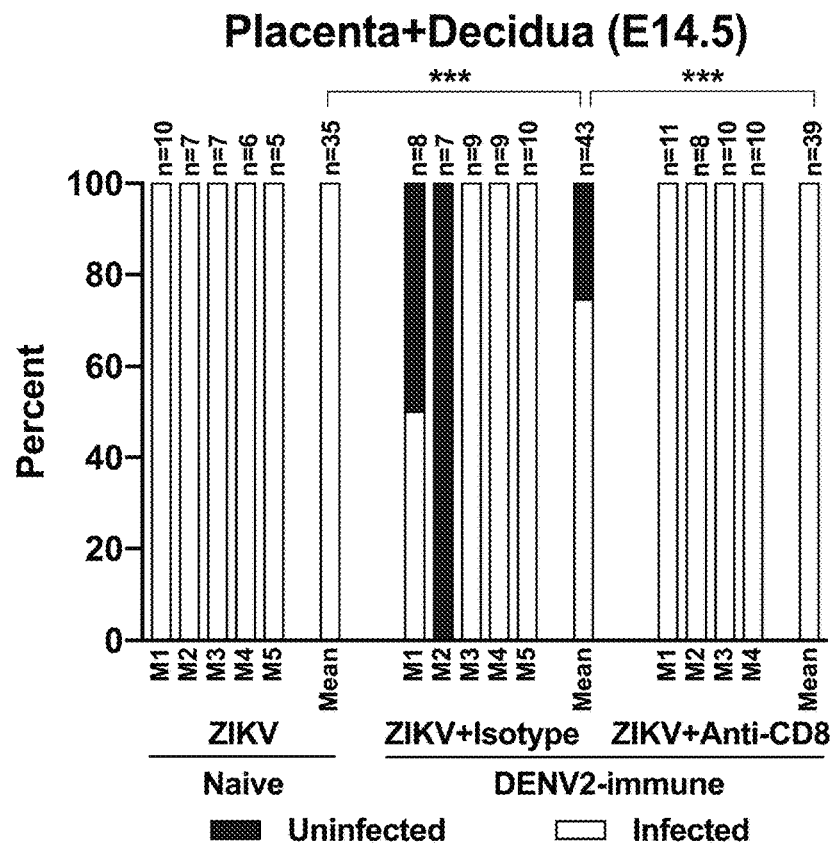
Figure 16J:
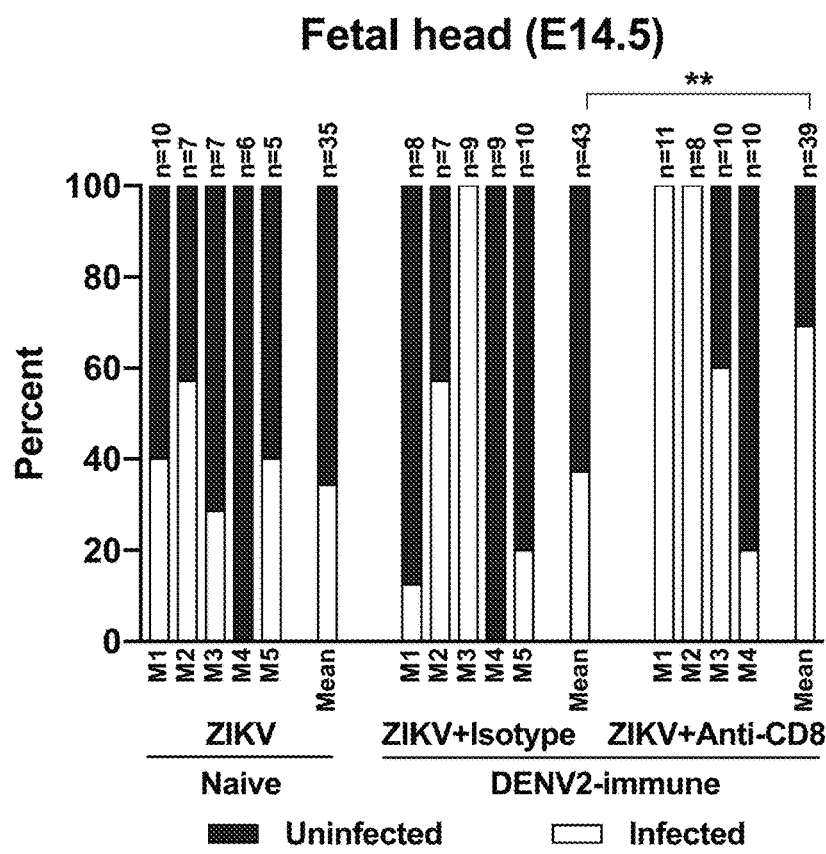
Figure 16K:
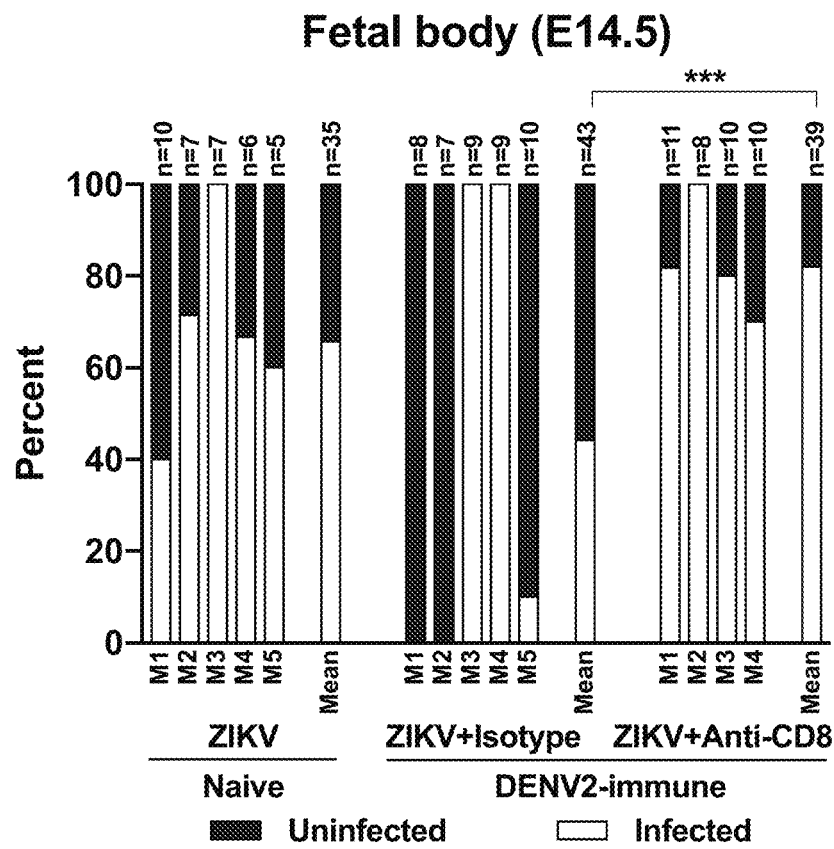
Figure 23:
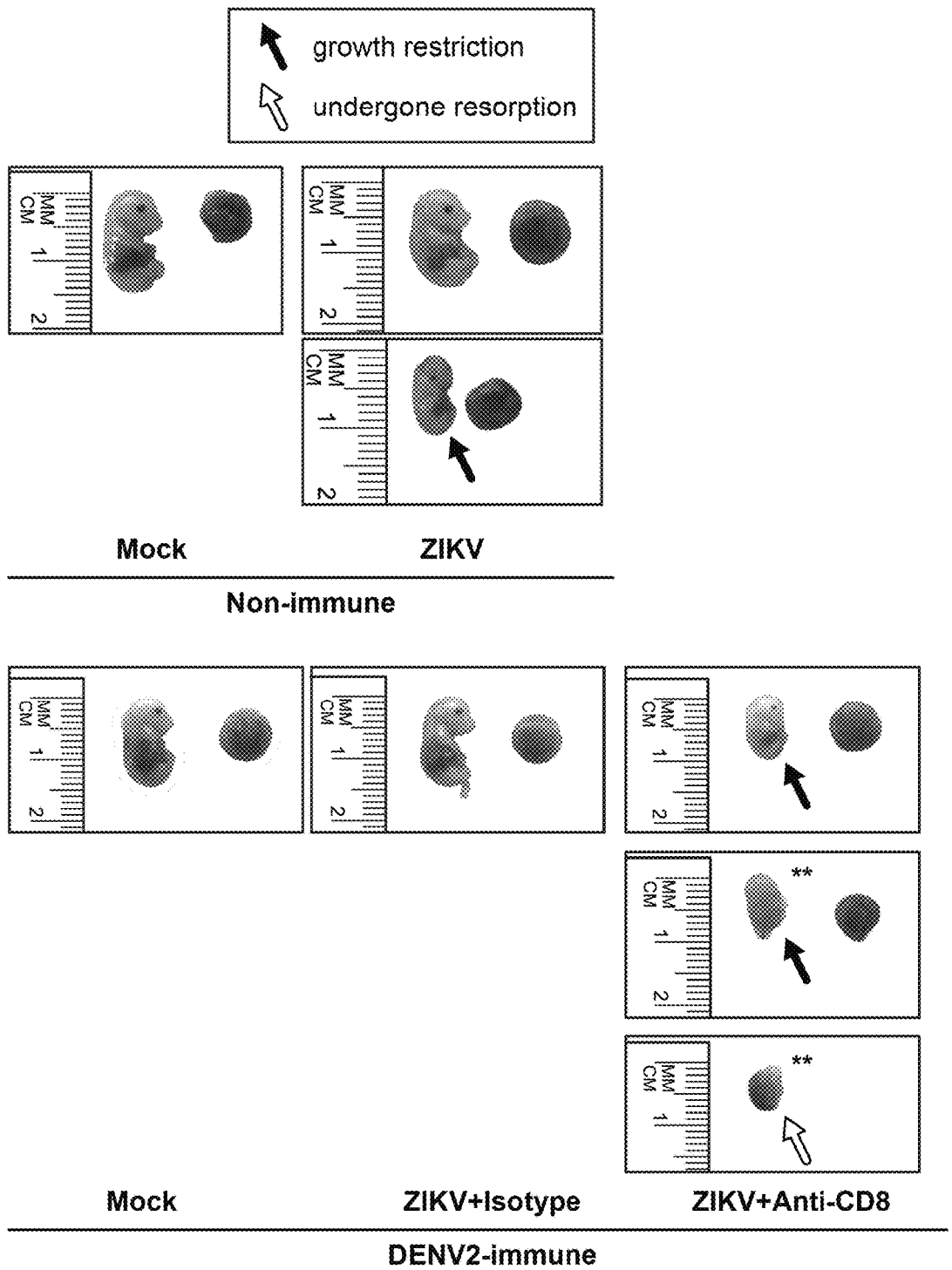
FIG. 23: shows graphs that illustrate non-limiting results of a phenotype of fetuses at E14.5 from non-immune or DENV2-immune WT dams treated with Ifnar1-blocking Ab with or without CD8+ T cell depletion in accordance with an embodiment of the present disclosure.

The results obtained are as follows:

As seen in the Ifnar1$^{-/-}$ mouse model, decreased fetal weight and size was observed in ZIKV infected non-immune mice, whereas prior DENV immunity prevented fetal growth restriction with the fetal size and weight comparable to the mock-infected control group (FIG. 16A and FIG. 16B). Again, fetal growth restriction and resorption were observed in DENV-immune mice treated with anti-CD8 Ab (FIG. 16A and FIG. 16B, and FIG. 23). These results demonstrate that, in WT mice with transient Ifnar1 blockade, prior DENV immunity affords protection against ZIKV-induced fetal growth restriction in a CD8$^+$ T cell-dependent manner.

In FIG. 23, non-immune or DENV2-immune WT dams that were treated with Ifnar1-blocking Ab were challenged with ZIKV at E7.5 as described in A-K. Tissues were harvested 7 days post-infection at E14.5. Representative images of fetuses and placentas from non-immune or DENV2-immune dams with or without anti-CD8 Ab administration are shown. The populations used are as follows:

TABLE 8

| n mothers | Feature |
| --- | --- |
| 6 separate mothers | Non-immune-Mock |
| 5 separate mothers | Non-immune-ZIKV |
| 4 separate mothers | DENV2-immune-Mock |
| 5 separate mothers | DENV2-immune-ZIKV + isotype |
| 4 separate mothers | DENV2-immune-ZIKV + Anti-CD8 |

Dark grey and light grey arrows indicate the presence of fetal growth restriction and resorption, respectively.

Analysis of viral burden revealed that ZIKV RNA was consistently present in maternal spleens, placentas with decidua, and fetal bodies, with reduced levels in DENV-immune mice relative to non-immune dams. Administration of anti-CD8 Ab abrogated the protective effect of DENV immunity, with significantly higher viral RNA levels detected in both maternal and fetal tissues compared to isotype control Ab-treated DENV-immune dams (FIG. 16C-FIG. 16H). The efficiency of anti-CD8 Ab-mediated CD8$^+$ T cell depletion in the spleen and decidua/placenta were >95% (FIG. 24A and FIG. 24B).

Figure 24A:
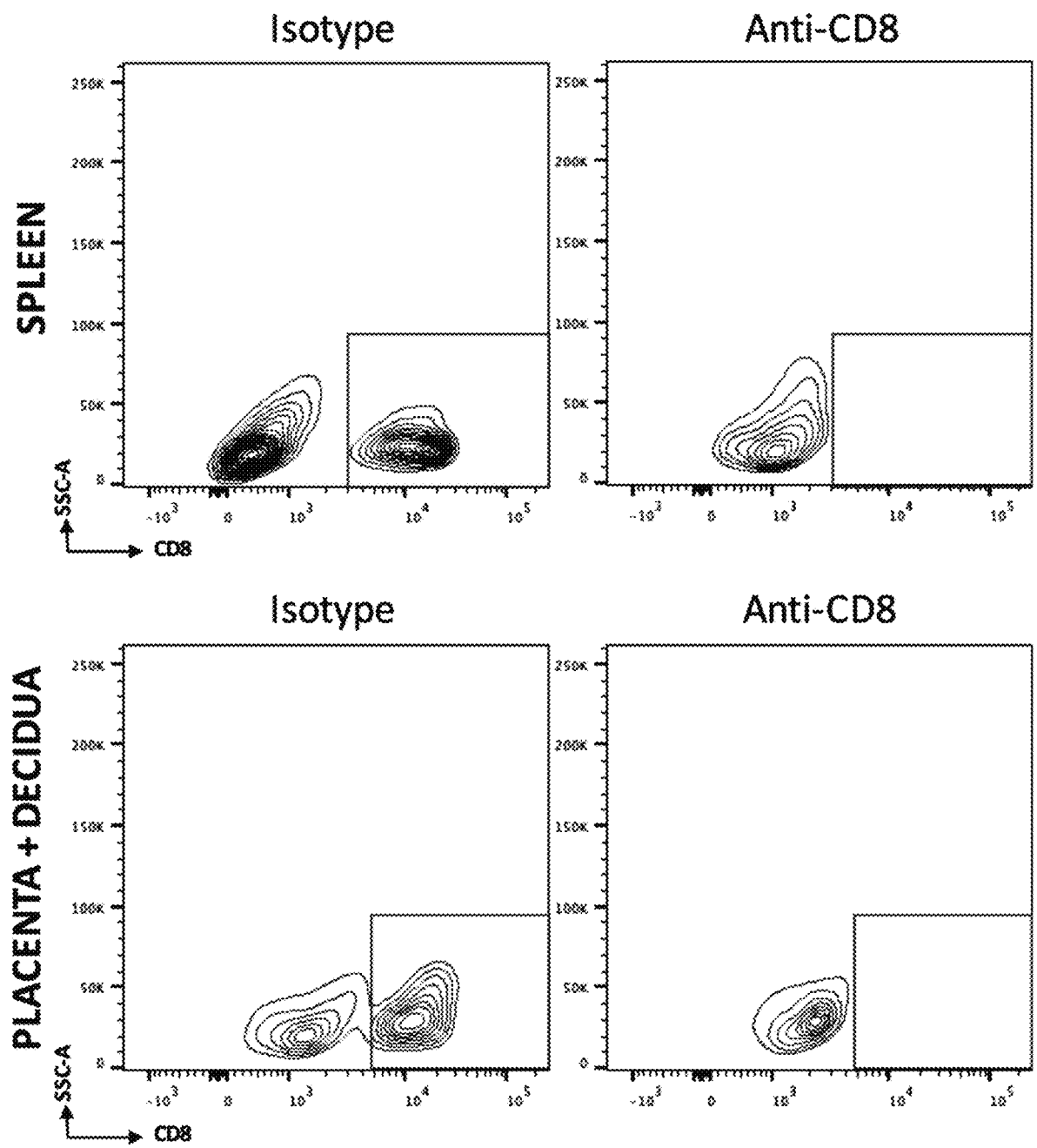
FIGS. 24A-24B: shows graphs that illustrate non-limiting results of efficiency of CD8+ T cell depletion in WT dams administered anti-CD8 Ab in accordance with an embodiment of the present disclosure.
Figure 24B:
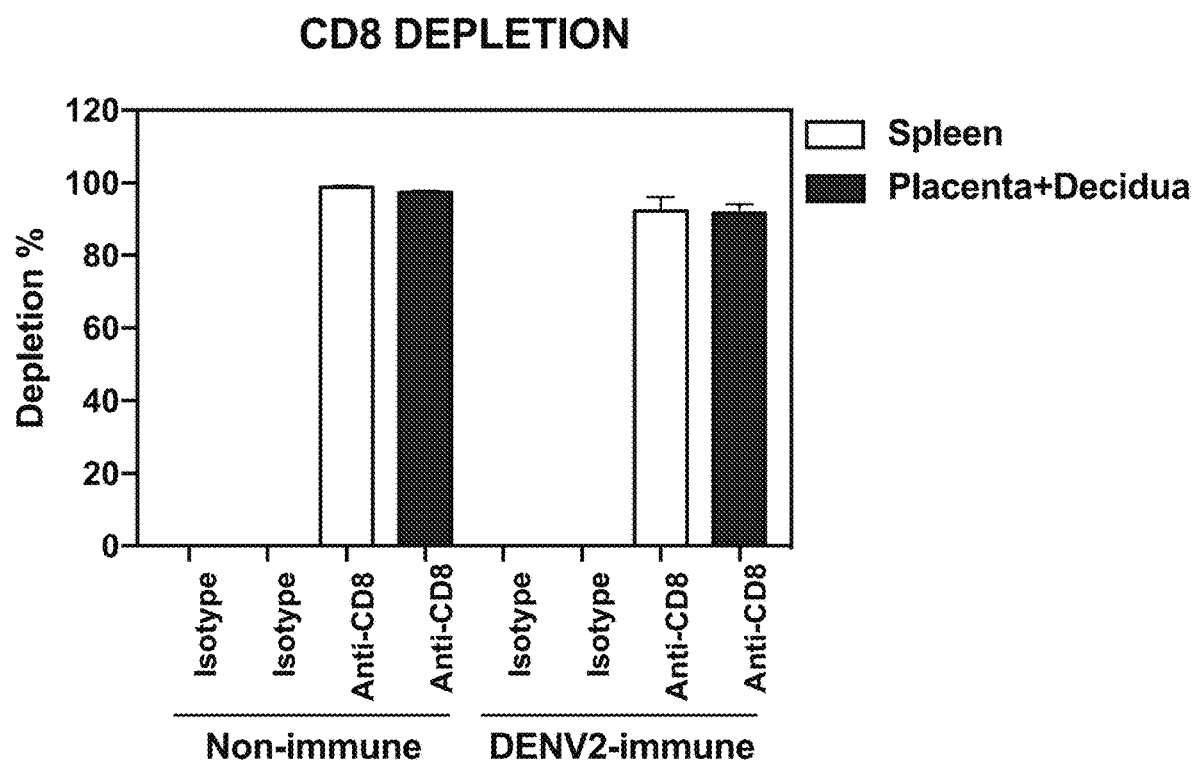

In FIG. 24, pregnant non-immune or DENV2-immune WT mice were challenged with ZIKV at E7.5 as described in FIG. 16A to FIG. 16K. In FIG. 24A, the gating strategy used to analyze the presence of CD8$^+$ T cells by flow cytometry in the spleen and decidua/placenta is illustrated. All plots represented were first gated on CD3+ cells. In FIG. 24B, the percentages of CD8$^+$ T cell depletion in spleen and decidua/placenta are represented for isotype control or anti-CD8 Ab-treated dams in both non-immune and DENV-2 immune groups.

In DENV-immune dams, anti-CD8 Ab treatment resulted in a greater percentage of ZIKV infection in placentas with decidua and fetal heads and bodies compared with isotype control Ab treatment, with 100% versus 74% in placentas with decidua, 69% versus 37% in fetal heads, and 82% versus 44% in fetal bodies. The differences between the isotype and anti-CD8 Ab treated DENV immune mice were significant for all three tissues (FIG. 16I to FIG. 16K) (Two-sided Fisher's exact test: p<0.001 for placenta with decidua, p<0.01 for fetal head, and p<0.001 for fetal body).

As decreased maternal ZIKV viremia may lead to lower ZIKV levels in the maternal-fetal interface, the present inventors compared viral burden in maternal and fetal tissues of DENV-immune mice treated with isotype control Ab versus anti-CD8 at early time points after ZIKV challenge.

The present results are with respect to FIG. 17A to FIG. 17E, where DENV2-immune WT dams were treated with anti-Ifnar1 mAb and challenged with ZIKV at E7.5 as described in FIG. 16A to FIG. 16K. Mice were administered isotype control or anti-CD8 Ab, also as described in FIG. 16A to FIG. 16K. On days 2 and 3 after ZIKV challenge (E9.5 and E10.5), ZIKV RNA levels in maternal (FIG. 17A) serum, (FIG. 17B) brain, and (FIG. 17C) spleen and (FIG. 17D) fetus+placenta+decidua were measured by qRT-PCR. The populations were as follows:

TABLE 9

| n fetuses | Feature |
| --- | --- |
| 19 fetuses from 3 separate mothers | ZIKV + isotype |
| 35 fetuses from 4 separate mothers | ZIKV + Anti-CD8 at E9.5 |
| 46 fetuses from 6 separate mothers | ZIKV + isotype |
| 48 fetuses from 6 separate mothers | ZIKV + Anti-CD8 at E10.5 |

Data were pooled from two independent experiments. Data are expressed as mean±SEM. *p<0.05, p<0.01, **p<0.00001. Two-tailed Mann Whitney test was used.

Figure 17A:
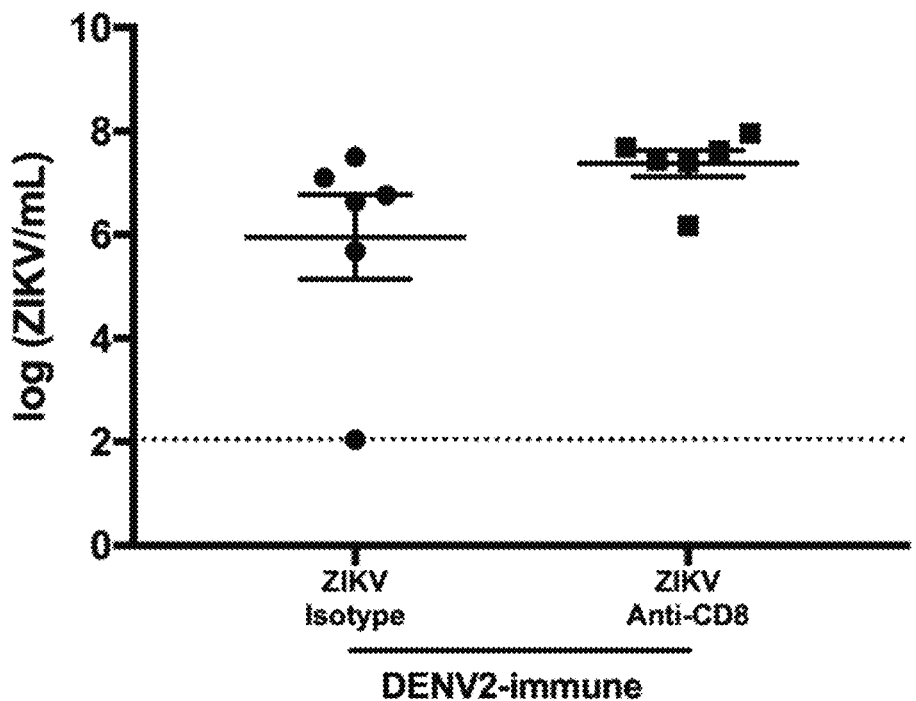
FIGS. 17A-17E: shows graphs that illustrate non-limiting results of ZIKV burden in Ifnar1-blocking Ab-treated WT dams and their fetuses on day 2 and 3 after ZIKV infection in accordance with an embodiment of the present disclosure.
Figure 17B:
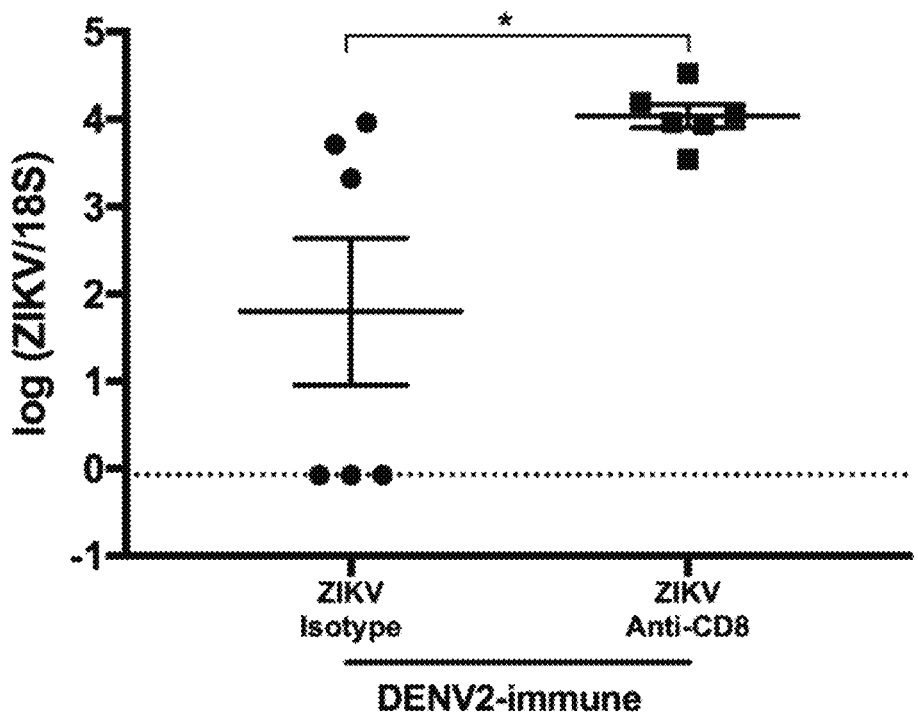
Figure 17C:
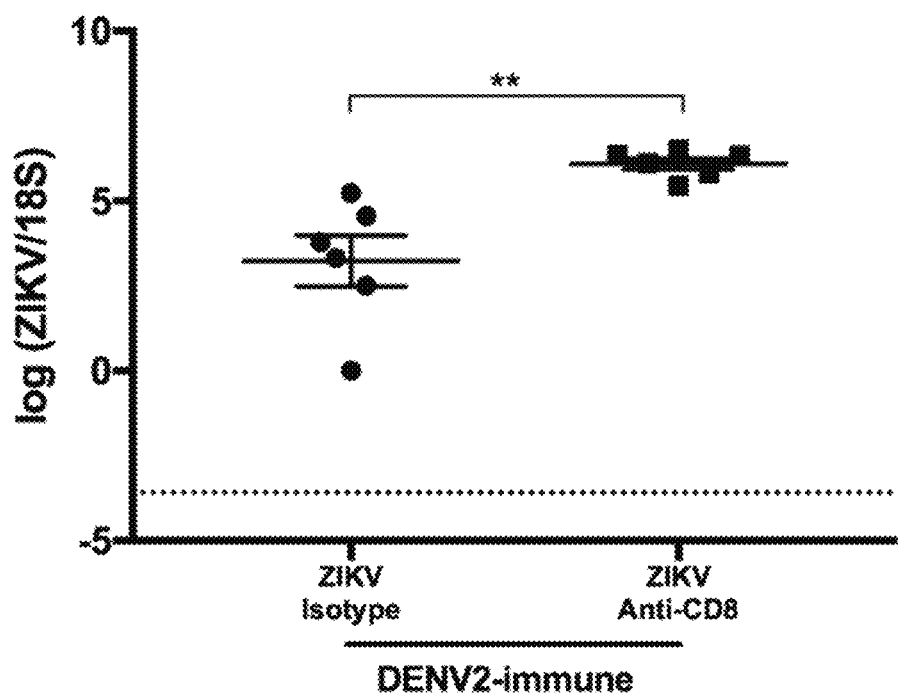
Figure 17D:
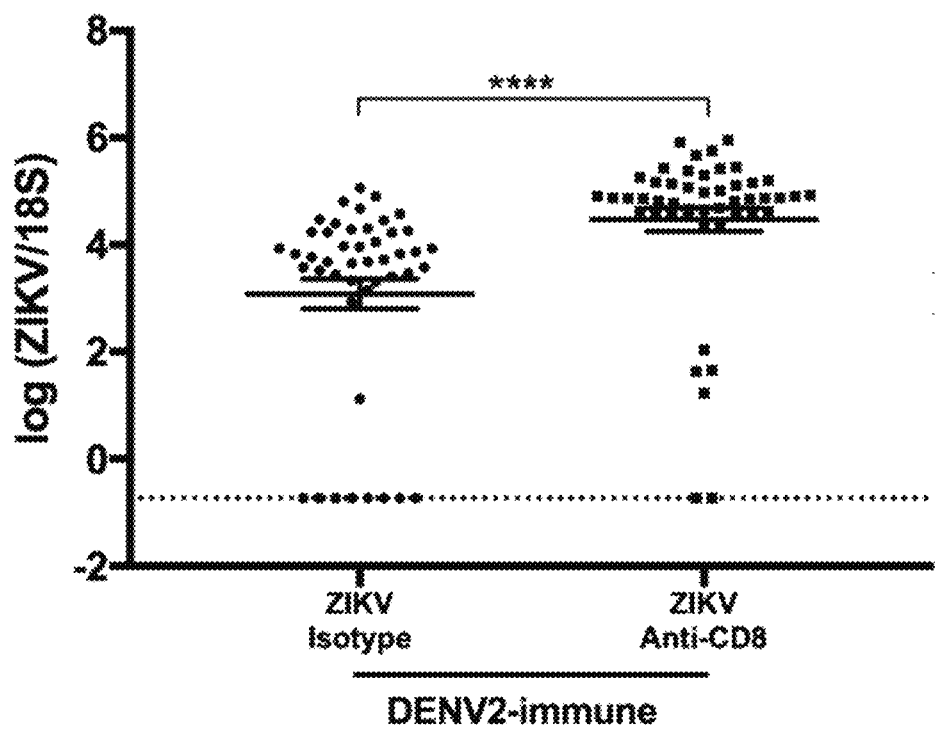
Figure 17E:
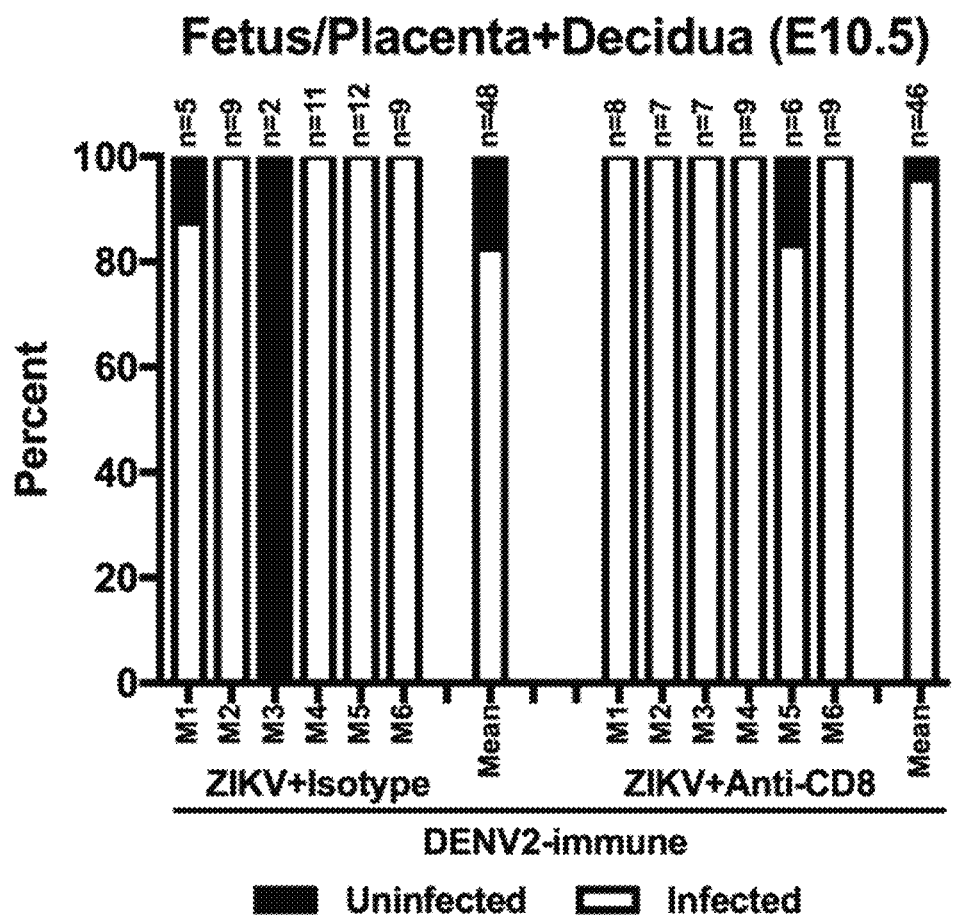

The results obtained are as follows:

At E9.5 and E10.5 (2 and 3 days after ZIKV challenge of E7.5 mothers), similar levels of ZIKV RNA were present in the maternal serum of DENV-immune mice treated with isotype control Ab or anti-CD8 (FIG. 17A). In contrast, higher ZIKV RNA levels were detected in the maternal brain and spleen at only E10.5 and in the placenta with decidua at both E9.5 and E10.5 in anti-CD8 Ab-treated than isotype control Ab-treated mice (FIG. 17B to FIG. 17D). No difference was observed in the percentages of infection of the placentas with decidua between the two groups despite higher levels of viral RNA in the placenta with decidua from the anti-CD8 group (FIG. 17E). Taken together, these data suggest that in WT mice with transient Ifnar1 blockade, prior DENV immunity controls ZIKV infection in both maternal and fetal tissues via DENV-exposed memory CD8$^+$ T cells. However, early during infection, ZIKV levels in circulation are not impacted by these T cells; once blood-borne ZIKV spreads and replicates in distal sites, including the maternal-fetal interface, DENV-elicited memory CD8$^+$ T cells assume an important role in limiting ZIKV infection of tissues.

8.3 Polyfunctionality of Cross-Reactive CD8$^+$ T Cells in the Maternal Spleen of DENV-Immune WT Mice with Transient Ifnar1 Blockade Five H-2$^b$ restricted ZIKV-derived CD8$^+$ T cell epitopes (prM$_{169-177}$ (SEQ ID NO: 19), E$_{294-302}$ (SEQ ID NO: 21), E$_{297-305}$ (SEQ ID NO: 25), NS3$_{1866-1874}$ (SEQ ID NO: 5), and NS5$_{2783-2792}$ (SEQ ID NO: 20)) have recently been identified by the present inventors that were cross-reactive with those induced in DENV2-infected mice (Wen et al., 2017a). To understand the contribution of DENV2-elicited CD8$^+$ T cells to protection against ZIKV infection during pregnancy in DENV-immune WT mice with transient Ifnar1 blockade, the present inventors assessed the quantity and phenotype of cross-reactive CD8$^+$ T cells in the maternal spleen by performing intracellular cytokine staining (ICS) analysis.

The following results are with respect to FIG. 18A to FIG. 18I, where non-immune or DENV2-immune WT dams with transient Ifnar1 blockade were challenged with ZIKV at E7.5 or injected 10% FBS-PBS (MOCK) as described in FIG. 16A to FIG. 16K. Seven days after ZIKV infection (E14.5), mice were sacrificed, and spleens were processed for ICS analysis. The percentages (FIG. 18A and FIG. 18B) and numbers (FIG. 18C) of CD44$^{high}$CD62L$^{low}$ CD8$^+$ T cells producing IFNγ are shown. The percentages (FIG. 18D and FIG. 18E) and numbers (FIG. 18F) of CD44$^{high}$CD62L$^{low}$ CD8$^+$ T cells producing both IFNγ and TNF are represented. The percentages (FIG. 18G and FIG. 18H) and numbers (FIG. 18I) of CD44$^{high}$CD62L$^{low}$ CD8$^+$ T cells expressing granzyme B are shown. The following numbers of dams were used: Non-immune (n=6 MOCK and n=5 ZIKV) and DENV2-immune (n=4 MOCK and n=5 ZIKV). Data were pooled from two independent experiments and are expressed as mean±SEM. *p<0.05, **p<0.01. Two-tailed Mann-Whitney test was used to compare MOCK versus ZIKV-infected or non-immune versus DENV2-immune mice for each stimulation condition in FIG. 18B to FIG. 18J.

Figure 18A:
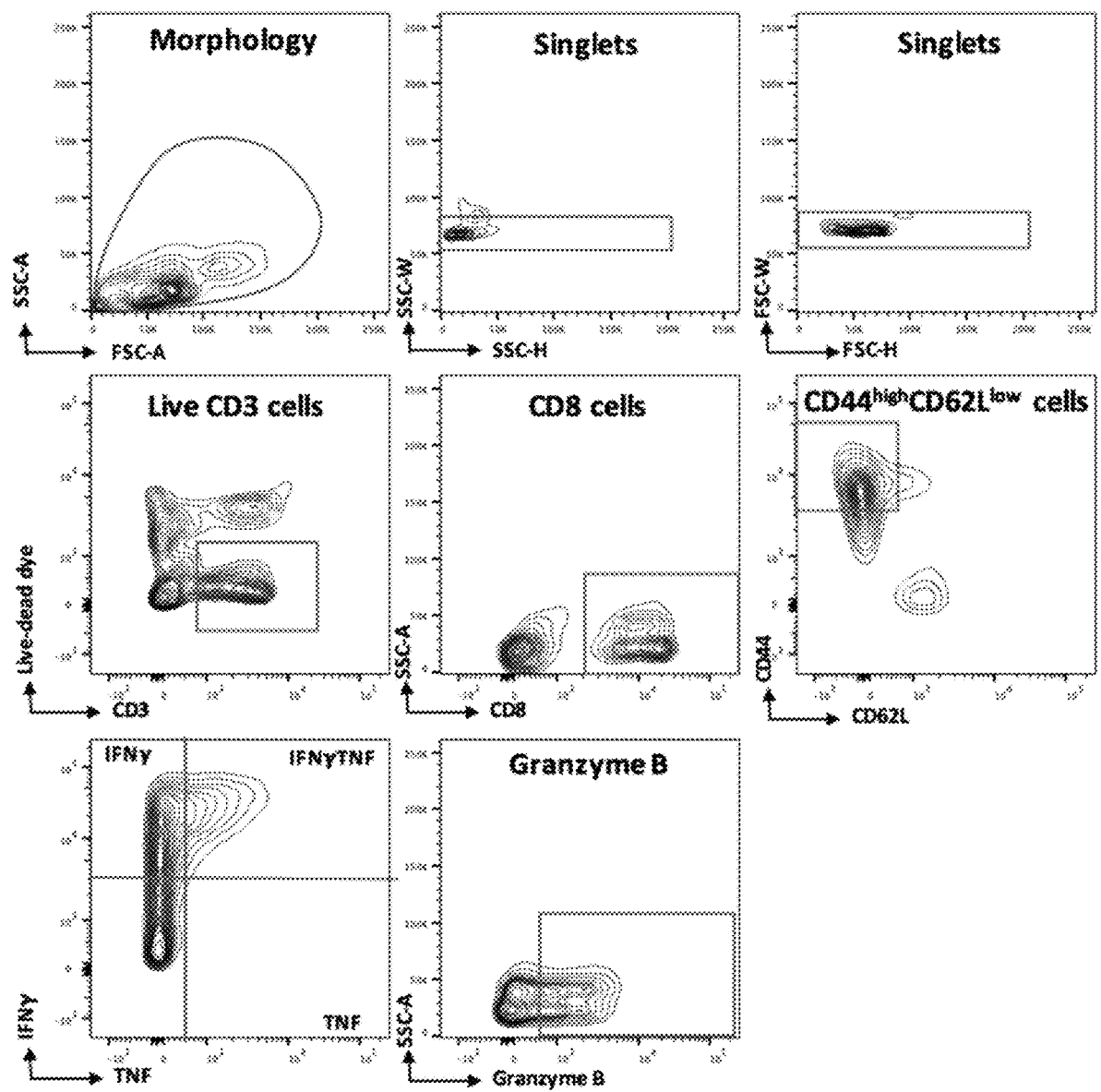
FIGS. 18A-18J: shows graphs that illustrate non-limiting results of cross-reactive epitope-specific CD8+ T cell response in spleens from Ifnar1-blocking Ab-treated WT dams on day 3 after ZIKV infection in accordance with an embodiment of the present disclosure.
Figure 18B:
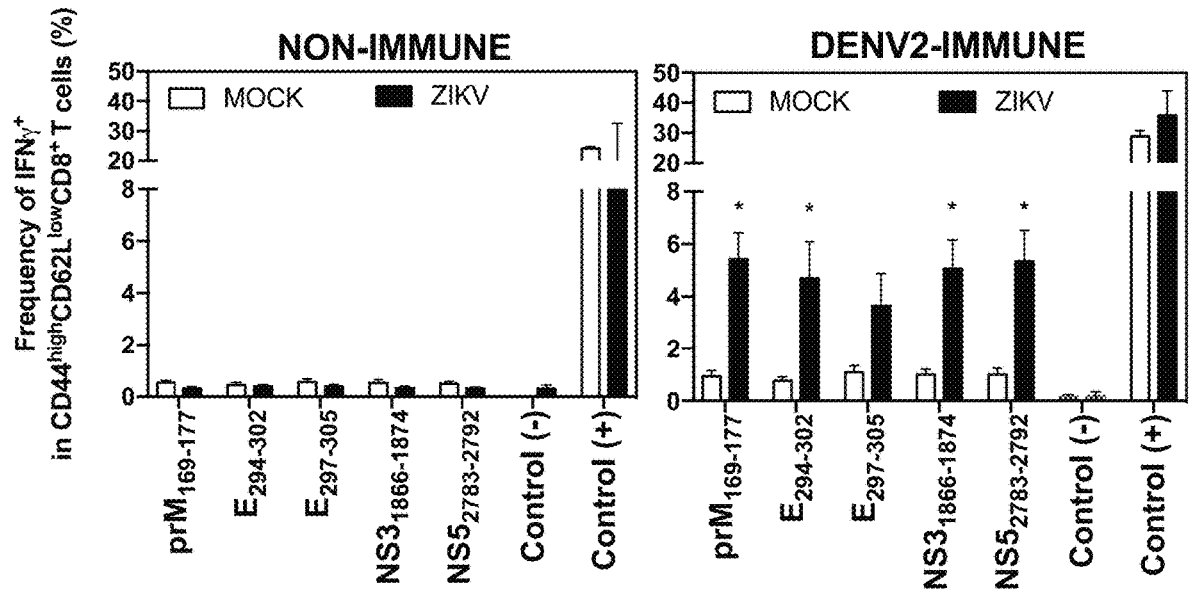
Figure 18C:
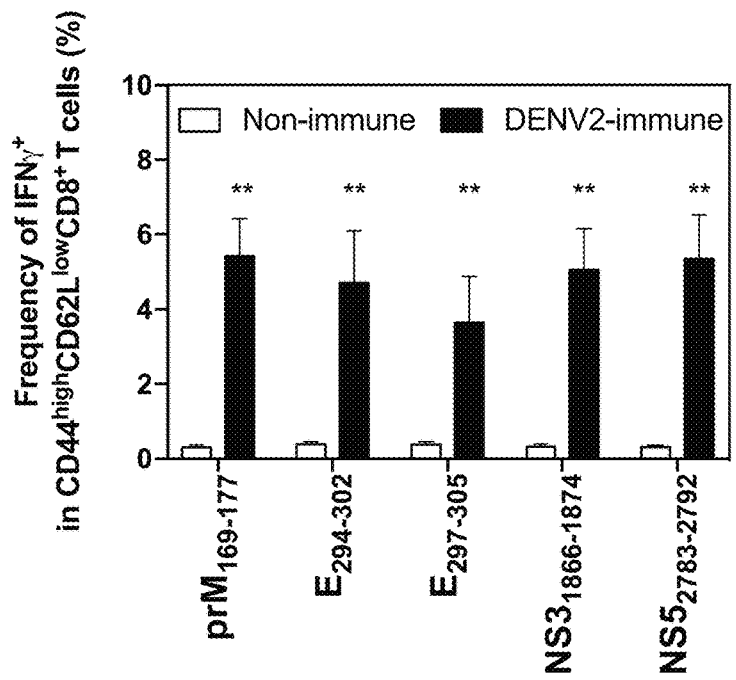
Figure 18D:
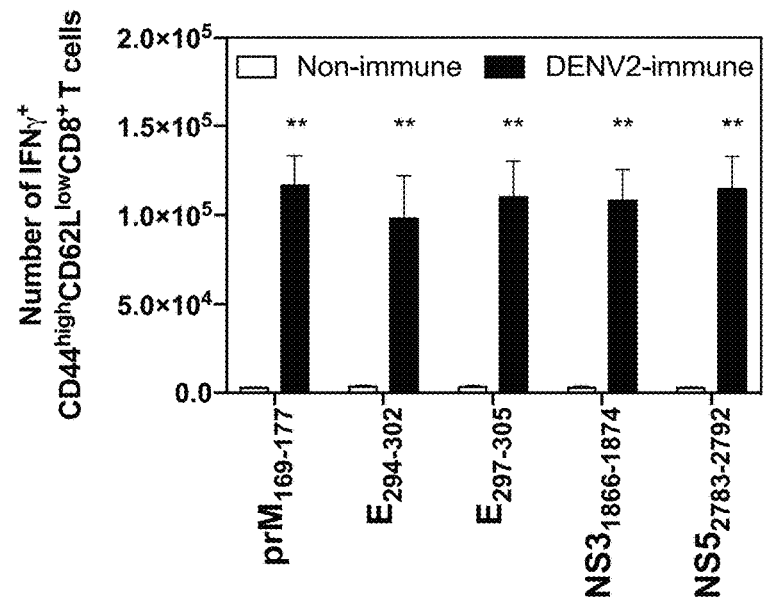
Figure 18E:
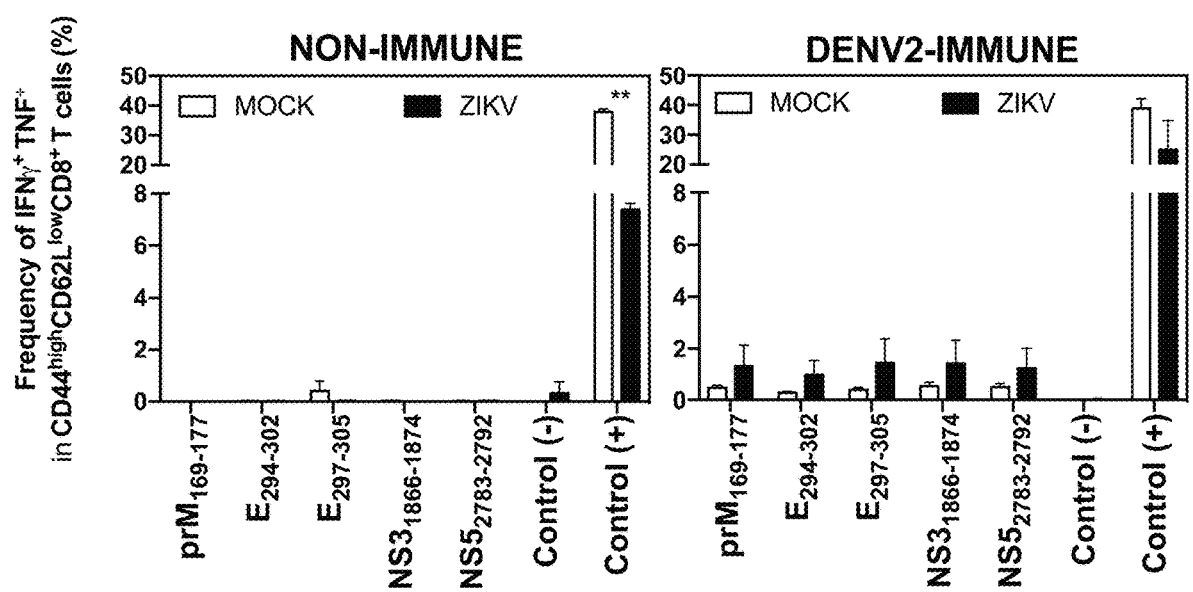
Figure 18F:
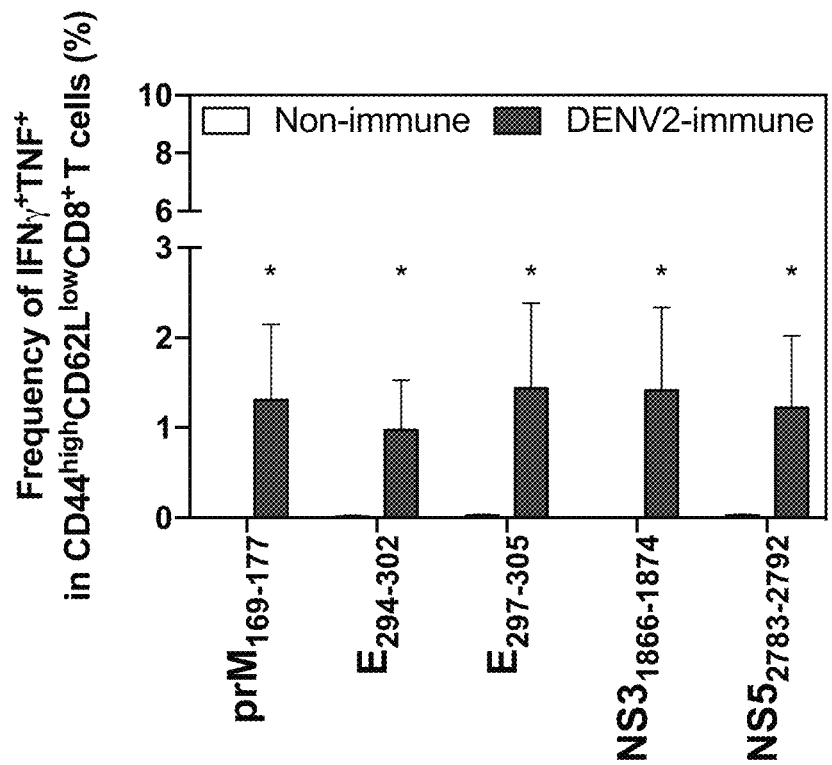
Figure 18G:
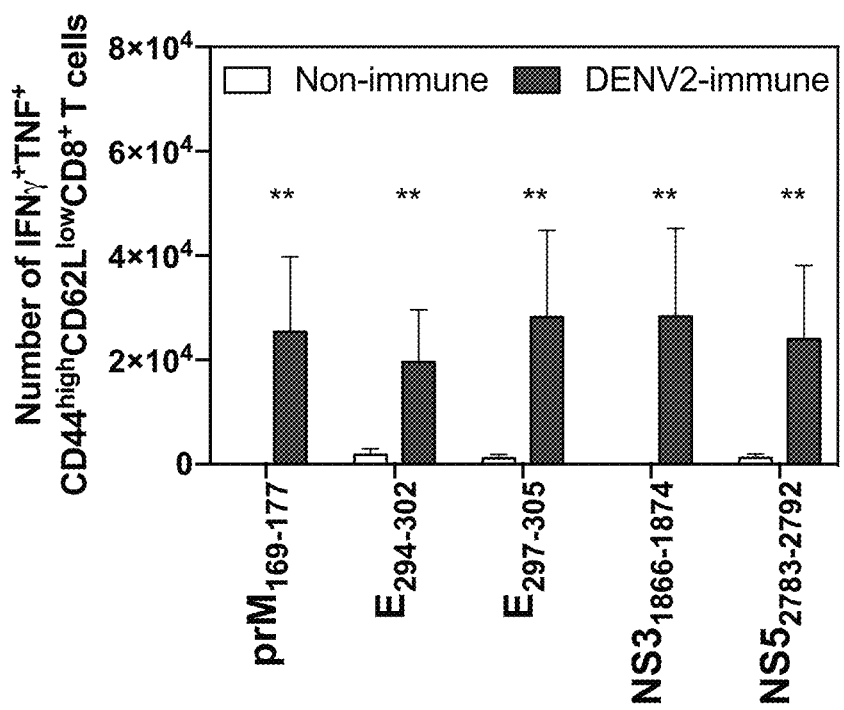
Figure 18H:
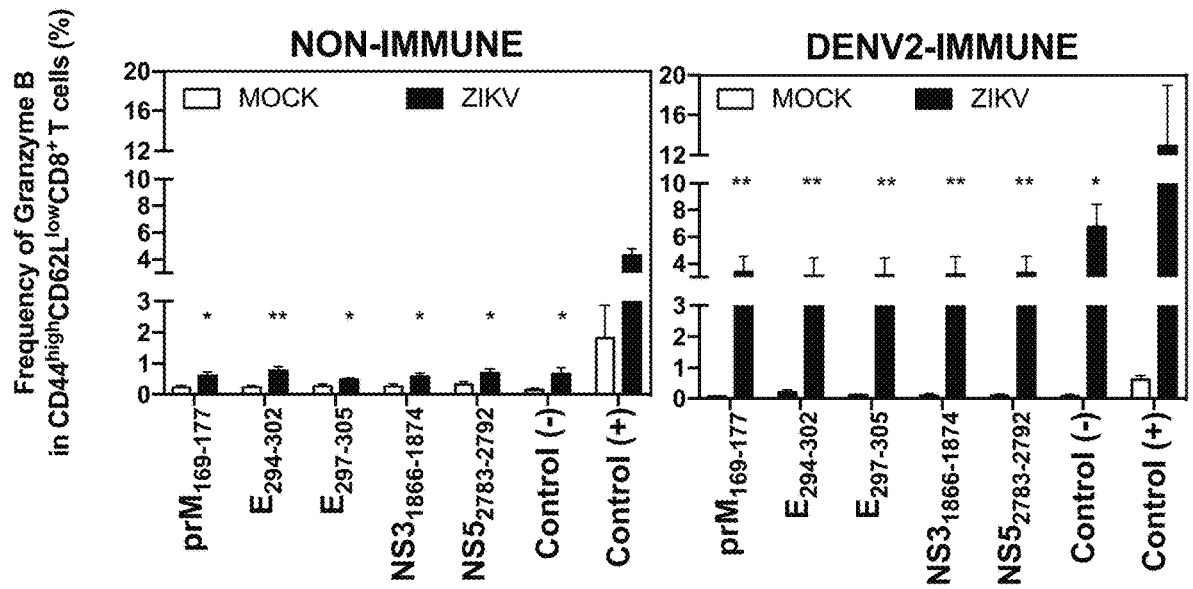
Figure 18I:
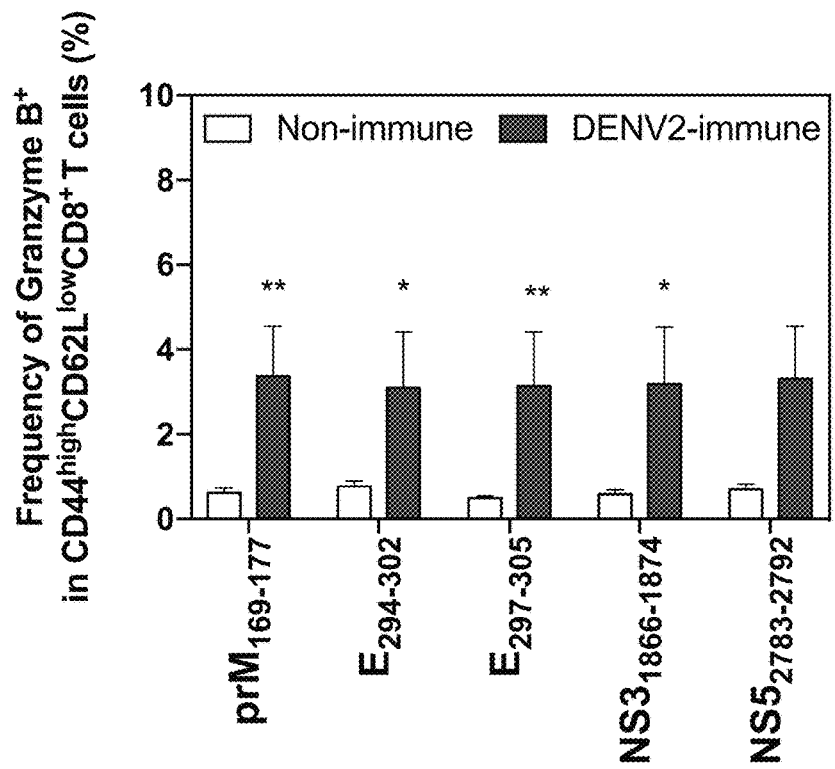
Figure 18J:
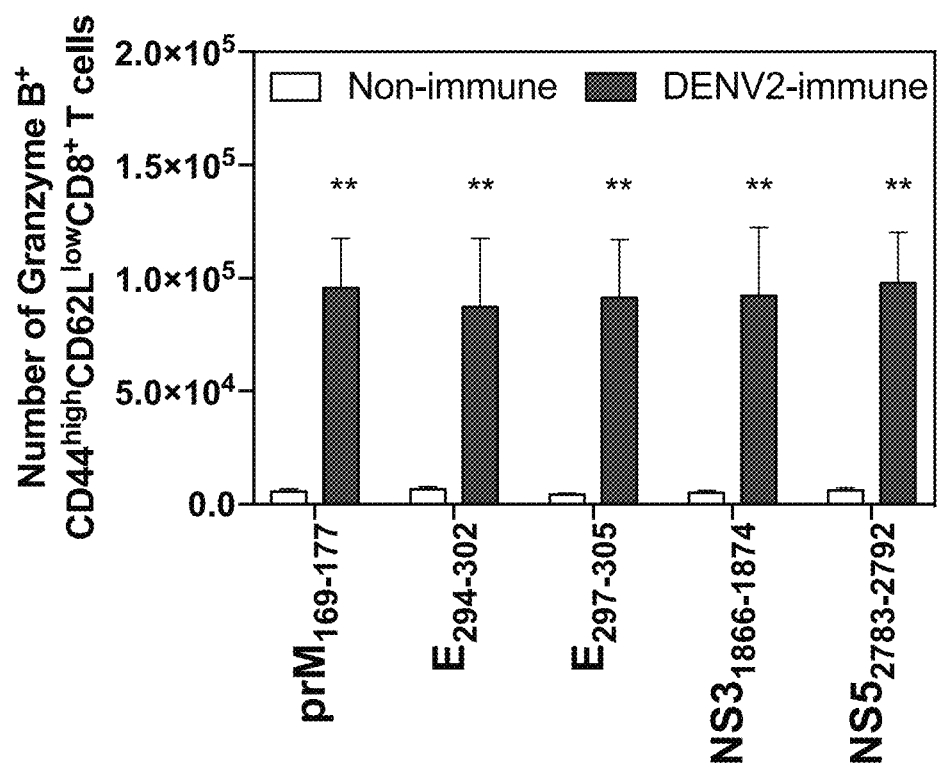

The results obtained are as follows:

The present inventors first confirmed the presence of cross-reactive antigen-specific CD8$^+$ T cells in DENV-immune dams three days after ZIKV challenge (E10.5); this time point was chosen because day 3 post-infection is too early for detection of the primary but not memory anti-ZIKV T cell response in adult male and virgin female mice (Elong Ngono et al., 2017; Wen et al., 2017b). The gating strategy used to identify cells of interest is illustrated in (FIG. 18A). Both frequencies and numbers of cross-reactive epitope-specific CD8$^+$ T cells that were CD44$^{hi}$ CD62L$^{low}$ (i.e. effector memory in DENV-immune and primary effectors in naïve mice) and expressed IFNγ alone (FIG. 18B—FIG. 18D), both IFNγ and TNF (FIG. 18E-FIG. 18G), or granzyme B (FIG. 18H-FIG. 18J) were higher in DENV-immune than non-immune dams. These results indicated that prior DENV exposure elicited cross-reactive effector memory CD8$^+$ T cell responses in the maternal spleen during subsequent ZIKV infection of WT dams with transient Ifnar1 blockade.

The following results are with respect to FIG. 19A to FIG. 19I, where non-immune or DENV2-immune WT dams with transient Ifnar1 blockade were challenged with ZIKV at E7.5 or injected 10% FBS-PBS (MOCK) as described in FIG. 16A to FIG. 16K. Seven days after ZIKV infection (E14.5), mice were sacrificed, and spleens were processed for ICS analysis. (FIG. 19A to FIG. 19C) The percentages (FIG. 19A and FIG. 19B) and numbers (FIG. 19C) of CD44$^{high}$CD62L$^{low}$ CD8$^+$ T cells producing IFNγ are shown. The percentages (FIG. 19D and FIG. 19E) and numbers (FIG. 19F) of CD44$^{high}$CD62L$^{low}$ CD8$^+$ T cells producing both IFNγ and TNF are represented. The percentages (FIG. 19G and FIG. 19H) and numbers (FIG. 19I) of CD44$^{high}$CD62L$^{low}$ CD8$^+$ T cells expressing granzyme B are shown. The following numbers of dams were used: Non-immune (n=6 MOCK and n=5 ZIKV) and DENV2-immune (n=4 MOCK and n=5 ZIKV). Data were pooled from two independent experiments and are expressed as mean±SEM. *p<0.05, **p<0.01. Two-tailed Mann-Whitney test was used to compare MOCK versus ZIKV-infected or non-immune versus DENV2-immune mice for each stimulation condition in FIG. 19A to FIG. 19I.

Figure 19A:
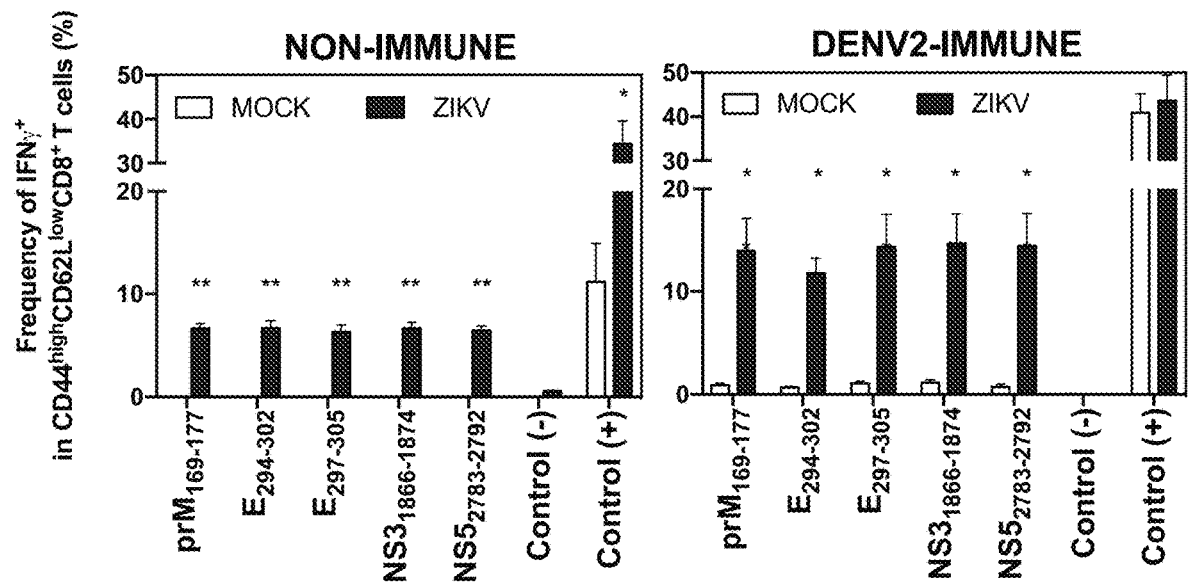
FIGS. 19A-19I: shows graphs that illustrate non-limiting results of cross-reactive epitope-specific CD8+ T cell response in spleens from Ifnar1-blocking Ab-treated WT dams on day 7 after ZIKV infection in accordance with an embodiment of the present disclosure.
Figure 19B:
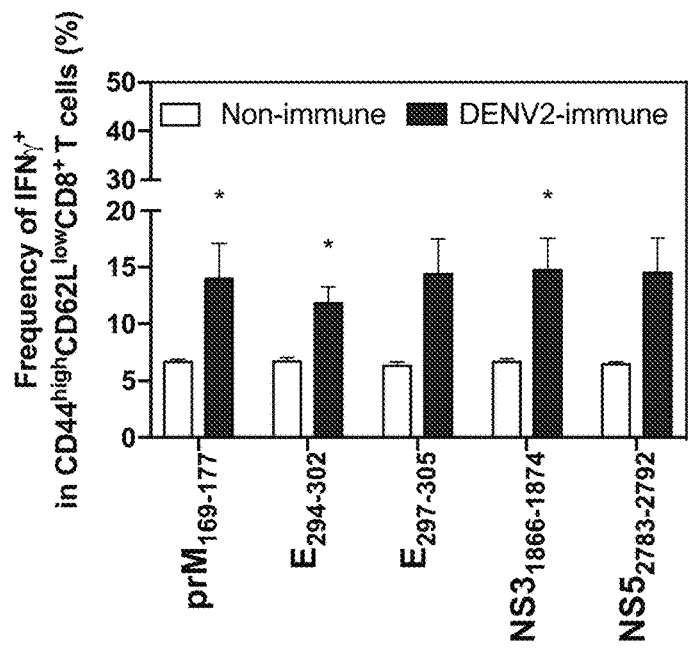
Figure 19C:
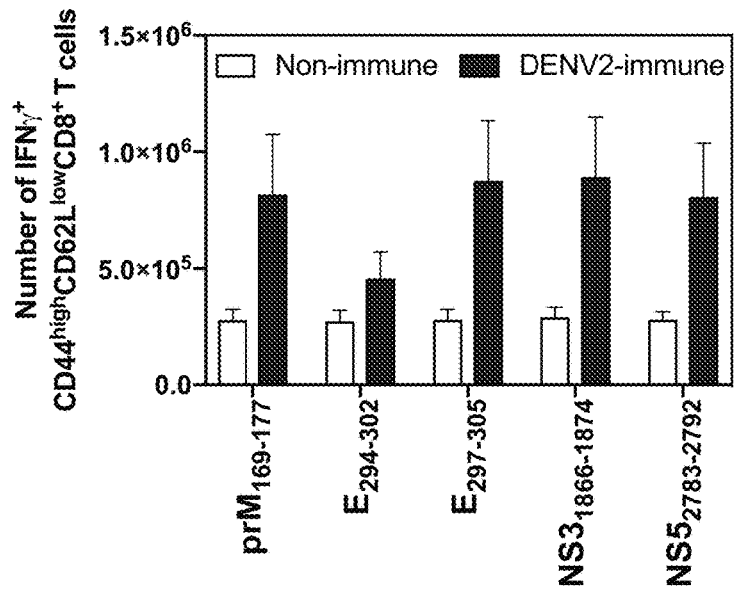
Figure 19D:
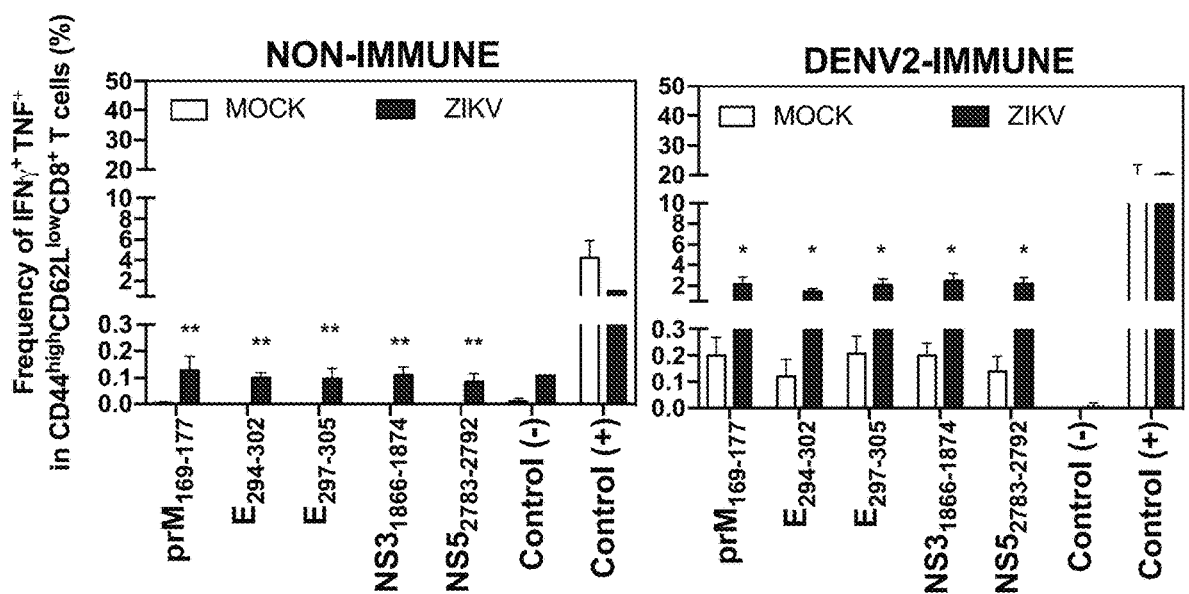
Figure 19E:
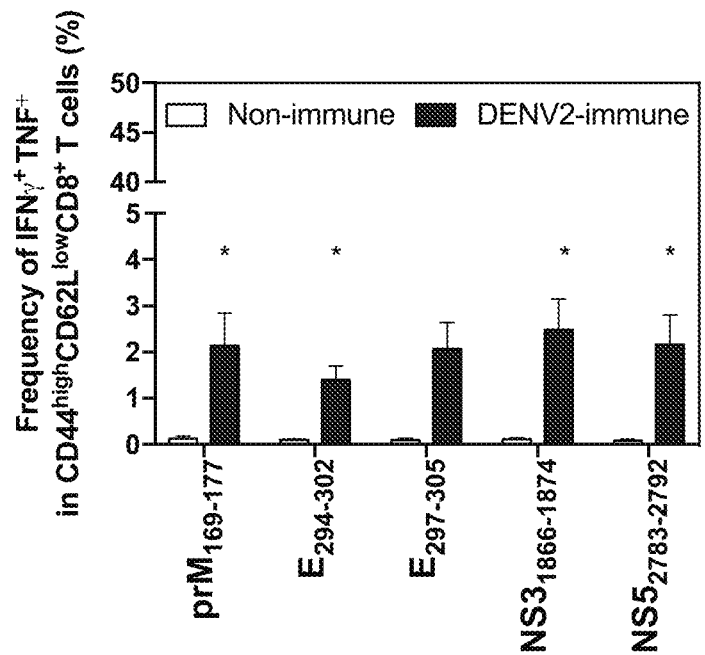
Figure 19F:
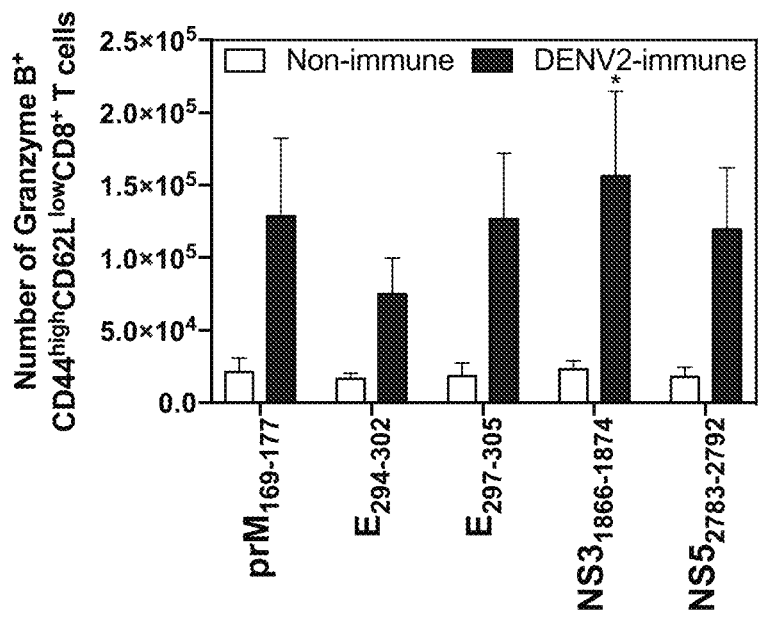
Figure 19G:
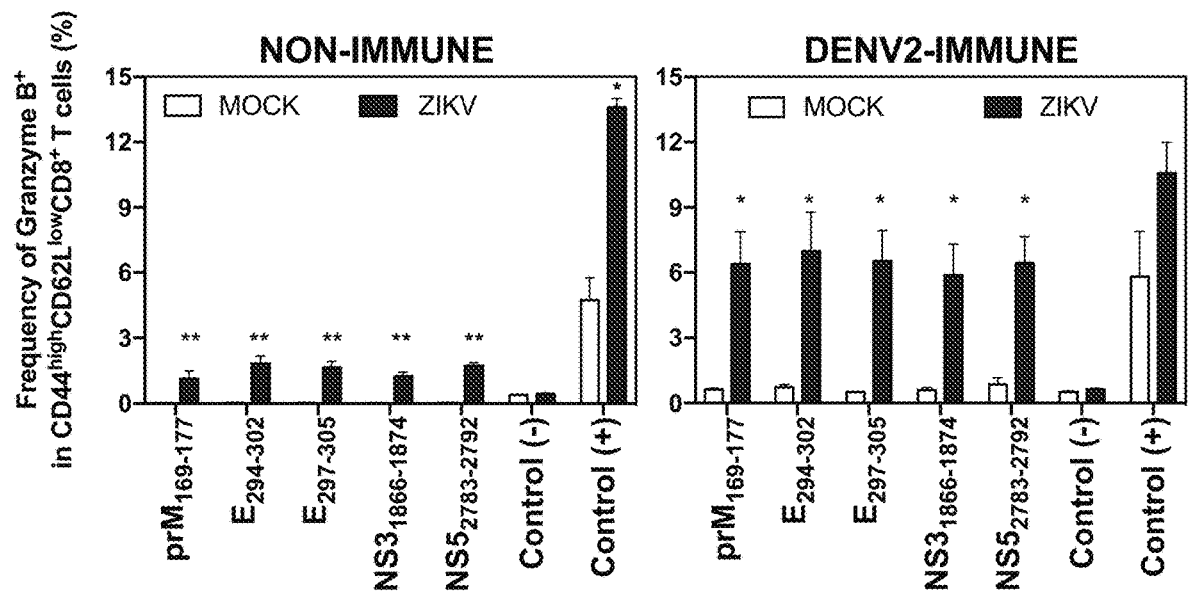
Figure 19H:
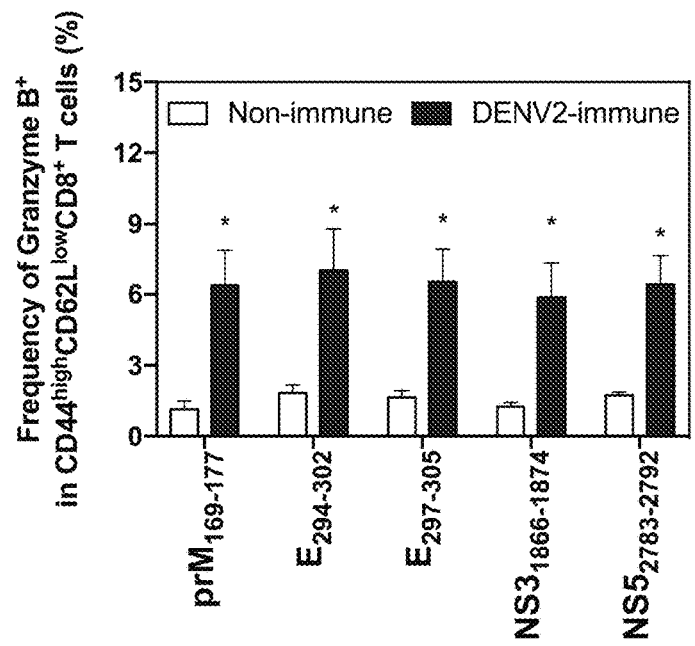
Figure 19I:
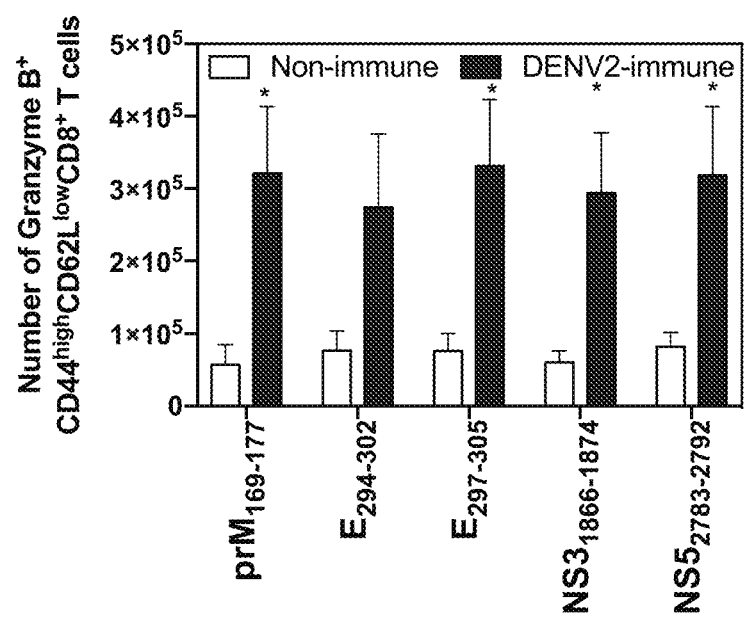

The results obtained are as follows:

Next, the 5 cross-reactive epitope-specific CD8$^+$ T cell responses in the maternal spleen from non-immune versus DENV-immune dams on day 7 after ZIKV challenge (E14.5) were compared, when the primary CD8$^+$ T cell response to ZIKV infection in non-immune animals should peak (Elong Ngono et al., 2017). The frequencies but not numbers of 3 of the 5 epitope-specific CD44$^{high}$CD62L$^{low}$ effector memory and effector CD8$^+$ T cells producing IFNγ were higher in DENV-immune than non-immune mice (FIG. 19A to FIG. 19C). In comparison, the frequencies of all 5 epitope-specific CD8$^+$ T cells and the number of some epitope-specific CD8$^+$ T cells producing both IFNγ and TNF were higher in DENV-immune than non-immune dams (FIG. 19D to FIG. 19F), and the percentages of all 5 epitope-specific and the numbers of 4 epitope-specific CD8$^+$ T cells expressing granzyme B were greater in DENV2-immune than non-immune animals (FIG. 19G to FIG. 19I). These results revealed an increased polyfunctional nature of the cross-reactive CD8$^+$ T cell response in DENV-immune relative to non-immune dams.

8.4 Presence of Cross-Reactive CD8$^+$ T Cells in the Decidua of DENV-Immune WT Mice with Transient Ifnar1 Blockade CD8$^+$ T cells are one of the key cell types that are present in the decidua, which is located on the maternal side of the placenta [60]. Therefore, the present inventors next addressed whether cross-reactive CD8$^+$ T cells were located at the maternal-fetal interface on day 7 after ZIKV challenge of non-immune and DENV-immune WT mice.

The following results are with respect to FIG. 20A to FIG. 20E, where non-immune or DENV2-immune WT dams with Ifnar1 blockade were challenged with ZIKV at E7.5 as described in FIG. 16A to FIG. 16K. Placentas with decidua were harvested 7 days post-infection at E14.5. Isolated cells were stimulated with a pool of 5 cross-reactive peptides for ICS. The gating strategy used to analyze the ICS data is illustrated. The numbers of CD44$^{high}$CD62L$^{low}$ CD8$^+$ T cells expressing IFNγ or both IFNγ and TNFα (FIG. 20B and FIG. 20C) or granzyme B (FIG. 20D and FIG. 20E) are shown. A total of 10 non-immune (n=6 MOCK and n=4 ZIKV) and 9 DENV2-immune (n=4 MOCK and n=5 ZIKV) dams were analyzed. Data were pooled from two independent experiments. All data were expressed as mean±SEM. *p<0.05, **p<0.01. Two-tailed Mann-Whitney test was used to compare MOCK versus ZIKV and non-immune versus DENV2-immune dams.

The results obtained are as follows

Figure 20A:
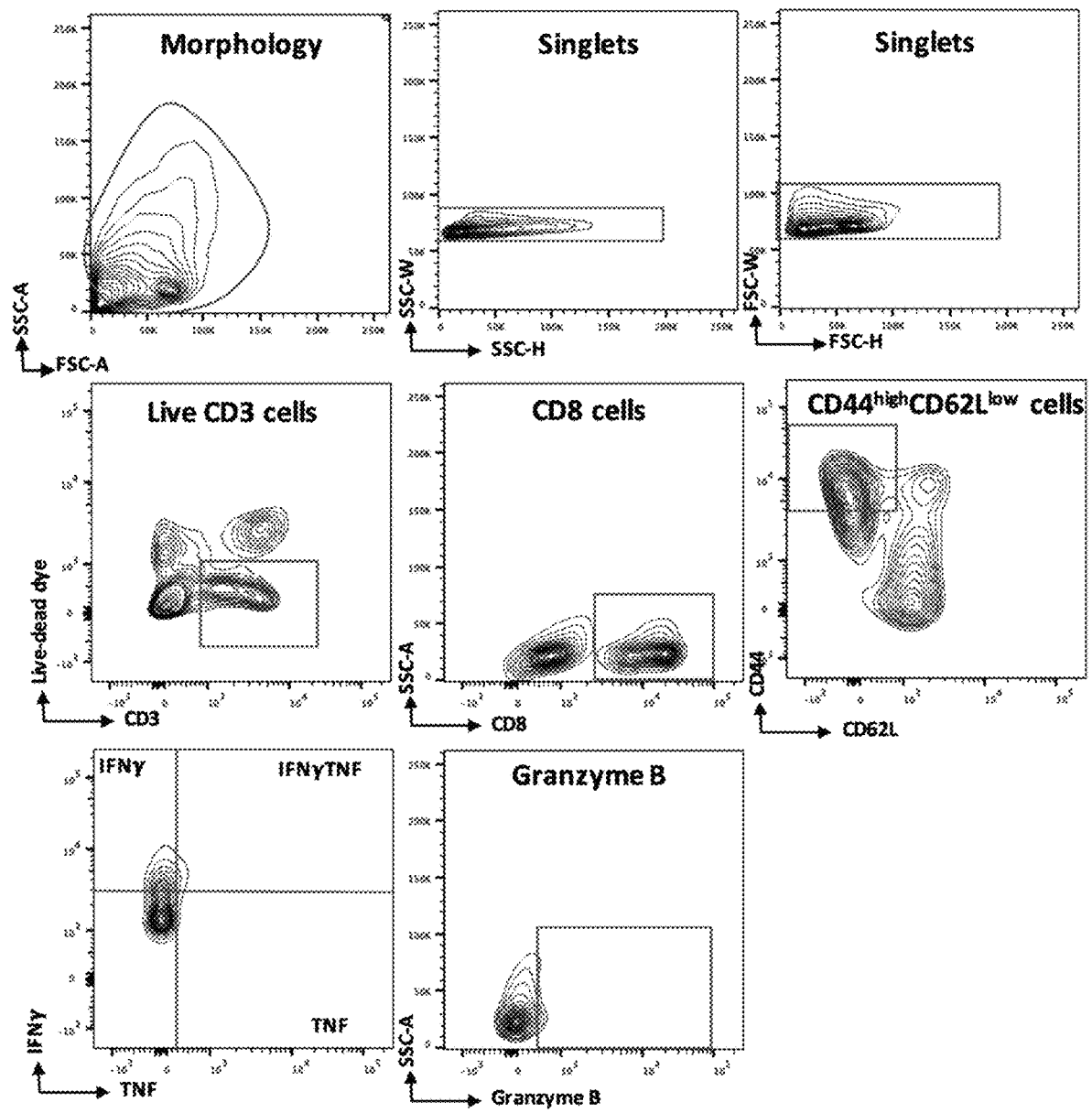
FIGS. 20A-20E: shows graphs that illustrate non-limiting results of cross-reactive epitope-specific CD8+ T cell response in placenta with decidua of non-immune or DENV2-immune Ifnar1 mAb-treated WT dams seven days after ZIKV infection in accordance with an embodiment of the present disclosure.
Figure 20B:
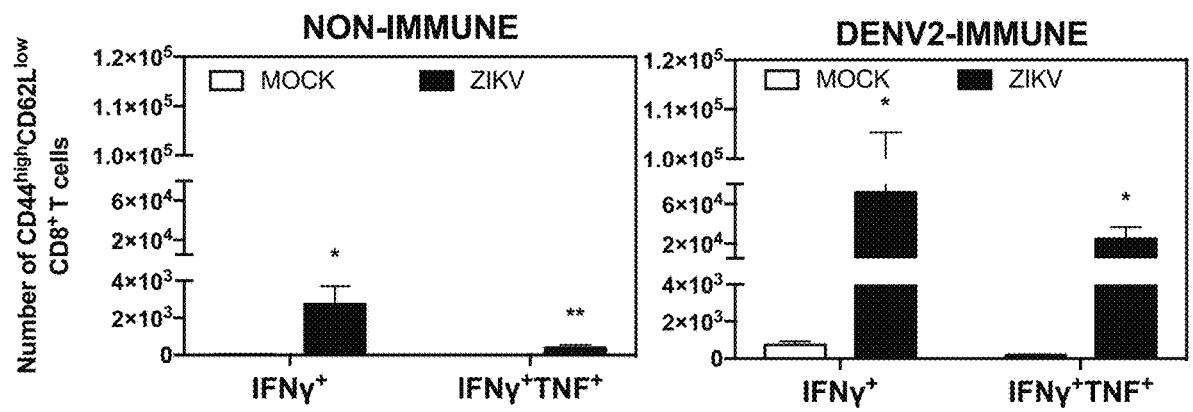
Figure 20C:
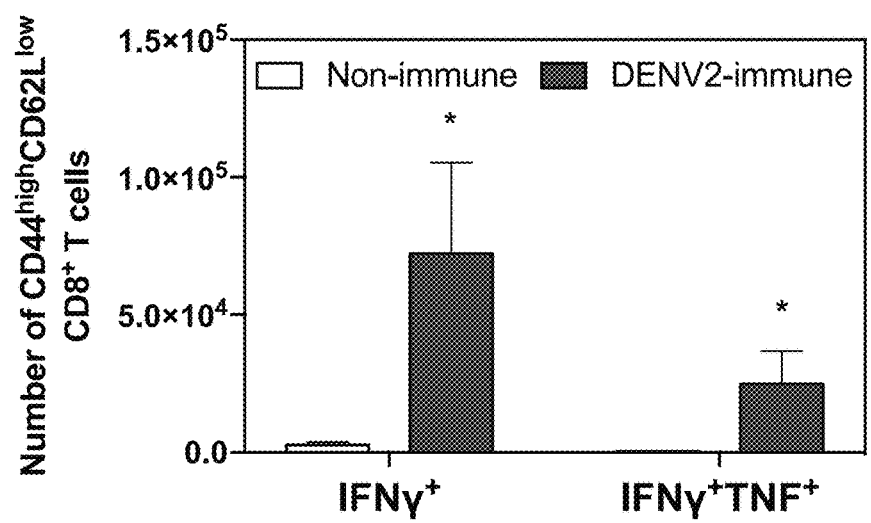
Figure 20D:
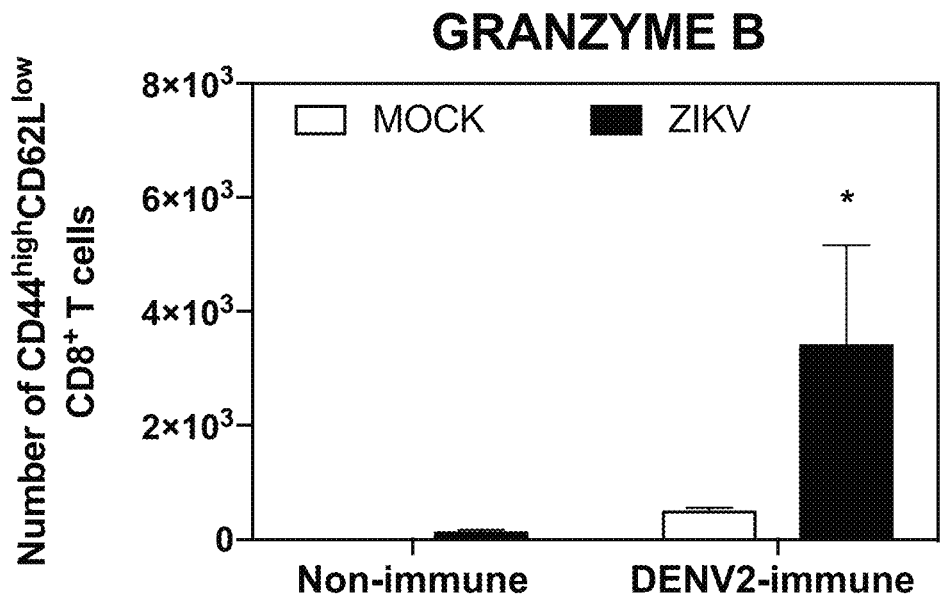
Figure 20E:
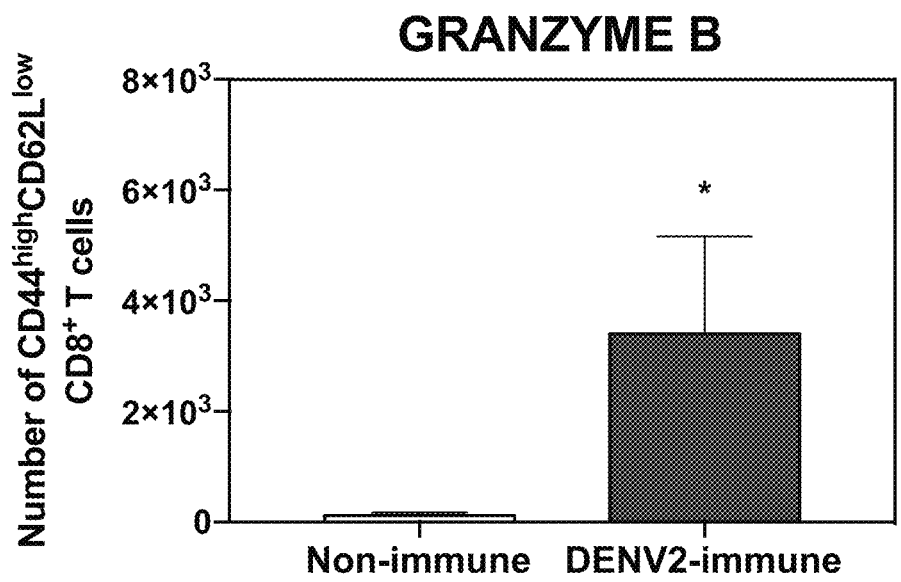

Although decidual T cells were rare compared to splenic T cells, perhaps due to epigenetic silencing of key chemokine genes that prevent influx of T cells to the decidua (Nancy et al., 2012), the present inventors detected polyfunctional effector memory and effector CD8$^+$ T cells in the decidua/placenta after restimulation with a mixture of the 5 cross-reactive epitopes (FIG. 20A). Although CD8$^+$ T cells producing IFNγ alone or both IFNγ and TNF were present in both non-immune and DENV-immune dams, significantly greater numbers were evident in the decidua of DENV-immune than non-immune mice (FIG. 20B and FIG. 20C). Similarly, higher numbers of CD8$^+$ T cells expressing granzyme B were present in DENV-immune compared to non-immune dams after ZIKV infection (FIG. 20D and FIG. 20E).

Thus, cross-reactive antigen-specific CD8$^+$ T cells with polyfunctional phenotype were present in the decidua/placenta of ZIKV-challenged DENV-immune mice, whereas very few antigen-specific CD8$^+$ T cells were observed in the decidua/placenta of ZIKV-infected non-immune dams.

9. Discussion on Example 3

As the number of ZIKV infections in pregnant women increases, more cases of Congenital ZIKV Syndrome likely will occur. As many of these infections will occur in DENV-endemic regions, there is an urgency to understand the effect of pre-existing DENV immunity on ZIKV. A major question in the field is whether prior DENV immunity contributes to protection against or pathogenesis of ZIKV infection during pregnancy. To address this question, the present inventors adapted established mouse models of ZIKV infection during pregnancy that rely on acquired or genetic deficiencies of type I IFN signaling (Miner et al., 2016; Yockey et al., 2016). The present inventors challenged DENV-immune dams with ZIKV to model sequential DENV-ZIKV infection. In DENV-immune mice, it was observed a reduction of ZIKV burden in maternal and fetal tissues, including the decidua/placenta, and an increase of fetal viability and growth compared to non-immune mice. Depletion of $CD8^+$ T cells abrogated this effect, demonstrating an essential role for $CD8^+$ T cells in protection against ZIKV during pregnancy in the context of prior DENV immunity. Cross-reactive, polyfunctional $CD8^+$ T cells during pregnancy may have the ability to overcome other pathogenic immune elements associated with prior DENV exposure, including ADE (Bardina et al., 2017). Indeed, it has been previously reported that DENV-reactive $CD8^+$ T cells can protect mice even under ADE conditions (Wen et al., 2017a; Zellweger et al., 2014; Zellweger et al., 2015).

At an early time point after ZIKV infection of pregnant dams, $CD8^+$ T cell depletion abrogated DENV-immune-mediated protection in maternal tissues and the maternal-fetal interface (i.e. decidua/placenta) despite having no effect on maternal viremia, suggesting that DENV-elicited memory $CD8^+$ T cells preferentially exert their effects in tissues rather than in circulation. Accordingly, analysis of T cells in the maternal spleen following ZIKV challenge revealed that the cross-reactive epitope-specific $CD8^+$ T cell response was of higher magnitude and polyfunctionality in DENV-immune than non-immune dams. Thus, at early stage of ZIKV infection, prior DENV exposure elicited cross-reactive $CD8^+$ T cells with greater functional activity compared to those expanded during primary ZIKV infection. Recent studies using blood samples from non-pregnant individuals have identified cross-reactive $CD8^+$ T cells in humans (Grifoni et al., 2017; Paquin-Proulx et al., 2017). One of these studies showed that DENV exposure prior to ZIKV infection influenced the magnitude and quality of the $CD8^+$ T cell response (Grifoni et al., 2017), suggesting that prior DENV immunity may shape the anti-ZIKV $CD8^+$ T cell response. A study with non-human primates suggested that prior DENV exposure may confer cross-protection against ZIKV infection (Pantoja et al., 2017), although a second study reported neither protective nor pathogenic effect of previous DENV exposure during subsequent ZIKV infection (McCracken et al., 2017). Notably, non-human primates in these studies were challenged 1-2 years following DENV exposure, as compared to our challenge of mice on day 30 after DENV priming. Going forward, a more detailed evaluation of the duration of cross-protection mediated by prior DENV-induced $CD8^+$ T cell responses against ZIKV infection during pregnancy is needed.

Consistent with the local effect of DENV-elicited $CD8^+$ T cells in each tissue, cross-reactive antigen-specific $CD8^+$ T cells also were detected in the decidua/placenta of DENV-immune mice. As $CD8^+$ T cell are one of the abundant cell types present in the decidua (Crespo et al., 2017; Lissauer et al., 2017; van Egmond et al., 2016), the T cells detected are likely decidual and thus of maternal origin. Future studies using CD45.1 C57BL/6 female mice with congenic CD45.2 sires should confirm the maternal versus fetal origin of these cells. At present, the precise specificity and origin of $CD8^+$ T cells and the mechanisms by which these cells balance immune tolerance of the fetus and antiviral immunity at the maternal-fetal interface are presently unclear, but both virus-specific and fetal antigen-specific $CD8^+$ T cells have been detected in human and mouse decidua (Constantin et al., 2007; Crespo et al., 2017; Lissauer et al., 2017; Nancy and Erlebacher, 2014; Powell et al., 2017; Tilburgs and Strominger, 2013; van Egmond et al., 2016). The decidual $CD8^+$ T cells in humans are primarily of effector memory phenotype and express reduced levels of granzyme B compared to peripheral blood $CD8^+$ T cells (Powell et al., 2017; Tilburgs et al., 2010; van Egmond et al., 2016). Consistent with this observation, cross-reactive antigen-specific $CD8^+$ T cells in the decidua/placenta of DENV-immune dams with ZIKV infection were effector memory, the majority of which had polyfunctional capacity, as defined by granzyme B or both IFNγ and TNF expression. Notably, despite the reported epigenetic silencing of chemokine genes in the decidua, which would limit T cells access during pregnancy (Nancy et al., 2012), more antigen-specific $CD8^+$ T cells were present in the decidua/placenta of DENV-immune than non-immune mice. Future studies are needed to determine the mechanisms by which these T cells were recruited or activated locally in the decidua.

Immune responses during pregnancy are complex and remain poorly understood, as the immune system needs to balance fetal tolerance with microbial defense at different stages of gestation. Little is known about the immune response to ZIKV infection during pregnancy, except for a recent study that reported a decreased frequency of granzyme B-expressing total $CD8^+$ T cells in pregnant dams compared to non-pregnant mice (Winkler et al., 2017), suggesting that the anti-ZIKV T cell response quantity or quality may be reduced during pregnancy. This published study and the present data have set the framework for comparing antigen-specific $CD8^+$ T cell responses in pregnant and non-pregnant mice with ZIKV infection. Given that gestational stage influences the susceptibility of ZIKV infection in the placenta and fetus (Jagger et al., 2017), it will be important also to evaluate the temporal component of the anti-ZIKV T cell response through the different stages of pregnancy.

The present inventors have previously demonstrated that $CD8^+$ T cells are necessary and sufficient to protect against systemic ZIKV challenge in both naïve and DENV-immune non-pregnant mice (Elong Ngono et al., 2017; Wen et al., 2017a; Wen et al., 2017b). Here, the present data demonstrates a similar requirement for $CD8^+$ T cells in protection against ZIKV in the context of pregnancy and prior DENV exposure. The present data also demonstrates a partially protective role for $CD4^+$ T cells, suggesting that $CD4^+$ T cell mediated-help may shape an optimal cross-reactive $CD8^+$ T cell response during ZIKV infection of DENV-immune pregnant females. Alternatively, $CD4^+$ T cells may exert their effect by regulating humoral immunity or $CD4^+$ regulatory T cells could minimize pathology at the maternal-fetal interface. The present data thus sets the foundation for investigating the precise role of $CD4^+$ and $CD8^+$ T cells in ZIKV infection during pregnancy in humans and animal models.

The present disclosure also raises key issues of epidemiologic relevance particularly in terms of the T cell response to ZIKV infection in individuals with previous DENV exposure. As $CD8^+$ T cell responses induced by a tetravalent live attenuated DENV vaccine also cross-reacted with ZIKV epitopes (Grifoni et al., 2017), further boosting of T cell responses could confer protection against ZIKV infection in pregnancy. Moreover, ZIKV vaccines that are designed to induce optimal T cell responses in addition to Abs may be more effective than those that focus solely on Ab responses for protection against ZIKV during pregnancy.

Example 4

Identification of ZIKV-Specific CD4+ T Cell Epitopes

Figures 25A, 25B, 25C:
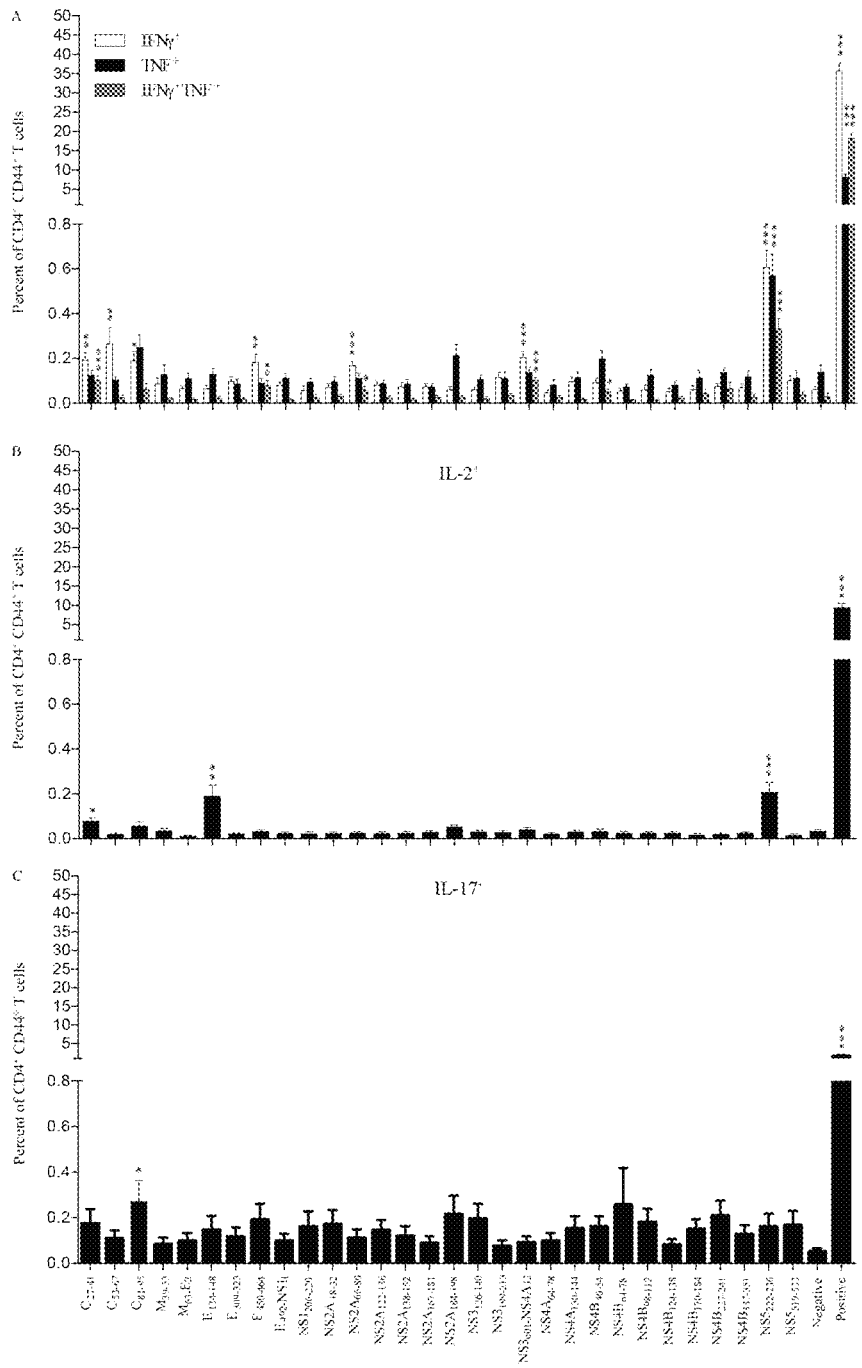
FIGS. 25A-25C: shows cytokine secretion pattern of ZIKV epitope-specific HLA-DRB1*0101-restricted CD4+ T cells. Ifnar1$^{-/-}$ HLA-DRB1*0101 mice were infected retro-orbitally with 1×10$^2$ FFU of ZIKV strain SD001 for 7 days. Splenocytes were stimulated in vitro with the indicated ZIKV-derived HLA-DRB1*0101-binding peptides for 6 h, and the frequency of CD44+ CD4+ T cells producing IFNγ, TNF, or IFNγ plus TNF (A), IL-2 (B), and IL-17 (C) were detected using the ICS assay. Data represent the mean±s.e.m. of four independent experiments (n=3-5 mice/experiment; total 16 mice). *P<0.05, P<0.01, *P<0.001, ****P<0.0001 by two-tailed Mann-Whitney test. Negative and positive refer to cells incubated alone or with PMA/ionomycin, respectively.
Figures 32A, 32B:
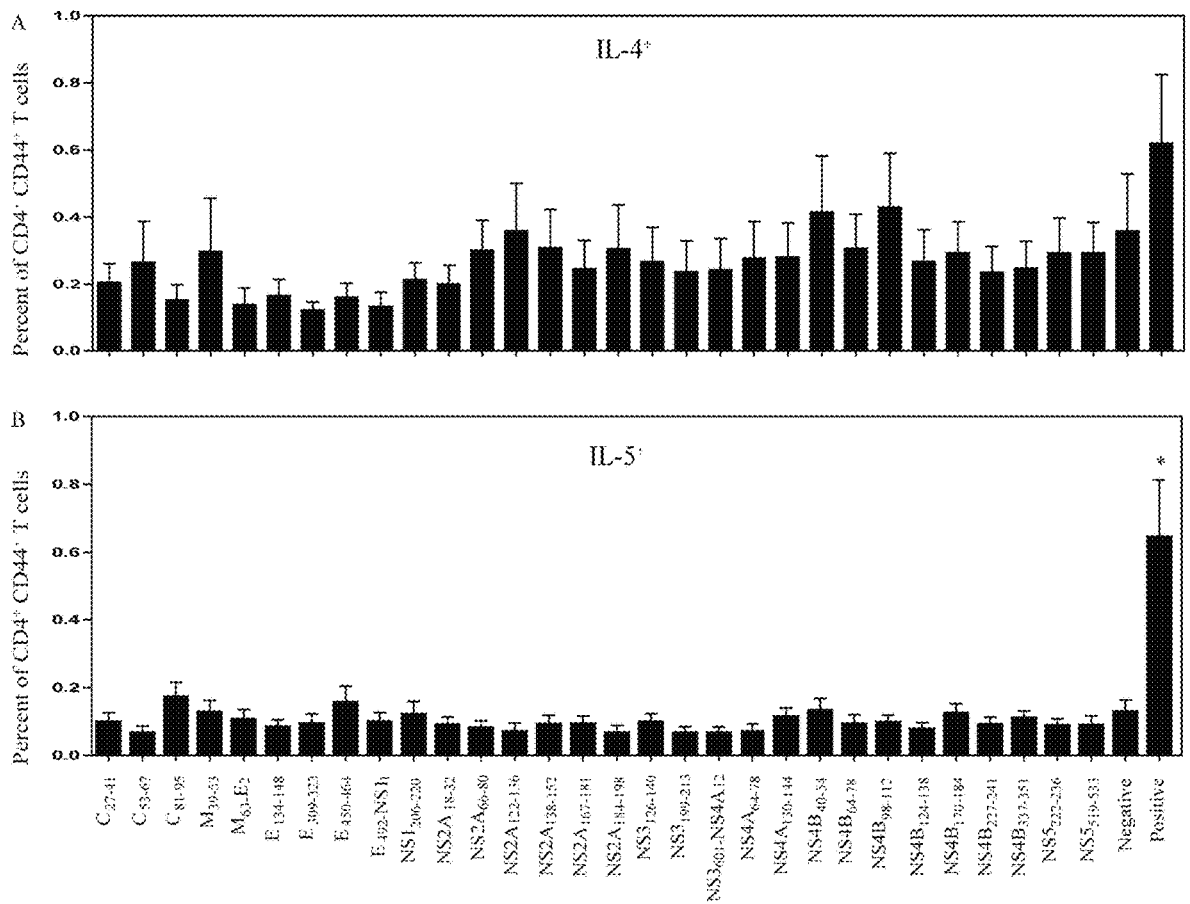
FIGS. 32A-32B: shows screening of IL-4 and IL-5 production in response to ZIKV-specific epitopes in an HLA-DRB1*0101 mouse model. Ifnar$^{-/-}$ HLA-DRB1*0101 mice were infected retro-orbitally with $1\times10^2$ FFU of ZIKV strain SD001 for 7 days. Splenocytes were stimulated in vitro with the indicated ZIKV-derived HLA-DRB1*0101-binding peptides for 6 h, and the frequency of CD44$^+$ CD4$^+$ T cells producing IL-4 (A) or IL-5 (B) were detected using the ICS assay. Data represent the mean±s.e.m. of four independent experiments, with a total of 13 mice. *P<0.05 by two-tailed Mann-Whitney test. Negative and positive refer to cells incubated alone or stimulated with PMA/ionomycin, respectively.

As the antigenic load dictates the magnitude of antiviral T cell responses[36,37], and wild-type mice are highly resistant to DENV and ZIKV infection due to the inability of these viruses to inhibit various components of the IFN system, Ifnar1$^{-/-}$ mice have been widely used to investigate the T cell responses to DENV and ZIKV[3,38]. Previous studies provided that vaccination of Ifnar1$^{-/-}$ mice with DENV peptide epitopes elicited CD4+ T cell-mediated protective immunity against subsequent DENV infection[39]. Therefore, here the Ifnar1$^{-/-}$ HLA-DRB1*0101 mouse model was used, which was previously employed to identify DENV-derived epitopes of relevance to human DENV infection[33]. Applicant selected a total of 30 ZIKV peptides from the top 2% of predicted HLA-DRB1*0101-binding epitopes from the predictive database IEDB-AR (Table 10). The 30 peptides were distributed in nine ZIKV proteins: three in C, two in M, four in E, one in NS1, six in NS2A, three in NS3, two in NS4A, seven in NS4B, and two in NS5. To test the reactivity of ZIKV-primed CD4+ T cells, Ifnar1$^{-/-}$ HLA-DRB1*0101 mice were infected with ZIKV SD001 for 7 days, and splenocytes were isolated, stimulated with the candidate epitopes for 6 h, and analyzed for production of canonical Th1 (IFNγ, TNF, IL-2), Th17 (IL-17), and Th2 (IL-4, IL-5) cytokines by flow cytometry using the ICS assay. Nine peptides ($C_{27-41}$ (SEQ ID NO: 97), $C_{53-67}$ (SEQ ID NO: 98), $C_{81-95}$ (SEQ ID NO: 99), $E_{134-148}$ (SEQ ID NO: 102), $E_{450-464}$ (SEQ ID NO: 104), NS2A66-so (SEQ ID NO:108), $NS3_{601}$-$NS4A_{12}$, (SEQ ID NO: 115), $NS4B_{40-54}$ (SEQ ID NO: 118), $NS5_{222-236}$ (SEQ ID NO: 125) were identified as Th1 epitopes (FIG. 25); two of which ($C_{53-67}$ (SEQ ID NO: 98), and $C_{81-95}$ (SEQ ID NO: 99)) stimulated CD4+ T cells to produce only IFNγ, four ($E_{450-464}$ (SEQ ID NO: 104), $NS2A_{66-80}$, (SEQ ID NO: 108), $NS3_{601}$-$NS4A_{12}$ (SEQ ID NO: 115), and $NS4B_{40-54}$ (SEQ ID NO:118) stimulated IFNγ plus TNF production, one ($E_{134-148}$ (SEQ ID NO: 102), stimulated only IL-2 production, and two ($C_{27-41}$ (SEQ ID NO: 97) and $NS5_{222-236}$ (SEQ ID NO: 125) stimulated IFNγ, TNF, and IL-2 production (FIG. 25 and Table 10). Additionally, one Th17 epitope, $C_{81-95}$ (SEQ ID NO: 99), was identified (FIG. 25C). Notably, none of the 30 peptides tested induced a Th2 cell response (FIG. 32). These data indicate that the primary response to ZIKV infection in HLA-DRB1*0101 transgenic mice is dominated by a Th1 CD4+ T cell response to nine peptides in non-structural and structural proteins.

Identification of ZIKV-Derived CD4+ T Cell Epitopes that Cross-React with DENV

Figures 26A, 26B:
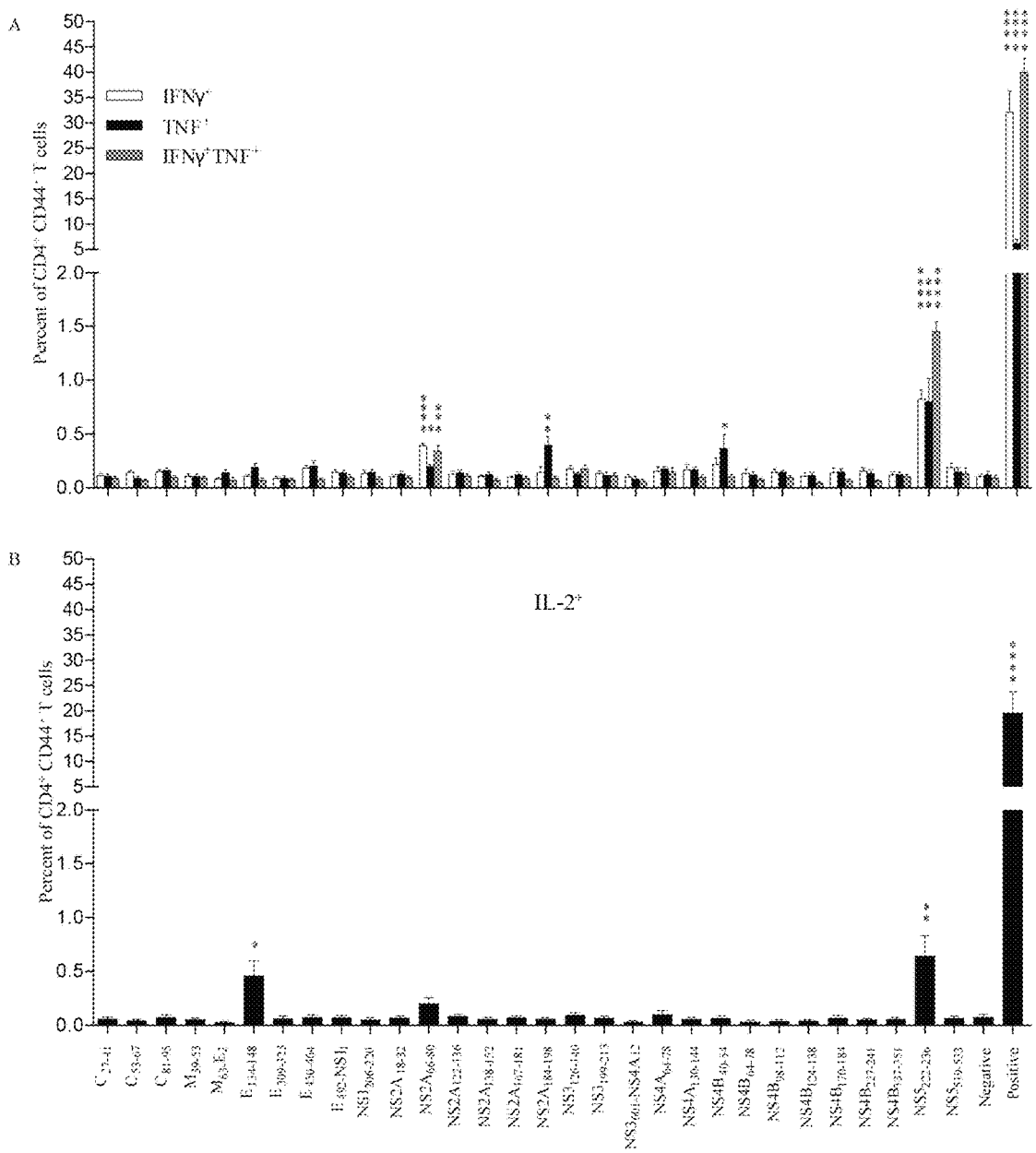
FIGS. 26A-26B: shows cross-reactivity of DENV2-primed CD4+ T cells to HLA-DRB1*0101-binding ZIKV peptides. Ifnar1$^{-/-}$ HLA-DRB1*0101 mice were infected intraperitoneally with 2×10$^3$ FFU of DENV2 strain S221 for 7 days. Splenocytes were stimulated in vitro with the indicated ZIKV-derived HLA-DRB1*0101-binding peptides for 6 h. The frequency of CD44+ CD4+ T cells producing IFNγ, TNF, or IFNγ plus TNF (A) or IL-2 (B) were detected using the ICS assay. Data represent the mean±s.e.m. of three independent experiments (n=3-4 mice/experiment; total 10 mice). *P<0.05, P<0.01, *P<0.001, ****P<0.0001 by two-tailed Mann-Whitney test. Negative and positive refer to cells incubated alone or with PMA/ionomycin, respectively.

Applicants previously found that DENV-exposed CD8+ T cells cross-react with ZIKV-derived peptides and that pre-existing DENV immunity shapes the magnitude and pattern of the subsequent CD8+ T cell response to ZIKV infection[13,26]. To investigate whether DENV-primed CD4+ T cells are stimulated by cross-reactive ZIKV peptides, Applicants isolated splenocytes from Ifnar1$^{-/-}$ HLA-DRB1*0101 mice on day 7 after infection with DENV2 S221, stimulated the cells in vitro for 6 h with the 30 ZIKV-derived candidate epitopes, and then analyzed cytokine production by ICS. Of the nine ZIKV CD4+ T cell epitopes identified above, four of them ($E_{134-148}$ (SEQ ID NO: 102), $NS2A_{66-80}$ (SEQ ID NO: 108), $NS4B_{40-54}$ (SEQ ID NO: 118) and $NS5_{222-236}$ (SEQ ID NO: 125) elicited cross-reactive responses by DENV2-primed CD4+ T cells (FIG. 26). In addition, Applicants identified one peptide, NS2A184-198 (SEQ ID NO: 112), which did not elicit a response by ZIKV-primed cells (FIG. 25) but did induce TNF production by DENV2-primed CD4+ T cells (FIG. 26A). Of the four DENV2/ZIKV-cross-reactive CD4+ T cell epitopes, $E_{134-148}$ (SEQ ID NO: 102), induced only IL-2-producing cells, $NS2A_{66-80}$ (SEQ ID NO: 108), induced IFNγ-plus TNF-producing cells, $NS4B_{40-54}$ (SEQ ID NO: 118), induced only TNF-producing cells, and $NS5_{222-236}$ (SEQ ID NO: 125) induced cells producing IFNγ, TNF, and IL-2 (FIG. 25, FIG. 26, and Table 10). These results show that structural and non-structural proteins in ZIKV contain epitopes that stimulate cross-reactive DENV-primed CD4+ T cells, although the majority of cross-reactive CD4+ T cell epitopes were located in ZIKV non-structural proteins. In addition, some of the cross-reactive cells produced only one cytokine, whereas others were multifunctional and produced two or more cytokines.

TABLE 10

Zika virus-derived potential HLA-DRB1*0101-restricted epitopes

| peptides[a] | Sequences | IEDB prediction percentile_rank | % CD4+ CD44+ T cells (ZIKV) | | | | % CD4+ CD44+ T cells (DENV) | | | |
|---|---|---|---|---|---|---|---|---|---|---|
| | | | INFγ+ | TNFα+ | INFγ+ TNFα+ | IL-2+ | INFγ+ | TNFα+ | INFγ+ TNFα+ | IL-2+ |
| $C_{27-41}$ | FGGLKRLPAGLLLGH | 0.25 | 0.191 | | 0.1 | 0.08 | | | | |
| $C_{53-67}$ | FLRFTAIKPSLGLIN | 0.19 | 0.265 | | | | | | | |
| $C_{81-95}$ | IKKFKKDLAAMLRII | 3.02 | 0.19 | | | | | | | |
| $M_{39-53}$ | NPGFALAAAAIAWLL | 0.13 | | | | | | | | |
| $M_{33}$-$E_{2}$ | YLVMILLIAPAYSIR | 0.96 | | | | | | | | |
| $E_{134-148}$ | NLEYRIMLSVHGSQH | 2.27 | | | | | | | 0.19 | 0.459 |
| $E_{309-323}$ | TAAFTFTKIPAETLH | 1.58 | | | | | | | | |
| $E_{450-464}$ | GAAFKSLFGGMSWFS | 2.51 | 0.183 | | 0.078 | | | | | |
| $E_{492}$-$NS3_{1}$ | GGVLIFLSTAVSADV | 1.99 | | | | | | | | |

TABLE 10-continued

Zika virus-derived potential HLA-DRB1*0101-restricted epitopes

| peptides[a] | Sequences | IEDB prediction percentile_rank | % CD4+ CD44+ T cells (ZIKV) | | | | % CD4+ CD44+ T cells (DENV) | | | |
|---|---|---|---|---|---|---|---|---|---|---|
| | | | IFNγ+ | TNFα+ | IFNγ+TNFα+ | IL-2+ | IFNγ+ | TNFα+ | IFNγ+TNFα+ | IL-2+ |
| NS1$_{205-220}$ | NDTWRLKRAHLIEMK | 2.73 | | | | | | | | |
| NS2A$_{18-32}$ | TTKIIISTSMAVLVA | 3.72 | | | | | | | | |
| NS2A$_{66-80}$ | LALIAAFKVRPALLV | 1.81 | 0.167 | | 0.058 | | 0.39 | 0.199 | 0.343 | |
| NS2A$_{123-136}$ | ALAWLAIRAMVVPRT | 1.24 | | | | | | | | |
| NS2A$_{138-152}$ | NITLAILAALTPLAR | 2.51 | | | | | | | | |
| NS2A$_{107-121}$ | GGFMLLSLKGKGSVK | 2.27 | | | | | | | | |
| NS2A$_{134-198}$ | LPFVMALGLTAVRLV | 0.28 | | | | | | | 0.397 | |
| NS3$_{125-140}$ | CGRVIGLYGNGVVIK | 4.77 | | | | | | | | |
| NS3$_{189-213}$ | RLRTVILAPTRVVAA | 1.81 | | | | | | | | |
| NS3$_{601}$-NS4A$_{12}$ | GAAFGVMEALGTLPG | 3.95 | 0.203 | | 0.102 | | | | | |
| NS4A$_{58-78}$ | GIPFVLMRNKGIGKM | 0.42 | | | | | | | | |
| NS4A$_{139-144}$ | QMAIIMVAVGLLGL | 0.96 | | | | | | | | |
| NS4B$_{40-54}$ | WAIYAALTTFITPAV | 3.95 | | | 0.049 | | | | 0.367 | |
| NS4B$_{58-78}$ | NYSLMAMATQAGVLF | 1.71 | | | | | | | | |
| NS4B$_{98-112}$ | IGCYSQLTPLTLIVA | 0.25 | | | | | | | | |
| NS4B$_{124-135}$ | IPGLQAAAARAAQKR | 1.06 | | | | | | | | |
| NS4B$_{178-184}$ | MGQVLLIAVAVSSAI | 2.05 | | | | | | | | |
| NS4B$_{327-343}$ | FRGSYLAGASLIYTV | 4.77 | | | | | | | | |
| NS4B$_{337-351}$ | GWSYYAATIRKVQEV | 1.53 | | | | | | | | |
| NS5$_{222-236}$ | RAIWYMWLGARFLEP | 0.88 | 0.607 | 0.571 | 0.333 | 0.21 | 0.82 | 0.8 | 1.451 | 0.643 |
| NS5$_{518-533}$ | HRRDLRLMANAICSS | 1.9 | | | | | | | | |

[a]The position of peptides was determined according to the amino acid sequences of ZIKV strain FSS13025.

Table 10 discloses SEQ ID NOS: 97-126, respectively, in order of appearance.

Influence of DENV2 Immunity on the CD4+ T Cell Response to ZIKV Challenge

Figures 27A, 27B, 27C, 27D, 27E:
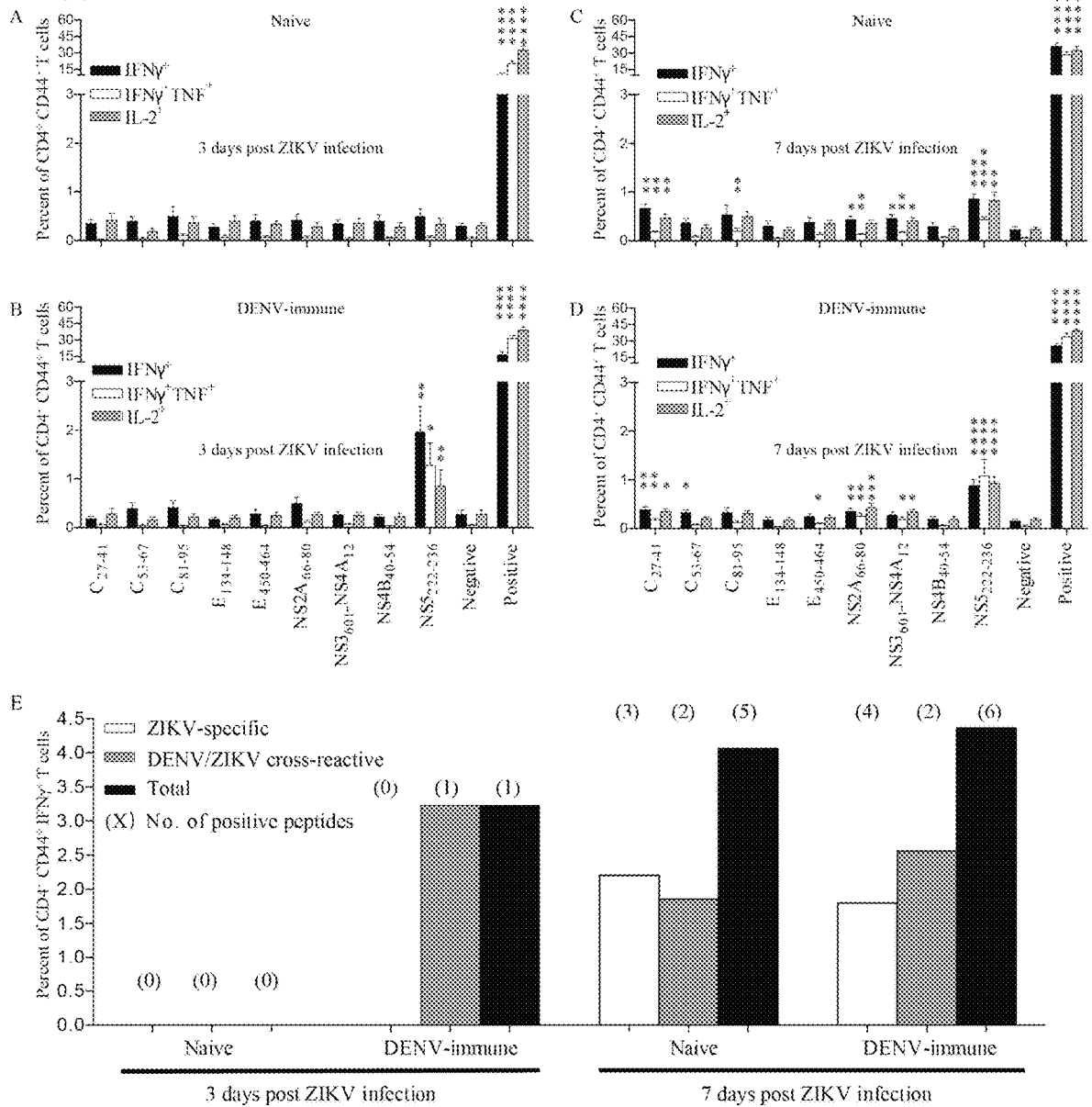
FIGS. 27A-27E: shows Alteration of CD4+ T cell responses to ZIKV infection by DENV2 immunity. Ifnar1−/−HLA-DRB1*0101 mice were primed intraperitoneally with 2×103 FFU of DENV2 S221 for 4 weeks. Naïve mice and DENV2-immune mice were challenged retro-orbitally with 1×10$^4$ FFU of ZIKV strain SD001 for 3 or 7 days. Splenocytes were stimulated in vitro with the indicated ZIKV-specific and DENV2/ZIKV-cross-reactive epitopes. The frequency of CD44+ CD4+ T cells producing IFNγ, IFNγ plus TNF, or IL-2 were detected using the ICS assay. (E) The combined data for positive peptide responses in (FIGS. 27A-27D). Numbers in parentheses indicate the number of positive peptides. Data represent the mean±s.e.m. of three or four independent experiments, with a total of 9 mice/group for A and C, 14/group for B, and 15/group for D. *P<0.05, P<0.01, *P<0.001, ****P<0.0001 by two-tailed Mann-Whitney test. Negative and positive refer to cells incubated alone or with PMA/ionomycin, respectively.

To examine the effects of prior DENV2 infection on the T cell response to subsequent ZIKV infection in this mouse model, Applicants primed Ifnar1$^{-/-}$ HLA-DRB1*0101 mice with DENV2 and then challenged groups of naïve or DENV2-primed mice with ZIKV 4 weeks later. Three or 7 days after ZIKV challenge, splenocytes were isolated and stimulated in vitro with the five ZIKV-specific peptides (C$_{27-41}$ (SEQ ID NO: 97), C$_{53-67}$ (SEQ ID NO: 98), C$_{81-95}$ (SEQ ID NO: 99), E$_{450-464}$ (SEQ ID NO: 104), and NS3$_{601}$-NS4A$_{12}$ (SEQ ID NO: 115)) and four DENV2/ZIKV-cross-reactive peptides (E$_{134-148}$ (SEQ ID NO: 102), NS2A$_{66-80}$ (SEQ ID NO: 108), NS4B$_{40-54}$ (SEQ ID NO: 118), and NS5$_{222-236}$ (SEQ ID NO: 125). CD4+ T cells producing IFNγ, IL-2, or both IFNγ and TNF were then quantified. Whereas CD4+ T cells from naïve mice harvested on day 3 after ZIKV infection showed no response to the peptides, cells harvested from DENV2-primed mice displayed a strong response to the DENV2/ZIKV-cross-reactive peptide NS5$_{222-236}$ (SEQ ID NO: 125), with significant expansion of cells producing IFNγ alone, IL-2 alone, and both IFNγ and TNF (FIGS. 27A and 27B). By day 7 after ZIKV challenge, naïve mice showed significant expansion of CD4+ T cells reactive with five ZIKV peptides (C$_{27-41}$ (SEQ ID NO: 97) C$_{81-95}$ (SEQ ID NO: 99), NS2A$_{66-80}$ (SEQ ID NO: 108) NS3$_{601}$-NS4A$_{12}$ (SEQ ID NO: 115), and NS5$_{222-236}$ (SEQ ID NO: 125), and cells from DENV2-immune mice showed increased responses to six ZIKV peptides (C$_{27-41}$ (SEQ ID NO: 97), C$_{53-67}$ (SEQ ID NO: 98), E$_{450-464}$ (SEQ ID NO: 104), NS2A$_{66-80}$ (SEQ ID NO: 108), NS3$_{601}$-NS4A$_{12}$ (SEQ ID NO: 115), and NS5$_{222-236}$ (SEQ ID NO: 125) (FIG. 27C and FIG. 27D). FIG. 27E summarizes the frequency and proportion of the CD4+ T cell response to ZIKV-specific, DENV2/ZIKV-cross-reactive, and total epitopes in naïve versus DENV-immune mice at 3 and 7 days following ZIKV challenge. These results showed that DENV2 priming induces DENV2/ZIKV-cross-reactive memory CD4+ T cells that are promptly activated after ZIKV challenge. Thus, prior DENV immunity appears to alter the kinetics and immunodominance pattern of the CD4+ T cell response to subsequent ZIKV infection.

Figures 28A, 28B, 28C, 28D, 28E, 28F:
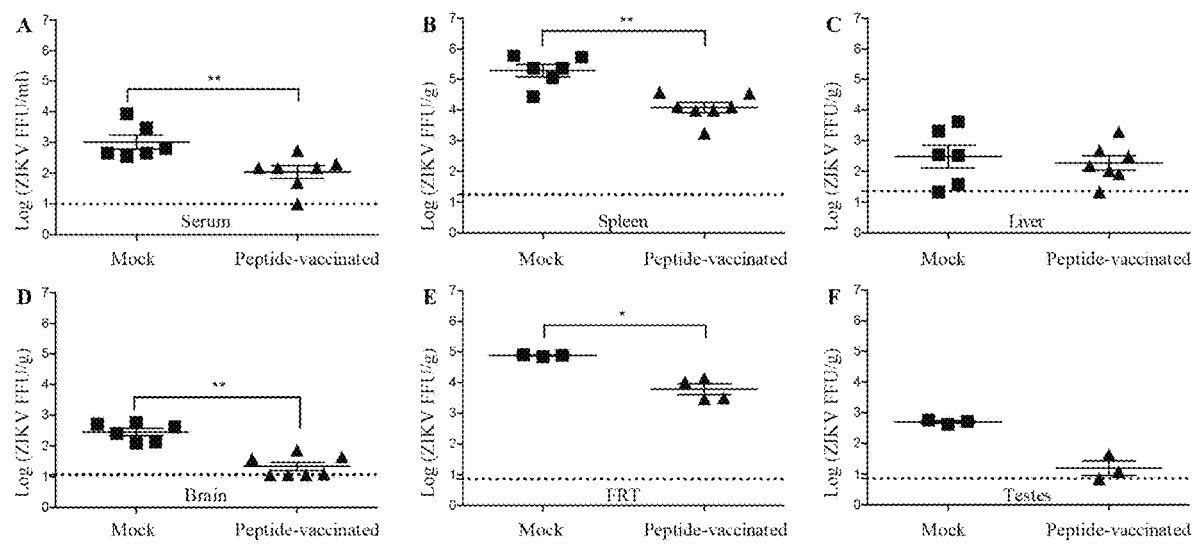
FIGS. 28A-28F: shows suppression of ZIKV infection induced by vaccination with immunodominant ZIKV peptides. Ifnar1$^{-/-}$ HLA-DRB1*0101 mice were injected subcutaneously with adjuvant alone (mock) or with a mixture of the five immunodominant ZIKV-derived HLA- DRB1*0101-binding peptides ($C_{27-41}$ (SEQ ID NO: 97), $E_{134-148}$ (SEQ ID NO: 102), $NS2A_{66-80}$, (SEQ ID NO: 108), $NS3_{601}$-$NS4A_{12}$ (SEQ ID NO: 115), and $NS5_{222-236}$ (SEQ ID NO: 125)) as described in the methods. Two weeks after the last immunization, all mice were challenged by retro-orbital injection with $1\times10^4$ FFU of ZIKV strain SD001. Three days later, serum, spleen, liver, brain, female reproductive tract (FRT), and testes were harvested, and levels of infectious ZIKV were determined using the focus-forming assay. Each point represents an individual mouse. Data represent the mean±s.e.m. of two independent experiments, with a total of 6 (mock; 3 females, 3 males) or 7 (peptide-vaccinated; 4 females, 3 males) mice/group. *P<0.05, **P<0.01 by two-tailed Mann-Whitney test.

Protective Effect of Vaccination with ZIKV-Specific and DENV2/ZIKV-Cross-Reactive Epitopes in ZIKV-Challenged Mice Ifnar1$^{-/-}$ HLA-DRB1*0101 transgenic mice were injected s.c. with adjuvant alone (mock-vaccinated) or with the five immunodominant ZIKV peptides ($C_{27-41}$ (SEQ ID NO: 97), $E_{134-148}$ (SEQ ID NO: 102), $NS2A_{66-80}$, (SEQ ID NO: 108), $NS3_{601}$-$NS4A_{12}$ (SEQ ID NO: 115), and $NS5_{222-236}$ (SEQ ID NO: 125) for 4 weeks and then challenged with ZIKV. Three days after ZIKV challenge, serum, spleen, liver, brain, FRT, and testes were harvested and viral titers were measured using the FFA. Infectious ZIKV titers were significantly lower in the serum, spleen, and brain of peptide-vaccinated mice compared with mock-vaccinated mice (12-, 17-, and 12-fold, respectively), whereas no significant differences were observed between the liver or FRT or testes titers in mock- and peptide-vaccinated mice (FIG. 28).

Figures 29A, 29B, 29C, 29D, 29E:
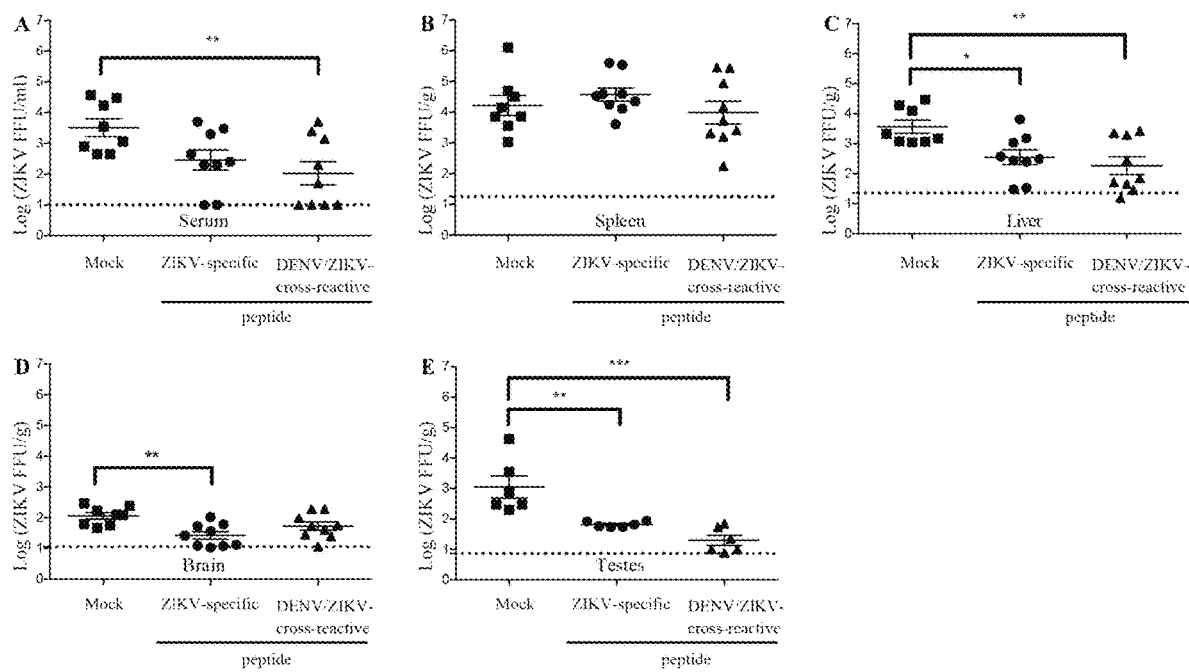
FIGS. 29A-29E: shows protection against ZIKV infection induced by vaccination with ZIKV-specific or DENV/ZIKV-cross-reactive peptides. Ifnar1$^{-/-}$ HLA-DRB1*0101 mice were injected subcutaneously with adjuvant, four ZIKV-specific peptides ($C_{27-41}$(SEQ ID NO: 97), $C_{81-95}$ (SEQ ID NO: 99), $E_{450-464}$ (SEQ ID NO: 104), and $NS3_{601}$-$NS4A_{12}$ (SEQ ID NO: 115), or four DENV2/ZIKV-cross-reactive peptides ($E_{134-148}$ (SEQ ID NO: 102), $NS2A_{66-80}$ (SEQ ID NO: 108), $NS4B_{40-54}$ (SEQ ID NO: 118), and $NS5_{222-236}$ (SEQ ID NO: 125)) as described in the Methods. Two weeks after the last immunization, all mice were challenged by retro-orbital injection with $1\times10^4$ FFU of ZIKV strain SD001. Three days later, serum, spleen, liver, brain, and testes were harvested, and levels of infectious ZIKV were determined using the focus-forming assay. Each point represents an individual mouse. Data represent the mean±s.e.m. of two independent experiments, with a total of 8 (mock; 2 females, 6 males) or 9 (ZIKV-specific; 3 females, 6 males) or 9 (DENV/ZIKV-cross-reactive; 3 females, 6 males) mice/group. *P<0.05, P<0.01, *P<0.001 by one-way ANOVA.
Figure 33:
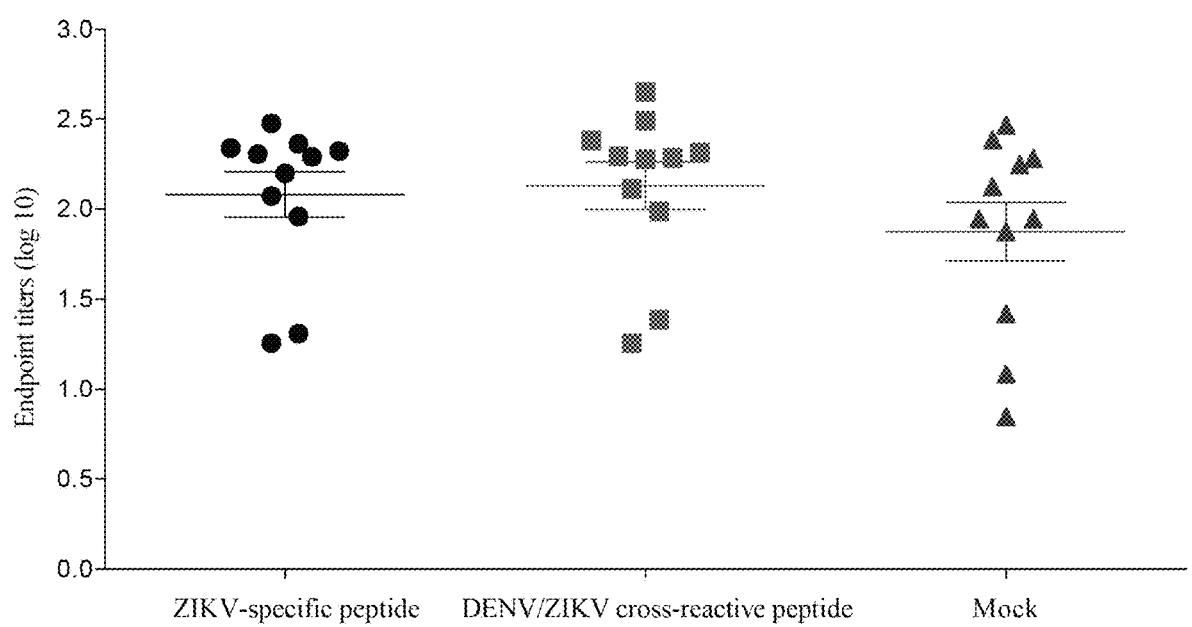
FIG. 33: shows ZIKV-reactive IgG ELISA screening of sera from mice vaccinated with DENV/ZIKV cross-reactive CD4$^+$ T cell epitopes. Ifnar1$^{-/-}$ HLA-DRB1*0101 mice were injected retro-orbitally with adjuvant alone (mock), four ZIKV-specific peptides ($C_{27-41}$ (SEQ ID NO: 97), $C_{81-95}$ (SEQ ID NO: 99), $E_{450-464}$ (SEQ ID NO: 104), and $NS3_{601}$-$NS4A_{12}$ (SEQ ID NO: 115)), or four DENV2/ZIKV-cross-reactive peptides ($E_{134-148}$ (SEQ ID NO: 102), $NS2A_{66-80}$, (SEQ ID NO: 108), $NS4B_{40-54}$ (SEQ ID NO: 118), and $NS5_{222-236}$ (SEQ ID NO: 125)) as described in the Methods. Two weeks after the last immunization, all mice were challenged by retro-orbital injection with $1\times10^4$ FFU of ZIKV strain SD001. Three days later, the mice were bled, and sera were tested for the presence of ZIKV E-reactive IgG by ELISA. Data are expressed as the mean±s.e.m. ****P<0.0001 by One-way ANOVA.

To further dissect the protective roles of ZIKV-specific and DENV2/ZIKV-cross-reactive CD4+ T cells, Applicants immunized the mice with four ZIKV-specific epitopes ($C_{27-41}$ (SEQ ID NO: 97), $C_{81-95}$ (SEQ ID NO: 99), $E_{450-464}$ (SEQ ID NO: 104), and $NS3_{601}$-$NS4A_{12}$ (SEQ ID NO: 115)), four DENV2/ZIKV-cross-reactive epitopes ($E_{134-148}$ (SEQ ID NO: 102), $NS2A_{66-80}$ (SEQ ID NO: 10), $NS4B_{40-54}$ (SEQ ID NO: 118), and $NS5_{222-236}$ (SEQ ID NO: 125), or adjuvant alone for 4 weeks, followed by ZIKV challenge. Three days after ZIKV challenge, Applicants bled the mice and measured ZIKV E-reactive IgG titers in the serum. No significant anti-ZIKV Ab response in mice vaccinated with either the ZIKV-specific or DENV2/ZIKV-cross-reactive peptides compared with mock-vaccinated mice was detected (FIG. 33), suggesting that vaccination with these ZIKV-derived CD4+ T cell epitopes does not induce a ZIKV-specific Ab response. Analysis of tissues harvested 3 days after ZIKV challenge revealed significantly lower infectious ZIKV levels in the liver, brain, and testes of mice vaccinated with ZIKV-specific epitopes compared with the mock-vaccinated mice (11-, 4-, and 17-fold, respectively; FIG. 29). Similarly, vaccination with DENV/ZIKV-cross-reactive peptides effectively suppressed ZIKV infection, with viral titers in the serum, liver, and testes reduced by 30-, 20-, and 56-fold, respectively, compared with the mock-vaccinated mice. Collectively, these results confirm that vaccination with either ZIKV-specific or DENV2/ZIKV-cross-reactive CD4+ T cell epitopes can protect against ZIKV infection in an Ab-independent manner.

Figure 30A:
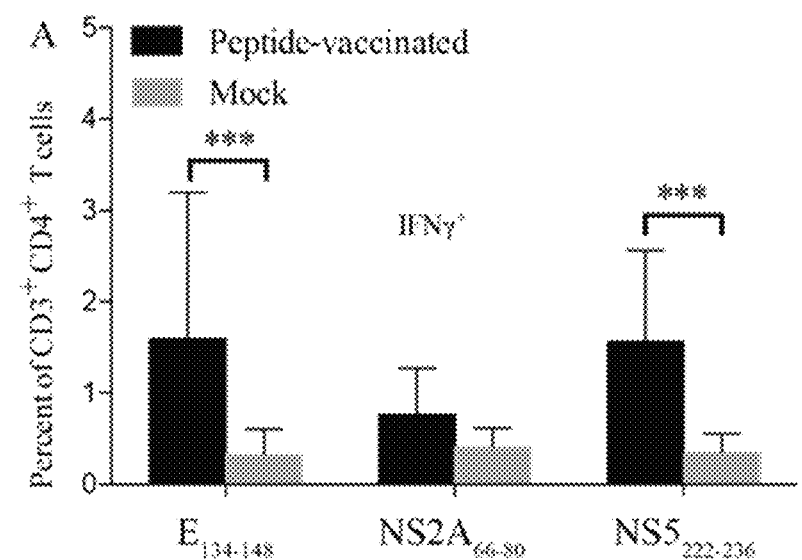
FIGS. 30A-30C: shows induction of a Th1 CD4$^+$ T cell response to ZIKV by vaccination with DENV/ZIKV-cross-reactive peptides. Ifnar1$^{-/-}$ HLA-DRB1*0101 mice were injected subcutaneously with adjuvant (mock) or four DENV2/ZIKV-cross-reactive peptides, E134-148 (SEQ ID NO: 102), $NS2A_{66-80}$ (SEQ ID NO: 108), $NS4B_{40-54}$(SEQ ID NO: 118), and $NS5_{222-236}$ (SEQ ID NO: 125), (Peptide-vaccinated) as described in the Methods. Two weeks after the last immunization, all mice were challenged by retro-orbital injection with $1\times10^4$ FFU of ZIKV strain SD001. Three days later, splenocytes were stimulated in vitro with each individual DENV/ZIKV-cross-reactive peptide for 6 h, and the frequency of CD3$^+$ CD4$^+$ T cells producing IFNγ (A), IFNγ plus TNF (B), and IFNγ plus IL-2 (C) were detected using the ICS assay. Data represent the mean s.e.m. of two independent experiments (n=5 mice/experiment; total 10 mice). P<0.01, *P<0.001, ****P<0.0001 by two-tailed Mann-Whitney test.
Figure 30B:
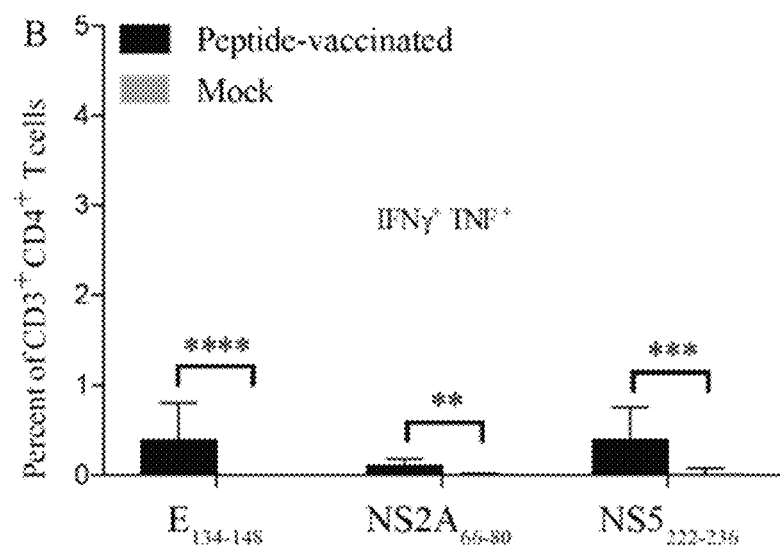
Figure 30C:
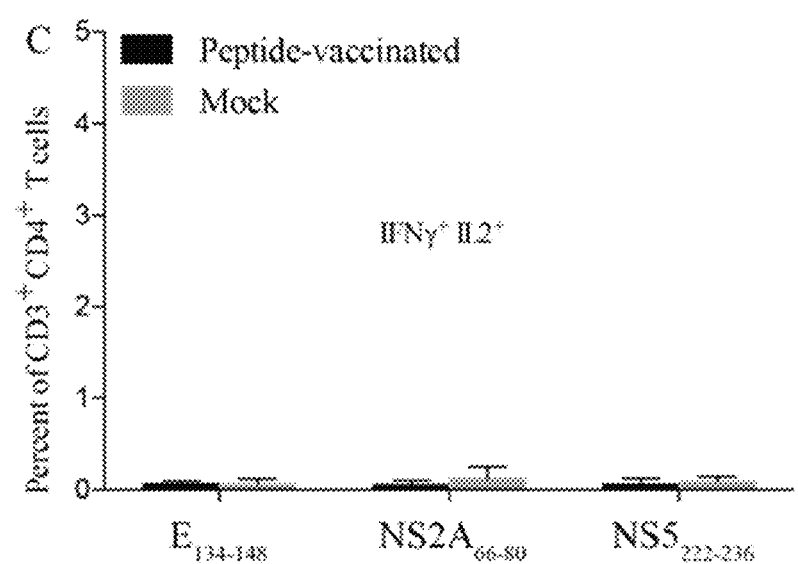
Figures 31A, 31B, 31C, 31D, 31E:
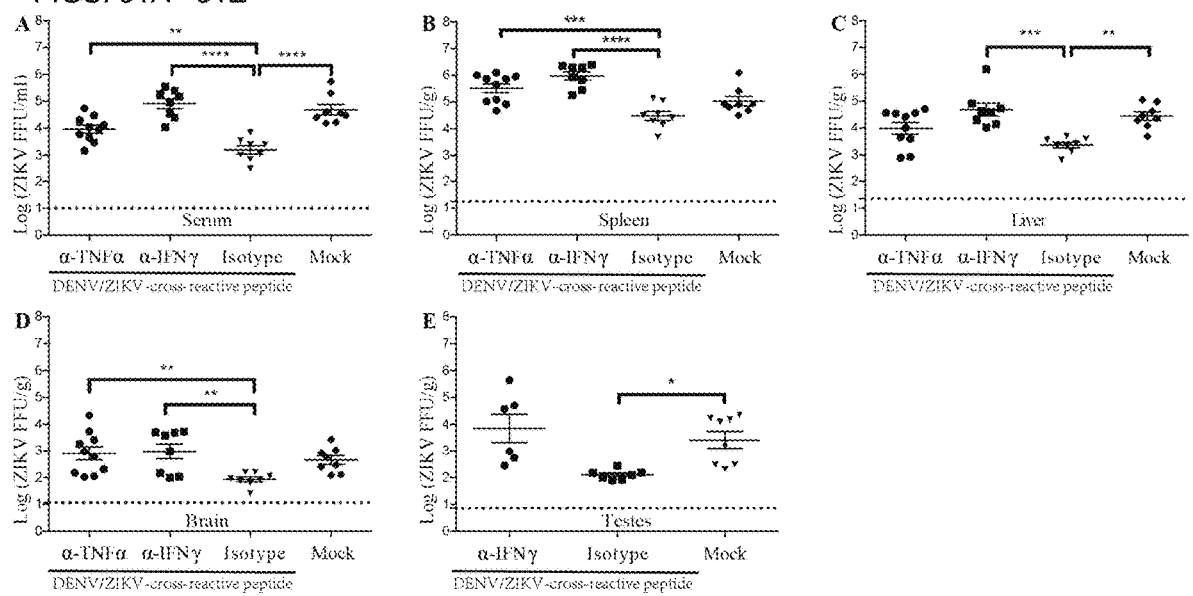
FIGS. 31A-31E: shows CD4$^+$ T cell-derived cytokine-mediated protective immunity against ZIKV infection induced by vaccination with DENV2/ZIKV-cross-reactive peptides. Ifnar1$^{-/-}$ HLA-DRB1*0101 mice were injected subcutaneously with adjuvant (mock) or four DENV2/ZIKV-cross-reactive peptides ($E_{134-148}$ (SEQ ID NO: 102), $NS2A_{66-80}$ (SEQ ID NO: 108), $NS4B_{40-54}$ (SEQ ID NO: 118), and $NS5_{222-236}$ (SEQ ID NO: 125)) as described in the Methods. Two weeks after the last immunization, all mice were challenged by retro-orbital injection with $1\times10^4$ FFU of ZIKV strain SD001. Mice were injected intraperitoneally with a neutralizing Ab against TNF or IFNγ or an isotype control Ab on days 3 and 1 before and 1 day after ZIKV infection. Three days after ZIKV challenge, serum, spleen, liver, brain, and testes were harvested, and levels of infectious ZIKV were determined using the focus-forming assay. Each point represents an individual mouse. Data represent the mean±s.e.m. of two independent experiments, with a total of 10 (α-TNF; 8 females, 2 males) or 8 (α-IFNγ; 2 females, 6 males) or 8 (Isotype; 1 females, 7 males) or 8 (Mock; 0 females, 8 males) mice/group. *P<0.05, P<0.01, *P<0.001, ****P<0.0001 by one-way ANOVA.
Figures 34A, 34B, 34C, 34D:
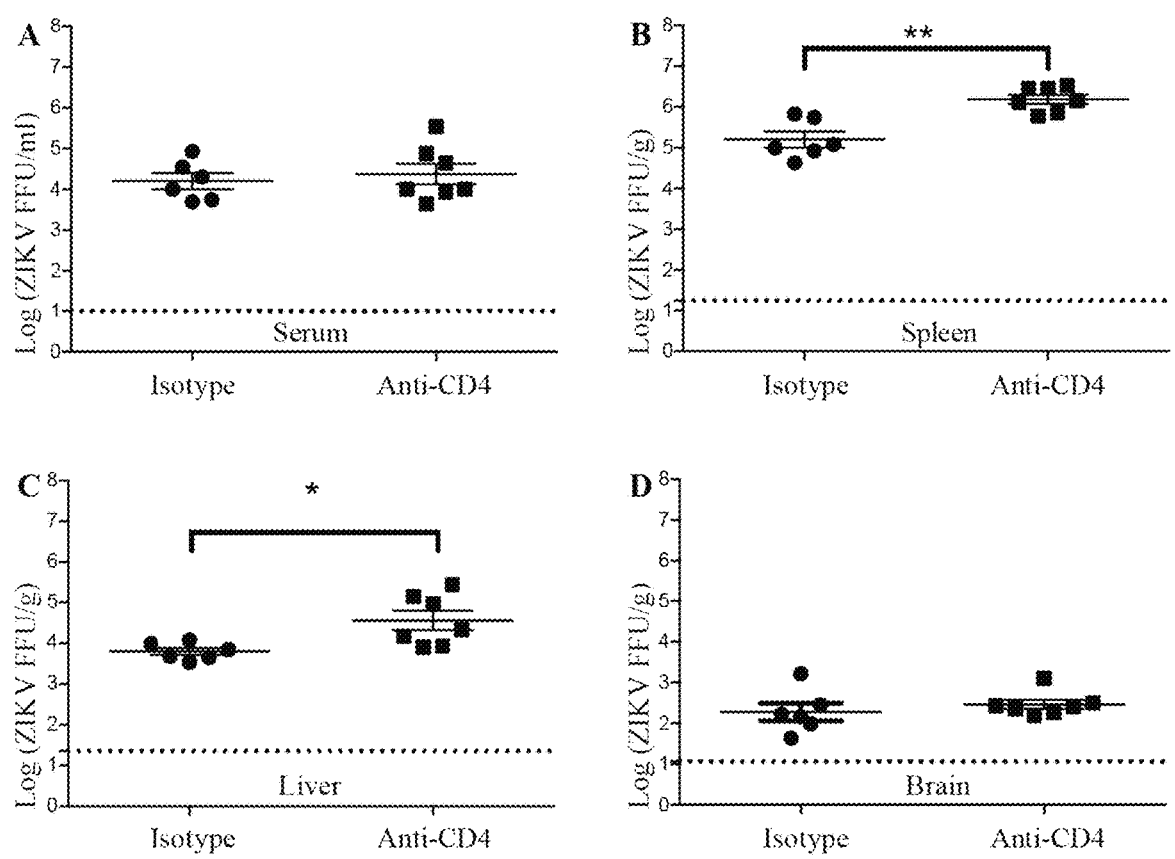
FIGS. 34A-34D: shows CD4$^+$ T cell-mediated protective immunity against ZIKV infection induced by vaccination with DENV/ZIKV cross-reactive peptides. Ifnar1$^{-/-}$ HLA-DRB1*0101 mice were injected subcutaneously with four DENV2/ZIKV-cross-reactive peptides ($E_{134-148}$ (SEQ ID NO: 102), $NS2A_{66-80}$ (SEQ ID NO: 108), $NS4B_{40-54}$ (SEQ ID NO: 118), and $NS5_{222-236}$ (SEQ ID NO: 125)) as described in the Methods. Two weeks after the last immunization, all mice were challenged by retro-orbital injection with $1\times10^4$ FFU of ZIKV strain SD001. Mice were injected intraperitoneally with isotype control Ab or anti-CD4 Ab on days 3 and 1 before and 1 day after ZIKV infection. Three days after ZIKV challenge, serum, spleen, liver, and brain were harvested, and levels of infectious ZIKV were determined using the focus-forming assay. Each point represents an individual mouse. Data represent the mean±s.e.m. of two independent experiments, with a total of 6 (isotype; 3 females, 3 males) or 7 (anti-CD4; 4 females, 3 males) mice/group. *P<0.05, **P<0.01 by two-tailed Mann-Whitney test.

CD4+ T Cells Elicited by DENV2/ZIKV-Cross-Reactive Epitopes Mediate Protection Against ZIKV Via Secretion of IFNγ and/or TNF To determine the potential mechanisms by which the cross-reactive CD4+ T cells contribute to anti-ZIKV immunity, Applicants analyzed their cytokine secretion patterns after vaccination with each of the four DENV2/ZIKV-cross-reactive epitopes followed by challenge with ZIKV, as described above. Upon in vitro re-stimulation with each of the DENV2/ZIKV-cross-reactive epitopes, splenocytes from the vaccinated mice mainly produced either IFNγ alone or both IFN-γ and TNF, whereas no IFN-γ plus IL-2-producing cells were detected (FIG. 30), revealing a strong Th1 effector CD4+ T cell response. To evaluate whether the protection conferred by vaccination with DENV2/ZIKV-cross-reactive epitopes was mediated by cytokine-producing CD4+ T cells, Applicants vaccinated the mice with DENV2/ZIKV-cross-reactive epitopes, treated them with a CD4+ T cell-depleting Ab (FIG. 34) or neutralizing Abs against either IFN-γ or TNF (FIG. 31), and then challenged the mice with ZIKV. Three days after ZIKV infection, blood and tissues were harvested and infectious ZIKV titers were determined. ZIKV titers were markedly higher in the spleen, liver, and brain (8-, 12-, and 1-fold, respectively) of CD4+ T cell-depleted compared with isotype Ab-treated mice (FIG. 34), showing that CD4+ T cells elicited by the DENV2/ZIKV-cross-reactive epitopes contributed to protection against subsequent ZIKV infection. Similarly, compared with the isotype control Ab-treated mice, ZIKV titers were significantly higher in the serum, spleen, and brain of mice treated with a neutralizing anti-TNF Ab (6-, 11-, and 10-fold, respectively) or anti-IFNγ Ab (53-, 31-, and 11-fold, respectively) (FIG. 31). ZIKV titers in the testes were also significantly inhibited by anti-IFN-γ Ab. Moreover, ZIKV titers in the liver were significantly suppressed by Ab-mediated depletion of IFN-γ, but not of TNF (FIG. 31). Taken together, these results identify TNF- and/or IFNγ-secreting CD4+ T cells as the likely effector cells that confer protection against subsequent ZIKV infection in mice vaccinated with DENV2/ZIKV-cross-reactive epitopes.

Materials & Methods

Viral Strains and Mice

Ifnar1$^{-/-}$ HLA-DRB1*0101 mice have been previously described[33]. Mice were bred under specific pathogen-free conditions at the La Jolla Institute for Immunology. Mouse experiments were approved by the Institutional Animal Care and Use Committee (protocol no. AP028-SS1-0615). Sample sizes were estimated based on experiments in similar studies, and the experiments were not randomized or blinded. ZIKV strain SD001 was isolated from the urine of a ZIKV-infected individual who traveled to Venezuela during the 2016 ZIKV epidemic. PCR sequencing showed that ZIKV SD001 belongs to the Asian lineage and is phylogenetically related to ZIKV isolates circulating in South American countries[34]. The mouse-adapted DENV2 strain S221 is a triple-plaque purified clone derived from DENV2 D251035. Both ZIKV and DENV2 were grown in C6/36 mosquito cells, and viral titers were measured using a focus-forming assay (FFA) with the baby hamster kidney (BHK)-21 cell line as described below.

Peptide Prediction and Synthesis

The online software Immune Epitope Database and Analysis Resource (IEDB-AR) (www.iedb.org) was used to predict HLA-DRB1*0101-binding peptides from ZIKV strain FSS13025 (Cambodia, 2010; Asian lineage). Thirty predicted epitope candidates were synthesized by Synthetic Biomolecules as crude peptides (>75% purity) for use in in vitro experiments. The four peptides identified as ZIKV-specific ($C_{27-41}$ (SEQ ID NO: 97), $C_{81-95}$ (SEQ ID NO: 99), $E_{450-464}$ (SEQ ID NO: 104), and $NS3_{601}$-$NS4A_{12}$(SEQ ID NO: 115)) and four as DENV2/ZIKV-cross-reactive ($E_{134-148}$ (SEQ ID NO: 102), $NS2A_{66-80}$ (SEQ ID NO: 108), $NS4B_{40-54}$ (SEQ ID NO: 118), and $NS5_{222-236}$ (SEQ ID NO: 125) CD4+ T cell epitopes (ZIKV sequence numbering; Table 1) were synthesized at high purity (>99%) for use in vitro and in mouse vaccination experiments. All peptides were dissolved in dimethyl sulfoxide (DMSO) at a concentration of 40 mg/ml and were stored at −20° C.

ZIKV Infection of Mice and Peptide Screening

For the 30-peptide epitope screen, 5-week-old female or male mice were infected retro-orbitally (r.o.) with either 1×10$^2$ focus-forming units (FFU) of ZIKV SD001 or 2×10$^3$ FFU of DENV2 S221 in 200 µl of 10% fetal bovine serum in phosphate-buffered saline (FBS/PBS). Seven days after infection, spleens were removed and single-cell splenocyte suspensions were prepared. A total of $1\times10^6$ splenocytes was plated in each well of a 96-well U-bottom plate and stimulated with individual peptides (20 µg crude peptide per well) for 6 h. One hour into the incubation, brefeldin A (GolgiPlug, BD Biosciences) was added to the cells. Positive and negative controls were splenocytes stimulated with phorbol-12-myristate-13-acetate (PMA, 0.1 µg/ml) and ionomycin (1 µg/ml) or incubated alone, respectively. Cells were harvested, washed, and processed for the ICS assay as described below.

ZIKV Challenge of DENV2-Immune Mice and Peptide Screening

Five-week-old female or male mice were inoculated intraperitoneally (i.p.) with $2\times10^3$ FFU of DENV2 S221. Four weeks later, the mice were challenged r.o. with $1\times10^4$ FFU of ZIKV SD001, and on day 3 or 7 after infection, splenocytes were prepared and stimulated in vitro as described above using 20 µg crude peptide or 1 µg purified peptide/well. Positive and negative controls were included in all experiments. Cells were harvested, washed, and processed for the ICS assay as described below.

ZIKV Challenge of Peptide-Vaccinated Mice

Mixtures of (i) the five ZIKV-specific and DENV2/ZIKV-cross-reactive immunodominant peptides ($C_{27-41}$ (SEQ ID NO: 97), $E_{134-148}$ (SEQ ID NO: 102), $NS2A_{66-80}$ (SEQ ID NO: 108), $NS3_{601}$-$NS4A_{12}$ (SEQ ID NO: 115), and $NS5_{222-236}$ (SEQ ID NO: 125); 50 µg of each peptide/mouse), (ii) the four ZIKV-specific peptides alone ($C_{27-41}$ (SEQ ID NO: 97), $C_{81-95}$ (SEQ ID NO: 99), $E_{450-464}$ (SEQ ID NO: 104), and $NS3_{601}$-$NS4A_{12}$ (SEQ ID NO: 115); 50 µg of each peptide/mouse), or (iii) the four DENV2/ZIKV-cross-reactive peptides alone ($E_{134-148}$ (SEQ ID NO: 102), $NS2A_{66-80}$ (SEQ ID NO: 108), (SEQ ID NO: 108,) $NS4B_{40-54}$ (SEQ ID NO: 118), and $NS5_{222-236}$ (SEQ ID NO: 125); 50 µg of each peptide/mouse) were emulsified in complete Freund's adjuvant and injected subcutaneously (s.c.) into 5-week-old female or male mice. Two weeks later, the mice were boosted by injection of the same peptides in incomplete Freund's adjuvant. Mock-vaccinated mice received the adjuvants in DMSO without peptides. Two weeks after the last immunization, all mice were challenged r.o. with $1\times10^4$ FFU of ZIKV SD001. For $CD4^+$ T cell-depletion experiments, mice were vaccinated with DENV2/ZIKV-cross-reactive peptides as described above and injected i.p. with 250 µg of a $CD4^+$ T cell-depleting Ab (clone GK1.5, BioXcell) or isotype control Ab (LTF-2, BioXcell) on days 3 and 1 before and 1 day after ZIKV infection. For IFNγ- or TNF-depletion experiments, mice were vaccinated with the cross-reactive peptides as described above and injected i.p. with 100 µg of neutralizing anti-TNF monoclonal Ab (mAb; clone XT3.11, BioXcell), anti-IFNγ mAb (clone XMG1.2, eBioscience), or isotype control mAb (clone HPRN, BioXcell) on days 3 and 1 before and 1 day after ZIKV infection. Three days after ZIKV challenge, all mice were sacrificed and serum samples were collected. After cardiac perfusion with PBS, the spleen, liver, brain, testes, and female reproductive tract (FRT) were harvested. Splenocytes were stimulated in vitro as described above using 1 µg purified peptide/well. Cells were harvested, washed, and processed for the ICS assay as described below. ZIKV-reactive IgG in serum was measured using a capture ELISA assay, and ZIKV viral titers in serum and tissues were measured using a FFA, both as described below.

ICS Assay

After incubation of splenocytes with peptides or PMA/ionomycin, cells were harvested, washed, and incubated with Fc Block (CD16/CD32 mAb 2.4G2, BD Biosciences), followed by staining with fixable Live/Dead blue viability stain (Life technologies) and the following antibodies: PerCP-Cy5.5-conjugated anti-CD3 mAb (clone 145-2C11, Tonbo), APC-eFluor780-conjugated anti-CD4 mAb (clone GK1.5, Invitrogen), Brilliant Violet (BV) 785-conjugated anti-CD44 mAb (clone IMT, Biolegend), PE-conjugated anti-CD11a (clone M17/4, Biolegend), BV605-conjugated anti-CD49d (clone 9C10(MFR4.B, Biolegend), PE-conjugated anti-CD25 mAb (clone PC61, Biolegend), PE-conjugated or biotin-conjugated anti-CD185 mAb (CXCR5, clone SPRC15; Invitrogen), BV 605-conjugated anti-CD27a mAb (PD1, clone $29F.1A_{12}$; Biolegend), and/or BV 421-conjugated streptavidin (#405225, Biolegend). Cells were then fixed and permeabilized using Cytofix/Cytoperm solution (BD Biosciences), followed by staining with FITC-conjugated anti-IFNγ mAb (clone XMG1.2, Tonbo), Alexa Fluor 700- or APC-conjugated anti-TNF mAb (clone MP6-XT22, eBioscience), PE-, BV 421-, or BV 711-conjugated anti-IL-2 mAb (clone JES6-5H4, Biolegend), APC-conjugated anti-IL-4 mAb (clone 11B11, Biolegend), PE-conjugated anti-IL-5 mAb (clone TRFK5, eBioscience), BV510-conjugated anti-IL-17A mAb (clone 17B7, eBioscience), and/or Alexa Fluor 700-conjugated anti-FoxP3 mAb (clone FJK-16S, eBioscience). Data were collected using an LSR Fortessa flow cytometer (BD Biosciences) and analyzed using FlowJo software X 10.0.7 (Tree Star).

ELISA Assay

To quantify ZIKV-reactive IgG, 96-well high-affinity ELISA plates (Costar) were coated with ZIKV E protein (1 mg/ml ZIKVSU-ENV, Native Antigen) in 100 µl coating buffer (0.1 M $NaHCO_3$) overnight at 4° C. and then blocked for 1 h at room temperature (RT) with 5% Blocker Casein in PBS (Thermo Fisher Scientific). Mouse serum samples were serially diluted three-fold from 1:30 to 1:65,610 in 1% bovine serum albumin (BSA)/PBS and added to the coated wells. 10 µg of the pan-flavivirus envelope protein-specific mAb 4G2 (BioXcell) in 1% BSA/PBS was titrated 1:3 like the sera and used as positive control. After 1.5 h incubation at RT, the wells were washed with washing buffer (0.05% Tween 20 in PBS) and then incubated with HRP-conjugated goat anti-mouse IgG (1:5000 in 1% BSA/PBS) for 1.5 h at RT. TMB chromogen solution (eBioscience) was added to the wells, the reaction was stopped by addition of 2N sulfuric acid, and the absorbance at 450 nm was read on a Spectramax M2E microplate reader (Molecular Devices). The ZIKV-specific IgG endpoint titers were calculated as the reciprocal of the highest serum dilution that gave a reading twice the cutoff absorbance of the negative control (1% BSA/PBS).

Focus-Forming Assay (FFA) of Viral Burden

BHK-21 cells ($2\times10^5$/well) were plated in 24-well culture plates and incubated at 37° C. in a $CO_2$ incubator overnight. Mouse spleen, liver, brain, eye, testes, and FRT were homogenized using TissueLyser II (Qiagen) and centrifuged at 6000 rpm for 10 min. Aliquots of the supernatants (100 µl) were serially diluted 10-fold in medium, added to the BHK-21 cells, and incubated at 37° C. for 1 h. The viral supernatant was aspirated, and a pre-warmed solution of 1% carboxymethyl cellulose medium was added to each well. After 2.5 days incubation, the cells were fixed with 4% paraformaldehyde solution for 30 min at RT, washed with PBS, permeabilized with 1% Triton X-100 for 20 min at RT, and washed again with PBS. Plates were blocked with 10% FBS/PBS for 40 min at RT and incubated with the pan-flavivirus envelope protein-specific mAb 4G2 (1 µg/ml) for 1 h at RT. Plates were washed with PBS and incubated with horseradish peroxidase-conjugated goat anti-mouse IgG mAb (1:1000 dilution) for 1.5 h at RT. Finally, the plates were washed with PBS and developed with TrueBlue peroxidase substrate for 20 min at RT. Foci were counted and the viral titers were expressed as FFU/ml serum or FFU/g tissue.

Statistical Analysis

All data were analyzed with Prism software version 6.0 (GraphPad Software) and are expressed as the mean±standard error (s.e.m.). Statistically significant differences between two groups were determined using the Mann-Whitney test, and one-way ANOVA was used for multiple comparisons. P<0.05 was considered significant.

Discussion

The co-circulation of DENV and ZIKV and the recent availability of a vaccine against DENV raise the need to understand the impact of prior DENV immunity during subsequent ZIKV infection. The goals of the present study were to (i) identify HLA-DRB1*0101-restricted DENV2/ZIKV-cross-reactive CD4$^+$ epitopes using Ifnar1$^{-/-}$ HLA-DRB1*0101 transgenic mice, (ii) determine the characteristics and functions of the CD4$^+$ T cells elicited by DENV2/ZIKV-cross-reactive epitopes, and (iii) determine the extent to and mechanism by which vaccination with DENV2/ZIKV-cross-reactive epitopes could protect the mice against subsequent ZIKV infection. Nine ZIKV epitopes able to stimulate CD4$^+$ T cells from ZIKV-primed mice are identified herein, six of which elicited Th1 CD4$^+$ T cells producing multiple cytokines (IFNγ, TNF, and/or IL-2). Four DENV2/ZIKV cross-reactive CD4$^+$ T cell epitopes were also identified, and Applicants show that vaccination of Ifnar1$^{-/-}$ HLA-DRB1*0101 transgenic mice with either the ZIKV-specific or DENV2/ZIKV cross-reactive epitopes induced CD4$^+$ T cell responses that contributed to viral clearance during a subsequent ZIKV challenge. Finally, Applicants showed that IFNγ- and/or TNF-secreting cross-reactive CD4$^+$ T cells were responsible for mediating the vaccination-induced protection against ZIKV infection. Thus, CD4$^+$ T cells producing the canonical Th1 effector cytokines represent one of the arms of DENV/ZIKV protective immunity against ZIKV.

Applicants showed the impact of preexisting DENV immunity on the development of the CD4$^+$ T cell response to ZIKV and revealed that cross-reactive CD4$^+$ T cells expanded early (day 3) after ZIKV challenge and remained dominant in the later phase of the response (day 7). This result is in agreement with human data showing that the cross-reactive CD4$^+$ T cells against ZIKV are rapidly activated in DENV-immune individuals[13]. It is also consistent with studies on the responses of cross-reactive CD8$^+$ T cells during sequential infections with DENV and ZIKV 13,26 or heterologous DENV serotypes[41]. Thus, both CD4$^+$ and CD8$^+$ T cell subsets that are elicited by previous DENV exposure and are reactive with ZIKV appear earlier during ZIKV infection in DENV-immune than DENV-naïve humans and Ifnar1$^{-/-}$ HLA transgenic mice. This finding further supports the use of the present mouse model for examining key features of human relevant, DENV/ZIKV-cross-reactive CD4$^+$ T cells against ZIKV infection.

Applicants identified four HLA-DRB1*0101-restricted ZIKV epitopes ($E_{134-148}$ (SEQ ID NO: 102), $NS2A_{66-80}$ (SEQ ID NO: 108), $NS4B_{40-54}$ (SEQ ID NO: 118), and $NS5_{222-236}$ (SEQ ID NO: 125) that were cross-reactive on DENV-primed CD4$^+$ T cells. The level of amino acid sequence homology between ZIKV and DENV2 proteomes can reach 56%13. In comparison, a 40-100% homology was observed between these four DENV2/ZIKV-cross-reactive epitopes and the corresponding sequences of DENV2 (Table 11). Therefore, Applicants conclude that the sequential exposure to DENV and ZIKV preferentially activates the T cell response targeting conserved epitopes between the viruses, which are consistent with recent animal and human studies[13,26] Reynolds and colleagues immunized HLA-DRB1*0101 transgenic mice with recombinant ZIKV proteins (E, NS1, NS3, and NS5) and mapped the CD4$^+$ T cell epitopes by in vitro stimulation of primed splenocytes with overlapping peptides spanning the ZIKV E protein. Analysis of IFNγ production in that study identified five immunodominant ZIKV epitopes in the E protein ($E_{1-20}$, $E_{131-150}$, $E_{301-320}$, $E_{401-420}$, and $E_{411-430}$)[32]. Furthermore, the $E_{1-20}$ and $E_{401-420}$ homologs in DENV1-4, WNV, and YFV were also shown to stimulate IFN-γ production by ZIKV-primed CD4$^+$ T cells[32]. Applicants identified RAIWYMWL (SEQ ID NO: 61) as a DENV2/ZIKV-cross-reactive epitope in $NS5_{222-236}$ (SEQ ID NO: 125), suggesting that this 8-mer is likely to be a core sequence recognized by human CD4$^+$ T cells as $NS5_{222-236}$ (SEQ ID NO: 125) is a highly conserved T cell epitope among the flaviviruses; the identical sequence is present in DENV1-4 and YFV, and the homologous sequence in JEV differs by only two residues. Similarly, Applicants previously identified an HLA-B*0702-restricted CD8$^+$ T cell epitope that is highly conserved among many flaviviruses, including ZIKV, DENV1-4, WNV, JEV, Usutu virus, Murray Valley encephalitis virus, and Kunjin virus[26]. The identification of such highly conserved CD4$^+$ T cell and CD8$^+$ T cell epitopes among flaviviruses demonstrates the effectiveness of pan-flavivirus vaccines, such as those provided herein, to elicit both CD4$^+$ and CD8$^+$ T cell-mediated protective immunity against multiple flaviviruses.

TABLE 11

ZIKV epitopes and DENV2 variants

| peptides[a] | Sequences[b] | Conservation[c] |
|---|---|---|
| ZIKV-$E_{134-148}$ | NLEYRIMLSVHGSQH | 40% |
| DENV2-$E_{134-148}$ | NLEYTIVITPHSGEE | |
| ZIKV-$NS2A_{66-80}$ | LALIAAFKVRPALLV | 67% |
| DENV2-$NS2A_{66-80}$ | LALLAAFKVRPTFAA | |
| ZIKV-$NS4B_{40-54}$ | WAIYAALTTFITPAV | 40% |
| DENV2-$NS4B_{40-54}$ | WALCEALTLATGPIS | |
| ZIKV-$NS5_{222-236}$ | RAIWYMWLGARFLEF | 100% |
| DENV2-$NS5_{222-236}$ | RAIWYMWLGARFLEF | |

[a]ZIKV peptides are identified as DENV2/ZIKV cross-reactive epitopes via ICS assays with cells from DENV2-infected mice
[b]Amino acid residues underlined are conserved between ZINKV epitope and DENV2 variant
[c]%shared amino acids between ZIKV and DENV2

Table 11 discloses SEQ ID NOS 102, 127, 108, 128, 118, 129, 125 and 125, respectively, in order of appearance.

The data provided herein demonstrate a protective role for DENV-elicited CD4$^+$ T cells against ZIKV infection. This data have revealed that these cross-reactive CD4$^+$ T cells mediate their antiviral function against ZIKV via secretion of IFNγ or TNF, revealing that the cross-reactive, canonical Th1 CD4$^+$ T cells represent a novel correlate of protection against flavivirus infections. The data provided herein demonstrate that a pan-flavivirus vaccine that induces canonical Th1 and CD8$^+$ T cell responses may, in certain embodiments, not only be effective against both DENV and ZIKV but also avoid ADE. This implication is important, as the DENV- and ZIKV-specific vaccines that are currently licensed or in clinical trials have been focused on eliciting antibody responses and may at least in theory cause ADE if the vaccine-induced Ab response is inefficient or wanes.

In summary, Applicants findings disclosed herein demonstrate that vaccination with DENV2/ZIKV-cross-reactive peptides elicits a Th1 CD4$^+$ T cell effector response that promotes protection against ZIKV infection in an IFNγ- and/or TNF-dependent manner. These findings demonstrate that inclusion of such cross-reactive epitopes can enhance the efficacy of vaccines to ZIKV.

Other examples of implementations will become apparent to the reader in view of the teachings of the present description and as such, will not be further described here.

Note that titles or subtitles may be used throughout the present disclosure for convenience of a reader, but in no way should these limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

All references cited throughout the specification are hereby incorporated by reference in their entirety for all purposes.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

Although various embodiments of the disclosure have been described and illustrated, it will be apparent to those skilled in the art in light of the present description that numerous modifications and variations can be made. The scope of the invention is defined more particularly in the appended claims.

REFERENCES

I—Example 1

Atkinson, B., Hearn, P., Afrough, B., Lumley, S., Carter, D., Aarons, E. J., Simpson, A. J., Brooks, T. J., and Hewson, R. (2016). Detection of Zika Virus in Semen. Emerg Infect Dis 22, 940.

Brasil, P., Pereira, J. P., Jr., Raja Gabaglia, C., Damasceno, L., Wakimoto, M., Ribeiro Nogueira, R. M., Carvalho de Sequeira, P., Machado Siqueira, A., Abreu de Carvalho, L. M., Cotrim da Cunha, D., et al. (2016). Zika Virus Infection in Pregnant Women in Rio de Janeiro—Preliminary Report. N Engl J Med.

Clausen, B. E., Burkhardt, C., Reith, W., Renkawitz, R., and Forster, I. (1999). Conditional gene targeting in macrophages and granulocytes using LysMcre mice. Transgenic research 8, 265-277.

Cugola, F. R., Fernandes, I. R., Russo, F. B., Freitas, B. C., Dias, J. L. M., Guimarães, K. P., Benazzato, C., Almeida, N., Pignatari, G. C., Romero, S., et al. (2016). The Brazilian Zika virus strain causes birth defects in experimental models. Nature advance online publication.

D' Ortenzio, E., Matheron, S., de Lamballerie, X., Hubert, B., Piorkowski, G., Maquart, M., Descamps, D., Damond, F., Yazdanpanah, Y., and Leparc-Goffart, I. (2016). Evidence of Sexual Transmission of Zika Virus. N Engl J Med.

Deckard, D. T., Chung, W. M., Brooks, J. T., Smith, J. C., Woldai, S., Hennessey, M., Kwit, N., and Mead, P. (2016). Male-to-Male Sexual Transmission of Zika Virus—Texas, January 2016. MMWR Morb Mortal Wkly Rep 65, 372-374.

Diamond, M. S., Kinder, M., Matsushita, H., Mashayekhi, M., Dunn, G. P., Archambault, J. M., Lee, H., Arthur, C. D., White, J. M., Kalinke, U., et al. (2011). Type I interferon is selectively required by dendritic cells for immune rejection of tumors. The Journal of experimental medicine 208, 1989-2003.

Dick, G. W. (1952). Zika virus. II. Pathogenicity and physical properties. Trans R Soc Trop Med Hyg 46, 521-534.

Dowall, S. D., Graham, V. A., Rayner, E., Atkinson, B., Hall, G., Watson, R. J., Bosworth, A., Bonney, L. C., Kitchen, S., and Hewson, R. (2016). A Susceptible Mouse Model for Zika Virus Infection. PLoS Negl Trop Dis 10, e0004658.

Elong Ngono, A., Chen, H. W., Tang, W. W., Joo, Y., King, K., Weiskopf, D., Sidney, J., Sette, A., and Shresta, S. (2016). Protective Role of Cross-Reactive CD8 T Cells Against Dengue Virus Infection. EBioMedicine 13, 284-293.

Foy, B. D., Kobylinski, K. C., Chilson Foy, J. L., Blitvich, B. J., Travassos da Rosa, A., Haddow, A. D., Lanciotti, R. S., and Tesh, R. B. (2011). Probable non-vector-borne transmission of Zika virus, Colorado, USA. Emerg Infect Dis 17, 880-882.

Govero, J., Esakky, P., Scheaffer, S. M., Fernandez, E., Drury, A., Platt, D. J., Gorman, M. J., Richner, J. M., Caine, E. A., Salazar, V., et al. (2016). Zika virus infection damages the testes in mice. Nature.

Guzman, M. G., Kouri, G., Valdes, L., Bravo, J., Alvarez, M., Vazques, S., Delgado, I., and Halstead, S. B. (2000). Epidemiologic studies on Dengue in Santiago de Cuba, 1997. American journal of epidemiology 152, 793-799; discussion 804.

Haddow, A. D., Schuh, A. J., Yasuda, C. Y., Kasper, M. R., Heang, V., Huy, R., Guzman, H., Tesh, R. B., and Weaver, S. C. (2012). Genetic characterization of Zika virus strains: geographic expansion of the Asian lineage. PLoS Negl Trop Dis 6, e1477.

Halstead, S. B. (2007). Dengue. Lancet (London, England) 370, 1644-1652.

Heang, V., Yasuda, C. Y., Sovann, L., Haddow, A. D., Travassos da Rosa, A. P., Tesh, R. B., and Kasper, M. R. (2012). Zika virus infection, Cambodia, 2010. Emerg Infect Dis 18, 349-351.

Hills, S. L., Russell, K., Hennessey, M., Williams, C., Oster, A. M., Fischer, M., and Mead, P. (2016). Transmission of Zika Virus Through Sexual Contact with Travelers to Areas of Ongoing Transmission—Continental United States, 2016. MMWR Morb Mortal Wkly Rep 65, 215-216.

Imrie, A., Meeks, J., Gurary, A., Sukhbataar, M., Kitsutani, P., Effler, P., and Zhao, Z. (2007). Differential functional avidity of dengue virus-specific T-cell clones for variant peptides representing heterologous and previously encountered serotypes. J Virol 81, 10081-10091.

Ioos, S., Mallet, H. P., Leparc Goffart, I., Gauthier, V., Cardoso, T., and Herida, M. (2014). Current Zika virus epidemiology and recent epidemics. Medecine et maladies infectieuses 44, 302-307.

Kim, Y., Ponomarenko, J., Zhu, Z., Tamang, D., Wang, P., Greenbaum, J., Lundegaard, C., Sette, A., Lund, O., Bourne, P. E., et al. (2012). Immune epitope database analysis resource. Nucleic acids research 40, W525-530.

Lanciotti, R. S., Lambert, A. J., Holodniy, M., Saavedra, S., and Signor Ldel, C. (2016). Phylogeny of Zika Virus in Western Hemisphere, 2015. Emerg Infect Dis 22, 933-935.

Lazear, H. M., and Diamond, M. S. (2016). Zika Virus: New Clinical Syndromes and its Emergence in the Western Hemisphere. J Virol.

Lazear, Helen M., Govero, J., Smith, Amber M., Platt, Derek J., Fernandez, E., Miner, Jonathan J., and Diamond, Michael S. (2016). A Mouse Model of Zika Virus Pathogenesis. Cell Host & Microbe.

Li, C., Xu, D., Ye, Q., Hong, S., Jiang, Y., Liu, X., Zhang, N., Shi, L., Qin, C. F., and Xu, Z. (2016a). Zika Virus Disrupts Neural Progenitor Development and Leads to Microcephaly in Mice. Cell stem cell 19, 120-126.

Li, H., Saucedo-Cuevas, L., Tang, W., Chai, G., J. A., R.-N., Sheets, N., A. V., T., S., S., and J. G., G. (2016b). Zika virus infection in adult brain shows tropism for neural progenitors and alters proliferation. Cell stem cell In Press.

Lopez, C. B., Yount, J. S., Hermesh, T., and Moran, T. M. (2006). Sendai virus infection induces efficient adaptive immunity independently of type I interferons. J Virol 80, 4538-4545.

Malone, R. W., Homan, J., Callahan, M. V., Glasspool-Malone, J., Damodaran, L., Schneider Ade, B., Zimler, R., Talton, J., Cobb, R. R., Ruzic, I., et al. (2016). Zika Virus: Medical Countermeasure Development Challenges. PLoS Negl Trop Dis 10, e0004530.

Mangada, M. M., Endy, T. P., Nisalak, A., Chunsuttiwat, S., Vaughn, D. W., Libraty, D. H., Green, S., Ennis, F. A., and Rothman, A. L. (2002). Dengue-specific T cell responses in peripheral blood mononuclear cells obtained prior to secondary dengue virus infections in Thai schoolchildren. J Infect Dis 185, 1697-1703.

Mangada, M. M., and Rothman, A. L. (2005). Altered cytokine responses of dengue-specific CD4$^+$ T cells to heterologous serotypes. J Immunol 175, 2676-2683.

Miner, J. J., Cao, B., Govero, J., Smith, A. M., Fernandez, E., Cabrera, O. H., Garber, C., Noll, M., Klein, R. S., Noguchi, K. K., et al. (2016). Zika Virus Infection during Pregnancy in Mice Causes Placental Damage and Fetal Demise. Cell 165, 1081-1091.

Mlakar, J., Korva, M., Tul, N., Popovic, M., Poljsak-Prijatelj, M., Mraz, J., Kolenc, M., Resman Rus, K., Vesnaver Vipotnik, T., Fabjan Vodusek, V., et al. (2016). Zika Virus Associated with Microcephaly. N Engl J Med 374, 951-958.

Mongkolsapaya, J., Dejnirattisai, W., Xu, X. N., Vasanawathana, S., Tangthawornchaikul, N., Chairunsri, A., Sawasdivorn, S., Duangchinda, T., Dong, T., Rowland-Jones, S., et al. (2003). Original antigenic sin and apoptosis in the pathogenesis of dengue hemorrhagic fever. Nat Med 9, 921-927.

Mongkolsapaya, J., Duangchinda, T., Dejnirattisai, W., Vasanawathana, S., Avirutnan, P., Jairungsri, A., Khemnu, N., Tangthawornchaikul, N., Chotiyarnwong, P., Sae-Jang, K., et al. (2006). T cell responses in dengue hemorrhagic fever: are cross-reactive T cells suboptimal? J Immunol 176, 3821-3829.

Musso, D., Roche, C., Robin, E., Nhan, T., Teissier, A., and Cao-Lormeau, V. M. (2015). Potential sexual transmission of Zika virus. Emerg Infect Dis 21, 359-361.

Oehler, E., Watrin, L., Lane, P., Leparc-Goffart, I., Lastere, S., Valour, F., Baudouin, L., Mallet, H., Musso, D., and Ghawche, F. (2014). Zika virus infection complicated by Guillain-Barre syndrome—case report, French Polynesia, December 2013. Euro surveillance: bulletin Europeen sur les maladies transmissibles=European communicable disease bulletin 19.

Oliveira Melo, A. S., Malinger, G., Ximenes, R., Szejnfeld, P. O., Alves Sampaio, S., and Bispo de Filippis, A. M. (2016). Zika virus intrauterine infection causes fetal brain abnormality and microcephaly: tip of the iceberg? Ultrasound in obstetrics & gynecology: the official journal of the International Society of Ultrasound in Obstetrics and Gynecology 47, 6-7.

Pinto, A. K., Brien, J. D., Lam, C. Y., Johnson, S., Chiang, C., Hiscott, J., Sarathy, V. V., Barrett, A. D., Shresta, S., and Diamond, M. S. (2015). Defining New Therapeutics Using a More Immunocompetent Mouse Model of Antibody-Enhanced Dengue Virus Infection. mBio 6, e01316-01315.

Prestwood, T. R., May, M. M., Plummer, E. M., Morar, M. M., Yauch, L. E., and Shresta, S. (2012a). Trafficking and replication patterns reveal splenic macrophages as major targets of dengue virus in mice. J Virol 86, 12138-12147.

Prestwood, T. R., Morar, M. M., Zellweger, R. M., Miller, R., May, M. M., Yauch, L. E., Lada, S. M., and Shresta, S. (2012b). Gamma interferon (IFN-gamma) receptor restricts systemic dengue virus replication and prevents paralysis in IFN-alpha/beta receptor-deficient mice. J Virol 86, 12561-12570.

Prestwood, T. R., Prigozhin, D. M., Sharar, K. L., Zellweger, R. M., and Shresta, S. (2008). A mouse-passaged dengue virus strain with reduced affinity for heparan sulfate causes severe disease in mice by establishing increased systemic viral loads. J Virol 82, 8411-8421.

Rossi, S. L., Tesh, R. B., Azar, S. R., Muruato, A. E., Hanley, K. A., Auguste, A. J., Langsjoen, R. M., Paessler, S., Vasilakis, N., and Weaver, S. C. (2016). Characterization of a Novel Murine Model to Study Zika Virus. Am J Trop Med Hyg.

Sangkawibha, N., Rojanasuphot, S., Ahandrik, S., Viriyapongse, S., Jatanasen, S., Salitul, V., Phanthumachinda, B., and Halstead, S. B. (1984). Risk factors in dengue shock syndrome: a prospective epidemiologic study in Rayong, Thailand. I. The 1980 outbreak. American journal of epidemiology 120, 653-669.

Sapparapu, G., Fernandez, E., Kose, N., Cao, B., Fox, J. M., Bombardi, R. G., Zhao, H., Nelson, C. A., Bryan, A. L., Barnes, T., et al. (2016). Neutralizing human antibodies prevent Zika virus replication and fetal disease in mice. Nature.

Screaton, G., Mongkolsapaya, J., Yacoub, S., and Roberts, C. (2015). New insights into the immunopathology and control of dengue virus infection. Nat Rev Immunol 15, 745-759.

Sheehan, K. C., Lai, K. S., Dunn, G. P., Bruce, A. T., Diamond, M. S., Heutel, J. D., Dungo-Arthur, C., Carrero, J. A., White, J. M., Hertzog, P. J., et al. (2006). Blocking monoclonal antibodies specific for mouse IFN-alpha/beta receptor subunit 1 (IFNAR-1) from mice immunized by in vivo hydrodynamic transfection. J Interferon Cytokine Res 26, 804-819.

Shrestha, B., and Diamond, M. S. (2004). Role of CD8+ T cells in control of West Nile virus infection. J Virol 78, 8312-8321.

Shrestha, B., Zhang, B., Purtha, W. E., Klein, R. S., and Diamond, M. S. (2008). Tumor necrosis factor alpha protects against lethal West Nile virus infection by promoting trafficking of mononuclear leukocytes into the central nervous system. J Virol 82, 8956-8964.

Tang, W. W., Grewal, R., and Shresta, S. (2015). Influence of antibodies and T cells on dengue disease outcome: insights from interferon receptor-deficient mouse models. Current opinion in virology 13, 61-66.

Tang, W. W., Young, M. P., Mamidi, A., Regla-Nava, J. A., Kim, K., and Shresta, S. (2016). A mouse model of Zika virus sexual transmission and vaginal viral replication. Cell Reports In Press.

Tetro, J. A. (2016). Zika and microcephaly: Causation, correlation, or coincidence? Microbes Infect.

Thompson, L. J., Kolumam, G. A., Thomas, S., and Murali-Krishna, K. (2006). Innate inflammatory signals induced by various pathogens differentially dictate the IFN-I dependence of CD8 T cells for clonal expansion and memory formation. J Immunol 177, 1746-1754.

Ventura, C. V., Maia, M., Bravo-Filho, V., Gois, A. L., and Belfort, R., Jr. (2016). Zika virus in Brazil and macular atrophy in a child with microcephaly. Lancet (London, England).

Venturi, G., Zammarchi, L., Fortuna, C., Remoli, M. E., Benedetti, E., Fiorentini, C., Trotta, M., Rizzo, C., Mantella, A., Rezza, G., et al. (2016). An autochthonous case of Zika due to possible sexual transmission, Florence, Italy, 2014. Euro surveillance: bulletin Europeen sur les maladies transmissibles=European communicable disease bulletin 21.

Weiskopf, D., Angelo, M. A., de Azeredo, E. L., Sidney, J., Greenbaum, J. A., Fernando, A. N., Broadwater, A., Kolla, R. V., De Silva, A. D., de Silva, A. M., et al. (2013). Comprehensive analysis of dengue virus-specific responses supports an HLA-linked protective role for CD8+ T cells. Proc Natl Acad Sci USA 110, E2046-2053.

Weiskopf, D., Bangs, D. J., Sidney, J., Kolla, R. V., De Silva, A. D., de Silva, A. M., Crotty, S., Peters, B., and Sette, A. (2015). Dengue virus infection elicits highly polarized CX3CR1+ cytotoxic CD4+ T cells associated with protective immunity. Proc Natl Acad Sci USA 112, E4256-4263.

Weiskopf, D., and Sette, A. (2014). T-cell immunity to infection with dengue virus in humans. Front Immunol 5, 93.

Yang, M., Rainone, A., Shi, X. Q., Fournier, S., and Zhang, J. (2014). A new animal model of spontaneous autoimmune peripheral polyneuropathy: implications for Guillain-Barre syndrome. Acta neuropathologica communications 2, 5.

Yauch, L. E., Prestwood, T. R., May, M. M., Morar, M. M., Zellweger, R. M., Peters, B., Sette, A., and Shresta, S. (2010). CD4+ T cells are not required for the induction of dengue virus-specific $CD8^+$ T cell or antibody responses but contribute to protection after vaccination. J Immunol 185, 5405-5416.

Yauch, L. E., Zellweger, R. M., Kotturi, M. F., Qutubuddin, A., Sidney, J., Peters, B., Prestwood, T. R., Sette, A., and Shresta, S. (2009). A protective role for dengue virus-specific CD8+ T cells. J Immunol 182, 4865-4873.

Zammarchi, L., Stella, G., Mantella, A., Bartolozzi, D., Tappe, D., Gunther, S., Oestereich, L., Cadar, D., Munoz-Fontela, C., Bartoloni, A., et al. (2015). Zika virus infections imported to Italy: clinical, immunological and virological findings, and public health implications. J Clin Virol 63, 32-35.

Zellweger, R. M., Eddy, W. E., Tang, W. W., Miller, R., and Shresta, S. (2014). CD8+ T cells prevent antigen-induced antibody-dependent enhancement of dengue disease in mice. J Immunol 193, 4117-4124.

Zellweger, R. M., Miller, R., Eddy, W. E., White, L. J., Johnston, R. E., and Shresta, S. (2013). Role of humoral versus cellular responses induced by a protective dengue vaccine candidate. PLoS Pathog 9, e1003723.

Zellweger, R. M., and Shresta, S. (2014). Mouse models to study dengue virus immunology and pathogenesis. Front Immunol 5, 151.

Zellweger, R. M., Tang, W. W., Eddy, W. E., King, K., Sanchez, M. C., and Shresta, S. (2015). CD8+ T Cells Can Mediate Short-Term Protection against Heterotypic Dengue Virus Reinfection in Mice. J Virol 89, 6494-6505.

REFERENCES

II—Example 2

1 Lazear, H. M. & Diamond, M. S. Zika Virus: New Clinical Syndromes and its Emergence in the Western Hemisphere. *Journal of virology*, doi: JVI.00252-16 [pii] 10.1128/JVI.00252-16 (2016).

2 Choumet, V. & Despres, P. Dengue and other flavivirus infections. *Rev Sci Tech* 34, 473-478, 467 472 (2015).

3 Faye, O. et al. Molecular evolution of Zika virus during its emergence in the 20(th) century. *PLoS neglected tropical diseases* 8, e2636, doi:10.1371/journal. pntd.0002636 (2014).

4 Cugola, F. R. et al. The Brazilian Zika virus strain causes birth defects in experimental models. *Nature* 534, 267-271, doi:10.1038/nature18296 (2016).

5 Miner, J. J. et al. Zika Virus Infection during Pregnancy in Mice Causes Placental Damage and Fetal Demise. *Cell* 165, 1081-1091, doi:10.1016/j. cell.2016.05.008 (2016).

6 Li, C. et al. Zika Virus Disrupts Neural Progenitor Development and Leads to Microcephaly in Mice. *Cell stem cell* 19, 120-126, doi:10.1016/j. stem.2016.04.017 (2016).

7 Oehler, E. et al. Zika virus infection complicated by Guillain-Barre syndrome—case report, French Polynesia, December 2013. *Euro surveillance: bulletin Europeen sur les maladies transmissibles=European communicable disease bulletin* 19 (2014).

8 D'Ortenzio, E. et al. Evidence of Sexual Transmission of Zika Virus. *N Engl J Med*, doi:10.1056/NEJMc1604449 (2016).

9 Musso, D. et al. Potential sexual transmission of Zika virus. *Emerging infectious diseases* 21, 359-361, doi: 10.3201/eid2102.141363 (2015).

10 Dupont-Rouzeyrol, M. et al. Co-infection with Zika and dengue viruses in 2 patients, New Caledonia, 2014. *Emerging infectious diseases* 21, 381-382, doi:10.3201/eid2102.141553 (2015).

11 Screaton, G., Mongkolsapaya, J., Yacoub, S. & Roberts, C. New insights into the immunopathology and control of dengue virus infection. *Nat Rev Immunol* 15, 745-759, doi:10.1038/nri3916 (2015).

12 Rothman, A. L., Medin, C. L., Friberg, H. & Currier, J. R. Immunopathogenesis Versus Protection in Dengue Virus Infections. *Current tropical medicine reports* 1, 13-20, doi:10.1007/s40475-013-0009-0 (2014).

13 Weiskopf, D. & Sette, A. T-cell immunity to infection with dengue virus in humans. *Frontiers in immunology* 5, 93, doi:10.3389/fimmu.2014.00093 (2014).

14 Halstead, S. B. Dengue. *Lancet* 370, 1644-1652, doi:10.1016/s0140-6736(07)61687-0 (2007).

15 Huang, X. et al. Antibody-dependent enhancement of dengue virus infection inhibits RLR-mediated Type-I IFN-independent signalling through upregulation of cellular autophagy. *Scientific reports* 6, 22303, doi:10.1038/srep22303 (2016).

16 Stettler, K. et al. Specificity, cross-reactivity, and function of antibodies elicited by Zika virus infection. *Science* (New York, N.Y.) 353, 823-826, doi:10.1126/science.aaf8505 (2016).

17 Barba-Spaeth, G. et al. Structural basis of potent Zika-dengue virus antibody cross-neutralization. *Nature* 536, 48-53, doi:10.1038/nature18938 (2016).

18 Dejnirattisai, W. et al. Dengue virus sero-cross-reactivity drives antibody-dependent enhancement of infection with zika virus. *Nature immunology*, doi:10.1038/ni.3515 (2016).

19 Priyamvada, L. et al. Human antibody responses after dengue virus infection are highly cross-reactive to Zika virus. *Proceedings of the National Academy of Sciences of the United States of America* 113, 7852-7857, doi:10.1073/pnas.1607931113 (2016).

20 Swanstrom, J. A. et al. Dengue Virus Envelope Dimer Epitope Monoclonal Antibodies Isolated from Dengue Patients Are Protective against Zika Virus. *mBio* 7, doi:10.1128/mBio.01123-16 (2016).

21 Elong Ngono, A. et al. Mapping and Role of the $CD8^+$ T Cell Response During Primary Zika Virus Infection in Mice. *Cell host & microbe*, doi:10.1016/j.chom.2016.12.010 (2017).

22 Weiskopf, D. et al. Insights into HLA-restricted T cell responses in a novel mouse model of dengue virus infection point toward new implications for vaccine design. *Journal of immunology* 187, 4268-4279, doi:10.4049/jimmunol.1101970 (2011).

23 Weiskopf, D. et al. Immunodominance changes as a function of the infecting dengue virus serotype and primary versus secondary infection. *Journal of virology* 88, 11383-11394, doi:10.1128/JVI.01108-14 (2014).

24 Ashour, J. et al. Mouse STAT2 restricts early dengue virus replication. *Cell host & microbe* 8, 410-421, doi:10.1016/j.chom.2010.10.007 (2010).

25 Aguirre, S. et al. DENV inhibits type I IFN production in infected cells by cleaving human STING. *PLoS pathogens* 8, e1002934, doi:10.1371/journal.ppat.1002934 (2012).

26 Yu, C. Y. et al. Dengue virus targets the adaptor protein MITA to subvert host innate immunity. *PLoS pathogens* 8, e1002780, doi:10.1371/journal.ppat.1002780 (2012).

27 Weiskopf, D. et al. Comprehensive analysis of dengue virus-specific responses supports an HLA-linked protective role for CD8+ T cells. *Proceedings of the National Academy of Sciences of the United States of America* 110, E2046-E2053, doi:10.1073/pnas.1305227110 (2013).

28 Weiskopf, D. et al. The human CD8+ T cell responses induced by a live attenuated tetravalent dengue vaccine are directed against highly conserved epitopes. *Journal of virology* 89, 120-128, doi:10.1128/jvi.02129-14 (2015).

29 Weiskopf, D. et al. Human CD8+ T-*Cell* Responses Against the 4 Dengue Virus Serotypes Are Associated With Distinct Patterns of Protein Targets. *The Journal of infectious diseases* 212, 1743-1751, doi:10.1093/infdis/jiv289 (2015).

30 Duangchinda, T. et al. Immunodominant T-cell responses to dengue virus NS3 are associated with DHF. *Proceedings of the National Academy of Sciences of the United States of America* 107, 16922-16927, doi:10.1073/pnas.1010867107 (2010).

31 Rivino, L. et al. Differential targeting of viral components by CD4+ versus CD8+ T lymphocytes in dengue virus infection. *Journal of virology* 87, 2693-2706, doi:10.1128/jvi.02675-12 (2013).

32 Grant, A. et al. Zika Virus Targets Human STAT2 to Inhibit Type I Interferon Signaling. *Cell host & microbe* 19, 882-890, doi:10.1016/j.chom.2016.05.009 (2016).

33 Rossi, S. L. et al. Characterization of a Novel Murine Model to Study Zika Virus. *The American journal of tropical medicine and hygiene* 94, 1362-1369, doi:10.4269/ajtmh.16-0111 (2016).

34 Dowall, S. D. et al. A Susceptible Mouse Model for Zika Virus Infection. *PLoS neglected tropical diseases* 10, e0004658, doi:10.1371/journal.pntd.0004658 (2016).

35 Lazear, Helen M. et al. A Mouse Model of Zika Virus Pathogenesis. *Cell host & microbe*, doi:10.1016/j.chom.2016.03.010 (2016).

36 Teixeira, M. G., Siqueira, J. B., Jr., Ferreira, G. L., Bricks, L. & Joint, G. Epidemiological trends of dengue disease in Brazil (2000-2010): a systematic literature search and analysis. *PLoS neglected tropical diseases* 7, e2520, doi:10.1371/journal.pntd.0002520 (2013).

37 Prestwood, T. R. et al. Gamma interferon (IFN-gamma) receptor restricts systemic dengue virus replication and prevents paralysis in IFN-alpha/beta receptor-deficient mice. *Journal of virology* 86, 12561-12570, doi:10.1128/JVI.06743-11 (2012).

38 Yauch, L. E. et al. A protective role for dengue virus-specific $CD8^+$ T cells. *Journal of immunology* (Baltimore, Md.: 1950) 182, 4865-4873, doi:10.4049/jimmunol.0801974 (2009).

39 Zellweger, R. M. et al. $CD8^+$ T Cells Can Mediate Short-Term Protection against Heterotypic Dengue Virus Reinfection in Mice. *Journal of virology* 89, 6494-6505, doi:10.1128/jvi.00036-15 (2015).

40 Elong Ngono, A. et al. Protective Role of Cross-Reactive CD8 T Cells Against Dengue Virus Infection. *EBioMedicine* In Press (2016).

41 Yockey, L. J. et al. Vaginal Exposure to Zika Virus during Pregnancy Leads to Fetal Brain Infection. *Cell* 166, 1247-1256 e1244, doi:10.1016/j.cell.2016.08.004 (2016).

42 Beckham, J. D., Pastula, D. M., Massey, A. & Tyler, K. L. Zika Virus as an Emerging Global Pathogen: Neurological Complications of Zika Virus. *JAMA neurology* 73, 875-879, doi:10.1001/jamaneurol.2016.0800 (2016).

43 Li, H. et al. Zika Virus Infects Neural Progenitors in the Adult Mouse Brain and Alters Proliferation. *Cell stem cell*, doi:10.1016/j.stem.2016.08.005 (2016).

44 Larocca, R. A. et al. Vaccine protection against Zika virus from Brazil. *Nature*, doi:10.1038/nature18952 (2016).

45 Dowd, K. A. et al. Rapid development of a DNA vaccine for Zika virus. *Science* (New York, N.Y.) 354, 237-240, doi:10.1126/science.aai9137 (2016).

46 Hunter, P., Erasmus, B. J. & Vorster, J. H. Teratogenicity of a mutagenised Rift Valley fever virus (MVP 12) in sheep. *The Onderstepoort journal of veterinary research* 69, 95-98 (2002).

47 Adams Waldorf, K. M. & McAdams, R. M. Influence of infection during pregnancy on fetal development. *Reproduction* 146, R151-162, doi:10.1530/REP-13-0232.

48 Yauch, L. E. et al. CD4+ T cells are not required for the induction of dengue virus-specific CD8$^+$ T cell or antibody responses but contribute to protection after vaccination. *Journal of immunology* (Baltimore, Md.: 1950) 185, 5405-5416, doi:10.4049/jimmunol.1001709 (2010).

49 Zellweger, R. M. et al. Role of humoral versus cellular responses induced by a protective dengue vaccine candidate. *PLoS pathogens* 9, e1003723, doi:10.1371/journal.ppat.1003723 (2013).

50 Zellweger, R. M., Eddy, W. E., Tang, W. W., Miller, R. & Shresta, S. CD8+ T cells prevent antigen-induced antibody-dependent enhancement of dengue disease in mice. *Journal of immunology* (Baltimore, Md.: 1950) 193, 4117-4124, doi:10.4049/jimmunol.1401597 (2014).

51 Weiskopf, D. et al. Dengue virus infection elicits highly polarized CX3CR1+ cytotoxic CD4+ T cells associated with protective immunity. *Proceedings of the National Academy of Sciences of the United States of America* 112, E4256-4263, doi:10.1073/pnas.1505956112 (2015).

52 Croft, M., Carter, L., Swain, S. L. & Dutton, R. W. Generation of polarized antigen-specific CD8 effector populations: reciprocal action of interleukin (IL)-4 and IL-12 in promoting type 2 versus type 1 cytokine profiles. *The Journal of experimental medicine* 180, 1715-1728 (1994).

REFERENCES

III—Example 3

1. Cao-Lormeau, V. M. and D. Musso, *Emerging arboviruses in the Pacific.* Lancet, 2014. 384(9954): p. 1571-2.
2. Duffy, M. R., et al., *Zika virus outbreak on Yap Island, Federated States of Micronesia.* N Engl J Med, 2009. 360(24): p. 2536-43.
3. Cao-Lormeau, V. M., et al., *Guillain-Barre Syndrome outbreak associated with Zika virus infection in French Polynesia: a case-control study.* Lancet, 2016. 387 (10027): p. 1531-1539.
4. Mlakar, J., et al., *Zika Virus Associated with Microcephaly.* N Engl J Med, 2016. 374(10): p. 951-8.
5. Driggers, R. W., et al., *Zika Virus Infection with Prolonged Maternal Viremia and Fetal Brain Abnormalities.* N Engl J Med, 2016. 374(22): p. 2142-51.
6. Hennessey, M., M. Fischer, and J. E. Staples, *Zika Virus Spreads to New Areas—Region of the Americas, May 2015-January 2016.* MMWR Morb Mortal Wkly Rep, 2016. 65(3): p. 55-8.
7. Rasmussen, S. A., et al., *Zika Virus and Birth Defects—Reviewing the Evidence for Causality.* N Engl J Med, 2016. 374(20): p. 1981-7.
8. Munoz-Suano, A., et al., *Regulatory T cells protect from autoimmune arthritis during pregnancy.* J Autoimmun, 2012. 38(2-3): p. J103-8.
9. Constantin, C. M., et al., *Normal establishment of virus-specific memory CD8 T cell pool following primary infection during pregnancy.* J Immunol, 2007. 179(7): p. 4383-9.
10. Erlebacher, A., *Mechanisms of T cell tolerance towards the allogeneic fetus.* Nat Rev Immunol, 2013. 13(1): p. 23-33.
11. Arora, N., et al., *Microbial Vertical Transmission during Human Pregnancy.* Cell Host Microbe, 2017. 21(5): p. 561-567.
12. King, N. J. C., M. M. Teixeira, and S. Mahalingam, *Zika Virus: Mechanisms of Infection During Pregnancy.* Trends Microbiol, 2017. 25(9): p. 701-702.
13. Anders, A. P., et al., *Current concepts in maternal-fetal immunology: Recognition and response to microbial pathogens by decidual stromal cells.* Am J Reprod Immunol, 2017. 77(3).
14. Miner, J. J., et al., *Zika Virus Infection during Pregnancy in Mice Causes Placental Damage and Fetal Demise.* Cell, 2016. 165(5): p. 1081-91.
15. Yockey, L. J., et al., *Vaginal Exposure to Zika Virus during Pregnancy Leads to Fetal Brain Infection.* Cell, 2016. 166(5): p. 1247-1256 e4.
16. Cugola, F. R., et al., *The Brazilian Zika virus strain causes birth defects in experimental models.* Nature, 2016. 534(7606): p. 267-71.
17. Quicke, K. M., et al., *Zika Virus Infects Human Placental Macrophages.* Cell Host Microbe, 2016. 20(1): p. 83-90.
18. Jurado, K. A., et al., *Zika virus productively infects primary human placenta-specific macrophages.* JCI Insight, 2016. 1(13).
19. Mysorekar, I. U. and M. S. Diamond, *Modeling Zika Virus Infection in Pregnancy.* N Engl J Med, 2016. 375(5): p. 481-4.
20. Li, C., et al., *Zika Virus Disrupts Neural Progenitor Development and Leads to Microcephaly in Mice.* Cell Stem Cell, 2016. 19(1): p. 120-6.
21. Wu, K. Y., et al., *Vertical transmission of Zika virus targeting the radial glial cells affects cortex development of offspring mice.* Cell Res, 2016. 26(6): p. 645-54.
22. Halstead, S. B., *Pathogenesis of dengue: challenges to molecular biology.* Science, 1988. 239(4839): p. 476-81.
23. Goncalvez, A. P., et al., *Monoclonal antibody-mediated enhancement of dengue virus infection in vitro and in vivo and strategies for prevention.* Proc Natl Acad Sci USA, 2007. 104(22): p. 9422-7.
24. Balsitis, S. J., et al., *Lethal antibody enhancement of dengue disease in mice is prevented by Fc modification.* PLoS Pathog, 2010. 6(2): p. e1000790.
25. Zellweger, R. M., T. R. Prestwood, and S. Shresta, *Enhanced infection of liver sinusoidal endothelial cells in a mouse model of antibody-induced severe dengue disease.* Cell Host Microbe, 2010. 7(2): p. 128-39.
26. Katzelnick, L. C., et al., *Antibody-dependent enhancement of severe dengue disease in humans.* Science, 2017.
27. Weiskopf, D., et al., *Comprehensive analysis of dengue virus-specific responses supports an HLA-linked protective role for CD8+ T cells.* Proc Natl Acad Sci USA, 2013. 110(22): p. E$_{2046-53}$.
28. Weiskopf, D., et al., *Human CD8+ T-Cell Responses Against the 4 Dengue Virus Serotypes Are Associated With Distinct Patterns of Protein Targets.* J Infect Dis, 2015. 212(11): p. 1743-51.
29. de Alwis, R., et al., *Immunodominant Dengue Virus-Specific CD8+ T Cell Responses Are Associated with a Memory PD-1+ Phenotype.* J Virol, 2016. 90(9): p. 4771-9.
30. Weiskopf, D., et al., *Dengue virus infection elicits highly polarized CX3CR1+ cytotoxic CD4+ T cells associated with protective immunity.* Proc Natl Acad Sci USA, 2015. 112(31): p. E4256-63.

31. Simon-Loriere, E., et al., *Increased adaptive immune responses and proper feedback regulation protect against clinical dengue.* Sci Transl Med, 2017. 9(405).
32. Rivino, L., et al., *Virus-specific T lymphocytes home to the skin during natural dengue infection.* Sci Transl Med, 2015. 7(278): p. 278ra35.
33. Elong Ngono, A., et al., *Protective Role of Cross-Reactive CD8 T Cells Against Dengue Virus Infection.* EBioMedicine, 2016. 13: p. 284-293.
34. Zellweger, R. M., et al., *CD8+ T Cells Can Mediate Short-Term Protection against Heterotypic Dengue Virus Reinfection in Mice.* J Virol, 2015. 89(12): p. 6494-505.
35. Yauch, L. E., et al., *A protective role for dengue virus-specific CD8+ T cells.* J Immunol, 2009. 182(8): p. 4865-73.
36. Yauch, L. E., et al., *CD4+ T cells are not required for the induction of dengue virus-specific CD8+ T cell or antibody responses but contribute to protection after vaccination.* J Immunol, 2010. 185(9): p. 5405-16.
37. Prestwood, T. R., et al., *Gamma interferon (IFN-gamma) receptor restricts systemic dengue virus replication and prevents paralysis in IFN-alpha/beta receptor-deficient mice.* J Virol, 2012. 86(23): p. 12561-70.
38. Zellweger, R. M., et al., *CD8+ T cells prevent antigen-induced antibody-dependent enhancement of dengue disease in mice.* J Immunol, 2014. 193(8): p. 4117-24.
39. Zellweger, R. M., et al., *Role of humoral versus cellular responses induced by a protective dengue vaccine candidate.* PLoS Pathog, 2013. 9(10): p. e1003723.
40. Dudley, D. M., et al., *A rhesus macaque model of Asian-lineage Zika virus infection.* Nat Commun, 2016. 7: p. 12204.
41. Elong Ngono, A., et al., *Mapping and Role of the CD8+ T Cell Response During Primary Zika Virus Infection in Mice.* Cell Host Microbe, 2017. 21(1): p. 35-46.
42. Priyamvada, L., et al., *Human antibody responses after dengue virus infection are highly cross-reactive to Zika virus.* Proc Natl Acad Sci USA, 2016. 113(28): p. 7852-7.
43. Stettler, K., et al., *Specificity, cross-reactivity, and function of antibodies elicited by Zika virus infection.* Science, 2016. 353(6301): p. 823-6.
44. Bardina, S. V., et al., *Enhancement of Zika virus pathogenesis by preexisting antiflavivirus immunity.* Science, 2017. 356(6334): p. 175-180.
45. Dejnirattisai, W., et al., *Dengue virus sero-cross-reactivity drives antibody-dependent enhancement of infection with zika virus.* Nat Immunol, 2016. 17(9): p. 1102-8.
46. Charles, A. S. and R. C. Christofferson, *Utility of a Dengue-Derived Monoclonal Antibody to Enhance Zika Infection In Vitro.* PLoS Curr, 2016. 8.
47. Swanstrom, J. A., et al., *Dengue Virus Envelope Dimer Epitope Monoclonal Antibodies Isolated from Dengue Patients Are Protective against Zika Virus.* MBio, 2016. 7(4).
48. Kawiecki, A. B. and R. C. Christofferson, *Zika Virus-Induced Antibody Response Enhances Dengue Virus Serotype 2 Replication In Vitro.* J Infect Dis, 2016. 214(9): p. 1357-1360.
49. Wen, J., et al., *Identification of Zika virus epitopes reveals immunodominant and protective roles for dengue virus cross-reactive CD8+ T cells.* Nat Microbiol, 2017. 2: p. 17036.
50. Grifoni, A., et al., *Prior Dengue virus exposure shapes T cell immunity to Zika virus in humans.* J Virol, 2017.
51. Paquin-Proulx, D., et al., *T-cell Responses in Individuals Infected with Zika Virus and in Those Vaccinated Against Dengue Virus.* Pathog Immun, 2017. 2(2): p. 274-292.
52. Wen, J., et al., *Dengue virus-reactive CD8+ T cells mediate-cross protection against subsequent Zika virus challenge.* Nat Commun, 2017. 8(1): p. 1459.
53. Pantoja, P., et al., *Zika virus pathogenesis in rhesus macaques is unaffected by pre-existing immunity to dengue virus.* Nat Commun, 2017. 8: p. 15674.
54. McCracken, M. K., et al., *Impact of prior flavivirus immunity on Zika virus infection in rhesus macaques.* PLoS Pathog, 2017. 13(8): p. e1006487.
55. Huang, H., et al., *CD8+ T Cell Immune Response in Immunocompetent Mice during Zika Virus Infection.* J Virol, 2017.
56. Swain, S. L., K. K. McKinstry, and T. M. Strutt, *Expanding roles for CD4(+) T cells in immunity to viruses.* Nat Rev Immunol, 2012. 12(2): p. 136-48.
57. Sheehan, K. C., et al., *Blocking monoclonal antibodies specific for mouse IFN-alpha/beta receptor subunit 1 (IFNAR-1) from mice immunized by in vivo hydrodynamic transfection.* J Interferon Cytokine Res, 2006. 26(11): p. 804-19.
58. Pinto, A. K., et al., *A temporal role of type I interferon signaling in CD8+ T cell maturation during acute West Nile virus infection.* PLoS Pathog, 2011. 7(12): p. e1002407.
59. Aguirre, S. and A. Fernandez-Sesma, *Collateral Damage during Dengue Virus Infection: Making Sense of DNA by cGAS.* J Virol, 2017. 91(14).
60. Crespo, A. C., et al., *Cytotoxic potential of decidual NK cells and CD8+ T cells awakened by infections.* J Reprod Immunol, 2017. 119: p. 85-90.
61. Nancy, P., et al., *Chemokine gene silencing in decidual stromal cells limits T cell access to the maternal-fetal interface.* Science, 2012. 336(6086): p. 1317-21.
62. Braga, C., et al., *Seroprevalence and risk factors for dengue infection in socio-economically distinct areas of Recife, Brazil.* Acta Trop, 2010. 113(3): p. 234-40.
63. de Araujo, T. V. B., et al., *Association between microcephaly, Zika virus infection, and other risk factors in Brazil: final report of a case-control study.* Lancet Infect Dis, 2017.
64. Johansson, M. A., et al., *Zika and the Risk of Microcephaly.* N Engl J Med, 2016. 375(1): p. 1-4.
65. van Egmond, A., et al., *The possible role of virus-specific CD8(+) memory T cells in decidual tissue.* J Reprod Immunol, 2016. 113: p. 1-8.
66. Lissauer, D., M. D. Kilby, and P. Moss, *Maternal effector T cells within decidua: The adaptive immune response to pregnancy?* Placenta, 2017.
67. Tilburgs, T. and J. L. Strominger, *CD8+ effector T cells at the fetal-maternal interface, balancing fetal tolerance and antiviral immunity.* Am J Reprod Immunol, 2013. 69(4): p. 395-407.
68. Nancy, P. and A. Erlebacher, *T cell behavior at the maternal-fetal interface.* Int J Dev Biol, 2014. 58(2-4): p. 189-98.
69. Powell, R. M., et al., *Decidual T Cells Exhibit a Highly Differentiated Phenotype and Demonstrate Potential Fetal Specificity and a Strong Transcriptional Response to IFN.* J Immunol, 2017. 199(10): p. 3406-3417.
70. Tilburgs, T., et al., *Human decidual tissue contains differentiated CD8+ effector-memory T cells with unique properties.* J Immunol, 2010. 185(7): p. 4470-7.
71. Winkler, C. W., et al., *Adaptive Immune Responses to Zika Virus Are Important for Controlling Virus Infection and Preventing Infection in Brain and Testes.* J Immunol, 2017. 198(9): p. 3526-3535.

72. Jagger, B. W., et al., *Gestational Stage and IFN-lambda Signaling Regulate ZIKV Infection In Utero*. Cell Host Microbe, 2017. 22(3): p. 366-376 e3.
73. Shresta, S., et al., *Murine model for dengue virus-induced lethal disease with increased vascular permeability*. J Virol, 2006. 80(20): p. 10208-17.
74. Lanciotti, R. S., et al., *Genetic and serologic properties of Zika virus associated with an epidemic, Yap State, Micronesia, 2007.* Emerg Infect Dis, 2008. 14(8): p. 1232-9.

REFERENCES

IV—Example 4

1. Lazear, H. M. & Diamond, M. S. Zika Virus: New Clinical Syndromes and Its Emergence in the Western Hemisphere. *Journal of virology* 90, 4864-4875 (2016).
2. Choumet, V. & Despres, P. Dengue and other flavivirus infections. *Rev Sci Tech* 34, 473-478, 467-472 (2015).
3. Ngono, A. E. & Shresta, S. Immune Response to Dengue and Zika. *Annu Rev Immunol* 36, 279-308 (2018).
4. Wen, J. & Shresta, S. Antigenic cross-reactivity between Zika and dengue viruses: is it time to develop a universal vaccine? *Current opinion in immunology* 59, 1-8 (2019).
5. Dejnirattisai, W. et al. Dengue virus sero-cross-reactivity drives antibody-dependent enhancement of infection with zika virus. *Nature immunology* 17, 1102-1108 (2016).
6. Castanha, P. M. S. et al. Dengue Virus-Specific Antibodies Enhance Brazilian Zika Virus Infection. *The Journal of infectious diseases* 215, 781-785 (2017).
7. Charles, A. S. & Christofferson, R. C. Utility of a Dengue-Derived Monoclonal Antibody to Enhance Zika Infection In Vitro. *PLoS Curr* 8 (2016).
8. Kawiecki, A. B. & Christofferson, R. C. Zika Virus-Induced Antibody Response Enhances Dengue Virus Serotype 2 Replication In Vitro. *The Journal of infectious diseases* 214, 1357-1360 (2016).
9. Paul, L. M. et al. Dengue virus antibodies enhance Zika virus infection. *Clinical & translational immunology* 5, e117 (2016).
10. Priyamvada, L. et al. Human antibody responses after dengue virus infection are highly cross-reactive to Zika virus. *Proceedings of the National Academy of Sciences of the United States of America* 113, 7852-7857 (2016).
11. Swanstrom, J. A. et al. Dengue Virus Envelope Dimer Epitope Monoclonal Antibodies Isolated from Dengue Patients Are Protective against Zika Virus. *mBio* 7 (2016).
12. Paquin-Proulx, D. et al. T-cell Responses in Individuals Infected with Zika Virus and in Those Vaccinated Against Dengue Virus. *Pathogens & immunity* 2, 274-292 (2017).
13. Grifoni, A. et al. Prior Dengue virus exposure shapes T cell immunity to Zika virus in humans. *Journal of virology* 91, e01469-01417 (2017).
14. Lim, M. Q. et al. Cross-Reactivity and Anti-viral Function of Dengue Capsid and NS3-Specific Memory T Cells Toward Zika Virus. *Frontiers in immunology* 9, 2225 (2018).
15. Fernandez, E. et al. Human antibodies to the dengue virus E-dimer epitope have therapeutic activity against Zika virus infection. *Nature immunology* 18, 1261-1269 (2017).
16. Kam, Y. W. et al. Cross-reactive dengue human monoclonal antibody prevents severe pathologies and death from Zika virus infections. *JCI insight* 2 (2017).
17. Slon Campos, J. L. et al. DNA-immunisation with dengue virus E protein domains I/II, but not domain III, enhances Zika, West Nile and Yellow Fever virus infection. *PLoS one* 12, e0181734 (2017).
18. Bardina, S. V. et al. Enhancement of Zika virus pathogenesis by preexisting antiflavivirus immunity. *Science* (2017).
19. Fowler, A. M. et al. Maternally Acquired Zika Antibodies Enhance Dengue Disease Severity in Mice. *Cell host & microbe* 24, 743-750 e745 (2018).
20. Katzelnick, L. C. et al. Antibody-dependent enhancement of severe dengue disease in humans. *Science* 358, 929-932 (2017).
21. Salje, H. et al. Reconstruction of antibody dynamics and infection histories to evaluate dengue risk. *Nature* 557, 719-723 (2018).
22. Halstead, S. B. Dengue. *Lancet* 370, 1644-1652 (2007).
23. Wen, J. & Shresta, S. T Cell Immunity to Zika and Dengue Viral Infections. *J Interferon Cytokine Res* 37, 475-479 (2017).
24. Elong Ngono, A. et al. Mapping and Role of the CD8$^+$ T Cell Response During Primary Zika Virus Infection in Mice. *Cell host & microbe* 21, 35-46 (2017).
25. Huang, H. et al. CD8(+) T Cell Immune Response in Immunocompetent Mice during Zika Virus Infection. *Journal of virology* 91 (2017).
26. Wen, J. et al. Identification of Zika virus epitopes reveals immunodominant and protective roles for dengue virus cross-reactive CD8+ T cells. *Nature microbiology* 2, 17036 (2017).
27. Wen, J. et al. Dengue virus-reactive CD8(+) T cells mediate cross-protection against subsequent Zika virus challenge. *Nature communications* 8, 1459 (2017).
28. Regla-Nava, J. A. et al. Cross-reactive Dengue virus-specific CD8(+) T cells protect against Zika virus during pregnancy. *Nature communications* 9, 3042 (2018).
29. Lucas, C. G. O. et al. Critical role of CD4+ T cells and IFNγ signaling in antibody-mediated resistance to Zika virus infection. *Nature communications* 9 (2018).
30. Elong, N. A. et al. CD4+ T cells promote humoral immunity and viral control during Zika virus infection. *PLoS pathogens* 15, e1007474 (2019).
31. Hassert, M. et al. CD4+ T cells mediate protection against Zika associated severe disease in a mouse model of infection. *PLoS pathogens* 14, e1007237 (2018).
32. Reynolds, C. J. et al. T cell immunity to Zika virus targets immunodominant epitopes that show cross-reactivity with other Flaviviruses. *Scientific reports* 8, 672 (2018).
33. Weiskopf, D. et al. Insights into HLA-restricted T cell responses in a novel mouse model of dengue virus infection point toward new implications for vaccine design. *Journal of immunology* 187, 4268-4279 (2011).
34. Carlin, A. F. et al. A longitudinal systems immunologic investigation of acute Zika virus infection in an individual infected while traveling to Caracas, Venezuela. *PLoS neglected tropical diseases* 12, e0007053 (2018).
35. Yauch, L. E. et al. A protective role for dengue virus-specific CD8+ T cells. Journal of *immunology* 182, 4865-4873 (2009).
36. Earl, P. L. et al. Immunogenicity of a highly attenuated MVA smallpox vaccine and protection against monkeypox. *Nature* 428, 182-185 (2004).
37. Salek-Ardakani, S. et al. The TNFR family members OX40 and CD27 link viral virulence to protective T cell vaccines in mice. *J Clin Invest* 121, 296-307 (2011).

38. Panagioti, E., Klenerman, P., Lee, L. N., van der Burg, S. H. & Arens, R. Features of Effective T Cell-Inducing Vaccines against Chronic Viral Infections. *Frontiers in immunology* 9, 276 (2018).
39. Grant, A. et al. Zika Virus Targets Human STAT2 to Inhibit Type I Interferon Signaling. *Cell host & microbe* 19, 882-890 (2016).
40. Yu, C. Y. et al. Dengue virus targets the adaptor protein MITA to subvert host innate immunity. *PLoS pathogens* 8, e1002780 (2012).
41. Aguirre, S. et al. DENV inhibits type I IFN production in infected cells by cleaving human STING. *PLoS pathogens* 8, e1002934 (2012).
42. Ding, Q. et al. Species-specific disruption of STING-dependent antiviral cellular defenses by the Zika virus NS2B3 protease. *Proceedings of the National Academy of Sciences of the United States of America* 115, E6310-E6318 (2018).
43. Tang, W. W., Grewal, R. & Shresta, S. Influence of antibodies and T cells on dengue disease outcome: insights from interferon receptor-deficient mouse models. *Curr Opin Virol* 13, 61-66 (2015).
44. Yauch, L. E. et al. CD4+ T cells are not required for the induction of dengue virus-specific CD8+ T cell or antibody responses but contribute to protection after vaccination. *Journal of immunology* 185, 5405-5416 (2010).
45. Koblischke, M. et al. Structural Influence on the Dominance of Virus-Specific CD4 T *Cell* Epitopes in Zika Virus Infection. *Frontiers in immunology* 9, 1196 (2018).
46. Weiskopf, D. et al. Immunodominance changes as a function of the infecting dengue virus serotype and primary versus secondary infection. *Journal of virology* 88, 11383-11394 (2014).
47. Weiskopf, D. et al. Insights into HLA-restricted T cell responses in a novel mouse model of dengue virus infection point toward new implications for vaccine design. *Journal of immunology* 187, 4268-4279 (2011).
48. Weiskopf, D. et al. Dengue virus infection elicits highly polarized CX3CR1+ cytotoxic CD4$^+$ T cells associated with protective immunity. *Proceedings of the National Academy of Sciences of the United States of America* 112, E4256-4263 (2015).
49. Weiskopf, D. et al. HLA-DRB1 Alleles Are Associated With Different Magnitudes of Dengue Virus-Specific CD4$^+$ T-*Cell* Responses. *The Journal of infectious diseases* 214, 1117-1124 (2016).
50. Elong Ngono, A. et al. Protective Role of Cross-Reactive CD8 T Cells Against Dengue Virus Infection. *EBioMedicine* 13, 284-293 (2016).
51. Weiskopf, D. et al. Comprehensive analysis of dengue virus-specific responses supports an HLA-linked protective role for CD8+ T cells. Proceedings of the National Academy of Sciences of the United States of America 110, E2046-2053 (2013).
52. Weiskopf, D. et al. Human CD8+ T-Cell Responses Against the 4 Dengue Virus Serotypes Are Associated With Distinct Patterns of Protein Targets. *The Journal of infectious diseases* 212, 1743-1751 (2015).
53. de Alwis, R. et al. Immunodominant Dengue Virus-Specific CD8+ T *Cell* Responses Are Associated with a Memory PD-1+ Phenotype. *Journal of virology* 90, 4771-4779 (2016).

What is claimed is:

1. A method of inducing, enhancing, or sustaining an immune response against Zika virus in a subject, the method comprising contacting T cells of the subject with an effective amount of a composition comprising an acceptable carrier or diluent, and one or more peptides selected from the group of a peptide consisting of an amino acid sequence set forth in any one of SEQ ID NO: 125 to SEQ ID NO: 129.

2. The method of claim 1, wherein the method is conducted following the date of suspected infection by or exposure to the Zika virus.

3. A method of stimulating, inducing, promoting, increasing, or enhancing an immune response against Zika virus in a subject, comprising administering to a subject an effective amount of a composition comprising an acceptable carrier or diluent, and one or more peptides selected from the group of a peptide consisting of an amino acid sequence set forth in any one of SEQ ID NO: 125 to SEQ ID NO: 129.

4. A method for treating, reducing or inhibiting susceptibility to Zika virus infection or pathology in a subject, comprising administering to a subject an amount of a composition an acceptable carrier or diluent, and one or more peptides selected from the group of a peptide consisting of an amino acid sequence set forth in any one of SEQ ID NO: 125 to SEQ ID NO: 129.

5. The method of claim 4, wherein the method elicits, stimulates, induces, promotes, increases, or enhances an anti-Zika virus T cell response or a CD4+ T cell response.

6. The method of claim 4, wherein the composition is administered prior to exposure to the virus or within 2-72 hours after a rash develops.

7. A method of inducing, increasing, promoting or stimulating anti-Zika virus activity of T cells in a subject, comprising administering to a subject an amount of composition comprising an acceptable carrier or diluent, and one or more peptides selected from the group of a peptide consisting of an amino acid sequence set forth in any one of SEQ ID NO: 125 to SEQ ID NO: 129.

8. A method of stimulating, inducing, promoting, increasing, or enhancing an immune response against Zika virus in a subject, comprising administering to a subject an amount of a composition comprising an acceptable carrier or diluent, and one or more peptides selected from the group of a peptide consisting of an amino acid sequence set forth in any one of SEQ ID NO: 125 to SEQ ID NO: 129.

9. A method of treating a subject for a Zika virus infection, comprising administering to a subject an amount of a composition comprising an acceptable carrier or diluent, and one or more peptides selected from the group of a peptide consisting of an amino acid sequence set forth in any one of SEQ ID NO: 125 to SEQ ID NO: 129.

10. The method of claim 9, wherein the method reduces Zika virus titer, increases or stimulates Zika virus clearance, reduces or inhibits Zika virus proliferation, reduces or inhibits increases in Zika virus titer or Zika virus proliferation, reduces the amount of a Zika virus protein or the amount of a Zika virus nucleic acid, or reduces or inhibits synthesis of a Zika virus protein or a Zika virus nucleic acid or reduces or improves one or more adverse physiological conditions, disorders, illness, diseases, symptoms or complications caused by or associated with Zika virus infection or pathology.

11. A method of inducing, increasing, promoting or stimulating anti-Zika virus activity of T cells in a subject, comprising administering to a subject an amount of a composition comprising an acceptable carrier or diluent, and one or more peptides selected from the group of a peptide consisting of an amino acid sequence set forth in any one of SEQ ID NO: 125 to SEQ ID NO: 129.

* * * * *

SEQUENCE LISTING

```
<160> NUMBER OF SEQ ID NOS: 157

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived epitopes, E protein 600-607

<400> SEQUENCE: 1

Ala Ala Phe Thr Phe Thr Lys Val
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes, NS2B protein 1489-1497

<400> SEQUENCE: 2

Ala Ala Gly Ala Trp Tyr Val Tyr Val
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes, PrM protein 145-153
```

```
<400> SEQUENCE: 3

Ile Ser Phe Ala Thr Thr Leu Gly Val
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived epitopes, PrM protein 171-178

<400> SEQUENCE: 4

Met Ser Tyr Glu Cys Pro Met Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes NS3 1866-1874

<400> SEQUENCE: 5

Pro Ser Val Arg Asn Gly Asn Glu Ile
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived epitopes NS5 2993-3000

<400> SEQUENCE: 6

Arg Ala Ile Trp Tyr Met Trp Leu
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      ZIKV-derived epitopes NS5 2892-2902

<400> SEQUENCE: 7

Arg Gln Val Met Asn Ile Val Ser Ser Trp Leu
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes NS3 1795-1803

<400> SEQUENCE: 8

Ser Ser Ile Ala Ala Arg Gly Tyr Ile
1               5

<210> SEQ ID NO 9
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      ZIKV-derived epitopes NS5 2839-2848

<400> SEQUENCE: 9

Ser Ser Leu Val Asn Gly Val Val Arg Leu
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived epitopes NS5 2899-2906

<400> SEQUENCE: 10

Ser Ser Trp Leu Trp Lys Glu Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes NS5 3220-3228

<400> SEQUENCE: 11

Thr Gly Trp Ser Asn Trp Glu Glu Val
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes E 338-346

<400> SEQUENCE: 12

Thr Thr Val Ser Asn Met Ala Glu Val
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes E 784-792

<400> SEQUENCE: 13

Val Met Ile Phe Leu Ser Thr Ala Val
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived epitopes NS1 969-978

<400> SEQUENCE: 14

Tyr Ser Leu Glu Cys Asp Pro Ala Val Ile
1               5                   10
```

```
<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived epitopes E 600-607

<400> SEQUENCE: 15

Ala Ala Phe Thr Phe Thr Lys Ile
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived epitopes NS5 2839-2848

<400> SEQUENCE: 16

Ser Ser Leu Ile Asn Gly Val Val Arg Leu
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes PrM 150-158

<400> SEQUENCE: 17

Thr Leu Gly Met Asn Lys Cys Tyr Ile
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived epitopes NS4A 2257-2264

<400> SEQUENCE: 18

Ile Met Val Ala Val Gly Leu Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes PrM 169-177

<400> SEQUENCE: 19

Ala Thr Met Ser Tyr Glu Cys Pro Met
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived epitopes NS5 2783-2792
```

```
<400> SEQUENCE: 20

Cys Ala Glu Ala Pro Asn Met Lys Val Ile
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes E 294-302

<400> SEQUENCE: 21

Ile Gly Val Ser Asn Arg Asp Phe Val
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      ZIKV-derived epitopes E 635-645

<400> SEQUENCE: 22

Met Ala Val Asp Met Gln Thr Leu Thr Pro Val
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes E 710-718

<400> SEQUENCE: 23

Arg Met Ala Val Leu Gly Asp Thr Ala
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes E 347-355

<400> SEQUENCE: 24

Arg Ser Tyr Cys Tyr Glu Ala Ser Ile
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes E 297-305

<400> SEQUENCE: 25

Ser Asn Arg Asp Phe Val Glu Gly Met
1               5

<210> SEQ ID NO 26
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      ZIKV-derived epitopes NS4B 2371-2379

<400> SEQUENCE: 26

Ser Gln Leu Thr Pro Leu Thr Leu Ile
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived epitopes NS2A 1336-1345

<400> SEQUENCE: 27

Ser Val Lys Lys Asn Leu Pro Phe Val Met
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived epitopes NS2A 1237-1244

<400> SEQUENCE: 28

Val Ser Phe Ile Phe Arg Ala Asn
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived epitopes NS3 1656-1664

<400> SEQUENCE: 29

Val Val Ile Lys Asn Gly Ser Tyr Val
1               5

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      ZIKV-derived HLA-restricted epitopes C 25-35

<400> SEQUENCE: 30

Ser Pro Phe Gly Gly Leu Lys Arg Leu Pro Ala
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA-restricted epitopes MR-M 4-12

<400> SEQUENCE: 31

Leu Pro Ser His Ser Thr Arg Lys Leu
```

```
<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived HLA-restricted epitopes MR-E 38-45

<400> SEQUENCE: 32

Lys Pro Thr Val Asp Ile Glu Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA-restricted epitopes MR-E 170-178

<400> SEQUENCE: 33

Thr Pro Asn Ser Pro Arg Ala Glu Ala
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived HLA-restricted epitopes MR-E 173-180

<400> SEQUENCE: 34

Ser Pro Arg Ala Glu Ala Thr Leu
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes MR-E 233-242

<400> SEQUENCE: 35

Thr Pro His Trp Asn Asn Lys Glu Ala Leu
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes E 337-347

<400> SEQUENCE: 36

Gly Pro Cys Lys Val Pro Ala Gln Met Ala Val
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
```

ZIKV-derived HLA restricted epitopes MR-NS 199-107

<400> SEQUENCE: 37

Gly Pro Gln Arg Leu Pro Val Pro Val
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS2A 31-40

<400> SEQUENCE: 38

Val Val Met Ile Leu Gly Gly Phe Ser Met
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes MR-NS2A 75-84

<400> SEQUENCE: 39

Arg Pro Ala Leu Leu Val Ser Phe Ile Phe
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes MR-NS2A 89-99

<400> SEQUENCE: 40

Thr Pro Arg Glu Ser Met Leu Leu Ala Leu
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS2A 133-141

<400> SEQUENCE: 41

Val Pro Arg Thr Asp Asn Ile Thr Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS2A 133-141

<400> SEQUENCE: 42

Val Pro Arg Thr Asp Asn Ile Ala Leu
1               5

<210> SEQ ID NO 43

```
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS2A 141-150

<400> SEQUENCE: 43

Leu Pro Ile Leu Ala Ala Leu Thr Pro Leu
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS2A 148-155

<400> SEQUENCE: 44

Thr Pro Leu Ala Arg Gly Thr Leu
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS2B 68-75

<400> SEQUENCE: 45

Ser Pro Arg Leu Asp Val Ala Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 188-196

<400> SEQUENCE: 46

Leu Pro Glu Ile Val Arg Glu Ala Ile
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 206-215

<400> SEQUENCE: 47

Ala Pro Thr Arg Val Val Ala Ala Glu Met
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 309-317

<400> SEQUENCE: 48
```

Phe Pro Asp Ser Asn Ser Pro Ile Met
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 405-413

<400> SEQUENCE: 49

Arg Val Ile Asp Ser Arg Arg Cys Leu
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 427-436

<400> SEQUENCE: 50

Gly Pro Met Pro Val Thr His Ala Ser Ala
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 492-501

<400> SEQUENCE: 51

Arg Pro Glu Ala Asp Lys Val Ala Ala Ile
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 574-582

<400> SEQUENCE: 52

Lys Pro Arg Trp Met Asp Ala Arg Val
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 581-589

<400> SEQUENCE: 53

Arg Val Cys Ser Asp His Ala Ala Leu
1               5

<210> SEQ ID NO 54
<211> LENGTH: 9
<212> TYPE: PRT
<213> ORGANISM: Artificial Sequence
<220> FEATURE:

<223> OTHER INFORMATION: Description of Artificial Sequence: Synthetic
ZIKV-derived HLA restricted epitopes NS 3596-NS4A1

<400> SEQUENCE: 54

Ala Ala Gly Lys Arg Gly Ala Ala Leu
1               5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
ZIKV-derived HLA restricted epitopes NS4A 36-45

<400> SEQUENCE: 55

Arg Pro Tyr Lys Ala Ala Ala Ala Gln Leu
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
ZIKV-derived HLA restricted epitopes NS4A 125-133

<400> SEQUENCE: 56

Ser Pro Gln Asp Asn Gln Met Ala Ile
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
ZIKV-derived HLA restricted epitopes NS4B 35-44

<400> SEQUENCE: 57

Arg Pro Ala Ser Ala Trp Ala Ile Tyr Ala
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
ZIKV-derived HLA restricted epitopes NS4B 105-115

<400> SEQUENCE: 58

Thr Pro Leu Thr Leu Ile Val Ala Ile Ile Leu
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
ZIKV-derived HLA restricted epitopes NS4B 210-220

<400> SEQUENCE: 59

Ser Pro Asn Lys Tyr Trp Asn Ser Ser Thr Ala
1               5                   10

```
<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS4B 426-435

<400> SEQUENCE: 60

Arg Pro Gly Ala Phe Cys Ile Lys Val Leu
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS5 61-70

<400> SEQUENCE: 61

Ala Pro Thr Gln Gly Ser Ala Ser Ser Leu
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS5 140-149

<400> SEQUENCE: 62

Arg Pro Arg Val Cys Thr Lys Glu Glu Phe
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS5 332-341

<400> SEQUENCE: 63

Arg Pro Ala Glu Gly Gly Lys Thr Val Met
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS5 539-546

<400> SEQUENCE: 64

Val Pro Thr Gly Arg Thr Thr Trp
1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS5 587-596

<400> SEQUENCE: 65
```

Ile Pro Tyr Leu Gly Lys Arg Glu Asp Leu
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS5 605-614

<400> SEQUENCE: 66

Arg Pro Arg Thr Thr Trp Ala Glu Asn Ile
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes C125-prM8

<400> SEQUENCE: 67

Val Thr Arg Arg Gly Asn Ala Tyr Tyr
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes prM 40-48

<400> SEQUENCE: 68

His Met Cys Asp Ala Thr Met Ser Tyr
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes E 81-90

<400> SEQUENCE: 69

Tyr Leu Asp Lys Gln Ser Asp Thr Gln Tyr
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes E 159-167

<400> SEQUENCE: 70

Glu Thr Asp Glu Asn Arg Ala Lys Val
1               5

<210> SEQ ID NO 71
<211> LENGTH: 9
<212> TYPE: PRT
<213> ORGANISM: Artificial Sequence

```
<220> FEATURE:
<223> OTHER INFORMATION: Description of Artificial Sequence: Synthetic
      ZIKV-derived HLA restricted epitopes E 195-203

<400> SEQUENCE: 71

Gly Leu Asp Phe Ser Asp Leu Tyr Tyr
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes E 198-206

<400> SEQUENCE: 72

Phe Ser Asp Leu Tyr Tyr Leu Thr Met
1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes E 377-386

<400> SEQUENCE: 73

Glu Leu Asp Pro Pro Phe Gly Asp Ser Tyr
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS1 23-31

<400> SEQUENCE: 74

Asp Val Glu Ala Trp Arg Asp Arg Tyr
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS3 272-280

<400> SEQUENCE: 75

Phe Thr Asp Pro Ser Ser Ile Ala Ala
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      ZIKV-derived HLA restricted epitopes NS4A 14-22

<400> SEQUENCE: 76

Met Thr Glu Arg Phe Gln Glu Ala Ile
1               5
```

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
     ZIKV-derived HLA restricted epitopes NS4B 231-239

<400> SEQUENCE: 77

Tyr Leu Ala Gly Ala Ser Leu Ile Tyr
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
     ZIKV-derived HLA restricted epitopes NS4B 270-278

<400> SEQUENCE: 78

Met Ser Ala Leu Glu Phe Tyr Ser Tyr
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
     ZIKV-derived HLA restricted epitopes NS5 509-517

<400> SEQUENCE: 79

Tyr Ala Gln Met Trp Gln Leu Leu Tyr
1               5

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
     Hepatitis C virus (HCV)-core helper peptide
     restricted by mouse MHC molecule I-Ab

<400> SEQUENCE: 80

Thr Pro Pro Ala Tyr Arg Arg Pro Pro Asn Ala Pro Ile Leu
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
     DENV2-NS2A 74-83

<400> SEQUENCE: 81

Arg Pro Thr Phe Ala Ala Gly Leu Leu Leu
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
     DENV2-NS3 575-583

<400> SEQUENCE: 82

Lys Pro Arg Trp Leu Asp Ala Arg Ile
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      DENV2-NS4B 423-432

<400> SEQUENCE: 83

Asn Thr Gln Phe Cys Ile Lys Val Leu
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      DENV2-NS5 538-545

<400> SEQUENCE: 84

Val Pro Thr Ser Arg Thr Thr Trp
1               5

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      DENV2-NS5 140-149

<400> SEQUENCE: 85

Thr Pro Arg Met Cys Thr Arg Glu Glu Phe
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      DENV2-NS3187-195

<400> SEQUENCE: 86

Leu Pro Ala Ile Val Arg Glu Ala Ile
1               5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      DENV2-NS2A 31-40

<400> SEQUENCE: 87

Val Thr Leu Ile Thr Gly Asn Met Ser Phe
1               5                   10

<210> SEQ ID NO 88
<211> LENGTH: 10

```
<212> TYPE: PRT
<213> ORGANISM: Artificial Sequence
<220> FEATURE:
<223> OTHER INFORMATION: Description of Artificial Sequence: Synthetic
      DENV2-NS2A 87-97

<400> SEQUENCE: 88

Thr Ser Lys Glu Leu Met Met Thr Thr Ile
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      DENV2-NS3 428-437

<400> SEQUENCE: 89

Gly Pro Met Pro Val Thr His Ser Ser Ala
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      DENV2-NS4B 208-218

<400> SEQUENCE: 90

Asn Pro Gly Arg Phe Trp Asn Thr Thr Ile Ala
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      DENV2-NS5 61-70

<400> SEQUENCE: 91

Thr Lys Gln Thr Gly Ser Ala Ser Ser Met
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      DENV2-E 38-45

<400> SEQUENCE: 92

Lys Pro Thr Leu Asp Phe Glu Leu
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      DENV2-NS3 582-590

<400> SEQUENCE: 93

Arg Ile Tyr Ser Asp Pro Leu Ala Leu
```

```
<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      forward primer to detect ZIKV RNA

<400> SEQUENCE: 94
ttggtcatga tactgctgat tgc                                            23

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      Reverse primer to detect ZIKV RNA

<400> SEQUENCE: 95
ccttccacaa agtccctatt gc                                             22

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      Probe to detect ZIKV RNA
<220> FEATURE:
<223> OTHER INFORMATION: 5' 6-FAM
<220> FEATURE:
<223> OTHER INFORMATION: 3' TAMRA-Q

<400> SEQUENCE: 96
cggcatacag catcaggtgc ataggag                                        27

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Phe Gly Gly Leu Lys Arg Leu Pro Ala Gly Leu Leu Leu Gly His
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Phe Leu Arg Phe Thr Ala Ile Lys Pro Ser Leu Gly Leu Ile Asn
1               5                   10                  15

<210> SEQ ID NO 99
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 99

Ile Lys Lys Phe Lys Lys Asp Leu Ala Ala Met Leu Arg Ile Ile
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asn Pro Gly Phe Ala Leu Ala Ala Ala Ile Ala Trp Leu Leu
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Leu Val Met Ile Leu Leu Ile Ala Pro Ala Tyr Ser Ile Arg
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Leu Glu Tyr Arg Ile Met Leu Ser Val His Gly Ser Gln His
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Ala Ala Phe Thr Phe Thr Lys Ile Pro Ala Glu Thr Leu His
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Ala Ala Phe Lys Ser Leu Phe Gly Gly Met Ser Trp Phe Ser
1               5                   10                  15
```

```
<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Gly Val Leu Ile Phe Leu Ser Thr Ala Val Ser Ala Asp Val
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asn Asp Thr Trp Arg Leu Lys Arg Ala His Leu Ile Glu Met Lys
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Thr Lys Ile Ile Ile Ser Thr Ser Met Ala Val Leu Val Ala
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Ala Leu Ile Ala Ala Phe Lys Val Arg Pro Ala Leu Leu Val
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Leu Ala Trp Leu Ala Ile Arg Ala Met Val Val Pro Arg Thr
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110
```

Asn Ile Thr Leu Ala Ile Leu Ala Ala Leu Thr Pro Leu Ala Arg
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Phe Met Leu Leu Ser Leu Lys Gly Lys Gly Ser Val Lys
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Leu Pro Phe Val Met Ala Leu Gly Leu Thr Ala Val Arg Leu Val
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Gly Arg Val Ile Gly Leu Tyr Gly Asn Gly Val Val Ile Lys
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Leu Arg Thr Val Ile Leu Ala Pro Thr Arg Val Val Ala Ala
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Ala Ala Phe Gly Val Met Glu Ala Leu Gly Thr Leu Pro Gly
1               5                   10                  15

<210> SEQ ID NO 116
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 116

Gly Ile Phe Phe Val Leu Met Arg Asn Lys Gly Ile Gly Lys Met
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Met Ala Ile Ile Ile Met Val Ala Val Gly Leu Leu Gly Leu
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Ala Ile Tyr Ala Ala Leu Thr Thr Phe Ile Thr Pro Ala Val
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asn Tyr Ser Leu Met Ala Met Ala Thr Gln Ala Gly Val Leu Phe
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Gly Cys Tyr Ser Gln Leu Thr Pro Leu Thr Leu Ile Val Ala
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Pro Gly Leu Gln Ala Ala Ala Ala Arg Ala Ala Gln Lys Arg
1               5                   10                  15
```

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Met Gly Gln Val Leu Leu Ile Ala Val Ala Val Ser Ser Ala Ile
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Phe Arg Gly Ser Tyr Leu Ala Gly Ala Ser Leu Ile Tyr Thr Val
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Trp Ser Tyr Tyr Ala Ala Thr Ile Arg Lys Val Gln Glu Val
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ala Ile Trp Tyr Met Trp Leu Gly Ala Arg Phe Leu Glu Phe
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

His Arg Arg Asp Leu Arg Leu Met Ala Asn Ala Ile Cys Ser Ser
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 127

Asn Leu Glu Tyr Thr Ile Val Ile Thr Pro His Ser Gly Glu Glu
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Ala Leu Leu Ala Ala Phe Lys Val Arg Pro Thr Phe Ala Ala
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Trp Ala Leu Cys Glu Ala Leu Thr Leu Ala Thr Gly Pro Ile Ser
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ile Arg Cys Ile Gly Val Ser Asn Arg Asp Phe Val Glu Gly Met
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Val Ser Asn Arg Asp Phe Val Glu Gly Met Ser Gly Gly Thr Trp
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Val Thr Thr Thr Val Ser Asn Met Ala Glu Val Arg Ser Tyr Cys
1               5                   10                  15

<210> SEQ ID NO 133
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 133

Ser Asn Met Ala Glu Val Arg Ser Tyr Cys Tyr Glu Ala Ser Ile
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Leu Val Glu Phe Lys Asp Ala His Ala Lys Arg Gln Thr Val
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Ala Leu Glu Ala Glu Met Asp Gly Ala Lys Gly Lys Leu Phe
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Lys Leu Arg Leu Lys Gly Val Ser Tyr Ser Leu Cys Thr Ala
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Gly Val Ser Tyr Ser Leu Cys Thr Ala Ala Phe Thr Phe Thr
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Leu Cys Thr Ala Ala Phe Thr Phe Thr Lys Val Pro Ala Glu
1               5                   10                  15
```

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Lys Val Pro Ala Glu Thr Leu His Gly Thr Val Thr Val Glu Val
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Thr Leu His Gly Thr Val Thr Val Glu Val Gln Tyr Ala Gly Thr
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Val Thr Val Glu Val Gln Tyr Ala Gly Thr Asp Gly Pro Cys Lys
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Gly Pro Cys Lys Ile Pro Val Gln Met Ala Val Asp Met Gln
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ile Pro Val Gln Met Ala Val Asp Met Gln Thr Leu Thr Pro Val
1               5                   10                  15

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 144

Asn Arg Asp Phe Val Glu Gly Met
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Met Ser Gly Gly Thr Trp
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Thr Ala Leu Ala Gly Ala Leu Glu Ala
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Gly Ala Lys Gly Arg Leu Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Lys Leu Arg Leu Lys Gly Val Ser Tyr
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Val Ser Tyr Ser Leu Cys Thr Ala
1               5

<210> SEQ ID NO 150
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Thr Ala Ala Phe Thr Phe Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Phe Thr Phe Thr Lys Ile Pro Ala Glu
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Ala Glu Thr Leu His Gly Thr
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

His Gly Thr Val Thr Val Glu Val
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Val Glu Val Gln Tyr Ala Gly Thr
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Gly Thr Asp Gly Pro Cys Lys
```

```
-continued

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Met Gln Thr Leu Thr Pro Val
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asn Pro Val Ile Thr Glu Ser Thr Glu
1               5
```